(12) United States Patent
Zhang et al.

(10) Patent No.: US 7,732,129 B1
(45) Date of Patent: Jun. 8, 2010

(54) METHOD FOR THE PRODUCTION AND PURIFICATION OF ADENOVIRAL VECTORS

(75) Inventors: Shuyuan Zhang, Sugar Land, TX (US); Capucine Thwin, Spring, TX (US); Zheng Wu, Sugar Land, TX (US); Toohyon Cho, Houston, TX (US); Shawn Gallagher, Missouri City, TX (US)

(73) Assignee: Crucell Holland B.V., Leiden (NL)

( * ) Notice: Subject to any disclaimer, the term of this patent is extended or adjusted under 35 U.S.C. 154(b) by 1634 days.

(21) Appl. No.: 09/203,078

(22) Filed: Dec. 1, 1998
(Under 37 CFR 1.47)

(51) Int. Cl.
*C12Q 1/70* (2006.01)
(52) U.S. Cl. .......................................................... 435/5
(58) Field of Classification Search .............. 435/173.9, 435/235.1, 239, 320.1, 366, 380, 383, 475
See application file for complete search history.

(56) References Cited

U.S. PATENT DOCUMENTS

| | | | |
|---|---|---|---|
| 4,352,883 A | 10/1982 | Lim | |
| 4,725,547 A | 2/1988 | Sakamoto et al. | 435/239 |
| 4,797,368 A | 1/1989 | Carter et al. | 435/320 |
| 5,106,841 A * | 4/1992 | Scheer | 514/185 |
| 5,139,941 A | 8/1992 | Muzycka et al. | 435/172.3 |
| 5,552,309 A | 9/1996 | March | 435/172.3 |
| 5,607,851 A | 3/1997 | Pellegrini et al. | 435/236 |
| 5,670,488 A | 9/1997 | Gregory et al. | 514/44 |
| 5,733,720 A | 3/1998 | Olivo | 435/5 |
| 5,744,304 A | 4/1998 | Munford | 435/6 |
| 5,789,244 A | 8/1998 | Heidrum et al. | 435/320.1 |
| 5,824,544 A | 10/1998 | Armentano et al. | 435/320.1 |
| 5,837,520 A | 11/1998 | Shabram et al. | 435/239 |
| 5,932,210 A | 8/1999 | Gregory et al. | 424/93.2 |
| 5,965,358 A | 10/1999 | Carrion et al. | 435/5 |
| 6,143,290 A * | 11/2000 | Zhang et al. | 424/93.2 |
| 6,143,548 A | 11/2000 | O'Riordan et al. | 435/239 |
| 6,168,944 B1 | 1/2001 | Condon et al. | 435/239 |
| 6,194,191 B1 | 2/2001 | Zhang et al. | 435/239 |
| 6,194,210 B1 * | 2/2001 | Leu et al. | 435/403 |
| 6,261,823 B1 | 7/2001 | Tang et al. | 435/239 |
| 6,316,185 B1 | 11/2001 | Saifer et al. | 435/5 |
| 6,383,795 B1 | 5/2002 | Carrión et al. | 435/239 |
| 6,447,995 B1 | 9/2002 | Carrion et al. | 435/5 |
| 6,485,958 B2 | 11/2002 | Blanche et al. | 435/239 |
| 6,537,793 B2 | 3/2003 | Blanche et al. | 435/239 |
| 6,586,226 B2 | 7/2003 | Carrion et al. | 435/239 |
| 6,689,600 B1 * | 2/2004 | Wu et al. | 435/235.1 |
| 6,726,904 B2 | 4/2004 | Krauss et al. | 424/78.17 |
| 7,125,706 B2 | 10/2006 | Zhang et al. | 435/235.1 |
| 2002/0018723 A1 | 2/2002 | Mera et al. | 417/222.2 |
| 2002/0045160 A1 | 4/2002 | Carrion et al. | 435/5 |
| 2002/0182723 A1 * | 12/2002 | Zhang et al. | 435/320.1 |

FOREIGN PATENT DOCUMENTS

| | | |
|---|---|---|
| EP | 0273085 | 12/1986 |
| EP | 0475623 | 3/1992 |
| JP | 1279843 | 11/1989 |
| JP | 4-9338 | 1/1992 |
| WO | WO 93/18790 | 9/1993 |
| WO | WO 93/25224 | 12/1993 |
| WO | WO 94/06910 | 3/1994 |
| WO | WO 94/17178 | 8/1994 |
| WO | WO 95/06743 | 3/1995 |
| WO | WO 95/10601 | 4/1995 |
| WO | WO 95/19427 | 7/1995 |
| WO | WO 95/24468 | 9/1995 |
| WO | WO 95/25789 | 9/1995 |
| WO | WO 96/09399 | 3/1996 |
| WO | WO 96/27677 | 9/1996 |
| WO | WO 96/32116 | 10/1996 |
| WO | WO 97/04803 | 2/1997 |
| WO | WO 97/08298 | 3/1997 |
| WO | WO/98/00524 | 1/1998 |
| WO | WO 98/22588 * | 5/1998 |
| WO | WO 98/26048 | 6/1998 |
| WO | WO 98/35554 | 8/1998 |
| WO | WO 99/12568 | 3/1999 |
| WO | WO 99/41416 | 8/1999 |
| WO | WO 99/43843 | 9/1999 |
| WO | WO 98/54441 | 10/1999 |
| WO | WO 99/54441 | 10/1999 |
| WO | WO 00/32754 | 6/2000 |
| WO | WO 00/34444 | 6/2000 |
| WO | WO 00/40702 | 7/2000 |
| WO | WO 02/29388 | 4/2002 |

OTHER PUBLICATIONS

Kraft et al. Archives of Virology 1978. 57 (3): 243-54. (Abstract only.).*

Murphy et al. Virus Taxonomy . In B.N. Fields et al. (ed.), Fields Virology, 3rd ed. Philadelphia: Lippencott-Raven Publishers; 1996: Table 6, pp. 51-54.*

(Continued)

*Primary Examiner*—Ali R. Salimi
(74) *Attorney, Agent, or Firm*—Fulbright & Jaworski LLP

(57) ABSTRACT

The present invention addresses the need to improve the yields of viral vectors when grown in cell culture systems. In particular, it has been demonstrated that for adenovirus, the use of low-medium perfusion rates in an attached cell culture system provides for improved yields. In other embodiments, the inventors have shown that there is improved Ad-p53 production with cells grown in serum-free conditions, and in particular in serum-free suspension culture. Also important to the increase of yields is the use of detergent lysis. Combination of these aspects of the invention permits purification of virus by a single chromatography step that results in purified virus of the same quality as preparations from double CsCl banding using an ultracentrifuge.

59 Claims, 50 Drawing Sheets

OTHER PUBLICATIONS

Aboud et al., "Rapid purification of extracellular and intracellular moloney murine leukemia virus," *Arch. Virol.*, 71:185-195, 1982.

Arap et al., "Replacement of the *p16/CDKN2* gene suppresses human glioma cell growth," *Cancer Res.*, 55:1351-1354, 1995.

Baichwal and Sugden, *In*: Kucherlapati R, ed. Gene transfer. New York: Plenum Press, pp. 117-148, 1986.

Benvenisty and Neshif, "Direction introduction of genes into rats and expression of the genes," *Proc. Nat'l Acad. Sci. USA*, 83:9551-9555, 1986.

Berg et al., "High-level expression of secreted proteins from cells adapted to serum-free suspension culture," *BioTechniques*, 14(6):972-978, 1993.

Bett, "An efficient and flexible system for construction of adenovirus vectors with insertions or deletions in early regions 1 and 3," *Proc. Natl. Acad. Sci. USA*, 91(19):8802-8806, 1994.

Bussemakers et al., "Decreased expression of E-cadherin in the progression of rat prostatic cancer," *Cancer Res.*, 52:2916-2922, 1992.

Caldas et al., "Frequent somatic mutations and homozygous deletions of the p16 (MTS1) gene in pancreatic adenocarcinoma," *Nat. Genet.*, 8:27-32, 1994.

Casey et al., "Growth suppression of human breast cancer cells by the introduction of a wild-type p53 gene," *Oncogene*, 6:1791-1797, 1991.

Chen and Okayama, "High-efficiency transfection of mammalian cells by plasmid DNA," *Mol. Cell Biol.*, 7:2745-2752, 1987.

Cheng et al., "*p16* Alterations and deletion mapping of 9p21-p22 in malignant mesothelioma," Cancer *Res.*, 54:5547-5551, 1994.

Cheung et al., "Structure and function of C-CAM1," *J Biol Chem.* 268(32):24303-24310, 1993.

Cheung et al., "The cytoplaxmic domain of C-CAM is required for C-CAM-mediated adhesion function: studies of a C-CAM transcript containing an unspliced intron", *Biochem. J.*, 295:427-435, 1993.

Cheung et al., "Cell-CAM105 isoforms with different adhesion functions are coexpressed in adult rat tissues and during liver development", *J. Biol. Chem.*, 268:6139-6146, 1993.

Coffin, "Retroviridae and their replication," *In: Virology*, Fields et al. (eds.), New York: Raven Press, pp. 1437-1500, 1990.

Coupar et al., "A general method for the construction of recombinant vaccinia virus expressing multiple foreign genes," *Gene*, 68:1-10, 1988.

Crooks et al., "Purification and analysis of infections virions and native non-structural antigens from cells infected with tick-borne encephalitis virus," *J. Chrom.*, 502:59-68, 1990.

Dubensky et al,. "Direct transfection of viral and plasmid DNA into the liver or spleen of mice," *Proc. Nat. Acad. Sci. USA*, 81:7529-7533, 1984.

Edelman and Crossin, "Cell adhesion molecules: implications for a molecular histology," *Annu. Rev. Biochem.*, 60:155-190, 1991.

Edelman, "Cell adhesion and the molecular processes of morphogenesis," *Annu. Rev. Biochem.*, 54:135-169, 1985.

Fechheimer et al., "Transfection of mammalian cells with plasmid DNA by scrape loading and sonication loading," *Proc. Nat'l Acad. Sci. USA*, 84:8463-8467, 1987.

Ferkol et al., "Regulation of the phosphoenolpyruvatecarboxykinase/humanfactor IX gene introduced into the livers of adult rats by receptor-mediatedgene transfer," *FASEB J.*, 7:1081-1091, 1993.

Fraley et al., "Entrapment of a bacterial plasmid in phospholipid vesicles: Potential for gene transfer," *Proc. Nat'l Acad. Sci. USA*, 76:3348-3352, 1979.

Freshney, "Animal Cell Culture: a Practical Approach", Second Edition, Oxford/New York, IRL Press, Oxford University Press, 1992.

Frixen et al., "E-cadherin-mediated cell-cell adhesion prevents invasiveness of human carcinoma cells," *J. Cell Biol.*, 113:173-185, 1991.

Garnier et al., "Scale-up of the adenovirus expression system for the production of recombinant protein in human 293S cells," *Cytotechnol.*, 15:145-155, 1994.

Ghosh and Bachhawat, *In: Liver Diseases, Targeted Diagnosis and Therapy Using Specific Receptors and Ligands*, Wu G, Wu C (ed.), Marcel Dekker, New York, pp. 87-104, 1991.

Giancotti and Ruoslahti, "Elevated levels of the $\alpha_5\beta_1$ fibronectin receptor suppress the transformed phenotype of Chinese hamster ovary cells," *Cell*, 60:849-859, 1990.

Gilbert, "Adaptation of cells to serum free culture for production of adenovirus vectors and recombinant proteins," *Williamsburg BioProcessing Conference*, Nov. 18-21, 1996.

Gopal, "Gene transfer method for transient gene expression, stable transfection, and cotransfection of suspension cell cultures," *Mol. Cell Biol.*, 5:1188-1190, 1985.

Graham and Prevec, "Manipulation of adenovirus vectors," *In: Methods in Molecular Biology: Gene Transfer and Expression Protocols 7*, (Murray, Ed.), Humana Press, Clifton, NJ, pp. 109-128, 1991.

Graham and Van Der Eb, "A new technique for the assay of infectivity of human adenovirus 5 DNA", *Virology*, 52:456-467, 1973.

Graham et al, "Characteristics of a human cell line transformed by DNA from human adenovirus type 5," *J. Gen. Virol.*, 36:59-72, 1977.

Graham, "Growth of 293 Cells in Suspension Culture," *J. Gen. Virol.*, 68:937-940, 1987.

Griffiths, "Overview of cell culture systems and their scale-up," *In: Animal Cell Biotechnology*, vol. 3, p. 179-220, (Spier and Griffiths, eds.), Academic Press, London, 1986.

Harland and Weintraub, "Translation of mammalian mRNA injected into Xenopus oocytes is specifically inhibited by antisense RNA," *J. Cell Biol.*, 101:1094-1099, 1985.

Hay et al., "Replication of adenovirus mini-chromosomes," *J. Mol. Biol.*, 175:493-510, 1984.

Hearing and Shenk, "Functional analysis of the nucleotide sequence surrounding the cap site for adenovirus type 5 region E1A messenger RNAs," *J. Mol. Biol.*, 167:809-822, 1983.

Hearing et al., "Identification of a repeated sequence element required for efficient encapsidation of the adenovirus type 5 chromosome," *J. Virol.*, 61:2555-2558, 1987.

Hearing et al., "Identification of a repeated sequence element required for efficient encapsidation of the adenovirus type 5 chromosome", *Journal of Virology*, 67:2555-2558, 1987.

Hermonat and Muzycska, "Use of adenoassociated virus as a mammalian DNA cloning vector: Transduction of neomycin resistance into mammalian tissue culture cells," *Proc. Nat'l Acad. Sci. USA*, 81:6466-6470, 1984.

Hollstein et al., "p53 mutations in human cancers," *Science*, 253:49-53, 1991.

Hussussian et al., "Germline p16 mutations in familial melanoma," *Nature Genetics*, 8(1):15-21, 1994.

Huyghe et al., "Purification of a type 5 recombinant adenovirus encoding human p53 by column chromatography," *Hum. Gene Ther.*, 6:1403-1416, 1996.

International Search Report dated Jul. 16, 1998 (PCT/US97/21504) (INGN:058P).

Jones and Shenk, "Isolation of deletion and substitution mutants of adenovirus type 5," *Cell*, 13:181-188, 1978.

Kamb et al., "A cell cycle regulator potentially involved in genesisi of many tumor types," *Science*, 264:436-440, 1994.

Kamb et al., "Analysis of the p16 gene (*CDKN2*) as a candidate for the chromosome 9p melanoma susceptibility locus," *Nature Genetics*, 8:22-26, 1994.

Kaneda et al., "Increased expression of DNA cointroduced with nuclear protein in adult rat liver," *Science*, 243:375-378, 1989.

Kato et al., "Expression of hepatitis b virus surface antigen in adult rat liver," *J. Biol. Chem.*, 266:3361-3364, 1991.

Klein et al., "High-velocity microprojectilesfor delivering nucleic acids into living cells," *Nature*, 327:70-73, 1987.

Larsson and Litwin, "The growth of polio virus in human diploid fibroblasts grown with cellulose microcarriers in suspension cultures," *Dev. Biol. Standard.*, 66:385-390, 1987.

Levrero et al., "Defective and nondefective adenovirus vectors for expressing foreign genes in vitro and in vivo," *Gene*, 101:195-202, 1991.

Lin and Guidotti, "Cloning and expression of a cDNA coding for a rat liver plasma membrane ecto-ATpase," *J. Biol. Chem.*, 264:14408-14414, 1989.

Mann et al., "Construction of a retrovirus packaging mutant and its use to produce helper-free defective retrovirus," *Cell*, 33:153-159, 1983.

Matsuura et al., "Altered expression of e-cadherin in gastric cancer tissues and carcinomatous fluid," *Brit. J. Cancer*, 66:1122-1130, 1992.

McGrath et al., "Retrovirus purification: method that conserves envelope glycoprotein and maximizes infectivity," *J. Virol.*, 25:923-927, 1978.

Mercer, "Cell cycle regulation and the p53 tumor suppressor protein," *Critic. Rev. Eukar. Gene Express.* 2:251-263, 1992.

Mizrahi, "Production of human interferons—an overview," *Proc. Biochem.*, (August):9-12, 1983.

Morris et al., "Serum-free production of adenoviral vectors for gene therapy," *Williamsburg BioProcessing Conference*, Nov. 18-21, 1996.

Nicolas and Rubenstein, "Vectors: a survey of molecular cloning vectors and their uses," *In: Vectors: A Survey of Molecular Cloning Vectors and Their Uses*, Rodriguez and Denhardt, (eds.), Stoneham: Butterworth, pp. 493-513, 1988.

Nicolau and Sene, "Liposome-mediated DNA transfer in eukaryotic cells," *Biochem. Biophys. Acta*, 721:185-190, 1982.

Nicolau et al., "Liposomes as carriers for in vivo gene transfer and expression," *Methods Enzymol.*, 149:157-176, 1987.

Nilsson and Mosbach, "Immobilized animal cells," *Dev. Biol. Standard*, 66:183-193.

Nobori et al., "Deletions fo the cyclin-dependent kinase-4 inhibitor gene in multiple human cancers," *Nature*, 368:753-756, 1994.

O'Neil and Balkovic, "Virus harvesting and affinity-based liquid chromatography," *Bio. Technol.*, 11:173-178, 1993.

Obrink, "C-CAM (cell-CAM 105)—a member of the growing immunogloublin superfamily of cell adhesion proteins," *BioEssays*, 13:227-233, 1991.

Odin and Obrink, "Quantitative determination of the organ distribution of the cell adhesion molecule cell-CAM 105 by radioimmunoassay," *Exp. Cell Res.*, 171:1-15, 1987.

Okamoto et al., "Mutations and altered expression of $p16^{INK4}$ in human cancer," *Proc. Nat'l Acad. Sci. USA*, 91:11045-11049, 1994.

Orlow et al., "Chromosome 9 allelic losses and microsatellite alterations in human bladder tumors," *Cancer Res.*, 54:2848-2851, 1994.

Paskind et al., "Dependence of moloney murine leukemia virus production on cell growth," *Virology*, 67:242-248, 1975.

Perales et al., "Gene transfer in vivo: sustained expression and regulation of genes introduced into the liver by receptor-targeted uptake," *Proc. Natl. Acad. Sci. USA*, 91:4086-4090, 1994.

Perrin et al., "An experimental rabies vaccine produced with a new BHK-21 suspension cell culture process: use of serum-free medium and perfusion-reactor system," *Vaccine*, 13(13):1244-1250, 1995.

Petricciani, "Should continuous cell lines be used as substrates for biological products?," *Dev. Biol. Standard*, 66:3-12, 1985.

Phillips et al., "Experience in the cultivation of mammalian cells on the 8000 1 scale," *In: Large Scale Mammalian Cell Culture* (Feder and Tolbert, eds.), Academic Press, Orlando, FL, U.S.A., 1985.

Potter et al., "Enhancer-dependent expression of human k immunoglobulin genes introduced into mouse pre-B lymphocytes by electroporation," *Proc. Nat'l Acad. Sci. USA*, 81:7161-7165, 1984.

U.S. Appl. No. 60/026,667, Entitled: "Method for the Production of Recombinant Adenoviruses," RPR File No. 096021-U.S., Translated from the French by the Medical Documentation Service® Institute for Scientific Information® Philadelphia, Pennsylvania.

Renan, "Cancer genes: current status, future prospects, and applications in radiotherapy/oncology," *Radiother. Oncol.*, 19:197-218, 1990.

Ridgeway, "Mammalian expression vectors," *In*: Rodriguez RL, Denhardt DT, ed. Vectors: A survey of molecular cloning vectors and their uses. Stoneham: Butterworth, pp. 467-492, 1988.

Rippe et al., "DNA-mediated gene transfer into adult rat hepatocytes in primary culture," *Mol. Cell Biol.*, 10:689-695, 1990.

Roux et al., "A versatile and potentially general approach to the targeting of specific cell types by retroviruses: application to the infection of human cells by means of major histocompatibility complex class I and class II antigens by mouse ecotropic murine leukemia virus-derived viruses," *Proc. Nat'l Acad. Sci. USA*, 86:9079-9083, 1989.

Serrano et al., "A New Regulatory Motif in Cell-Cycle Control Causing Specific Ihyibition of Cyclin D/CDK4," *Nature*, 366:704-707, 1993.

Serrano et al., "Inhibition of Ras-Induced Proliferation and Cellular Transformation by $p16^{INK}4$," *Science*, 267:249-252, 1995.

Smith and Lee, "Large-scale isolation and partial purification of type C RNA viruses on hydroxyapatite," *Analytical Biochem.*, 86: 252-263, 1978.

Takahasi et al., "Wild-type but not mutant p53 suppresses the growth of human lung cancer cells bearing multiple genetic lesions," *Cancer Res.*, 52:2340-2342,1992.

Temin, "Retrovirus vectors for gene transfer: efficient integration into and expression of exogenous DNA in vertebrate cell genomes," *In: Gene Transfer*, (Kucherlapati, ed.), Plenum Press, New York, pp. 149-188, 1986.

Tibbetts, "Viral DNA sequences from incomplete particles of human adenovirus type 7," *Cell*, 12:243-249, 1977.

Tur-Kaspa et al., "Use of electroporationto introduce biologically active foreign genes into primary rat hepatocytes," *Mol. Cell Biol.*, 6:716-718, 1986.

Umbas et al., "Expression of the cellular adhesion molecule E-cadherin is reduced or absent in high-grade prostate cancer," *Cancer Res.*, 52:5104-5109, 1992.

van Wezel, "Growth of cell-strains and primary cells on micro-carriers in homogeneous culture," *Nature*, 216:64-65, 1967.

Wagner et al., "Transferrin-polycation conjugates as carriers for DNA uptake into cells", *Proc. Nat'l. Acad. Sci.*, 87(9):3410-3414, 1990.

Wagner et al., "Antisense gene inhibition by oligonucleotidescontaining C-5 propyne pyrimidines," *Science*, 260:1510-1513,1990.

Wang et al., "High cell density perfusion culture of hybridoma cells for production of monoclonal antibodies in the celligen packed bed reactor," *In: Animal Cell Technology: Basic & Applied Aspects*, (Kaminogawa et al., eds), Kluwer Academic Publishers, Netherlands, vol. 5, pp. 463-469, 1993.

Wang et al., "Modified CelliGen-packed bed bioreactors for hybridoma cell cultures," *Cytotechnol.*, 9:41-49, 1992.

Watt et al.,"Human prostate-specific antigen: structural and functional similarity with serine proteases", *Proc. Nat'l Acad. Sci.*, 83(2):3166-3170, 1986.

Weinberg, "Tumor Suppressor Genes," *Science*, 254:1138-1145, 1991.

Wong et al., "Appearance of b-lactamase activity in animal cells upon liposome mediated gene transfer," *Gene*, 10:87-94, 1980.

Wu and Wu, "Receptor mediated in vitro gene transfections by a soluble DNA courier system," *J. Biol. Chem*, 262:4429-4432,1987.

Wu and Wu, "Evidence for targeted gene delivery to HepG2 hepatoma cells in vitro," *Biochemistry*, 27:887-892, 1988.

Wu and Wu, "Liver-directed gene delivery", *Adv. Drug Delivery Rev.*, 12:159-167, 1993.

Yang et al., "In vivo and in vitro gene transfer to mammalian somatic cells by particle bombardment," *Proc. Nat'l Acad. Sci. USA*, 87:9568-9572, 1990.

Complaint *Aventis Pharmaceuticals Products Inc. and Aventis Pharma, S.A., Plaintiffs,* v. *Introgen Therapeutics, Inc., Defendant.* Civil Action No. 01-451 from the U.S. District Court for the District of Delaware, Jun. 29, 2001.

Shabram et al., "Analytical anion-exchange HPLC of recombinant type-5 adenoviral particles," *Human Gene Therapy*, 8:453-465, 1997.

Cartwright, "Fermenter design for animal cell cultures," Animal Cells as Bioreactors, Cambridge University Press, 58-63, 1994.

Carver et al., "Transgenic livestock as bioreactors: stable expression of human alpha-1-antitrypsin by a flock of sheep," *Biotechnology NY*, 11:1263-1270, 1993.

Corveleyn and Remon, "Maltodextrins as lyoprotectants in the lyophilization of a model protein, LDH," *Pharm. Res.*, 13:146-150, 1996.

Croyle et al., "Factors that influence stability of recombinant adenoviral preparations for human gene therapy," *Pharm. Dev. Technol.*, 3(3):373-383, 1998.

Fried and Bromberg, "Factors that affect the stability of protein-DNA complexes during gel electrophoresis," *Electrophoresis*, 18:6-11, 1997.

Hall et al., "Stabilizing effect of sucrose against irreversible denaturation of rabbit muscle lactate dehydrogenase," *Biophys. Chem.*, 57:47-54, 1995.

Herman et al., "The effect of bulking agent on the solid-state stability of freeze-dried methylprednisolone sodium succinate," *Pharm. Res.*, 11:1467-1473, 1994.

Kotani et al., "Improved methods of retroviral vector transduction and production for gene therapy," *Human Gene Therapy*, 5:19-28, 1994.

Lentfer and Conde, "A rapid and inexpensive procedure for the purification of adenovirions," *Archives of Virology*, 56:189-193, 1978.

Lu et al., "Coat protein interactions involved in tobacco mosaic tobamovirus cross-protection," *Virology*, 248:188-198, 1998.

Lueckel et al., "Formulations of sugars with amino acids or mannitol—influence of concentration ratio on the properties of the freeze-concentrate and the lyophilizate," *Pharm. Dev. Technol.*, 3:326-336, 1998.

Montagnon, "Polio and rabies vaccines produced in continuous cell lines: a reality for vero cell line," *Develop. Biol. Standard.*, 70:27-47, 1989.

Mori et al., "Frequent somatic mutation of the MTS1/CDK4I (Multiple Tumor suppressor/Cyclin dependent Kinase 4 Inhibitor) gene in esophageal squamous cell carcinoma," *Cancer Res.*, 54:3396-3397, 1994.

Nadeau et al., *Biotechnology and Bioengineering*, 51:613-623, 1996.

Payment et al., In: *Biotechnology Current Progress*, ed. P.N. Cheremisinoff et al., Technomic Publishing, 1991.

Racher et al., "Culture of 293 cells in different culture systems: cell growth and recombinant adenovirus production," *Biotechnology Techniques*, 9:169-174, 1995.

Sagrera et al., "Study of the influence of salt concentration on Newcastle disease virus matrix protein aggregation," *Biochem. Mol. Biol. Int.*, 46:429-435, 1998.

Trepanier et al., *Journal of Virological Methods*, 3:201-211, 1981.

Vanlandschoot et al, "pH-dependent aggregation and secretion of soluble monomeric influenza hemagglutinin," *Arch. Virol.*, 143:227-239, 1998.

Vossen and Fried, "Sequestration stabilizes lac repressor-DNA complexes during gel electrophoresis," *Anal. Biochem.*, 245:85-92, 1997.

Wills and Menzel, "Adenovirus Vectors for Gene Therapy of Cancer," *J. of Cellular Biochem.*, Suppl: 17E, S216:206, 1993.

Kotani, "Serum-free production of adenoviral vectors for gene therapy," Williamsburg BioProcessing Conference, Nov. 18-21, 1996.

U.S. Appl. No. 60/026,667, filed Sep. 25, 1996, Guillaume et al.

Batra et al., "IkappaBalpha gene transfer is cytotoxic to squamous-cell lung cancer cells and sensitizes them to tumor necrosis factor-alpha-mediated cell death," *Am J Respir Cell Mol Biol*, 21:238-245, 1999.

Blackwell et al., "Retargeting to EGFR enhances adenovirus infection efficiency of squamous cell carcinoma," *Arch Otolaryngol Head Neck Surg.*, 125:856-863, 1999.

Butman et al., "High Sensibitivity HPLC Method for Determining Viral Particle Concentration," Presentation, 2000.

Carrion et al., "Intrinsic Fluorescence of Adenovirus Type S: A Sensitive Detection Alternative," *Molecular Ther.*, 3:438, 2001.

Chillon et al., "Group D Adenoviruses Infect Primary Central Nervous System Cells More Efficiently than Those from Group C," *J Virol*, 73:2537-2540, 1990.

Chroboczek et al., "The Sequence of the Genome of Adenovirus Type 5 and Its Comparison with the Genome of Adenovirus Type 2," *Virology*, 186:280-285, 1992.

Cristiano et al., "Viral and nonviral gene delivery vectors for cancer gene therapy," *Cancer Detect Prev*, 22:445-454, 1998.

Dorai et al., "A recombinant defective adenoviral agent expressing anti-bcl-2 ribozyme promotes apoptosis of bcl-2-expressing human prostate cancer cells," *Int J Cancer*, 82:846-852, 1999.

Feldman et al., "Perspectives of arterial gene therapy for the prevention of restenosis," *Cardiovasc Res.*, 32:194-204, 1996.

Graham and Prevec, "Methods for construction of adenovirus vectors," *Mol. Biotechnol.*, 3:207-220, 1995.

Hermens and Verhaagen, "Viral vectors, tools for gene transfer in the nervous system," *Prog. Neurobiol.*, 55:399-432, 1998.

Hurwitz et al., "Suicide Gene Therapy for Treatment of Retinoblastoma in a Murine Model," *Human Gene Therapy*, 10:441-448, 1999.

Irie et al., "Therapeutic efficacy of an adenovirus-mediated anti-H-ras ribozyme in experimental bladder cancer," *Antisense Nucleic Acid Drug Dev*, 9:341-349, 1999.

Ishibashi et al., "Hypercholesterolemia in low density lipoprotein receptor knockout mice and its reversal by adenovirus-mediated gene delivery," *J. Clin Invest*, 92:883-893, 1993.

Jardon and Garnier, "PH, pCO2, and temperature effect on R-adenovirus production," *Biotechnol. Prog.*, 19:202-208, 2003.

Jiang et al., "The melanoma differentiation associated gene mda-7 suppresses cancer cell growth," *Proc Nat'l Acad Sci USA*, 93:9160-9165, 1996.

Lesch, "Gene transfer to the brain: emerging therapeutic strategy in psychiatry?," *Biol. Psychiatry*, 45:247-253, 1999.

Marienfeld et al., "'Autoreplication' of the vector genome in recombinant adenoviral vectors with different E1 region deletions and transgenes," *Gene Ther.*, 6:1101-1113, 1999.

Mincheff et al., "Naked DNA and adenoviral immunizations for immunotherapy of prostate cancer: a phase I/II clinical trial," *Eur. Urol.*, 38:208-217, 2000.

Morrison et at., "Complete DNA sequence of canine adenovirus type 1," *J. Gen Virol.*, 78:873-878, 1997.

Murakami et al., "Quantitation of adenovirus DNA and virus particles with the PicoGreen fluorescent Dye," *Analytical Biochemistry*, 274:283-288, 1999.

Parks et al., "A helper-dependent system for adenovirus vector production helps define a lower limit for efficient DNA packaging," *J Virol.*, 71:3293-3298, 1997.

Petrof, "Respiratory muscles as a target for adenovirus-mediated gene therapy," *Eur. Respir J*, 11:492-497, 1998.

Reddy et al., "Nucleotide sequence and transcription map of porcine adenovirus type 3," *Virology*, 251:414-426, 1998.

Robbins and Ghivizzani, "Viral vectors for gene therapy," *Pharmacol. Ther.*, 80:35-47, 1998.

Robbins et al., "Viral vectors for gene therapy," *Trends Biotechnol.*, 16:35-40, 1998.

Stewart et al., "Adenovector-mediated gene delivery of interleukin-2 in metastatic breast cancer and melanoma: results of a phase 1 clinical trial," *Gene Ther.*, 6:350-363, 1999.

Vanderkwaak and Alvarez, "Immune directed therapy for ovarian carcinoma," *Curr. Opin Obstet Gynecol*, 11:29-34, 1999.

Wilson, "Vehicles for gene therapy," *Nature*, 365: 691-692, 1993.

Wilson, "When Bad Gene Transfer is Good," *J. Clin. Invest.*, 98:2435, 1996.

Yotnda et al., "Efficient infection of primitive hematopoietic stem cells by modified adenovirus," *Gene Ther.*, 8:930-937, 2001.

Zheng et al., "Transcription units of E1a, E1b and pIX regions of bovine adenovirus type 3," *J. Gen. Virol.*, 80:1735-1742, 1999.

U.S. Appl. No. 60/082,628, filed Apr. 22, 1998, Carrión et al.

Haruna et al., "Separation of adenovirus by chromatography on DEAE-cellulose," *Virology*, 13:264-267, 1961.

Cartwright, T., *Animal cells as bioreactors*, In: Cambridge Studies in Biotechnology, Cambridge University Press, No. 11:58-63, 1994.

Jul. 17, 2006: Minutes of Oral Proceedings Before the Examining Division with decision to grant European Patent Application No. 97950677.1.

Côté et al., "Study of Adenovirus Production in Serum-Free 293SF Suspension Culture by GFP-Expression Monitoring", Biotechnol. Prog., 13:709-714, 1997.

Massie et al., "Improved Adenovirus Vector Provides Herpes Simplex Virus Ribonuocleotide Reductase R1 and R2 Subunites Very Efficiently", Bio/Technology 13:602, 1995.

Zhang et al, "Adenovirus Inhibition of Cell Translation Facilitates Release of Virus Particles and Enhances Degradation of the Cytokeratin Network", Journal of Virology, 2544-2555, 1994.

\* cited by examiner

```
Cube   (low perfusion rate,          Titer      Vol. (ml)  Yield       Recovery
       keep glucose > 1g/L)          (PFU/ml)              (PFU)       %
  │  1% Tween-20 in
  │  buffer A                                                          Step   Acc.
  ▼
Harvest
  │  Clarification and
  │  Filtration (0.22 um)
  ▼
Virus solution                       $2.6 \times 10^9$   1900   $4.9 \times 10^{12}$
  │  Conc./diaf.
  │  (10-fold conc., diaf.
  │  into 1m NaCl buffer A)
  ▼
Conc. sup                            $2.5 \times 10^{10}$  200   $5 \times 10^{12}$   102%
  │  Benzonase treatment
  │  (O/N, RT, 100u/ml)
  ▼
Treated sup
  │  Diluted with water to
  │  conductivity = 22-25
  │  mS/cm
  ▼
Diluted virus solution               $7 \times 10^9$   700   $4.9 \times 10^{12}$   98%   100%
  │
  ▼
purified virus                       $1.5 \times 10^{10}$   240   $3.6 \times 10^{12}$   73%   73%
  │  conc./diaf (5-fold conc.)
  ▼
Final purified product               $7 \times 10^{10}$   50   $3.5 \times 10^{12}$   97%   71%
```

*FIG. 23*

| Date (Temp.) | PFU x 10⁹/ml | | | HPLC viral particles (x10¹⁰)/ml | | | Water Content (W%) | | | |
|---|---|---|---|---|---|---|---|---|---|---|
| | SET 10-6 | SET 10-7 | SET 10-8 | SET 10-9 | SET 10-6 | SET 10-7 | SET 10-8 | SET 10-9 | SET 10-6 | SET 10-7 | SET 10-8 | SET 10-9 |
| 4/11/97 | 5.5 | 6 | 5.8 | 6.5 | 24.5 | 24.6 | 24.9 | 26.7 | 2.2 | 2.5 | 2.7 | 3.3 |
| 5/15/97 (-20°C) | 7.6 | 7.1 | 7.5 | 8.1 | 22.4 | 25.6 | 26.8 | 28.5 | 2.2 | 2.5 | 2.8 | 3.3 |
| 5/15/97 (4°C) | 6.5 | 6.3 | 6.5 | 10 | 22 | 23 | 24 | 27.5 | 2.4 | 2.6 | 3 | 3.4 |
| 5/15/96 (R.T.) | 7.1 | 7.1 | 6.7 | 3.3 | 14.5 | 16.5 | 6.2 | 4.2 | 2.7 | 2.9 | 3.2 | 3.5 |
| 7/18/97 (-20°C) | 6.8 | 6.4 | 6.8 | 7.2 | 28.7 | 28.9 | 28.6 | 31.2 | 2.3 | 2.5 | 2.8 | 3.3 |
| 7/18/97 (4°C) | 6 | 5.8 | 7.3 | 9 | 25 | 26.6 | 27.6 | 31.1 | 2.5 | 2.8 | 3 | 3.6 |
| 7/18/97 (R.T.) | 1.2 | 0.8 | 4 | 1.4 | 0.9 | 1.8 | 0.7 | 0.7 | 2.7 | 2.9 | 3 | 3.4 |
| 10/22/97 (-20°C) | 7.9 | 7.5 | 7.9 | 7.8 | 25.5 | 25 | 25.4 | 26.2 | 2.4 | 2.6 | 2.8 | 3.1 |
| 10/22/97 (4°C) | 6.8 | 6.8 | 5.8 | 8 | 22 | 23 | 24.7 | 24.2 | 2.7 | 2.9 | 3.2 | 3.6 |
| 10/22/97 (R.T) | <0.01 | <0.01 | <0.01 | <0.01 | N.D. | N.D. | N.D. | 0.7 | 2.7 | 2.9 | 3.1 | 3.4 |
| 4/16/98 (-20°C) | 6 | 5.8 | 7.1 | 7.2 | 19.3 | 20.3 | 23.5 | 26.1 | 2.4 | 2.6 | 2.8 | 3.4 |
| 4/16/98 (4°C) | 5.4 | 7.2 | 6.1 | 6.3 | 21.7 | 22.8 | 22.9 | 24.6 | 2.9 | 3.1 | 3.3 | 3.8 |
| 4/16/98 (R.T.) | 0.0003 | 0.001 | 0.0007 | 0.001 | N.D. | N.D. | N.D. | N.D. | 2.7 | 2.9 | 3.1 | 3.4 |

N.D.: Not detectable

*FIG. 30A-1*

CONTROLS

| Date | PFU x 10⁹/ml | | | | HPLC viral particles (x10¹⁰)/ml | | | |
|---|---|---|---|---|---|---|---|---|
| | SET 10-6 | SET 10-7 | SET 10-8 | SET 10-9 | SET 10-6 | SET 10-7 | SET 10-8 | SET 10-9 |
| 4/11/97 | 5.5 | 7 | 7 | 7 | 35.5 | 35.8 | 36 | 36.9 |

*FIG. 30A-2*

| Date (Temp.) | PFU × 10⁹/ml | | | | HPLC viral particles (×10¹⁰)/ml | | | | Water Content (W%) | | | |
|---|---|---|---|---|---|---|---|---|---|---|---|---|
| | SET 11-6 | SET 11-7 | SET 11-8 | SET 11-9 | SET 11-6 | SET 11-7 | SET 11-8 | SET 11-9 | SET 11-6 | SET 11-7 | SET 11-8 | SET 11-9 |
| 5/2/97 | 7 | 6 | 6.3 | 5.8 | 28.5 | 28.8 | 28.4 | 29.5 | 2.3 | 2.7 | 3.5 | 4 |
| 6/20/97 (-20°C) | 6.2 | 6.6 | 6.9 | 6.5 | 26.3 | 25 | 27 | 27.3 | 2.2 | 2.8 | 3.4 | 4.6 |
| 6/20/97 (4°C) | 6.1 | 6 | 6.5 | 6.5 | 24.1 | 22.1 | 25.6 | 26.6 | 2.5 | 2.8 | 3.5 | 4.8 |
| 6/20/97 (R.T.) | 3.3 | 3 | 1 | <0.1 | 20.5 | 17.4 | 5.2 | 9.1 | 2.7 | 3.1 | 3.5 | 4.7 |
| 8/18/97 (-20°C) | 8 | 7.2 | 7.5 | 7.6 | 21.6 | 21.8 | 25.3 | 24.9 | 2.3 | 2.8 | 3.7 | 4.9 |
| 8/18/97 (4°C) | 8 | 7.3 | 8 | 8 | 22.7 | 22.7 | 24.9 | 25 | 2.6 | 3 | 3.9 | 4.2 |
| 8/18/97 (R.T.) | <0.1 | <0.1 | <0.1 | <0.1 | N.D. | N.D. | 0.2 | 13.1 | 2.7 | 3 | 3.5 | 4.4 |
| 10/22/97 (-20°C) | 7.9 | 7.5 | 7.9 | 6.7 | 21 | 22 | 25.1 | 24 | 2.4 | 3 | 3.9 | 4.4 |
| 10/22/97 (4°C) | 6 | 6.9 | 6.8 | 7.3 | 21.4 | 22 | 23.1 | 23.1 | 2.6 | 3 | 3.3 | 4.6 |
| 10/22/97 (R.T.) | <0.01 | <0.01 | <0.01 | <0.01 | N.D. | N.D. | N.D. | 9 | 2.7 | 2.9 | 3.9 | 5 |
| 5/8/98 (-20°C) | 8.3 | 7.5 | 8 | 8.7 | 19 | 18.2 | 19.9 | 21.1 | 2.6 | 3.1 | 4 | 4.6 |
| 5/8/98 (4°C) | 7 | 7.1 | 7.8 | 6.5 | 17.3 | 17.1 | 18.2 | 17.8 | 2.8 | 3.2 | 4.1 | 5.1 |
| 5/8/87 (R.T.) | 0.00033 | 0.000065 | 0.00045 | 0.000016 | N.D. | N.D. | N.D. | N.D. | 2.7 | 2.9 | 4 | 4.9 |

N.D.: Not detectable

FIG. 30B-1

CONTROLS

| Date | PFU × 10⁹/ml | | | | HPLC viral particles (×10¹⁰)/ml | | | |
|---|---|---|---|---|---|---|---|---|
| | SET 11-6 | SET 11-7 | SET 11-8 | SET 11-9 | SET 11-6 | SET 11-7 | SET 11-8 | SET 11-9 |
| 5/2/97 | 6.4 | 6.8 | 6.5 | 6.5 | 37.7 | 36.7 | 37.3 | 36 |

FIG. 30B-2

| Date (Temp.) | PFU x 10⁹/ml | | | | HPLC viral particles (x10¹⁰)/ml | | | | Water Content (W%) | | | |
|---|---|---|---|---|---|---|---|---|---|---|---|---|
| | SET 10-6 | SET 10-7 | SET 10-8 | SET 10-9 | SET 10-6 | SET 10-7 | SET 10-8 | SET 10-9 | SET 10-6 | SET 10-7 | SET 10-8 | SET 10-9 |
| 5/15/97 | 6.5 | 5.6 | 6.1 | 6 | 18 | 18.6 | 21.9 | 23.3 | 0.8 | 1.1 | 1.3 | 1.5 |
| 6/20/97 (4 °C) | 5.4 | 5.6 | 5.5 | 5.5 | 14.6 | 14.9 | 17.2 | 16.6 | 0.8 | 1.2 | 1.5 | 1.6 |
| 6/20/97 (R.T.) | 4.5 | 5 | 5.5 | 6 | 10.8 | 11.8 | 15 | 15.4 | 1.3 | 1.4 | 1.6 | 1.9 |
| 8/18/97 (4 °C) | 7 | 6.7 | 6.8 | 7 | 15.3 | 17.1 | 17.9 | 17.7 | 1.3 | 1.5 | 1.5 | 1.7 |
| 8/18/97 (R.T.) | 2.4 | 2.2 | 4.8 | 5.8 | 4.3 | 7.2 | 11.7 | 14.2 | 1.3 | 1.6 | 1.7 | 2.1 |
| 11/20/97 (4 °C) | 5.5 | 5.5 | 5.3 | 5.7 | 16.8 | 16.8 | 20.6 | 20.1 | 1.1 | 1.4 | 1.6 | 1.9 |
| 11/20/97 (R.T.) | 0.45 | 0.9 | 2.3 | 3.1 | 1.5 | 5.5 | 7.3 | 10.7 | 1.3 | 1.7 | 1.8 | 2.2 |
| 5/14/98 (4 °C) | 4.9 | 4.7 | 5.4 | 6.5 | 9.7 | 11.9 | 12.6 | 14.2 | 1.2 | 1.6 | 2.2 | 1.4 |
| 5/14/98 (R.T.) | 0.000006 | 0.00006 | 0.00004 | 0.000024 | N.D. | N.D. | N.D. | N.D. | 1.4 | 1.6 | 1.3 | 2 |

N.D.: Not detectable

*FIG. 31A-1*

CONTROLS

| Date | PFU x 10⁹/ml | | | | HPLC viral particles (x10¹⁰)/ml | | | |
|---|---|---|---|---|---|---|---|---|
| | SET 10-6 | SET 10-7 | SET 10-8 | SET 10-9 | SET 10-6 | SET 10-7 | SET 10-8 | SET 10-9 |
| 5/15/97 | 7 | 5.6 | 7 | 7 | 31.2 | 30.6 | 31.6 | 31.4 |

*FIG. 31A-2*

| Date (Temp.) | PFU x 10⁹/ml | | | | HPLC viral particles (x10¹⁰)/ml | | | | Water Content (W%) | | | |
|---|---|---|---|---|---|---|---|---|---|---|---|---|
| | SET 11-6 | SET 11-7 | SET 11-8 | SET 11-9 | SET 11-6 | SET 11-7 | SET 11-8 | SET 11-9 | SET 11-6 | SET 11-7 | SET 11-8 | SET 11-9 |
| 5/22/97 | 7.5 | 6.3 | 7.3 | 6.5 | 17.4 | 16.6 | 20.3 | 24.7 | 1 | 1.2 | 1.6 | 1.9 |
| 6/20/97 (4°C) | 5.5 | 6.3 | 6 | 7.5 | 14.8 | 16.1 | 17.5 | 21.1 | 1.2 | 1.3 | 1.7 | 1.8 |
| 6/20/97 (R.T.) | 5 | 6 | 6 | 7.5 | 12.6 | 14.9 | 17.2 | 20.3 | 1.4 | 1.6 | 1.9 | 2 |
| 8/18/97 (4°C) | 6.3 | 6.7 | 6.8 | 7.5 | 15.7 | 17.2 | 18.5 | 22.6 | 1.2 | 1.5 | 1.8 | 1.9 |
| 8/18/97 (R.T.) | 3.3 | 4.5 | 5.5 | 7 | 7.4 | 10.5 | 15.8 | 21.2 | 1.6 | 1.7 | 1.9 | 2.2 |
| 11/20/97 (4°C) | 5.3 | 5.6 | 5.3 | 6.6 | 17.3 | 20 | 22.6 | 26.3 | 1.2 | 1.4 | 1.9 | 1.9 |
| 11/20/97 (R.T.) | 0.8 | 1.9 | 3 | 0.2 | 3.2 | 7.9 | 14.2 | 1.3 | 1.6 | 1.7 | 2 | 2.1 |
| 5/14/98 (4°C) | 6.7 | 7.2 | 6.9 | 7.6 | 12.4 | 13.9 | 15.5 | 18.5 | 1.3 | 1.6 | 2 | 2.2 |
| 5/14/98 (R.T.) | 0.0013 | 0.00005 | 0.00031 | 0.00045 | N.D. | N.D. | N.D. | N.D. | 1.6 | 1.8 | 1.6 | 2 |

N.D.: Not detectable

*FIG. 31B-1*

CONTROLS

| Date | PFU x 10⁹/ml | | | | HPLC viral particles (x10¹⁰)/ml | | | |
|---|---|---|---|---|---|---|---|---|
| | SET 11-6 | SET 11-7 | SET 11-8 | SET 11-9 | SET 11-6 | SET 11-7 | SET 11-8 | SET 11-9 |
| 5/22/97 | 8 | 7.4 | 8.3 | 7.6 | 26.7 | 27.6 | 27.5 | 32.4 |

| Date (Temp.) | PFU x 10⁹/ml | | | | HPLC viral particles (x10¹⁰)/ml | | | | Water Content (W%) | | | |
|---|---|---|---|---|---|---|---|---|---|---|---|---|
| | SET 10-6 | SET 10-7 | SET 10-8 | SET 10-9 | SET 10-6 | SET 10-7 | SET 10-8 | SET 10-9 | SET 10-6 | SET 10-7 | SET 10-8 | SET 10-9 |
| 6/13/97 | 3.4 | 4.3 | 4.1 | 4.2 | 16 | 16.5 | 16.1 | 18.1 | 0.8 | 1.1 | 1.3 | 1.4 |
| 7/18/97 (4°C) | 6.3 | 6.3 | 6 | 6 | 17.9 | 19.5 | 19.9 | 20.6 | 0.9 | 1.2 | 1.4 | 1.6 |
| 7/18/97 (R.T.) | 4.1 | 5.5 | 5 | 5.5 | 11.4 | 15.5 | 18.2 | 20.6 | 1.2 | 1.4 | 1.7 | 1.8 |
| 9/16/97 (4°C) | 4.2 | 5.5 | 4.5 | 5.1 | 15.3 | 16.1 | 16.4 | 17.8 | 1 | 1.3 | 1.5 | 1.7 |
| 9/16/97 (R.T.) | 0.7 | 1.2 | 5 | 4 | 2.9 | 5 | 9.5 | 13 | 1.3 | 1.5 | 1.8 | 2 |
| 12/4/97 (4°C) | 5.5 | 5.3 | 5.4 | 5.9 | 16.1 | 16.2 | 18.1 | 18.5 | 1.1 | 1.4 | 1.6 | 1.7 |
| 12/4/97 (R.T.) | 0.3 | 0.5 | 2.5 | 3.4 | N.D. | 1.7 | 4.7 | 8.8 | 1.4 | 1.6 | 1.8 | 2 |
| 6/29/98 (4°C) | 3.8 | 5.1 | 5.3 | 5.4 | 10.6 | 10.8 | 12 | 12.9 | 1.3 | 1.5 | 1.8 | 1.9 |
| 6/29/98 (R.T.) | 0.00003 | 0.00006 | 0.0001 | 0.0001 | N.D. | N.D. | N.D. | N.D. | 1.4 | 1.6 | 1.7 | 1.8 |

N.D.: Not detectable

CONTROLS

FIG. 32A-2

| Date | PFU x 10⁹/ml | | | | HPLC viral particles (x10¹⁰)/ml | | | |
|---|---|---|---|---|---|---|---|---|
| | SET 10-6 | SET 10-7 | SET 10-8 | SET 10-9 | SET 10-6 | SET 10-7 | SET 10-8 | SET 10-9 |
| 6/13/97 | 4.7 | 3.8 | 5.5 | 6.2 | 26 | 26.2 | 27.4 | 27.5 |

| Date (Temp.) | PFU x 10⁹/ml | | | | HPLC viral particles (x10¹⁰)/ml | | | | Water Content (W%) | | | |
|---|---|---|---|---|---|---|---|---|---|---|---|---|
| | SET 11-6 | SET 11-7 | SET 11-8 | SET 11-9 | SET 11-6 | SET 11-7 | SET 11-8 | SET 11-9 | SET 11-6 | SET 11-7 | SET 11-8 | SET 11-9 |
| 6/13/97 | 3.4 | 4.2 | 3.6 | 4.4 | 16.1 | 16.3 | 18.4 | 19.3 | 0.9 | 1.3 | 1.8 | 1.9 |
| 7/18/97 (4 °C) | 5.5 | 6.2 | 6.5 | 6.2 | 18 | 19.5 | 23 | 23.9 | 1 | 1.4 | 1.8 | 2.1 |
| 7/18/97 (R.T.) | 3.7 | 6 | 6.7 | 7.3 | 13.7 | 18.7 | 21.8 | 22.8 | 1.3 | 1.7 | 2 | 2.2 |
| 9/16/97 (4 °C) | 3.9 | 4 | 4.6 | 6 | 15.6 | 17.3 | 19.5 | 20.6 | 1.3 | 1.5 | 1.9 | 2.1 |
| 9/16/97 (R.T.) | 0.8 | 2.2 | 4 | 5.3 | 3.6 | 6.8 | 13.8 | 14.6 | 1.5 | 1.9 | 2.3 | 2.4 |
| 12/4/97 (4 °C) | 4.6 | 5.3 | 8 | 6.1 | 15.7 | 18.2 | 21.4 | 21.6 | 1.2 | 1.6 | 2.1 | 2.2 |
| 12/4/97 (R.T.) | 0.4 | 0.6 | 0.3 | <0.01 | N.D. | N.D. | 1.7 | N.D | 1.6 | 1.8 | 2.1 | 2.1 |
| 6/29/98 (4 °C) | 4.9 | 5 | 5.4 | 6.4 | 11.4 | 14.2 | 13.7 | 16 | 1.5 | 1.7 | 2.1 | 2.6 |
| 6/29/98 (R.T.) | 0.0001 | 0.00015 | 0.00085 | 0.0012 | N.D. | N.D. | N.D. | N.D. | 1.6 | 1.7 | 2.2 | 2.3 |

N.D.: Not detectable

*FIG. 32B-1*

CONTROLS

| Date | PFU x 10⁹/ml | | | | HPLC viral particles (x10¹⁰)/ml | | | |
|---|---|---|---|---|---|---|---|---|
| | SET 11-6 | SET 11-7 | SET 11-8 | SET 11-9 | SET 11-6 | SET 11-7 | SET 11-8 | SET 11-9 |
| 6/13/97 | 4.5 | 5 | 4 | 5 | 26.5 | 26.9 | 26.6 | 27.1 |

*FIG. 32B-2*

| Date (Storage Cond.) | PFU x10⁹/ml ||||| HPCL viral particles (x10¹⁰)/ml |||||
|---|---|---|---|---|---|---|---|---|---|---|
| | 10%-G | 5%-S,5%-HSA | 5%-S,%-PEG | 5%-T,1%-PEG | 10%-G | 10%-G | 5%-S,5%-HSA | 5%-S,%-PEG | 5%-T,1%-PEG |
| 8/1/97 | 5.8 | 4.7 | 4.3 | 4.4 | 16.9 | 14.5 | 16.1 | 16.7 |
| 8/28/97 (4°C, N₂) | 5.8 | 5.8 | 6.4 | 6.3 | 13.3 | 14.9 | 13.8 | 13.4 |
| 8/28/97 (4°C, AIR) | 5 | 5.9 | 6 | 5.9 | 12.9 | 14.2 | 12.9 | 12.9 |
| 8/28/97 (R.T., N₂) | 4.4 | 4.8 | 5 | 6 | 12.6 | 14.5 | 13.5 | 12.9 |
| 8/28/97 (R.T., AIR) | 4.3 | 5 | 5 | 5.6 | 12.3 | 13.7 | 13 | 13 |
| 10/30/97 (4°C, N₂) | 3.8 | 4 | 4.7 | 3.8 | 14 | 15.5 | 14.7 | 14.8 |
| 10/30/97 (4°C, AIR) | 3 | 4.1 | 3.7 | 4.7 | 12.6 | 14.9 | 14.3 | 14.4 |
| 10/30/97 (R.T., N₂) | 1.5 | 3.4 | 3.5 | 3.6 | 13.8 | 15.1 | 14.6 | 14.4 |
| 10/30/97 (R.T., AIR) | 1.5 | 3.6 | 2.2 | 3.1 | 12.7 | 14.7 | 14.8 | 14.4 |
| 1/12/98 (4°C, N₂) | 3.2 | 4.1 | 3.3 | 3.4 | 7.3 | 11.1 | 9.5 | 9.5 |
| 1/12/98 (4°C, AIR) | 1.5 | 3.8 | 3.9 | 3.4 | 7.7 | 10.8 | 10.2 | 10 |
| 1/12/98 (R.T., N₂) | 0.1 | 1.4 | 0.7 | 0.7 | 10 | 10.8 | 11.1 | 10.4 |
| 1/12/98 (R.T., AIR) | 0.4 | 1.6 | 1 | 0.4 | 9.9 | 11 | 10 | 10.4 |
| 4/30/98 (4°C, N₂) | 0.08 | 4.3 | 4 | 5.3 | 5.1 | 12.3 | 12.3 | 12.1 |
| 4/30/98 (4°C, AIR) | 1.5 | 3.6 | 4.4 | 4.5 | 5 | 11.6 | 11.8 | 11.9 |
| 4/30/98 (R.T., N₂) | 0.0025 | 0.23 | 0.11 | 0.17 | 11.1 | 12.3 | 12.6 | 12.5 |
| 4/30/98 (R.T., AIR) | 0.0015 | 0.21 | 0.063 | 0.007 | 11 | 12.4 | 12.3 | 11 |

FIG. 33

PFU x 10^9/ml

| Date (Temp.) | AQF2-1 | AQF2-2 | AQF2-3 | AQF2-4 | AQF2-5 | AQF2-6 | AQF2-7 | AQF2-8 | AQF2-9 | AQF2-10 | AQF2-11 | AQF2-12 |
|---|---|---|---|---|---|---|---|---|---|---|---|---|
| 9/25/97 | 2.8 | 2.8 | 2.8 | 3 | 2.8 | 2.8 | 2.7 | 2.8 | 2.7 | 3.3 | 3.1 | 2.7 |
| 11/05/97 (4°C) | 2.3 | 3.2 | 2.4 | 3.6 | 2.7 | 2 | 3.6 | 3.8 | 2.7 | 3 | 3.5 | 2.5 |
| 11/05/97 (R.T.) | 2.2 | 0.1 | 2.4 | 2.7 | 2.1 | 2.1 | 3.2 | 2.1 | 3 | 3 | 3.4 | 2.9 |
| 12/12/97 (4°C) | 2.2 | 0.1 | 2.4 | 2.7 | 2.1 | 2.1 | 3.2 | 2.1 | 3 | 3 | 3.4 | 2.9 |
| 01/09/98 (R.T.) | 1.2 | <0.1 | 0.2 | 1.2 | 0.2 | 0.1 | 1.3 | 1.1 | 0.2 | <0.1 | 2 | 1.1 |
| 3/27/98 (4°C) | 1.8 | <0.1 | 1.9 | 2 | <0.1 | 1.7 | 2 | <0.1 | 2.6 | 2.9 | 2.6 | 1.8 |
| 3/27/98 (R.T.) | 0.6 | <0.1 | <0.1 | 0.8 | <0.1 | <0.1 | 1 | <0.1 | <0.1 | <0.1 | 1.1 | 0.7 |

FIG. 34A-1

HPLC viral particles (x10^10/ml)

| Date (Temp.) | AQF2-1 | AQF2-2 | AQF2-3 | AQF2-4 | AQF2-5 | AQF2-6 | AQF2-7 | AQF2-8 | AQF2-9 | AQF2-10 | AQF2-11 | AQF2-12 |
|---|---|---|---|---|---|---|---|---|---|---|---|---|
| 9/25/97 | 10.9 | 9.6 | 9.7 | 11.3 | 10.7 | 10.6 | 10.9 | 10.8 | 10.7 | 11.4 | 11.8 | 10.7 |
| 11/05/97 (4°C) | 7.9 | 7.6 | 8.7 | 8.8 | 8.9 | 7.5 | 8.6 | 9.1 | 9.2 | 10.3 | 11.2 | 9.6 |
| 11/05/97 (R.T.) | 8.2 | 6.6 | 7.6 | 8.6 | 7.7 | 9.3 | 9 | 8 | 9.3 | 10.3 | 11.1 | 9.6 |
| 12/12/97 (4°C) | 6.7 | 1.5 | 8 | 6.9 | 5.2 | 7.5 | 7.5 | 6.1 | 7.6 | 8.8 | 7.3 | 7.7 |
| 12/17/98 (R.T.) | 7 | 1.2 | 7 | 7.5 | 4.1 | 7.1 | 7 | 3 | 8.2 | 7.6 | 8.4 | 7.5 |
| 3/13/98 (4°C) | 5.6 | N.D. | 6.2 | 6.7 | N.D. | 6.5 | 6.8 | N.D. | 7.1 | 8 | 8.9 | 7.2 |
| 3/13/98 (R.T.) | 6.2 | N.D. | 6.5 | 6.9 | N.D. | 7.3 | 6.8 | N.D. | 6.9 | 7.8 | 7.5 | 7.1 |

FIG. 34A-2

| Excipients | AQF2-1 | AQF2-2 | AQF2-3 | AQF2-4 | AQF2-5 | AQF2-6 | AQF2-7 | AQF2-8 | AQF2-9 | AQF2-10 | AQF2-11 | AQF2-12 |
|---|---|---|---|---|---|---|---|---|---|---|---|---|
| Mannitol (W%) | 5 | 5 | 5 | | | | 5 | 5 | 5 | 5 | 5 | |
| Sucrose (W%) | | | | 5 | 5 | 5 | 5 | 5 | 5 | 5 | 5 | 10 |
| Glycine (M) | 0.25 | | | 0.25 | | | 0.25 | | | | 0.25 | 0.25 |
| Arginine (M) | | 0.25 | | | 0.25 | | | 0.25 | | | 0.25 | |
| Urea (W%) | | | 1 | | | 1 | | | 1 | | 1 | |
| Peg (W%) | | | | | | | | | | 1 | 1 | |

FIG. 34B

| Date (Temp.) | PFU x 10^9 | | | | HPLC viral particles (x 10^10/ml) | | | |
|---|---|---|---|---|---|---|---|---|
| | F10-7 | F10-8 | F11-7 | F11-8 | F10-7 | F10-8 | F11-7 | F11-8 |
| 10/3/97 | 2.2 | 3.3 | 2.1 | 2.8 | 12.1 | 12 | 11.8 | 12 |
| 11/6/97 (-20°C) | 3.4 | 4 | 2.8 | 3.4 | 10.6 | 10.5 | 10.1 | 10.3 |
| 11/6/97 (4°C) | 3.5 | 3.6 | 4.3 | 2.8 | 10 | 9.7 | 9.9 | 10.3 |
| 1/15/98 (-20°C) | 3.8 | 4.8 | 3.2 | 3.7 | 7.3 | 7.4 | 7.7 | 8 |
| 1/15/98 (4°C) | 3.5 | 3.1 | 2.9 | 3.1 | 7.5 | 7.4 | 7.6 | 7.5 |

FIG. 35-1

| Excipients | F10-7 | F10-8 | F11-7 | F11-8 |
|---|---|---|---|---|
| Mannitol (W%) | 6 | 6 | 5 | 5 |
| Sucrose (W%) | 7 | 8 | 7 | 8 |
| HSA (W%) | 0.5 | 0.5 | 0.5 | 0.5 |
| Gglycerol (W%) | 1 | 1 | 1 | 1 |
| $MgCl_2$ (mM) | 1 | 1 | 1 | 1 |

FIG. 35-2

| Date (Temp.) | PFU x 10⁹ | | | | | | |
|---|---|---|---|---|---|---|---|
| | AQF4-1 | AQF4-2 | AQF4-3 | AQF4-4 | AQF4-5 | AQF4-6 | AQF4-7 |
| 1/13/98 | 3 | 2.5 | 3.6 | 3.4 | 2.7 | 3.1 | 3.4 |
| 2/11/98 (4°C) | 2.5 | 3.2 | 3.3 | 2.9 | 2.6 | 2.9 | 2.6 |
| 2/11/98 (R.T.) | 1.8 | 2.7 | 1.6 | 3.6 | 2.6 | 1.6 | 1.7 |
| 4/10/98 (4°C) | 2.2 | 2 | 2.6 | 3 | 2.4 | 1.9 | 2.2 |
| 4/10/98 (R.T.) | 0.4 | 0.4 | 0.3 | 0.5 | 0.4 | <0.1 | 1.1 |
| 7/24/98 (4°C) | 2.4 | 2.8 | 2.6 | 3.5 | 1.9 | 2.2 | 2.6 |
| 7/24/98 (R.T.) | 0.002 | 0.005 | 0.006 | 0.005 | 0.005 | 0.005 | 0.001 |

FIG. 36-1

| Date (Temp.) | HPCL Intergrated Area | | | | | | |
|---|---|---|---|---|---|---|---|
| | AQF4-1 | AQF4-2 | AQF4-3 | AQF4-4 | AQF4-5 | AQF4-6 | AQF4-7 |
| 1/13/98 | 8.7 | 10.9 | 11.5 | 11.1 | 9.5 | 9.7 | 11.3 |
| 2/16/98 (4°C) | 9.1 | 9.3 | 9.2 | 9.5 | 8.2 | 8.4 | 9.6 |
| 2/16/98 (R.T.) | 6.8 | 9 | 9.5 | 9 | 8.7 | 8.4 | 9.3 |
| 4/10/98 (4°C) | 7.1 | 9.2 | 9.6 | 9.6 | 8.9 | 9.1 | 9.9 |
| 4/10/98 (R.T.) | 7.5 | 9.5 | 10.1 | 9.7 | 8.9 | 8.9 | 9.5 |
| 7/24/98 (4°C) | 8.1 | 9.9 | 11.1 | 10.3 | 9.2 | 7.4 | 9.3 |
| 7/24/98 (R.T.) | 7.3 | 3 | 10.7 | 8.9 | 10.4 | 10.45 | 3.5 |

FIG. 36-2

| Excipients | AQF4-1 | AQF4-2 | AQF4-3 | AQF4-4 | AQF4-5 | AQF4-6 | AQF4-7 |
|---|---|---|---|---|---|---|---|
| Mannitol (W%) | 5 | 5 | 5 | 5 | 5 | 5 | 5 |
| Sucrose (W%) | 5 | 5 | 5 | 5 | 5 | 5 | 5 |
| Tween 80 (W%) | | 0.02 | 0.1 | 0.5 | | | |
| Chap (W%) | | | | | 0.02 | 0.1 | 0.5 |

FIG. 36-3

METHOD FOR THE PRODUCTION AND PURIFICATION OF ADENOVIRAL VECTORS

The entire texts of U.S. patent application Ser. No. 08/975,519 filed Nov. 29, 1997, now U.S. Pat. No. 6,194,191, and U.S. Provisional Patent Application Ser. No. 60/031,329 filed Nov. 20, 1996, are specifically incorporated by reference herein without disclaimer.

BACKGROUND OF THE INVENTION

1. Field of the Invention

The present invention relates generally to the fields of cell culture and virus production. More particularly, it concerns improved methods for the culturing of mammalian cells, infection of those cells with adenovirus and the production of infectious adenovirus particles therefrom.

2. Description of Related Art

Adenoviral vectors, which carry transgenes that can be transcribed and translated to express therapeutic proteins, are currently being evaluated in the clinic for the treatment of a variety of cancer indications, including lung and head and neck cancers. As the clinical trials progress, the demand for clinical grade adenoviral vectors is increasing dramatically. The projected annual demand for a 300 patient clinical trial could reach approximately $1.08 \times 10^{16}$ viral particles.

Traditionally, adenoviruses are produced in commercially available tissue culture flasks, "cellfactories," or RB. Virus infected cells are harvested and subjected to multiple freeze-thaws to release the viruses from the cells in the form of crude cell lysate. The produced crude cell lysate (CCL) is then purified by multiple CsCl gradient ultracentrifugation steps. The typically reported virus yield from 100 single tray cell-factories is about $1 \times 10^{14}$ viral particles. Clearly, it becomes unfeasible to produce the required amount of virus using this traditional process. New scaleable and validatable production and purification processes have to be developed to meet the increasing demand.

The purification throughput of CsCl gradient ultracentrifugation is so limited that it cannot meet the demand for adenoviral vectors for gene therapy applications. Therefore, in order to achieve large scale adenoviral vector production, purification methods other than CsCl gradient ultracentrifugation have to be developed. Reports on the chromatographic purification of viruses are very limited, despite the wide application of chromatography for the purification of recombinant proteins. Size exclusion, ion exchange and affinity chromatography have been evaluated for the purification of retroviruses, tick-borne encephalitis virus, and plant viruses with varying degrees of success (Crooks, et al., 1990; Aboud, et al., 1982; McGrath et al., 1978, Smith and Lee, 1978; O'Neil and Balkovic, 1993). Even less research has been done on the chromatographic purification of adenovirus. This lack of research activity may be partially attributable to the existence of the effective, albeit non-scalable, CsCl gradient ultracentrifugation purification method for adenoviruses.

Recently, Huyghe et al. (1996) reported adenoviral vector purification using ion exchange chromatography in conjunction with metal chelate affinity chromatography. Virus purity similar to that from CsCl gradient ultracentrifugation was reported. Unfortunately, only 23% of virus was recovered after the double column purification process. Process factors that contribute to this low virus recovery are the freeze/thaw step utilized by the authors to lyse cells in order to release the virus from the cells and the two column purification procedure.

Clearly, there is a demand for an effective and scaleable method of adenoviral vector production that will result in a high yield of product to meet the ever increasing demand for such products. Recently Blanche et al in WO 98/00524, based on U.S. Ser. No. 60/026,667, describe adenoviral production methods that are useful as descriptive art. PCT publication No. WO 98/00524 and U.S. Ser. No. 60/026,667 are specifically herein incorporated by reference for their description of techniques for production and purification of recombinant adenovirus.

SUMMARY OF THE INVENTION

The present invention describes a new large scale process for the production and purification of adenovirus. This new production process offers not only scalability and validatability but also virus purity comparable to that achieved using CsCl gradient ultracentrifugation.

The present invention relates to a process for preparing large scale quantities of adenovirus. Indeed, it is believed that very large quantities of adenovirus particles can be produced using the processes of the present invention, quantities of up to about $1 \times 10^{18}$ particles, and preferably at least about $5 \times 10^{14}$ particles. This is highly desirable, as there are currently no techniques available to produce the very large, commercial quantities of adenovirus particles required for clinical applications at the high level of purity needed.

In one embodiment, the process generally involves preparing a culture of producer cells by seeding producer cells into a culture medium, infecting cells in the culture after they have reached a mid-log phase growth with a selected adenovirus (e.g., a recombinant adenovirus), and harvesting the adenovirus particles from the cell culture. This is because it has surprisingly been discovered by the inventors that maximal virus production is achieved in the producer cells when they are infected in the later part of log phase growth and prior to stationary growth. Preferably, the adenovirus particles so obtained are then subjected to purification techniques either known in the art or set forth herein.

In certain preferred embodiments of the present invention, therefore, the producer cells are infected with adenovirus at between about mid-log phase and stationary phase of growth. The log phase of the growth curve is where the cells reach their maximum rate of cell division (i.e. growth). The term mid-log phase of growth refers to the transition mid-point of a logarithmic growth curve. Stationary phase growth refers to the time on a growth curve (i.e. a plateau) in which cell growth and cell death have come to equilibrium.

In even more preferred embodiments, the producer cells are infected with the adenovirus during or after late-log phase of growth and before stationary phase. Late-log phase is defined as cell growth approaching the end of logarithmic growth, and before reaching the stationary phase of growth. Late-log phase can typically be identified on a growth curve as a secondary or tertiary point of inflection that occurs as the log-growth phase slows, approaching stationary growth.

In a preferred embodiment of the present invention, the producer cells are seeded into the cell culture medium using an essentially homogeneous pool of cells. The inventors have surprisingly discovered that the use of a homogeneous pool of cells for seeding can provide much improved confluency and cell density as well as better maturation of the virus, which in turn provides for larger production quantities and ultimate purity of the virus recovered. Indeed, seeding through the use of separate rather than homogeneous cell populations, for example from individual cell culture devices used in the cell expansion phase, can result in uneven cell density, and therefore uneven confluency levels at the time of infection. It is believed that the use of a homogeneous cell pool for seeding overcomes these problems.

In another preferred embodiment of the present invention, the culture medium is at least partially perfused during a portion of time during cell growth of the producer cells or following infection. Perfusion is used in order to maintain desired levels of certain metabolites and to remove and thereby reduce impurities in the culture medium. Perfusion rates can be measured in various manners, such as in terms of replacement volumes/unit time or in terms of levels of certain metabolites that are desired to be maintained during times of perfusion. Of course, it is typically the case that perfusion is not carried out at all times during culturing, etc., and is generally carried out only from time to time during culturing as desired. For example, perfusion is not typically initiated until after certain media components such as glucose begin to become exhausted and need to be replaced.

The inventors have discovered that low perfusion rates are particularly preferred, in that low perfusion rates tend to improve one's ability to obtain highly purified virus particles. The inventors prefer to define perfusion rate in terms of the glucose level that is achieved or maintained by means of the perfusion. For example, in the present invention the glucose concentration in the medium is preferably maintained at a concentration of between about 0.5 g/L and about 3.0 g/L. In a more preferred embodiment, the glucose concentration is maintained at between about 0.70 g/L and 2.0 g/L. In a still more preferred embodiment, the glucose concentration is maintained at between about 1.0 g/L and 1.5 g/L.

Also in certain preferred embodiments, the inventors prefer to recirculate the cell culture media while carrying out processes in accordance with the present invention, and even more preferably, the recirculation is carried out continuously. Recirculation is desirable in that it affords a more even distribution of nutrients throughout the cell growth chamber.

In certain other embodiments, the cells are seeded into the culture medium and allowed to attach to a culture surface for between about 3 hours and about 24 hours prior to initiation of medium recirculation. Attachment of cells to a cell surface generally allows for a more consistent and uniform cell growth and higher virus production rate, which in turn allows for the production of higher quality virus. It has been found by the inventors that recirculation can sometimes impede consistent and uniform cell attachment, and that ceasing recirculation during cell attachment phases can provide significant advantages.

With respect to seeding, in a preferred embodiment of the present invention, the cell culture medium is seeded with between about $0.5 \times 10^4$ and about $3 \times 10^4$ cells/cm$^2$, and more preferably with from about $1$-$2 \times 10^4$ cells/cm$^2$. The reason for this is that it has been found that in order to achieve maximal cell expansion and growth, it is most preferable to inoculate the selected growth chamber with a lower number of cells that one might typically use in other cell growth situations. The inventors have found that higher numbers of cells used in the cell inoculation step results in a cell density that is too high and can result in an over-confluence of cells at the time of viral infection, thus lowering yields. It is well within one of skill in the art to determine that in other types of cell culturing systems, similar optimization of the seeding density for a particular system could easily be determined. Nevertheless, in a particularly preferred embodiment, the cell culture medium is seeded with between about $7.5 \times 10^3$ and about $2.0 \times 10^4$ cell/cm$^2$. In an even more preferred embodiment, the cell culture medium is seeded with between about $9 \times 10^3$ and $1.5 \times 10^4$ cells/cm$^2$.

In another preferred embodiment of the present invention, the harvested adenovirus is purified and placed in a pharmaceutically acceptable composition. A pharmaceutically acceptable composition is defined as one that meets the minimal safety required set forth by the FDA or other similar pharmaceutical governing body, and can thus be administered safely to a patient. The present invention provides processes for the purification of the adenovirus. For example, the adenovirus is purified by steps that include chromatographic separation. While more than one chromatography step can be used in accordance with the present invention to purify the adenovirus, this will often result in significant losses in terms of yield. Thus, the inventors have discovered that surprising levels of purity can be achieved where only a single chromatography step is carried out, particularly where that chromatography step is carried out using ion-exchange chromatography. Ion-exchange chromatography is an excellent choice for purification of adenovirus particles due to the presence of a net negative charge on the surface of adenoviruses at physiological pH, permitting high purity isolation of adenovirus particles.

In particular embodiments of the present invention, the recombinant adenovirus is a replication-deficient adenovirus encoding a therapeutic gene operably linked to a promoter. A replication deficient adenovirus carrying a therapeutic gene linked to a promoter allows the controlled expression of the therapeutic gene by activating the promoter. The precise choice of a promoter further allows tissue specific regulation and expression of the therapeutic gene. In particular embodiments, the promoter is an SV40 IE, RSV LTR, β-actin, CMV-IE, adenovirus major late, polyoma F9-1, or tyrosinase promoter.

In other embodiments the replication deficient adenovirus is lacking at least a portion of the E1 region of the adenoviral genome. Replication deficient adenoviruses lacking a portion of the E1 region are desired to reduce toxicity and immunologic reaction to host cells. In another embodiment of the present invention, the producer cells complement the growth of replication deficient adenoviruses. This is an important feature of producer cells required to maintain high viral particle number of the replication deficient adenovirus. In certain such embodiments, the producer cells are 293, PER.C6, 911 or IT293SF cells. In a preferred embodiment, the producer cells are 293 cells. This allows In a preferred embodiment of the present invention it is contemplated that the recombinant adenovirus encodes a therapeutic recombinant gene. For example, the therapeutic gene may encode antisense ras, antisense myc, antisense raf, antisense erb, antisense src, antisense fins, antisense jun, antisense trk, antisense ret, antisense gsp, antisense hst, antisense bcl antisense abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF, mda-7, thymidine kinase or p53. In an even more preferred embodiment, the therapeutic gene is p53. One of the most frequent abnormalities resulting in human cancer are mutations in p53, thus the ability to replace a deficient p53 gene using the present invention is highly desirable.

In another particular embodiment of the present invention, the adenovirus is harvested by steps that include lysing the producer cells by means other than freeze-thaw. The reason for this is that the freeze-thaw method is somewhat cumbersome and not particularly suited to production of commercial quantities. In preferred embodiments the producer cells are lysed by means of detergent lysis or autolysis. The harvesting of the adenovirus by detergent lysis and autolysis results in a much higher virus recovery than the freeze-thaw process and is therefore an improvement in the large scale production of adenoviruses.

In a particular embodiment of the present invention the purified recombinant adenovirus has one or more of the following properties. For example, the property may be a virus titer of between about $1 \times 10^9$ and about $1 \times 10^{13}$ pfu/ml, a virus particle concentration between about $1 \times 10^{10}$ and about $2 \times 10^{13}$ particles/ml, a particle:pfu ratio between about 10 and about 60, less than 50 ng BSA per $1 \times 10^{12}$ viral particles, between about 50 pg and 1 ng of contaminating human DNA per $1 \times 10^{12}$ viral particles or a single HPLC elution peak consisting essentially of 97 to 99% of the area under the peak. These criteria select for a highly purified adenovirus.

To further impose limits on the purification process of the adenovirus, between about $5 \times 10^{14}$ and $1 \times 10^{18}$ viral particles are desired. In addition, one or more of the following properties further improve the selection for high purity adenovirus particles. For example the property may be a virus titer of between about $1 \times 10^9$ and about $1 \times 10^{13}$ pfu/ml, more preferably $1 \times 10^{11}$ and about $1 \times 10^{13}$ pfu/ml, and most preferably $1 \times 10^{12}$ and about $1 \times 10^{13}$ pfu/ml. Further, a virus particle concentration between about $1 \times 10^{10}$ and about $2 \times 10^{13}$ particles/ml, more preferably $1 \times 10^{11}$ and about $2 \times 10^{13}$ particles/ml, and most preferably $1 \times 10^{12}$ and about $1 \times 10^{13}$ particles/ml.

Additionally, a particle:pfu ratio between about 10 and about 60, more preferably a particle:pfu ratio between about 10 and about 50, even more preferable a particle:pfu ratio between about 10 and about 40, and most preferably a particle:pfu ratio between about 20 and about 40.

To limit the BSA concentration, it is preferable to have less than 50 ng BSA per $1 \times 10^{12}$ viral particles, for example, between about 1 ng to 50 ng BSA per $1 \times 10^{12}$ viral particles, and more preferably between about 5 ng and 40 ng of BSA per $1 \times 10^{12}$ viral particles.

Low concentrations of DNA contamination are also desired. Thus, between about 50 pg and 1 ng of contaminating human DNA per $1 \times 10^{12}$ viral particles is acceptable, even more preferable is between about 50 pg and 500 pg of contaminating human DNA per $1 \times 10^{12}$ viral particles, and most preferable is between about 100 pg and 500 pg of contaminating human DNA per $1 \times 10^{12}$ viral particles. Finally, an adenovirus that elutes as a single HPLC peak is desired, more preferably is an adenovirus that elutes as an HPLC peak that contains between about 97 and 99% of the total area under the peak.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A Thesit®. FIG. 3B Triton® X-100. FIG. 3C. NP-40®. FIG. 3D. Brij® 80. FIG. 3E. Tween® 20. Detergent concentration: 1% (w/v) lysis temperature: room temperature. (solid line $A_{260}$; dotted line $A_{280}$).

FIG. 8B fraction 4, FIG. 8C fraction 8. (solid line $A_{260}$; dotted line $A_{280}$).

FIG. 10A Crude virus solution. FIG. 10B Flow through. FIG. 10C. Peak number 1. FIG. 10D. Peak number 2. FIG. 10E. CsCl purified virus. (solid line $A_{260}$; dotted line $A_{280}$).

FIG. 16A HPLC profiles of virus fraction from first purification step. FIG. 16B HPLC profiles of virus fraction from second purification. (solid line $A_{260}$; dotted line $A_{280}$).

FIG. 19A SDS-PAGE analysis. FIG. 19B Western blot for BSA. FIG. 19C nucleic acid slot blot to determine the contaminating nucleic acid concentration.

FIG. 20A Flow through from loading ratio of 1:1. FIG. 20B. Purified virus from loading ratio of 1:1. FIG. 20C Flow through of loading ratio of 2:1. FIG. 20D. Purified virus from the loading ratio of 2:1. FIG. 20E Flow through from loading ratio of 3:1. FIG. 20F. Purified virus from the loading ratio of 3:1. (solid line $A_{260}$; dotted line $A_{280}$).

FIG. 23. A production and purification flow chart for AdC-MVp53

FIG. 30A and FIG. 30B. Storage stability data using secondary drying at 10° C. without $N_2$ blanketing. FIG. 30A, secondary drying at 10° C. without $N_2$ blanketing for formulation set 10. FIG. 30B, secondary drying at 10° C. without $N_2$ blanketing for formulation set 11.

FIG. 31A and FIG. 31B. Storage stability data using secondary drying at 30° C. without $N_2$ blanketing. FIG. 31A, secondary drying at 30° C. without $N_2$ blanketing for formulation set 10. FIG. 31B, secondary drying at 30° C. without $N_2$ blanketing for formulation set 11.

FIG. 32A and FIG. 32B. Storage stability data using secondary drying at 30° C. with $N_2$ blanketing. FIG. 32A, secondary drying at 30° C. with $N_2$ blanketing for formulation set 10. FIG. 32B, secondary drying at 30° C. with $N_2$ blanketing for formulation set 11.

FIG. 33. Stability data for liquid formulation set #1.
FIG. 34. Stability data for liquid formulation set #2.
FIG. 35. Stability data for liquid formulation set #3.
FIG. 36. Stability data for liquid formulation set #4.

DESCRIPTION OF ILLUSTRATIVE EMBODIMENTS

Figure 1A:
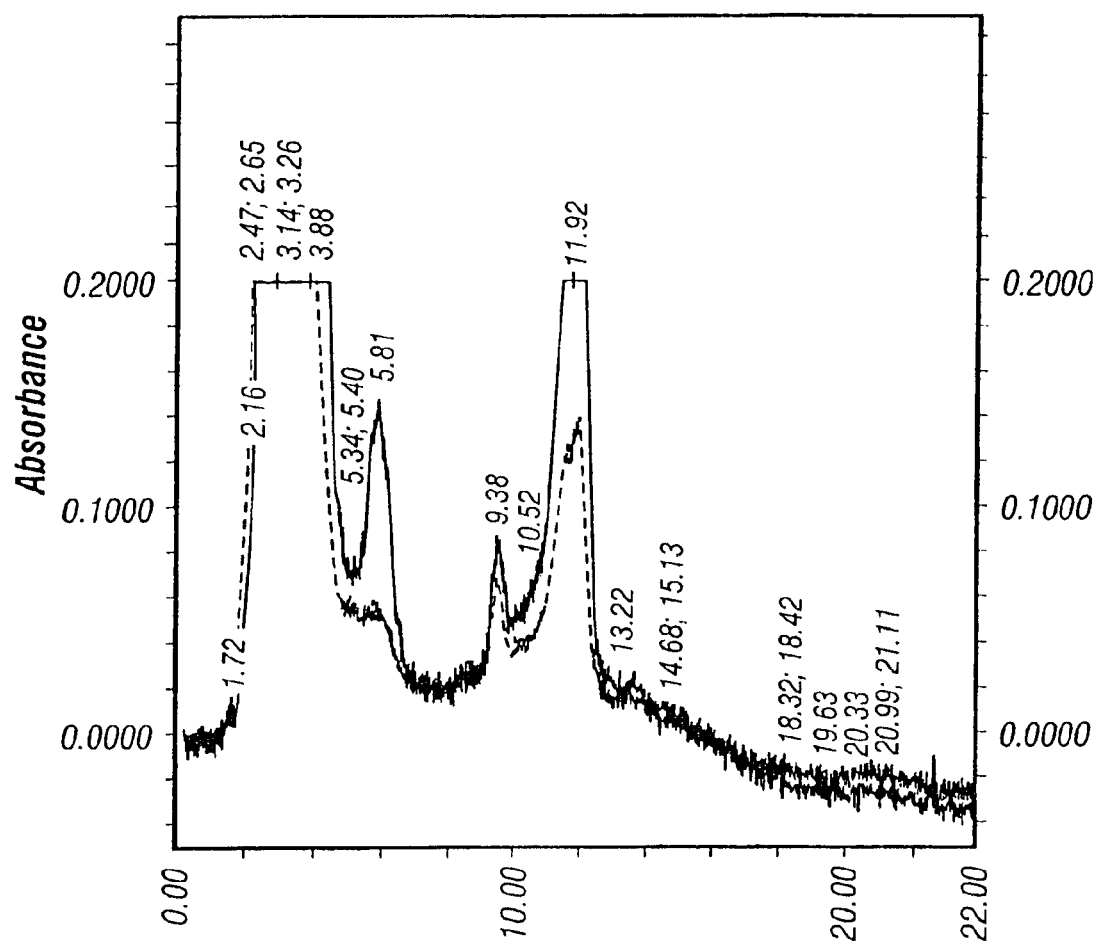
FIG. 1A and FIG. 1B. HPLC profiles of the viral solutions from production runs using medium perfusion rates characterized as "high" (FIG. 1A) and "low" (FIG. 1B).

It has been shown that adenoviral vectors can successfully be used in eukaryotic gene expression and vaccine development. Recently, animal studies have demonstrated that recombinant adenovirus could be used for gene therapy. Successful studies in administering recombinant adenovirus to different tissues have proven the effectiveness of adenoviral vectors in therapy. This success has led to the use of such vectors in human clinical trials. There now is an increased demand for the production of adenoviral vectors to be used in various therapies. The techniques currently available are insufficient to meet such a demand. The present invention provides methods for the production of large amounts of adenovirus for use in such therapies.

The present invention involves a process that has been developed for the production and purification of a replication deficient recombinant adenovirus. The production process is based on the use of a cell culture bioreactor for cell growth and virus production. After viral infection of the producer cells, virus can be harvested by any number of methods, including virus autolysis or chemical lysis. The harvested crude virus solution can then be purified using a single ion exchange chromatography run, after concentration/diafiltration and nuclease treatment to reduce the contaminating nucleic acid concentration in the crude virus solution. The column purified virus has equivalent purity relative to that of virus purified by cesium banding. The total process recovery of the virus product is 70%±10%. This is a significant improvement over the results reported by Huyghe et al. (1996). Compared to double CsCl gradient ultracentrifugation, column purification has the advantage of being more consistent, scaleable, validatable, faster and less expensive. This new process represents a significant improvement in the technology for manufacturing of adenoviral vectors for gene therapy.

Therefore, the present invention is designed to take advantage of these improvements in large scale culturing systems and purification for the purpose of producing and purifying adenoviral vectors. The various components for such a system, and methods of producing adenovirus therewith, are set forth in detail below.

1. HOST CELLS

A) Cells

In a preferred embodiment, the generation and propagation of the adenoviral vectors depend on a unique helper cell line, designated 293, which was transformed from human embryonic kidney cells by Adenovirus serotype 5 (Ad5) DNA fragments and constitutively expresses E1 proteins (Graham et al., 1977). Since the E3 region is dispensable from the Ad genome (Jones and Shenk, 1978), the current Ad vectors, with the help of 293 cells, carry foreign DNA in either the E1, the E3 or both regions (Graham and Prevec, 1991; Bett et al., 1994).

A first aspect of the present invention is the recombinant cell lines which express part of the adenoviral genome. These cells lines are capable of supporting replication of adenovirus recombinant vectors and helper viruses having defects in certain adenoviral genes, i.e., are "permissive" for growth of these viruses and vectors. The recombinant cell also is referred to as a helper cell because of the ability to complement defects in, and support replication of, replication-incompetent adenoviral vectors. The prototype for an adenoviral helper cell is the 293 cell line, which contains the adenoviral E1 region. 293 cells support the replication of adenoviral vectors lacking E1 functions by providing in trans the E1-active elements necessary for replication. Other cell lines which also support the growth of adenoviruses lacking E1 function include PER.C6 (IntroGene, NL), 911 (IntroGene, NL), and IT293SF.

Helper cells according to the present invention are derived from a mammalian cell and, preferably, from a primate cell such as human embryonic kidney cell. Although various primate cells are preferred and human or even human embryonic kidney cells are most preferred, any type of cell that is capable of supporting replication of the virus would be acceptable in the practice of the invention. Other cell types might include, but are not limited to Vero cells, HeLa cells or any eukaryotic cells for which tissue culture techniques are established as long as the cells are adenovirus permissive. The term "adenovirus permissive" means that the adenovirus or adenoviral vector is able to complete the entire intracellular virus life cycle within the cellular environment.

The helper cell may be derived from an existing cell line, e.g., from a 293 cell line, or developed de novo. Such helper cells express the adenoviral genes necessary to complement in trans deletions in an adenoviral genome or which support replication of an otherwise defective adenoviral vector, such as the E1, E2, E4, E5 and late functions. A particular portion of the adenovirus genome, the E1 region, has already been used to generate complementing cell lines. Whether integrated or episomal, portions of the adenovirus genome lacking a viral origin of replication, when introduced into a cell line, will not replicate even when the cell is superinfected with wild-type adenovirus. In addition, because the transcription of the major late unit is after viral DNA replication, the late functions of adenovirus cannot be expressed sufficiently from a cell line. Thus, the E2 regions, which overlap with late functions (L1-5), will be provided by helper viruses and not by the cell line. Typically, a cell line according to the present invention will express E1 and/or E4.

As used herein, the term "recombinant" cell is intended to refer to a cell into which a gene, such as a gene from the adenoviral genome or from another cell, has been introduced. Therefore, recombinant cells are distinguishable from naturally-occurring cells which do not contain a recombinantly-introduced gene. Recombinant cells are thus cells having a gene or genes introduced through "the hand of man."

Replication is determined by contacting a layer of uninfected cells, or cells infected with one or more helper viruses, with virus particles, followed by incubation of the cells. The formation of viral plaques, or cell free areas in the cell layer, is the result of cell lysis caused by the expression of certain viral products. Cell lysis is indicative of viral replication.

Examples of other useful mammalian cell lines that may be used with a replication competent virus or converted into complementing host cells for use with replication deficient virus are Vero and HeLa cells and cell lines of Chinese hamster ovary, W138, BHK, COS-7, HepG2, 3T3, RIN, MDCK and A549 cells.

B) Growth in Selection Media

In certain embodiments, it may be useful to employ selection systems that preclude growth of undesirable cells. This may be accomplished by virtue of permanently transforming a cell line with a selectable marker or by transducing or infecting a cell line with a viral vector that encodes a selectable marker. In either situation, culture of the transformed/transduced cell with an appropriate drug or selective compound will result in the enhancement, in the cell population, of those cells carrying the marker.

Examples of markers include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; and hygro, that confers resistance to hygromycin.

C. Growth in Serum Weaning

Serum weaning adaptation of anchorage-dependent cells into serum-free suspension cultures have been used for the production of recombinant proteins (Berg, 1993) and viral vaccines (Perrin, 1995). There have been few reports on the adaptation of 293A cells into serum-free suspension cultures until recently. Gilbert reported the adaptation of 293A cells into serum-free suspension cultures for adenovirus and recombinant protein production (Gilbert, 1996). A similar adaptation method had been used for the adaptation of A549 cells into serum-free suspension culture for adenovirus production (Morris et al., 1996). Cell-specific virus yields in the adapted suspension cells, however, are about 5-10-fold lower than those achieved in the parental attached cells.

Using the similar serum weaning procedure, the inventors have successfully adapted the 293A cells into serum-free suspension culture (293SF cells). In this procedure, the 293 cells were adapted to a commercially available 293 media by sequentially lowering down the FBS concentration in T-flasks. Briefly, the initial serum concentration in the media was approximately 10% FBS DMEM media in T-75 flask and the cells were adapted to serum-free IS 293 media in T-flasks by lowering down the FBS concentration in the media sequentially. After 6 passages in T-75 flasks the FBS % was estimated to be about 0.019% in the 293 cells. The cells were subcultured two more times in the T flasks before they were transferred to spinner flasks. The results described herein below show that cells grow satisfactorily in the serum-free medium (IS293 medium, Irvine Scientific, Santa Ana, Calif.). Average doubling time of the cells were 18-24 h achieving stationary cell concentrations in the order of $4\text{-}10 \times 10^6$ cells/ml without medium exchange.

D. Adaptation of Cells for Suspension Culture

Two methodologies have been used to adapt 293 cells into suspension cultures. Graham adapted 293A cells into suspension culture (293N3S cells) by 3 serial passages in nude mice (Graham, 1987). The suspension 293N3S cells were found to be capable of supporting El$^-$ adenoviral vectors. However, Garnier et al. (1994) observed that the 293N3S cells had a relatively long initial lag phase in suspension, a low growth rate, and a strong tendency to clump.

The second method that has been used is a gradual adaptation of 293A cells into suspension growth (Cold Spring Harbor Laboratories, 293S cells). Garnier et al. (1994) reported the use of 293S cells for production of recombinant proteins from adenoviral vectors. The authors found that 293S cells were much less clumpy in calcium-free media and a fresh medium exchange at the time of virus infection could significantly increase the protein production. It was found that glucose was the limiting factor in culture without medium exchange.

In the present invention, the 293 cells adapted for growth in serum-free conditions were adapted into a suspension culture. The cells were transferred in a serum-free 250 mL spinner suspension culture (100 mL working volume) for the suspension culture at an initial cell density of between about 1.18E+5 vc/mL and about 5.22E+5 viable cells/mL. The media may be supplemented with heparin to prevent aggregation of cells. This cell culture systems allows for some increase of cell density whilst cell viability is maintained. Once these cells are growing in culture, the cells are subcultured in the spinner flasks approximately 7 more passages. It may be noted that the doubling time of the cells is progressively reduced until at the end of the successive passages the doubling time is about 1.3 day, i.e. comparable to 1.2 day of the cells in 10% FBS media in the attached cell culture. In the serum-free IS 293 media supplemented with heparin almost all the cells existed as individual cells not forming aggregates of cells in the suspension culture.

2. CELL CULTURE SYSTEMS

In any cell culture system, there is a characteristic growth pattern following inoculation that includes a lag phase, an accelerated growth phase, an exponential or "log" phase, a negative growth acceleration phase and a plateau or stationary phase. The log and plateau phases give vital information about the cell line, the population doubling time during log growth, the growth rate, and the maximum cell density achieved in plateau. In the log phase, as growth continues, the cells reach their maximum rate of cell division. Numbers of cells increase in log relationship to time. During this period of most active multiplication, the logarithms of the numbers of cells counted at short intervals, plotted against time, produce a straight line. By making one count at a specified time and a second count after an interval during the log phase of growth and knowing the number of elapsed time units, one can calculate the total number of cell divisions or doublings, and both the growth rate and generation time. Within a few hours or days after the commencement of the log phase, the rate of cell division begins to decline and some of the cells begin to die. This is reflected on the growth curve by a gradual flattening out of the line. Eventually the rate of cells dying is essentially equal to the rate of cells dividing, and the total viable population remains the same for a period of time. This is known as the stationary or plateau phase and is represented on the growth curve as a flattening out of the line where the slope approaches zero.

Measurement of the population doubling time can be used to quantify the response of the cells to different inhibitory or stimulatory culture conditions such as variations in nutrient concentration, hormonal effects, or toxic drugs. It is also a good monitor of the culture during serial passage and enables the calculation of cell yields and the dilution factor required at subculture.

The population doubling time is an average figure and describes the net result of a wide range of cell division rates, including zero, within the culture. The doubling time will also differ with varying cell types, culture conditions, and culture vessels. Single time points are unsatisfactory for monitoring growth when the shape of the cell growth curve is not known. Thus it is important to determine the growth curve for each cell type being used in the conditions that are being used for the cell culture. Typical growth curves are sigmoidal in shape, with the first part of the curve representing the lag phase, the center part of the curve representing the log phase, and the last part of the curve representing the plateau phase. The log phase is when the cells are growing at the highest rate, and as the cells reach their saturation density, their growth will slow and the culture will enter the plateau phase. A detailed description of cell culture techniques and theory can be found in Freshney, 1992 and Freshney, 1987.

An important aspect of the present invention is infection of the producer cells with recombinant adenovirus at an appropriate time to achieve maximal virus production. The inventors have found that maximal virus production is obtained when the producer cells are infected between about when the cells reach the first inflection point on the log phase of the cell growth curve, i.e. mid-log phase, and before the $2^{nd}$ inflection point on the plateau phase of the cell growth curve, i.e. mid-plateau phase. This range can be determined easily for any cell type and any culture conditions with any cell culturing apparatus. The inflection points on a cell growth curve are when the shape of the line changes from a convex to a concave shape, or from a concave to a convex shape.

For most growth curves plotted on semi-log scales, the log phase of growth can be approximately represented by a linear increase in the slope of the line over time. That is, at any short interval between two points on the line of the logarithmic phase of the curve, the log of cell number is increasing in a linear fashion relative to time. Thus mid log phase can be approximately defined as the point or interval within the log phase in which the cells are dividing at their maximal rate, and the increase in logs of cell number is linear with respect to time. Late log phase can be defined as approximately the point or interval of time in which the rate of cell division has slowed, and the log of number of cells is no longer increasing in a linear fashion with respect to time. When looking at a growth curve, this area would be represented by gradual falling or flattening of the slope of the line. At early stationary phase, the rate of cell growth is decreasing and getting nearer the rate of cell death, and thus the slope of the line on the growth curve is even less than that at late log phase. At mid-stationary phase, the rate of cell growth is approximately equal to the rate of cell division and thus the line on the growth curve is relatively flat and has a slope approaching zero. It will be understood that the skilled artisan can formulate growth curves for any such cell line and identify the aforementioned regions on the curve.

The ability to produce infectious viral vectors is increasingly important to the pharmaceutical industry, especially in the context of gene therapy. Over the last decade, advances in biotechnology have led to the production of a number of important viral vectors that have potential uses as therapies, vaccines and protein production machines. The use of viral vectors in mammalian cultures has advantages over proteins produced in bacterial or other lower lifeform hosts in their ability to post-translationally process complex protein structures such as disulfide-dependent folding and glycosylation.

Development of cell culture for production of virus vectors has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector.

Frequently, factors which affect the downstream (in this case, beyond the cell lysis) side of manufacturing scale-up were not considered before selecting the cell line as the host for the expression system. Also, development of bioreactor systems capable of sustaining very high density cultures for prolonged periods of time have not lived up to the increasing demand for increased production at lower costs.

The present invention will take advantage of the recently available bioreactor technology. Growing cells according to the present invention in a bioreactor allows for large scale production of fully biologically-active cells capable of being infected by the adenoviral vectors of the present invention. By operating the system at a low perfusion rate and applying a different scheme for purification of the infecting particles, the invention provides a purification strategy that is easily scaleable to produce large quantities of highly purified product.

Bioreactors have been widely used for the production of biological products from both suspension and anchorage dependent animal cell cultures. The most widely used producer cells for adenoviral vector production are anchorage dependent human embryonic kidney cells (293 cells). Bioreactors to be developed for adenoviral vector production should have the characteristic of high volume-specific culture surface area in order to achieve high producer cell density and high virus yield. Microcarrier cell culture in stirred tank bioreactor provides very high volume-specific culture surface area and has been used for the production of viral vaccines (Griffiths, 1986). Furthermore, stirred tank bioreactors have industrially been proven to be scaleable. The multiplate Cellcube™ cell culture system manufactured by Corning-Costar also offers a very high volume-specific culture surface area. Cells grow on both sides of the culture plates hermetically sealed together in the shape of a compact cube. Unlike stirred tank bioreactors, the Cellcube™ culture unit is disposable. This is very desirable at the early stage production of clinical product because of the reduced capital expenditure, quality control and quality assurance costs associated with disposable systems. In consideration of the advantages offered by the different systems, both the stirred tank bioreactor and the Cellcube™ system were evaluated for the production of adenovirus.

Table 1 list several exemplary techniques for cell culturing and viral particle production. Currently, there are no methods employed that result in both high purity and a high number of viral particles. Thus, the following methods are considered in combination with the large scale process for the production and purification of adenovirus described in the present invention.

TABLE 1

|  | Virus Particles | | | | |
| --- | --- | --- | --- | --- | --- |
|  | $5 \times 10^{14}$ | $1 \times 10^{15}$ | $1 \times 10^{16}$ | $1 \times 10^{17}$ | $1 \times 10^{18}$ |
| Exemplary Techniques for Viral Particle Production | Cellcube ™ | Cellcube ™ | Packed Bed per 10 L | 1000-5000 L Stirred Tank Airlift Reactor | 10,000-20,000 L Stirred Tank |
| Total Cell Number | $5 \times 10^{10}$ | $1 \times 10^{11}$ | $1 \times 10^{12}$ | $1 \times 10^{13}$ | $1 \times 10^{14}$ |

A) Anchorage-Dependent Versus Non-Anchorage-Dependent Cultures.

Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively simple to operate and straightforward to scale up. Homogeneous conditions can be provided in the reactor which allows for precise monitoring and control of temperature, dissolved oxygen, and pH, and ensures that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1985; Larsson, 1987). Viruses propagated in suspension cultures as opposed to anchorage-dependent cultures can sometimes cause rapid changes in viral markers, leading to reduced immunogenicity (Bahnemann, 1980). Finally, sometimes even recombinant cell lines can secrete considerably higher amounts of products when propagated as anchorage-dependent cultures as compared with the same cell line in suspension (Nilsson and Mosbach, 1987). For these reasons, different types of anchorage-dependent cells are used extensively in the production of different biological products.

B) Reactors and Processes for Suspension.

Large scale suspension culture of mammalian cells in stirred tanks was undertaken. The instrumentation and controls for bioreactors adapted, along with the design of the fermentors, from related microbial applications. However, acknowledging the increased demand for contamination control in the slower growing mammalian cultures, improved aseptic designs were quickly implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are available. Maximum cell densities obtainable in suspension cultures are relatively low at about $2\text{-}4 \times 10^6$ cells/ml of medium (which is less than 1 mg dry cell weight per ml), well below the numbers achieved in microbial fermentation.

Two suspension culture reactor designs are most widely used in the industry due to their simplicity and robustness of operation—the stirred reactor and the airlift reactor. The stirred reactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a variety of devices (e.g. fine mesh spin filter, hollow fiber or flat plate membrane filters, settling tubes). Spin filter cultures can produce cell densities of approximately $5 \times 10^7$ cells/ml. A true open system and the simplest perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cell mass from the reactor). Culture fluid containing cells and cell products and byproducts is removed at the same rate.

C) Non-Perfused Attachment Systems.

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottles, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling key process parameters and difficulty in maintaining homogeneous environmental conditions throughout the culture.

Despite these drawbacks, a commonly used process for large scale anchorage-dependent cell production is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to approximately $10^9$ cells/bottle or almost $10^7$ cells/ml of culture media).

D) Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency on the microcarrier surface. In fact, this large scale culture system upgrades the attachment dependent culture from a single disc process to a unit process in which both monolayer and suspension culture have been brought together. Thus, combining the necessary surface for a cell to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2 \times 10^7$ cells/ml when cultures are propagated in a perfused reactor mode. Second, cells can be propagated in one unit process vessels instead of using many small low-productivity vessels (i.e., flasks or dishes). This results in far better nutrient utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, $pO_2$, and concentration of medium components), thus leading to more reproducible cell propagation and product recovery. Fourth, it is possible to take a representative sample for microscopic observation, chemical testing, or enumeration. Fifth, since microcarriers settle out of suspension quickly, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

E) Microencapsulation of Mammalian Cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982, U.S. Pat. No. 4,352,883, incorporated herein by reference) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150-1500 µm in diameter, are easily retained in a perfused reactor using a fine-meshed screen. The ratio of capsule volume to total media volume can be maintained from as dense as 1:2 to 1:10. With intracapsular cell densities of up to $10^8$, the effective cell density in the culture is $1-5 \times 10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

The current invention includes cells which are anchorage-dependent in nature. 293 cells, for example, are anchorage-dependent, and when grown in suspension, the cells will attach to each other and grow in clumps, eventually suffocating cells in the inner core of each clump as they reach a size that leaves the core cells unsustainable by the culture conditions. Therefore, an efficient means of large-scale culture of anchorage-dependent cells is needed in order to effectively employ these cells to generate large quantities of adenovirus.

F) Perfused Attachment Systems

Perfused attachment systems are a preferred form of the present invention. Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential.

The current use of perfused culture is in response to the challenge of growing cells at high densities (i.e., $0.1\text{-}5 \times 10^8$ cells/ml). In order to increase densities beyond $2\text{-}4 \times 10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

The development of a perfused packed-bed reactor using a bed matrix of a non-woven fabric has provided a means for maintaining a perfusion culture at densities exceeding $10^8$ cells/ml of the bed volume (CelliGen™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 μm to 100 μm, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al.), which is hereby incorporated by reference in its entirety.

The Cellcube™ (Corning-Costar) module provides a large styrenic surface area for the immobilization and growth of substrate attached cells. It is an integrally encapsulated sterile single-use device that has a series of parallel culture plate joined to create thin sealed laminar flow spaces between adjacent plates.

The Cellcube™ module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Cells within the system reach a higher density of solution (cells/ml) than in traditional culture systems. Many typically used basal media are designed to support $1\text{-}2 \times 10^6$ cells/ml/day. A typical Cellcube™, run with an 85,000 $cm^2$ surface, contains approximately 6 L media within the module. The cell density often exceeds $10^7$ cells/mL in the culture vessel. At confluence, 2-4 reactor volumes of media are required per day.

The timing and parameters of the production phase of cultures depends on the type and use of a particular cell line. Many cultures require a different media for production than is required for the growth phase of the culture. The transition from one phase to the other will likely require multiple washing steps in traditional cultures. However, the Cellcube™ system employs a perfusion system. On of the benefits of such a system is the ability to provide a gentle transition between various operating phases. The perfusion system negates the need for traditional wash steps that seek to remove serum components in a growth medium.

In an exemplary embodiment of the present invention, the CellCube™ system is used to grow cells transfected with AdCMVp53. 293 cells were inoculated into the Cellcube™ according to the manufacturer's recommendation. Inoculation cell densities were in the range of $1\text{-}1.5 \times 10^4/cm^2$. Cells were allowed to grow for 7 days at 37° C. under culture conditions of pH=7.20, DO=60% air saturation. The medium perfusion rate was regulated according to the glucose concentration in the Cellcube™. One day before viral infection, medium for perfusion was changed from a buffer comprising 10% FBS to a buffer comprising 0% FBS. On day 8, cells were infected with virus at a multiplicity of infection (MOI) of 5. Medium perfusion was stopped for 1 hr immediately after infection then resumed for the remaining period of the virus production phase. Culture was harvested 45-48 hr post-infection. Of course these culture conditions are exemplary and may be varied according to the nutritional needs and growth requirements of a particular cell line. Such variation may be performed without undue experimentation and are well within the skill of the ordinary person in the art.

G) Serum-Free Suspension Culture

In particular embodiments, adenoviral vectors for gene therapy are produced from anchorage-dependent culture of 293 cells (293A cells) as described above. Scale-up of adenoviral vector production is constrained by the anchorage-dependency of 293A cells. To facilitate scale-up and meet future demand for adenoviral vectors, significant efforts have been devoted to the development of alternative production processes that are amenable to scale-up. Methods include growing 293A cells in microcarrier cultures and adaptation of 293A producer cells into suspension cultures. Microcarrier culture techniques have been described above. This technique relies on the attachment of producer cells onto the surfaces of microcarriers which are suspended in culture media by mechanical agitation. The requirement of cell attachment may present some limitations to the scalability of microcarrier cultures.

Until the present application there have been no reports on the use of 293 suspension cells for adenoviral vector production for gene therapy. Furthermore, the reported suspension 293 cells require the presence of 5-10% FBS in the culture media for optimal cell growth and virus production. Historically, presence of bovine source proteins in cell culture media has been a regulatory concerns, especially recently because of the outbreak of Bovine Spongiform Encephalopathy (BSE) in some countries. Rigorous and complex downstream purification process has to be developed to remove contaminating proteins and any adventitious viruses from the final product. Development of serum-free 293 suspension culture is deemed to be a major process improvement for the production of adenoviral vector for gene therapy.

Results of virus production in spinner flasks and a 3 L stirred tank bioreactor indicate that cell specific virus productivity of the 293SF cells was approximately $2.5 \times 10^4$ vp/cell, which is approximately 60-90% of that from the 293A cells. However, because of the higher stationary cell concentration, volumetric virus productivity from the 293SF culture is essentially equivalent to that of the 293A cell culture. The inventors also observed that virus production increased significantly by carrying out a fresh medium exchange at the time of virus infection. The inventors are going to evaluate the limiting factors in the medium. These findings allow for a scaleable, efficient, and easily validatable process for the production of adenoviral vector. This adaptation method is not limited to 293A cells only and will be equally useful when applied to other adenoviral vector producer cells.

3. METHODS OF CELL HARVEST AND LYSIS

Adenoviral infection results in the lysis of the cells being infected. The lytic characteristics of adenovirus infection permit two different modes of virus production. One is harvesting infected cells prior to cell lysis. The other mode is harvesting virus supernatant after complete cell lysis by the produced virus. For the latter mode, longer incubation times are required in order to achieve complete cell lysis. This prolonged incubation time after virus infection creates a serious concern about increased possibility of generation of replication competent adenovirus (RCA), particularly for the current first generation adenoviral vectors (E1-deleted vector). Therefore, harvesting infected cells before cell lysis was chosen as the production mode of choice. Table 2 lists the most common methods that have been used for lysing cells after cell harvest.

TABLE 2

| Methods used for cell lysis | | |
|---|---|---|
| Methods | Procedures | Comments |
| Freeze-thaw | Cycling between dry ice and 37° C. water bath | Easy to carry out at lab scale. High cell lysis efficiency Not scaleable Not recommended for large scale manufacturing |
| Solid Shear | French Press Hughes Press | Capital equipment investment Virus containment concerns Lack of experience |
| Detergent lysis | Non-ionic detergent solutions such as Tween, Triton, NP-40, etc. | Easy to carry out at both lab and manufacturing scale Wide variety of detergent choices Concerns of residual detergent in finished product |
| Hypotonic solution lysis | water, citric buffer | Low lysis efficiency |
| Liquid Shear | Homogenizer Impinging Jet Microfluidizer | Capital equipment investment Virus containment concerns Scaleability concerns |
| Sonication | Ultrasound | Capital equipment investment Virus containment concerns Noise pollution Scaleability concern |

A) Detergents

Cells are bounded by membranes. In order to release components of the cell, it is necessary to break open the cells. The most advantageous way in which this can be accomplished, according to the present invention, is to solubilize the membranes with the use of detergents. Detergents are amphipathic molecules with an apolar end of aliphatic or aromatic nature and a polar end which may be charged or uncharged. Detergents are more hydrophilic than lipids and thus have greater water solubility than lipids. They allow for the dispersion of water insoluble compounds into aqueous media and are used to isolate and purify proteins in a native form.

Detergents can be denaturing or non-denaturing. The former can be anionic such as sodium dodecyl sulfate or cationic such as ethyl trimethyl ammonium bromide. These detergents totally disrupt membranes and denature the protein by breaking protein-protein interactions. Non denaturing detergents can be divided into non-anionic detergents such as Triton® X-100, bile salts such as cholates and zwitterionic detergents such as CHAPS. Zwitterionics contain both cationic and anion groups in the same molecule, the positive electric charge is neutralized by the negative charge on the same or adjacent molecule.

Denaturing agents such as SDS bind to proteins as monomers and the reaction is equilibrium driven until saturated. Thus, the free concentration of monomers determines the necessary detergent concentration. SDS binding is cooperative i.e. the binding of one molecule of SDS increase the probability of another molecule binding to that protein, and alters proteins into rods whose length is proportional to their molecular weight.

Non-denaturing agents such as Triton® X-100 do not bind to native conformations nor do they have a cooperative binding mechanism. These detergents have rigid and bulky apolar moieties that do not penetrate into water soluble proteins. They bind to the hydrophobic parts of proteins. Triton® X100 and other polyoxyethylene nonanionic detergents are inefficient in breaking protein-protein interaction and can cause artifactual aggregations of protein. These detergents will, however, disrupt protein-lipid interactions but are much gentler and capable of maintaining the native form and functional capabilities of the proteins.

Detergent removal can be attempted in a number of ways. Dialysis works well with detergents that exist as monomers.

Dialysis is somewhat ineffective with detergents that readily aggregate to form micelles because the micelles are too large to pass through dialysis. Ion exchange chromatography can be utilized to circumvent this problem. The disrupted protein solution is applied to an ion exchange chromatography column and the column is then washed with buffer minus detergent. The detergent will be removed as a result of the equilibration of the buffer with the detergent solution. Alternatively the protein solution may be passed through a density gradient. As the protein sediments through the gradients the detergent will come off due to the chemical potential.

Often a single detergent is not versatile enough for the solubilization and analysis of the milieu of proteins found in a cell. The proteins can be solubilized in one detergent and then placed in another suitable detergent for protein analysis. The protein detergent micelles formed in the first step should separate from pure detergent micelles. When these are added to an excess of the detergent for analysis, the protein is found in micelles with both detergents. Separation of the detergent-protein micelles can be accomplished with ion exchange or gel filtration chromatography, dialysis or buoyant density type separations.

Triton® X-Detergents: This family of detergents (Triton® X-100, X114 and NP-40) have the same basic characteristics but are different in their specific hydrophobic-hydrophilic nature. All of these heterogeneous detergents have a branched 8-carbon chain attached to an aromatic ring. This portion of the molecule contributes most of the hydrophobic nature of the detergent. Triton® X detergents are used to solubilize membrane proteins under non-denaturing conditions. The choice of detergent to solubilize proteins will depend on the hydrophobic nature of the protein to be solubilized. Hydrophobic proteins require hydrophobic detergents to effectively solubilize them.

Triton® X-100 and NP-40 are very similar in structure and hydrophobicity and are interchangeable in most applications including cell lysis, delipidation protein dissociation and membrane protein and lipid solubilization. Generally 2 mg detergent is used to solubilize 1 mg membrane protein or 10 mg detergent/1 mg of lipid membrane. Triton® X-114 is useful for separating hydrophobic from hydrophilic proteins.

Brij® Detergents: These are similar in structure to Triton® X detergents in that they have varying lengths of polyoxyethylene chains attached to a hydrophobic chain. However, unlike Triton® X detergents, the Brij® detergents do not have an aromatic ring and the length of the carbon chains can vary. The Brij® detergents are difficult to remove from solution using dialysis but may be removed by detergent removing gels. Brij® 58 is most similar to Triton® X100 in its hydrophobic/hydrophilic characteristics. Brij®-35 is a commonly used detergent in HPLC applications.

Dialyzable Nonionic Detergents: η-Octyl-β-D-glucoside (octylglucopyranoside) and η-Octyl-β-D-thioglucoside (octylthioglucopyranoside, OTG) are nondenaturing nonionic detergents which are easily dialyzed from solution. These detergents are useful for solubilizing membrane proteins and have low UV absorbances at 280 nm. Octylglucoside has a high CMC of 23-25 mM and has been used at concentrations of 1.1-1.2% to solubilize membrane proteins.

Octylthioglucoside was first synthesized to offer an alternative to octylglucoside. Octylglucoside is expensive to manufacture and there are some inherent problems in biological systems because it can be hydrolyzed by β-glucosidase.

Tween® Detergents: The Tween® detergents are nondenaturing, nonionic detergents. They are polyoxyethylene sorbitan esters of fatty acids. Tween® 20 and Tween® 80 detergents are used as blocking agents in biochemical applications and are usually added to protein solutions to prevent nonspecific binding to hydrophobic materials such as plastics or nitrocellulose. They have been used as blocking agents in ELISA and blotting applications. Generally, these detergents are used at concentrations of 0.01-1.0% to prevent nonspecific binding to hydrophobic materials.

Tween® 20 and other nonionic detergents have been shown to remove some proteins from the surface of nitrocellulose. Tween® 80 has been used to solubilize membrane proteins, present nonspecific binding of protein to multiwell plastic tissue culture plates and to reduce nonspecific binding by serum proteins and biotinylated protein A to polystyrene plates in ELISA.

The difference between these detergents is the length of the fatty acid chain. Tween® 80 is derived from oleic acid with a $C_{18}$ chain while Tween® 20 is derived from lauric acid with a $C_{12}$ chain. The longer fatty acid chain makes the Tween® 80 detergent less hydrophilic than Tween® 20 detergent. Both detergents are very soluble in water.

The Tween® detergents are difficult to remove from solution by dialysis, but Tween® 20 can be removed by detergent removing gels. The polyoxyethylene chain found in these detergents makes them subject to oxidation (peroxide formation) as is true with the Triton® X and Brij® series detergents.

Zwitterionic Detergents: The zwitterionic detergent, CHAPS, is a sulfobetaine derivative of cholic acid. This zwitterionic detergent is useful for membrane protein solubilization when protein activity is important. This detergent is useful over a wide range of pH (pH 2-12) and is easily removed from solution by dialysis due to high CMCs (8-10 mM). This detergent has low absorbances at 280 nm making it useful when protein monitoring at this wavelength is necessary. CHAPS is compatible with the BCA Protein Assay and can be removed from solution by detergent removing gel. Proteins can be iodinated in the presence of CHAPS CHAPS has been successfully used to solubilize intrinsic membrane proteins and receptors and maintain the functional capability of the protein. When cytochrome P-450 is solubilized in either Triton® X-100 or sodium cholate aggregates are formed.

B) Non-Detergent Methods

Various non-detergent methods, though not preferred, may be employed in conjunction with other advantageous aspects of the present invention:

Freeze-Thaw: This has been a widely used technique for lysis cells in a gentle and effective manner. Cells are generally frozen rapidly in, for example, a dry ice/ethanol bath until completely frozen, then transferred to a 37° C. bath until completely thawed. This cycle is repeated a number of times to achieve complete cell lysis.

Sonication: High frequency ultrasonic oscillations have been found to be useful for cell disruption. The method by which ultrasonic waves break cells is not fully understood but it is known that high transient pressures are produced when suspensions are subjected to ultrasonic vibration. The main disadvantage with this technique is that considerable amounts of heat are generated. In order to minimize heat effects specifically designed glass vessels are used to hold the cell suspension. Such designs allow the suspension to circulate away from the ultrasonic probe to the outside of the vessel where it is cooled as the flask is suspended in ice.

High Pressure Extrusion: This is a frequently used method to disrupt microbial cell. The French pressure cell employs pressures of $10.4 \times 10^7$ Pa (16,000 p.s.i) to break cells open. These apparatus consists of a stainless steel chamber which opens to the outside by means of a needle valve. The cell suspension is placed in the chamber with the needle valve in the closed position. After inverting the chamber, the valve is opened and the piston pushed in to force out any air in the chamber. With the valve in the closed position, the chamber is restored to its original position, placed on a solid based and the required pressure is exerted on the piston by a hydraulic press. When the pressure has been attained the needle valve is opened fractionally to slightly release the pressure and as the cells expand they burst. The valve is kept open while the pressure is maintained so that there is a trickle of ruptured cell which may be collected.

Solid Shear Methods: Mechanical shearing with abrasives may be achieved in Mickle shakers which oscillate suspension vigorously (300-3000 time/min) in the presence of glass beads of 500 nm diameter. This method may result in organelle damage. A more controlled method is to use a Hughes press where a piston forces most cells together with abrasives or deep frozen paste of cells through a 0.25 mm diameter slot in the pressure chamber. Pressures of up to $5.5 \times 10^7$ Pa (8000 p.s.i.) may be used to lyse bacterial preparations.

Liquid Shear Methods: These methods employ blenders, which use high speed reciprocating or rotating blades, homogenizers which use an upward/downward motion of a plunger and ball and microfluidizers or impinging jets which use high velocity passage through small diameter tubes or high velocity impingement of two fluid streams. The blades of blenders are inclined at different angles to permit efficient mixing. Homogenizers are usually operated in short high speed bursts of a few seconds to minimize local heat. These techniques are not generally suitable for microbial cells but even very gentle liquid shear is usually adequate to disrupt animal cells.

Hypotonic/Hypertonic Methods: Cells are exposed to a solution with a much lower (hypotonic) or higher (hypertonic) solute concentration. The difference in solute concentration creates an osmotic pressure gradient. The resulting flow of water into the cell in a hypotonic environment causes the cells to swell and burst. The flow of water out of the cell in a hypertonic environment causes the cells to shrink and subsequently burst.

Viral Lysis Methods: In some situations, the method of viral lysis may be advantageous to use, and with modifications to the experimental protocol, the formation of RCA may be minimized. Since adenoviruses are lytic viruses, after infection of the host cells the mature viruses lyse the cell and are released into the supernatant and then can be harvested by conventional methods. One of the advantages to using the viral lysis method is the generation of more mature viral particles, since early lysis by mechanical or chemical means may lead to increased numbers of defective particles. In addition, the process permits an easier and more precise follow-up of the production kinetics directly on the homogeneous samples of supernatant, which produces better reproducibility of the production runs. Chemical lysis also presents an additional step in the process and requires the removal of the lysis agent, both of which may lead to potential losses of product and/or diminished activity.

In utilizing the viral lysis method, the kinetics of the liberation of virions can be followed in different ways and will be able to indicate the optimal time for supernatant harvest. For example, HPLC, IEC, PCR, dye exclusion, spectrophotometry, ELISA, RIA or nephelometric methods may be used. Harvesting is preferably performed when approximately 50% of the virions have been released. More preferably, the supernatant is harvested when at least 70% of the virions are released, and most preferably, the supernatant is harvested when at least 90% of the virions are released, or when the viral release reaches a plateau as measured by one of the methods indicated above. Variations in the time needed for the virus release to reach a plateau may be observed when using modification of gene transfer vector, however the harvest schedule can easily be modified by the skilled artisan when using one or more of the methods above to follow the kinetics of virus release.

4. METHODS OF CONCENTRATION AND FILTRATION

One aspect of the present invention employs methods of crude purification of adenovirus from a cell lysate. These methods include clarification, concentration and diafiltration. The initial step in this purification process is clarification of the cell lysate to remove large particulate matter, particularly cellular components, from the cell lysate. Clarification of the lysate can be achieved using a depth filter or by tangential flow filtration. In a preferred embodiment of the present invention, the cell lysate is passed through a depth filter, which consists of a packed column of relatively non-adsorbent material (e.g. polyester resins, sand, diatomeceous earth, colloids, gels, and the like). In tangential flow filtration (TFF), the lysate solution flows across a membrane surface which facilitates back diffusion of solute from the membrane surface into the bulk solution. Membranes are generally arranged within various types of filter apparatus including open channel plate and frame, hollow fibers, and tubules.

After clarification and prefiltration of the cell lysate, the resultant virus supernatant is first concentrated and then the buffer is exchanged by diafiltration. The virus supernatant is concentrated by tangential flow filtration across an ultrafiltration membrane of 100-300K nominal molecular weight cutoff. Ultrafiltration is a pressure-modified convective process that uses semi-permeable membranes to separate species by molecular size, shape and/or charge. It separates solvents from solutes of various sizes, independent of solute molecular size. Ultrafiltration is gentle, efficient and can be used to simultaneously concentrate and desalt solutions. Ultrafiltration membranes generally have two distinct layers: a thin (0.1-1.5 μm), dense skin with a pore diameter of 10-400 angstroms and an open substructure of progressively larger voids which are largely open to the permeate side of the ultrafilter. Any species capable of passing through the pores of the skin can therefore freely pass through the membrane. For maximum retention of solute, a membrane is selected that has a nominal molecular weight cut-off well below that of the species being retained. In macromolecular concentration, the membrane enriches the content of the desired biological species and provides filtrate cleared of retained substances. Microsolutes are removed convectively with the solvent. As concentration of the retained solute increases, the ultrafiltration rate diminishes.

Diafiltration, or buffer exchange, using ultrafilters is an ideal way for removal and exchange of salts, sugars, non-aqueous solvents separation of free from bound species, removal of material of low molecular weight, or rapid change of ionic and pH environments. Microsolutes are removed most efficiently by adding solvent to the solution being ultrafiltered at a rate equal to the ultrafiltration rate. This washes microspecies from the solution at constant volume, purifying the retained species. The present invention utilizes a diafiltration step to exchange the buffer of the virus supernatant prior to Benzonase® treatment.

5. VIRAL INFECTION

The present invention employs, in one example, adenoviral infection of cells in order to generate therapeutically significant vectors. Typically, the virus will simply be exposed to the appropriate host cell under physiologic conditions, permitting uptake of the virus. Though adenovirus is exemplified, the present methods may be advantageously employed with other viral vectors, as discussed below.

A) Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. Elimination of large portions of the adenoviral genome, and providing the delete gene products in trans, by helper virus and/or helper cells, allows for the insertion of large portions of heterologous DNA into the vector. This strategy also will result in reduced toxicity and immunogenicity of the adenovirus gene products.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194-385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

B) Retrovirus

Although adenoviral infection of cells for the generation of therapeutically significant vectors is a preferred embodiments of the present invention, it is contemplated that the present invention may employ retroviral infection of cells for the purposes of generating such vectors. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Y, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Y components is constructed (Mann et al., 1983). When a recombinant plasmid containing a human cDNA, together with the retroviral LTR and Y sequences is introduced into this cell line (by calcium phosphate precipitation for example), the Y sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

C) Adeno Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996;

Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994;

D) Herpesvirus

Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1995). The expression of α genes, the first set of genes to be expressed after infection, is enhanced by the virion protein number 16, or α-transinducing factor (Post et al., 1981; Batterson and Roizman, 1983; Campbell, et al., 1983). The expression of β genes requires functional a gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

E) Vaccinia Virus

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

F) SV40 Virus

Simian virus 40 (SV40) was discovered in 1960 as a contaminant in polio vaccines prepared from rhesus monkey kidney cell cultures. It was found to cause tumors when injected into newborn hamsters. The genome is a double-stranded, circular DNA of about 5000 bases encoding large (708 AA) and small T antigens (174 AA), agnoprotein and the structural proteins VP1, VP2 and VP3. The respective size of these molecules is 362, 352 and 234 amino acids.

Little is known of the nature of the receptors for any polyoma virus. The virus is taken up by endocytosis and transported to the nucleus where uncoating takes place. Early mRNA's initiate viral replication and is necessary, along with DNA replication, for late gene expression. Near the origin of replication, promoters are located for early and late transcription. Twenty-one base pair repeats, located 40-103 nucleotides upstream of the initiation transcription site, are the main promoting element and are binding sites for Sp1, while 72 base pair repeats act as enhancers.

Large T antigen, one of the early proteins, plays a critical role in replication and late gene expression and is modified in a number of ways, including N-terminal acetylation, phosphorylation, poly-ADP ribosylation, glycosylation and acylation. The other T antigen is produced by splicing of the large T transcript. The corresponding small T protein is not strictly required for infection, but it plays a role in the accumulation of viral DNA.

DNA replication is controlled, to an extent, by a genetically defined core region that includes the viral origin of replication. The SV40 element is about 66 bp in length and has subsequences of AT motifs, GC motifs and an inverted repeat of 14 bp on the early gene side. Large T antigen is required for initiation of DNA replication, and this protein has been shown to bind in the vicinity of the origin. It also has ATPase, adenylating and helicase activities.

After viral replication begins, late region expression initiates. The transcripts are overlapping and, in some respect, reflect different reading frames (VP1 and VP2/3). Late expression initiates is the same general region as early expression, but in the opposite direction. The virion proteins are synthesized in the cytoplasm and transported to the nucleus where they enter as a complex. Virion assembly also takes place in the nucleus, followed by lysis and release of the infectious virus particles.

It is contemplated that the present invention will encompass SV40 vectors lacking all coding sequences. The region from about 5165-5243 and about 0-325 contains all of the control elements necessary for replication and packaging of the vector and expression of any included genes. Thus, minimal SV40 vectors are derived from this region and contain at least a complete origin of replication.

Because large T antigen is believed to be involved in the expression of late genes, and no large T antigen is expressed in the target cell, it will be desired that the promoter driving the heterologous gene be a polyomavirus early promoter, or more preferably, a heterologous promoter. Thus, where heterologous control elements are utilized, the SV40 promoter and enhancer elements are dispensable.

D) Other Viral Vectors

Other viral vectors may be employed as expression constructs in the present invention. Vectors derived from viruses such as papillomaviruses, papovaviruses and lentivirus may be employed. These viruses offer several features for use in gene transfer into various mammalian cells, and it will be understood that various modifications to such viruses can be made to enhance for example infectivity and targeting. Chimeric viruses, employing advantageous portions of different viruses, may also be constructed by one of skill in the art.

6. ENGINEERING OF VIRAL VECTORS

In certain embodiments, the present invention further involves the manipulation of viral vectors. Such methods involve the use of a vector construct containing, for example, a heterologous DNA encoding a gene of interest and a means for its expression, replicating the vector in an appropriate helper cell, obtaining viral particles produced therefrom, and infecting cells with the recombinant virus particles. The gene could simply encode a protein for which large quantities of the protein are desired, i.e., large scale in vitro production methods. Alternatively, the gene could be a therapeutic gene, for example to treat cancer cells, to express immunomodulatory genes to fight viral infections, or to replace a gene's function as a result of a genetic defect. In the context of the gene therapy vector, the gene will be a heterologous DNA, meant to include DNA derived from a source other than the viral genome which provides the backbone of the vector. Finally, the virus may act as a live viral vaccine and express an antigen of interest for the production of antibodies thereagainst. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA may also include a regulatory sequence which may be derived from one source and the gene from a different source.

A) Therapeutic Genes p53 currently is recognized as a tumor suppressor gene (Montenarh, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 393-amino-acid phosphoprotein that can form complexes with host proteins such as large-T antigen and E1B. The protein is found in normal tissues and cells, but at concentrations which are generally minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or directly or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 is not detrimental to normal cells with endogenous wild-type p53. Thus, such constructs might be taken up by normal cells without adverse effects. It is thus proposed that the treatment of p53-associated cancers with wild-type p53 expression constructs will reduce the number of malignant cells or their growth rate. Furthermore, recent studies suggest that some p53 wild-type tumors are also sensitive to the effects of exogenous p53 expression.

The major transitions of the eukaryotic cell cycle are triggered by cyclin-dependent kinases, or CDK's. One CDK, cyclin-dependent kinase 4 (CDK4), regulates progression through the $G_1$ phase. The activity of this enzyme may be to phosphorylate Rb at late $G_1$. The activity of CDK4 is controlled by an activating subunit, D-type cyclin, and by an inhibitory subunit, e.g. p16$^{INK4}$, which has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p21$^{WAF1, CIP1, SDI1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993a; 1993b and 1993c) demonstrated that the first Ig domain of C-CAM is critical for cell adhesion activity.

Cell adhesion molecules, or CAMs are known to be involved in a complex network of molecular interactions that regulate organ development and cell differentiation (Edelman, 1985). Recent data indicate that aberrant expression of CAMs may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention include RB, APC, DCC, NF-1, NF-2, WT-1, MEN-I, MEN-II, zac1, p73, BRCA1, VHL, FCC, MMAC1, MCC, p16, p21, p57, pTEN, C-CAM, p27, mda-7 and BRCA2. Inducers of apoptosis, such as Bax, Bak, Bcl-$X_5$, Bik, Bid, Harakiri, Ad E1B, Bad and ICE-CED3 proteases, similarly could find use according to the present invention.

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

Hormones are another group of gene that may be used in the vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1-40), parathyroid hormone-related protein (107-139) (PTH-rP), parathyroid hormone-related protein (107-111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

Other classes of genes that are contemplated to be inserted into the vectors of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

Examples of diseases for which the present viral vector would be useful include, but are not limited to, adenosine deaminase deficiency, human blood clotting factor IX deficiency in hemophilia B, and cystic fibrosis, which would involve the replacement of the cystic fibrosis transmembrane receptor gene. The vectors embodied in the present invention could also be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also be used in the treatment of hyperploiferative disorders, including cancer.

B) Antisense Constructs

Oncogenes such as ras, myc, neu, raf, erb, src, fms, jun, trk, ret, gsp, hst, bcl and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementarity rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes can either be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

C) Antigens for Vaccines

Other therapeutics genes might include genes encoding antigens such as viral antigens, bacterial antigens, fungal antigens or parasitic antigens. Viruses include picornavirus, coronavirus, togavirus, flavirviru, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths. Also, tumor markers, such as fetal antigen or prostate specific antigen, may be targeted in this manner. Preferred examples include HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

D) Control Regions

In order for the viral vector to effect expression of a transcript encoding a therapeutic gene, the polynucleotide encoding the therapeutic gene will be under the transcriptional control of a promoter and a polyadenylation signal. A "promoter" refers to a DNA sequence recognized by the synthetic machinery of the host cell, or introduced synthetic machinery, that is required to initiate the specific transcription of a gene. A polyadenylation signal refers to a DNA sequence recognized by the synthetic machinery of the host cell, or introduced synthetic machinery, that is required to direct the addition of a series of nucleotides on the end of the mRNA transcript for proper processing and trafficking of the transcript out of the nucleus into the cytoplasm for translation. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constituitively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 3).

TABLE 3

Tissue specific promoters

| Tissue | Promoter |
| --- | --- |
| Pancreas | Insulin |
|  | elastin |
|  | amylase |
|  | pdr-1 pdx-1 |
|  | glucokinase |
| Liver | albumin PEPCK |
|  | HBV enhancer |
|  | alpha fetoprotein |
|  | apolipoprotein C |
|  | alpha-1 antitrypsin |
|  | vitellogenin, NF-AB |
|  | Transthyretin |
| Skeletal muscle | myosin H chain |
|  | muscle creatine kinase |
|  | dystrophin |
|  | calpain p94 |
|  | skeletal alpha-actin |
|  | fast troponin 1 |
| Skin | keratin K6 |
|  | keratin K1 |
| Lung | CFTR |
|  | human cytokeratin 18 (K18) |
|  | pulmonary surfactant proteins A, B and C |
|  | CC-10 |
|  | P1 |
| Smooth muscle | sm22 alpha |
|  | SM-alpha-actin |
| Endothelium | endothelin-1 |
|  | E-selectin |
|  | von Willebrand factor |
|  | TIE (Korhonen et al., 1995) |
|  | KDR/flk-1 |
| Melanocytes | Tyrosinase |
| Adipose tissue | lipoprotein lipase (Zechner et al., 1988) |
|  | adipsin (Spiegelman et al., 1989) |
|  | acetyl-CoA carboxylase (Pape and Kim, 1989) |
|  | glycerophosphate dehydrogenase (Dani et al., 1989) |
|  | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor specific promoters such as osteocalcin, hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g. MDR), and heat (hyperthermia) inducible promoters, Radiation-inducible (e.g., EGR (Joki et al., 1995)), Alpha-inhibin, RNA pol III tRNA met and other amino acid promoters, U1 snRNA (Bartlett et al., 1996), MC-1, PGK, -actin and alpha-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein. A further list of promoters is provided in the Table 4.

TABLE 4

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |

TABLE 4-continued

| PROMOTER |
| --- |
| c-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-RegulatedProteins(GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

The promoter further may be characterized as an inducible promoter. An inducible promoter is a promoter which is inactive or exhibits low activity except in the presence of an inducer substance. Some examples of promoters that may be included as a part of the present invention include, but are not limited to, MT II, MMTV, Colleganse, Stromelysin, SV40, Murine MX gene, α-2-Macroglobulin, MHC class I gene h-2 kb, HSP70, Proliferin, Tumor Necrosis Factor, or Thyroid Stimulating Hormone a gene. The associated inducers are shown in Table 5. It is understood that any inducible promoter may be used in the practice of the present invention and that all such promoters would fall within the spirit and scope of the claimed invention.

TABLE 5

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

In various embodiments, the human cytomegalovirus (CMV) immediate early gene promoter, the SV40 early promoter and the Rous sarcoma virus long terminal repeat can be used to obtain high-level expression of the polynucleotide of interest. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of the therapeutic gene.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base (EPDB)) could also be used to drive expression of a particular construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Such polyadenylation signals as that from SV40, bovine growth hormone, and the herpes simplex virus thymidine kinase gene have been found to function well in a number of target cells.

7. METHODS OF GENE TRANSFER

In order to create the helper cell lines of the present invention, and to create recombinant adenovirus vectors for use therewith, various genetic (i.e. DNA) constructs must be delivered to a cell. One way to achieve this is via viral transductions using infectious viral particles, for example, by transformation with an adenovirus vector of the present invention. Alternatively, retroviral or bovine papilloma virus may be employed, both of which permit permanent transformation of a host cell with a gene(s) of interest. In other situations, the nucleic acid to be transferred is not infectious, i.e., contained in an infectious virus particle. This genetic material must rely on non-viral methods for transfer.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularity applicable for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other expression constructs which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

8. REMOVING NUCLEIC ACID CONTAMINANTS

The present invention employs nucleases to remove contaminating nucleic acids. Exemplary nucleases include Benzonase®, Pulmozyme®; or any other DNase or RNase commonly used within the art.

Enzymes such as Benzonaze® degrade nucleic acid and have no proteolytic activity. The ability of Benzonase® to rapidly hydrolyze nucleic acids makes the enzyme ideal for reducing cell lysate viscosity. It is well known that nucleic acids may adhere to cell derived particles such as viruses. The adhesion may interfere with separation due to agglomeration, change in size of the particle or change in particle charge, resulting in little if any product being recovered with a given purification scheme. Benzonase® is well suited for reducing the nucleic acid load during purification, thus eliminating the interference and improving yield.

As with all endonucleases, Benzonase® hydrolyzes internal phosphodiester bonds between specific nucleotides. Upon complete digestion, all free nucleic acids present in solution are reduced to oligonucleotides 2 to 4 bases in length.

9. PURIFICATION TECHNIQUES

The present invention employs a number of different purification to purify adenoviral vectors of the present invention. Such techniques include those based on sedimentation and chromatography and are described in more detail herein below.

A) Density Gradient Centrifugation

There are two methods of density gradient centrifugation, the rate zonal technique and the isopycnic (equal density) technique, and both can be used when the quantitative separation of all the components of a mixture of particles is required. They are also used for the determination of buoyant densities and for the estimation of sedimentation coefficients.

Particle separation by the rate zonal technique is based upon differences in size or sedimentation rates. The technique involves carefully layering a sample solution on top of a performed liquid density gradient, the highest density of which exceeds that of the densest particles to be separated. The sample is then centrifuged until the desired degree of separation is effected, i.e., for sufficient time for the particles to travel through the gradient to form discrete zones or bands which are spaced according to the relative velocities of the particles. Since the technique is time dependent, centrifugation must be terminated before any of the separated zones pellet at the bottom of the tube. The method has been used for the separation of enzymes, hormones, RNA-DNA hybrids, ribosomal subunits, subcellular organelles, for the analysis of size distribution of samples of polysomes and for lipoprotein fractionations.

The sample is layered on top of a continuous density gradient which spans the whole range of the particle densities which are to be separated. The maximum density of the gradient, therefore, must always exceed the density of the most dense particle. During centrifugation, sedimentation of the particles occurs until the buoyant density of the particle and the density of the gradient are equal (i.e., where $p_p = p_m$ in equation 2.12). At this point no further sedimentation occurs, irrespective of how long centrifugation continues, because the particles are floating on a cushion of material that has a density greater than their own.

Isopycnic centrifugation, in contrast to the rate zonal technique, is an equilibrium method, the particles banding to form zones each at their own characteristic buoyant density. In cases where, perhaps, not all the components in a mixture of particles are required, a gradient range can be selected in which unwanted components of the mixture will sediment to the bottom of the centrifuge tube whilst the particles of interest sediment to their respective isopycnic positions. Such a technique involves a combination of both the rate zonal and isopycnic approaches.

Isopycnic centrifugation depends solely upon the buoyant density of the particle and not its shape or size and is independent of time. Hence soluble proteins, which have a very similar density (e.g., $p=1.3$ g cm$^{-3}$ in sucrose solution), cannot usually be separated by this method, whereas subcellular organelles (e.g., Golgi apparatus, $p=1.11$ g cm$^{-3}$, mitochondria, $p=1.19$ g cm$^{-3}$ and peroxisomes, $p=1.23$ g cm in sucrose solution) can be effectively separated.

As an alternative to layering the particle mixture to be separated onto a preformed gradient, the sample is initially mixed with the gradient medium to give a solution of uniform density, the gradient 'self-forming', by sedimentation equilibrium, during centrifugation. In this method (referred to as the equilibrium isodensity method), use is generally made of the salts of heavy metals (e.g., caesium or rubidium), sucrose, colloidal silica or Metrizamide.

The sample (e.g., DNA) is mixed homogeneously with, for example, a concentrated solution of caesium chloride. Centrifugation of the concentrated caesium chloride solution results in the sedimentation of the CsCl molecules to form a concentration gradient and hence a density gradient. The sample molecules (DNA), which were initially uniformly distributed throughout the tube now either rise or sediment until they reach a region where the solution density is equal to their own buoyant density, i.e. their isopycnic position, where they will band to form zones. This technique suffers from the disadvantage that often very long centrifugation times (e.g., 36 to 48 hours) are required to establish equilibrium. However, it is commonly used in analytical centrifugation to determine the buoyant density of a particle, the base composition of double stranded DNA and to separate linear from circular forms of DNA.

Many of the separations can be improved by increasing the density differences between the different forms of DNA by the incorporation of heavy isotopes (e.g., $^{15}N$) during biosynthesis, a technique used by Leselson and Stahl to elucidate the mechanism of DNA replication in *Esherichia coli*, or by the binding of heavy metal ions or dyes such as ethidium bromide. Isopycnic gradients have also been used to separate and purify viruses and analyze human plasma lipoproteins.

B) Chromatography

In certain embodiments of the invention, it will be desirable to produce purified adenovirus. Purification techniques are well known to those of skill in the art. These techniques tend to involve the fractionation of the cellular milieu to separate the adenovirus particles from other components of the mixture. Having separated adenoviral particles from the other components, the adenovirus may be purified using chromatographic and electrophoretic techniques to achieve complete purification. Analytical methods particularly suited to the preparation of a pure adenoviral particle of the present invention are ion-exchange chromatography, size exclusion chromatography; polyacrylamide gel electrophoresis. A particularly efficient purification method to be employed in conjunction with the present invention is HPLC.

Certain aspects of the present invention concern the purification, and in particular embodiments, the substantial purification, of an adenoviral particle. The term "purified" as used herein, is intended to refer to a composition, isolatable from other components, wherein the adenoviral particle is purified to any degree relative to its naturally-obtainable form. A purified adenoviral particle therefore also refers to an adenoviral component, free from the environment in which it may naturally occur.

Generally, "purified" will refer to an adenoviral particle that has been subjected to fractionation to remove various other components, and which composition substantially retains its expressed biological activity. Where the term "substantially purified" is used, this designation will refer to a composition in which the particle, protein or peptide forms the major component of the composition, such as constituting about 50% or more of the constituents in the composition.

Various methods for quantifying the degree of purification of a protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

There is no general requirement that the adenovirus, always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

Of course, it is understood that the chromatographic techniques and other purification techniques known to those of skill in the art may also be employed to purify proteins expressed by the adenoviral vectors of the present invention. Ion exchange chromatography and high performance liquid chromatography are exemplary purification techniques employed in the purification of adenoviral particles and are described in further detail herein below.

Ion-Exchange Chromatography. The basic principle of ion-exchange chromatography is that the affinity of a substance for the exchanger depends on both the electrical properties of the material and the relative affinity of other charged substances in the solvent. Hence, bound material can be eluted by changing the pH, thus altering the charge of the material, or by adding competing materials, of which salts are but one example. Because different substances have different electrical properties, the conditions for release vary with each bound molecular species. In general, to get good separation, the methods of choice are either continuous ionic strength gradient elution or stepwise elution. (A gradient of pH alone is not often used because it is difficult to set up a pH gradient without simultaneously increasing ionic strength.) For an anion exchanger, either pH and ionic strength are gradually increased or ionic strength alone is increased. For a cation exchanger, both pH and ionic strength are increased. The actual choice of the elution procedure is usually a result of trial and error and of considerations of stability. For example, for unstable materials, it is best to maintain fairly constant pH.

An ion exchanger is a solid that has chemically bound charged groups to which ions are electrostatically bound; it can exchange these ions for ions in aqueous solution. Ion exchangers can be used in column chromatography to separate molecules according to charge; actually other features of the molecule are usually important so that the chromatographic behavior is sensitive to the charge density, charge distribution, and the size of the molecule.

The principle of ion-exchange chromatography is that charged molecules adsorb to ion exchangers reversibly so that molecules can be bound or eluted by changing the ionic environment. Separation on ion exchangers is usually accomplished in two stages: first, the substances to be separated are bound to the exchanger, using conditions that give stable and tight binding; then the column is eluted with buffers of different pH, ionic strength, or composition and the components of the buffer compete with the bound material for the binding sites.

An ion exchanger is usually a three-dimensional network or matrix that contains covalently linked charged groups. If a group is negatively charged, it will exchange positive ions and is a cation exchanger. A typical group used in cation exchangers is the sulfonic group, $SO_3^-$. If an $H^+$ is bound to the group, the exchanger is said to be in the acid form; it can, for example, exchange on $H^+$ for one $Na^+$ or two $H^+$ for one $Ca^{2+}$. The sulfonic acid group is called a strongly acidic cation exchanger. Other commonly used groups are phenolic hydroxyl and carboxyl, both weakly acidic cation exchangers. If the charged group is positive—for example, a quaternary amino group—it is a strongly basic anion exchanger. The most common weakly basic anion exchangers are aromatic or aliphatic amino groups.

The matrix can be made of various material. Commonly used materials are dextran, cellulose, agarose and copolymers of styrene and vinylbenzene in which the divinylbenzene both cross-links the polystyrene strands and contains the charged groups. Table 6 gives the composition of many ion exchangers.

The total capacity of an ion exchanger measures its ability to take up exchangeable groups per milligram of dry weight. This number is supplied by the manufacturer and is important because, if the capacity is exceeded, ions will pass through the column without binding.

TABLE 6

| Matrix | Exchanger | Functional Group | Tradename |
| --- | --- | --- | --- |
| Dextran | Strong Cationic | Sulfopropyl | SP-Sephadex |
| | Weak Cationic | Carboxymethyl | CM-Sephadex |
| | Strong Anionic | Diethyl-(2-hydroxypropyl)-aminoethyl | QAE-Sephadex |
| Cellulose | Weak Anionic | Diethylaminoethyl | DEAE-Sephadex |
| | Cationic | Carboxymethyl | CM-Cellulose |
| | Cationic | Phospho | P-cel |
| | Anionic | Diethylaminoethyl | DEAE-cellulose |
| | Anionic | Polyethylenimine | PEI-Cellulose |
| | Anionic | Benzoylated-naphthoylated, deiethylaminoethyl | DEAE(BND)-cellulose |
| | Anionic | p-Aminobenzyl | PAB-cellulose |
| Styrene-divinyl-benzene | Strong Cationic | Sulfonic acid | AG 50 |
| | Strong Anionic | | AG 1-Source15Q |
| | Strong Cationic + Strong Anionic | Sulfonic acid + Tetramethylammonium | AG 501 |
| Acrylic | Weak Cationic | Carboxylic | Bio-Rex 70 |
| | Strong Anionic | Trimethylaminoethyl | E. Merk |
| | Strong Anionic | Trimethylamino group | Toso Haas TSK-Gel-Q-5PW |
| Phenolic | Strong Cationic | Sulfonic acid | Bio-Rex 40 |
| Expoxyamine | Weak Anionic | Tertiary amino | AG-3 |

The available capacity is the capacity under particular experimental conditions (i.e., pH, ionic strength). For example, the extent to which an ion exchanger is charged depends on the pH (the effect of pH is smaller with strong ion exchangers). Another factor is ionic strength because small ions near the charged groups compete with the sample molecule for these groups. This competition is quite effective if the sample is a macromolecule because the higher diffusion coefficient of the small ion means a greater number of encounters. Clearly, as buffer concentration increases, competition becomes keener.

The porosity of the matrix is an important feature because the charged groups are both inside and outside the matrix and because the matrix also acts as a molecular sieve. Large molecules may be unable to penetrate the pores; so the capacity will decease with increasing molecular dimensions. The porosity of the polystyrene-based resins is determined by the amount of cross-linking by the divinylbenzene (porosity decreases with increasing amounts of divinylbenzene). With the Dowex and AG series, the percentage of divinylbenzene is indicated by a number after an X—hence, Dowex 50-X8 is 8% divinylbenzene Ion exchangers come in a variety of particle sizes, called mesh size. Finer mesh means an increased surface-to-volume ration and therefore increased capacity and decreased time for exchange to occur for a given volume of the exchanger. On the other hand, fine mesh means a slow flow rate, which can increase diffusional spreading. The use of very fine particles, approximately 10 μm in diameter and high pressure to maintain an adequate flow is called high-performance or high-pressure liquid chromatography or simply HPLC.

Such a collection of exchangers having such different properties—charge, capacity, porosity, mesh—makes the selection of the appropriate one for accomplishing a particular separation difficult. How to decide on the type of column material and the conditions for binding and elution is described in the following Examples.

There are a number of choices to be made when employing ion exchange chromatography as a technique. The first choice to be made is whether the exchanger is to be anionic or cationic. If the materials to be bound to the column have a single charge (i.e., either plus or minus), the choice is clear. However, many substances (e.g., proteins, viruses), carry both negative and positive charges and the net charge depends on the pH. In such cases, the primary factor is the stability of the substance at various pH values. Most proteins have a pH range of stability (i.e., in which they do not denature) in which they are either positively or negatively charged. Hence, if a protein is stable at pH values above the isoelectric point, an anion exchanger should be used; if stable at values below the isoelectric point, a cation exchanger is required.

The choice between strong and weak exchangers is also based on the effect of pH on charge and stability. For example, if a weakly ionized substance that requires very low or high pH for ionization is chromatographed, a strong ion exchanger is called for because it functions over the entire pH range. However, if the substance is labile, weak ion exchangers are preferable because strong exchangers are often capable of distorting a molecule so much that the molecule denatures. The pH at which the substance is stable must, of course, be matched to the narrow range of pH in which a particular weak exchanger is charged. Weak ion exchangers are also excellent for the separation of molecules with a high charge from those with a small charge, because the weakly charged ions usually fail to bind. Weak exchangers also show greater resolution of substances if charge differences are very small. If a macromolecule has a very strong charge, it may be impossible to elute from a strong exchanger and a weak exchanger again may be preferable. In general, weak exchangers are more useful than strong exchangers.

The Sephadex and Bio-gel exchangers offer a particular advantage for macromolecules that are unstable in low ionic strength. Because the cross-links in these materials maintain the insolubility of the matrix even if the matrix is highly polar, the density of ionizable groups can be made several times greater than is possible with cellulose ion exchangers. The increased charge density means increased affinity so that adsorption can be carried out at higher ionic strengths. On the other hand, these exchangers retain some of their molecular sieving properties so that sometimes molecular weight differences annul the distribution caused by the charge differences; the molecular sieving effect may also enhance the separation.

Small molecules are best separated on matrices with small pore size (high degree of cross-linking) because the available capacity is large, whereas macromolecules need large pore size. However, except for the Sephadex type, most ion exchangers do not afford the opportunity for matching the porosity with the molecular weight.

The cellulose ion exchangers have proved to be the best for purifying large molecules such as proteins and polynucleotides. This is because the matrix is fibrous, and hence all functional groups are on the surface and available to even the largest molecules. In may cases however, beaded forms such as DEAE-Sephacel and DEAE-Biogel P are more useful because there is a better flow rate and the molecular sieving effect aids in separation.

Selecting a mesh size is always difficult. Small mesh size improves resolution but decreases flow rate, which increases zone spreading and decreases resolution. Hence, the appropriate mesh size is usually determined empirically.

Because buffers themselves consist of ions, they can also exchange, and the pH equilibrium can be affected. To avoid these problems, the rule of buffers is adopted: use cationic buffers with anion exchangers and anionic buffers with cation exchangers. Because ionic strength is a factor in binding, a buffer should be chosen that has a high buffering capacity so that its ionic strength need not be too high. Furthermore, for best resolution, it has been generally found that the ionic conditions used to apply the sample to the column (the so-called starting conditions) should be near those used for eluting the column.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

10. QUALITY CONTROL ASSAYS

Recombinant adenovirus vectors made according to the present invention are tested to ensure that they meet desired product release specifications. These specifications are defined by assays for biological activity, virus titer, final product purity, identity and physico-chemical characteristics. These assays are performed at various stages of production including analysis of the crude cell lysate, in-process bulk (pre-filter), in-process bulk (post-filter), and the final product. Crude cell lysate is defined as the material that is removed from the cell culture apparatus before any processing has been done. In-process bulk (prefilter) is defined as the material that has been processed through the HPLC purification step, but has not been sterile filtered prior to vialing. In-process bulk (post filter) is defined as the material that has been sterile filtered and is ready to be vialed. Final product is defined as the material that has been placed into individual vials and is ready for storage or use. It will be understood that similar protocols may be used as tests for Ad5CMV-p53 as well as other adenoviral vectors containing the same or different transgenes. The following section describes representative assays used for testing the recombinant adenovirus product.

A. Safety Assays

General Safety Assay

The general safety assay test (C.F.R. 610.11) is performed to detect the presence of extraneous toxic contaminants. Guinea pigs (Hartley albino, either sex) and mice (Swiss outbred, either sex) are inoculated intraperitoneally with the test article diluted in sterile water for injection and observed for overt signs of ill health, weight loss, or death for the test period. Their weights are measured just prior to and upon completion of the test period of 7 days. A passing test is one in which the controls perform as expected and the animals inoculated with the test article have satisfactory responses.

PCR Assay for the Detection of Adeno-associated virus (AAV) in Biological Samples This assay detects the presence of AAV nucleic acid sequences by PCR amplification with a set of primers targeted to a conserved region in the capsid gene. The amplified DNA from the test article is run on an agarose gel containing ethidium bromide and visualized by photography. Briefly, the DNA is extracted from the test sample, and 0.5 micrograms is analyzed by PCR. PCR amplification is performed using AAV oligonucleotides primers specific for the capsid region of AAV. Negative and positive control DNA is also analyzed. Assay acceptance is determined by the absence of any bands in the negative control sample, and the expected size band in the positive control sample. For the present assay, a specific 459 bp band is the expected size. A passing test for the test article is the absence of the 459 base pair band.

In Vitro Assay for the Presence of Viral Contaminants

This assay determines whether adventitious viral contaminants are present in the test article through the inoculation and observation of three types of indicator cells. The presence of viral contamination is determined by observations for cytopathic effect (CPE) or other visually discernible effects, hemagglutination, and hemadsorption. The indicator cells include MRC-5, a diploid human lung line; Vero, an African green monkey kidney line; and HeLa, a human epithelioid carcinoma cell line. Briefly, the three indicator cell lines are seeded into 6-well plates and maintained for approximately 24 hours. The cultures are then inoculated with 0.5 ml of the adenoviral sample or virus controls and allowed to absorb for 1 hours at 36 degrees Celsius. The virus is then removed and replaced with culture medium, and the wells observed for 14 days for evidence of CPE. Each well is also tested for hemadsorption and hemagglutination using three types of erythrocytes. All culture fluids are blind passaged onto additional culture plates of indicator cells and observed for CPE for another 14 days.

To accept this assay, certain criteria should preferably be met. These include: 1) each of the positive control viruses should preferably cause CPE in the indicator cell lines into which it is inoculated; 2) each of the positive control viruses should preferably produce hemadsorption and/or hemagglutination with at least one type of erythrocyte at 4 degrees Celsius and/or 36 degrees Celsius at one or more time points with each of the indicator cells lines into which it is inoculated; 3) The indicator cells lines inoculated with the negative control should preferably not exhibit any CPE, hemadsorption, or hemagglutination. A passing test for the test article is preferably the absence of CPE, hemadsorption and hemagglutination.

In Vivo Adventitious Virus Assay

This assay is designed to detect the presence of viruses which do not cause a discernible effect in in vitro cell culture systems, but may cause unwanted effects in vivo. The experimental design utilizes inoculations of adult and suckling mice, guinea pigs, and embryonated hens' eggs, and is similar to that used by the British Institute for Biological Standards and Control. This test includes blind passages of homogenates to successive animals and/or hens eggs to increase the likelihood of detection of low level viral contaminants.

The test method is as follows. Suckling mice will be inoculated intraperitoneally, per os, and intracranially and observed for 14 days. A single pool of emulsified tissue (minus skin and gastrointestinal tract) of all surviving mice will be used to inoculate additional mice using the same routes. Sham control mice will also be inoculated. Adult mice of both sexes will be inoculated intraperitoneally, per os, intradermally, and intracranially and observed for 28 days. Sham controls will also be inoculated. Adult guinea pigs of both sexes will be inoculated intraperitoneally and intracranially and observed for 28 days. Sham control guinea pigs will also be inoculated. The yolk sac of 6-7 days old embryonated hens' eggs will be inoculated and incubated at least nine days. The yolk sacs will be harvested, pooled, and a 10% suspension will be sub-passaged into new embryonated hens' eggs. Nine days later, the eggs are evaluated for viability.

Acceptance criteria for the assay include healthy animals at the start of the testing, and the tests will be considered valid if about 90% of control adult mice, about 80% of control suckling mice, about 80% of the embryonated hens' eggs, and about 75% of the control guinea pigs survive the incubation period and show no lesions at the site of inoculation or show no signs of viral infection. The test article will be considered not contaminated if about 80% of the animals remain healthy and survive the observation period and if about 95% the animals used in the test fail to show any lesions of any kind at the site of injection and fail to show any signs of viral infection.

B. Purity Assays

BCA Assay for Total Protein

This assay allows for a quantitative determination of total protein in the final product. The assay uses the Pierce BCA kit procedure. Briefly, replicate samples are prepared and placed in a microtiter plate. A Bovine Serum Albumin (BSA) standard is prepared and placed in a microliter plate as a control. For a negative control, diluent is placed in a microtiter plate. The BCA reagent is dispensed into the microtiter plates and the plates are incubated to allow color development. The plates are then read spectrophotometrically at 550 nm, and the test sample concentrations are calculated based on the BSA standard. Preferred protein content by BCA is 250 to 500 micrograms per $1 \times 10e12$ viral particles. Most preferable protein content is 260 to 320 micrograms per $1 \times 10e12$ viral particles. The protein concentration determined by this assay is used to calculate the amount of protein to load on the SDS-PAGE gel for restriction analysis.

Sterility Assay

Sterility assays (documented in U.S.P. XXIII <71>) are used at both the bulk and final product stage. Sterility testing is via membrane filtration and is performed in a soft-wall isolator system to minimize laboratory contamination of samples tested. All test articles should preferably pass the sterility test.

Bioburden Test

The bioburden test is used to detect microbial load in a test sample by filtering the test sample onto a membrane filter, placing the membrane filter onto Tryptic Soy agar and Sabouraud agar plates and observing for growth after 2-5 days incubation. Suspensions with known levels of *Bacillus subtilis* and *Candid albicans* are also assayed to confirm assay suitability.

Briefly the test method is as follows. Test samples may be stored up to 24 hours at 2-8 degree Celsius before testing. Reserve samples that are not to be tested within 24 hours may be frozen at less than −60 degrees Celsius. Negative controls (sterile diluent) are prepared by filtering 100 mL of sterile diluent through an analytical filter unit using a vacuum. The membrane filter is removed from the unit and placed on a pre-warmed Tryptic Soy agar plate. The process is repeated using a second filter unit and the filter is placed on a pre-warmed Sabouraud agar plate. In-process test samples are tested by filtering 5×10 mL of crude cell lysate onto 5 separate filters or 10 mL of prefiltered bulk product onto a single filter. Each membrane filter is removed from the unit and placed on a pre-warmed Tryptic Soy agar plate. The process is repeated using a second set of filter units and the filter is placed on a pre-warmed Sabouraud agar plate. *Bacillus subtilis* positive controls are prepared by filtering 50 mL of sterile diluent through an analytical filter unit using a vacuum. The membrane filter is removed from the unit and placed on a pre-warmed Tryptic Soy agar plate. The process is repeated using a *Candida albicans* positive control using a second filter unit and the filter is placed on a pre-warmed Sabouraud agar plate. Tryptic Soy agar plates are incubated at 30-35 degrees Celsius for 2-5 days. Sabouraud agar plates are incubated at 22-27 degrees Celsius for 5-7 days. Colonies on the membrane filters are counted after the incubation period. The assays are acceptable when the negative controls exhibit no growth and positive controls exhibit 1-100 colonies per membrane filter. The test article should preferably contain less than or equal to 1000 colony forming units per 100 mL of the crude cell lysate. It is more preferable that the crude cell lysate contain less than or equal to 500 colony forming units per 100 mL, and most preferable that the crude cell lysate contain less than or equal to 10 colony forming units per 100 mL. It is most preferable that the prefiltered bulk product contain less than or equal to one colony forming unit per 10 mL. Using purification techniques in accordance with the present disclosure, bioburden values less than 1 have been obtained at the crude cell lysate step, and less than 1 at the prefiltered bulk product step.

Bacterial Endotoxin Test

The purpose of this test is to measure the amount of gram negative bacterial endotoxin in a given sample. The *Limulus Amebocyte* Lysate (LAL) assay is performed in accordance with USPXXIII using a commercial chromogenic test kit. It is used to quantify the gram-negative bacterial endotoxin level in test samples. Dilutions of samples are run with and without a spike of endotoxin for evaluation of inhibition or enhancement effects.

The test method is performed according to the directions outlined in the test kit insert, and is as follows. The assay is performed in 96 well plates and LAL-free water is used as an assay blank. A standard curve ranging from 0.01 to 5.0 endotoxin units/mL is made using commercially available exdotoxin standard. Test samples are tested either neat or diluted appropriately in endotoxin free water. Positive controls are prepared by spiking test samples at each dilution with 0.05 EU/mL. All manipulations are performed in pyrogen free glass or polystyrene tubes using pyrogen free pipette tips. The 96 well plate is incubated with blank, standard curve, test samples, and positive control for 10 minutes, after which the LAL reagent is added to each well. The plate is read in a kinetic reader at 405 nm for 150 seconds and the results are expressed in EU/mL.

For the assay to be acceptable, the standard curve should preferably be linear with an r value of −0.980 to 1.000, the slope of the curve should preferably be −0.0 to −0.100, the Y-intercept should preferably be 2.5000 to 3.5000 and endotoxin recovery in the positive control should preferably be 5-150% of the spike. It is preferable that the sample have less than five (5) EU/mL, more preferably the sample have less than 3 EU/mL, and most preferable that the sample have less than 0.05 EU/mL. Using purification techniques in accordance with the present disclosure, endotoxin values as low as 0.15 have been obtained at the prefiltered bulk product step and as low as 0.3 at the final product step.

Test for the Presence of Agar-Cultivable and Non-Cultivable Mycoplasmas

This assay detects the presence of *Mycoplasma* in a test article based on the ability of *Mycoplasma* to grow in any one of the test systems: Agar isolation and Vero cell culture system. Growth is signified by colony formation, shift in pH indicators, or presence of *Mycoplasma* by staining, depending on the system used. The assay is performed using a large sample volume. The test methods are as follows. The test article and positive controls are inoculated directly onto *Mycoplasma* agar plates and into *Mycoplasma* semi-solid broth which is subcultured three times onto agar plates. The samples are incubated both aerobically and anaerobically. At 14 days post-infection the agar plates are examined for evidence of growth. The test article is also inoculated directly onto Vero cell cultures and incubated for 3-5 days. The cultures are stained with a DNA-binding fluorochrome and evaluated microscopically by epifluorescence for the presence of *Mycoplasma*.

For the Agar isolation assay, the positive controls should preferably show *Mycoplasma* growth in at least two out of five direct plates for each media type and for each incubation condition, and in the semi-broth. The negative control plates and bottles should preferably show absence of *Mycoplasma* growth. For the Vero cell culture assay, positive controls should preferably show the presence of *Mycoplasma*, negative controls should preferably show no presence of *Mycoplasma*, and all of the controls should preferably show the absence of bacterial or fungal contaminants. The test article will preferably be negative for the presence of *Mycoplasma*.

Contaminating Host Cell DNA Assay

This method allows evaluation of contaminating host cell DNA in a final product. Test samples are extracted and examined for contaminating DNA. The test method is as follows. Samples are extracted and transferred to nitrocellulose. Diluted reference samples are spiked with human DNA and transferred to nitrocellulose. Positive controls are prepared by spiking human DNA into aliquots of BSA and transferred to nitrocellulose. The nitrocellulose with all samples and controls is probed with a $^{32}$P-labeled human DNA probe. The filter is rinsed and the hybridized radioactivity is measured using an AMBIS Radioanalytic Imaging System. Acceptable performance of the assay is determined by the controls performing as expected, and a test article should preferably have less than or equal to 10 ng contaminating host cell DNA per $1 \times 10^{12}$ viral particles. It is more preferable that the level of contaminating human DNA be less than 7 ng/$1 \times 10^{12}$ viral particles, even more preferable that the level of contaminating human DNA be less than 5 ng/$1 \times 10^{12}$ viral particles, even more preferable that the level of contaminating human DNA be less than 3 ng/$1 \times 10^{12}$ viral particles and most preferable that the level of contaminating human DNA be less than 5 pg/$1 \times 10^{12}$ viral particles. Using purification techniques in accordance with the present disclosure, contaminating DNA values as low as 200 pg/mL have been obtained at the final product step and 80 pg/mL in a developmental batch.

Quantitative Replication Competent Adenovirus (RCA) Assay.

The RCA present in a recombinant-defective adenovirus population such as Ad5CMV-p53 are detected by infection of non-competent A549 human carcinoma cells. A549 cells are grown in cell culture dishes to give a monolayer of cells and are then infected with the adenovirus sample to be tested. After 4 hours of infection time, the supernatant is discarded and the A549 monolayer is covered by a mixture containing both culture media and agarose. After solidification, the agarose limits any infected cell to formation of a single plaque. After 14 days at 37 degrees Celsius, agarose is stained with neutral red and the visualized plaques are counted. Positive controls are run concomitantly and contain either wild type adenovirus alone or the test article spiked with wild type adenovirus such that any inhibitory effect coming from the sample could be detected. In order to characterize any observed RCA, all plaques are subcultured and PCR characterized. PCR analysis is performed using probes targeted against the E1 region in order to demonstrate the presence of E1 region in the vector, and against the E3 region to exclude the presence of wild type viruses. It has been demonstrated that the presence of E1 excludes the presence of the p53 gene and that the RCA consist of only double homologous constructions.

The test methodology is as follows. A human lung carcinoma line, A549, is grown to sub-confluence in cell culture dishes and then infected with the Ad5CMV-p53 sample to be tested at an MOI of less than 200 viral particles per cell. The cells are then exposed to the virus for a 4 hour infection time, the supernatant is discarded, and the cell monolayer is covered with a media/agarose overlay. One positive control containing wild type adenovirus and one containing the test sample spiked with wild type adenovirus are run concomitantly to assure assay sensitivity. After a 14 day incubation at 37 degrees Celsius the overlay is stained with neutral red to allow visualization of any plaques. Plaques are counted, picked and transferred to 0.8 mL of culture media and subjected to three freeze-thaw cycles to release virus. The plaque supernatant is then used to infect additional multi well dishes of A549 cells. The cells are observed for CPE and the supernatant from those dishes is harvested. The harvested supernatant is subjected to amplification by PCR using probes directed against the E1 region of the wild type adenovirus genome and against the E3 region of the wild type adenovirus virus. If the E3 region is present the RCA is scored as wild type. If only the E1 region is present the RCA is scored as a double homologous recombination product. For the assay to be considered valid, all controls must perform as expected. It is preferable that the test article contain less than 40 plaque forming units in $1\times10^{11}$ viral particles. It is more preferable that the test article contain less than 4 plaque forming units in $1\times10^{11}$ viral particles, and most preferable that the test article contain less than 0.4 plaque forming units in $1\times10^{11}$ viral particles. Using purification techniques in accordance with the present disclosure, RCA values $\leq 1$ in $2.5\times10^{11}$ virus particles have been obtained at the final product step.

Determination of BSA Levels

This assay is used to determine levels of contaminating bovine serum albumin (BSA) in adenoviral preparations. In certain recombinant adenovirus production runs, the vector is produced in a cell culture system containing bovine serum. This assay is an enzyme linked immunosorbent assay (ELISA) that detects the presence and quantity of low levels of BSA that remain in the final product.

The test method is as follows. A standard curve ranging from 1.9 ng to 1125 ng/mL of purified BSA is prepared. A positive control is prepared by spiking 0.2% gelatin with 3.9, 15, and 62.5 ng/mL BSA. A negative control sample is 0.2% gelatin in Tris buffered saline. The test sample is tested neat and at dilutions of 1:10 through 1:320. All samples and controls are transferred to an ELISA assay plate, and the BSA content is detected with a probe antibody specific for BSA. The plates are read at 492 nm. For the assay to be considered valid, the blank $OD_{492}$ should preferably be less than 0.350. The test article should preferably contain less than 100 ng BSA per $1\times10^{12}$ viral particles. It is more preferable that the test article contain less than 85 ng BSA per $1\times10^{12}$ viral particles, even more preferable that the test article contain less than 75 ng BSA per $1\times10^{12}$ viral particles, even more preferable that the test article contain less than 65 ng BSA per $1\times10^{12}$ viral particles and most preferable that the test article contain less than 1 ng BSA per $1\times10^{12}$ viral particles. Using purification techniques in accordance with the present disclosure, BSA values<1.9 ng/$1\times10^{12}$ virus particles have been obtained at the final product step.

P53 Mutation Assay

This assay is to demonstrate the ability of p53 expressed from Ad5CMV-p53 final product to activate transcription. The critical biochemical function of p53, which underlies its tumor suppressor activity, is the ability to activate transcription. Mutant proteins fail to activate transcription in mammalian cells. The transcriptional activity of human p53 is conserved in yeast, and mutant which are inactive in human cells are also inactive in yeast. The detection of p53 mutations is possible in yeast by testing the transcriptional competence of human p53 expressed in a *Saccharomyces cerevisiae* defective in adenine synthesis due to a mutation in ADE2 but which contains a second copy of ADE2 in an open reading frame controlled by a p53 responsive promoter. The *Saccharomyces cerevisiae* strain is cotransformed with a linearized plasmid and the isolated p53 fragment from Ad5CMV-p53. Recombinants will constituitively express p53. When grown on adenine poor media, the yeast strain will appear red. If the yeast carries a wild-type p53 gene the colonies will appear white.

The test method is as follows. DNA from the test article is extracted using a phenol/chloroform/isoamyl alcohol procedure and the p53 DNA insert from the adenoviral genome is isolated following restriction digestion. An expression vector containing the ADH1 promoter is linearized. Yeast (strain yIG397) is co-transformed with the DNA fragment bearing the p53 gene from the test article and the linearized expression vector. A p53 expression vector is formed in vivo by homologous recombination. The yeast cultures are grown for two to three days at 30 degrees Celsius. The ADH1 promoter causes recombinants to constituitively express p53. The yIG397 strain of yeast is defective in adenine synthesis because of a mutation in the endogenous ADE2 gene, but it contains a second copy of the ADE2 open reading frame controlled by the p53-responsive ADH1 promoter. The colonies of yIG397 that are ADE2 mutant turn red when grown on low adenine plates. Colonies of yIG397 with mutant p53 are also red, and colonies containing wild type p53 are white. Red and white colonies are counted at the end of the assay. The assay is considered valid if all the controls perform as expected, and the test article should preferably contain p53 mutations at a frequency of less than 3% to pass product release specifications. It is more preferable that the test article contain less than 2% p53 mutations, and most preferable that the test article contain 0% p53 mutations. Using purification techniques in accordance with the present disclosure, p53 mutations values 1% have been obtained at the final product step.

Plaque Assay for Adenoviral Vectors

This assay is used to determine the titer of adenoviral material in the final product by measuring the development of plaques on human 293 cells, which are derived from human embryonic kidney. Ad5CMV-p53 is replication deficient on normal cells due to deletion of the E1 region. The E1 function is provided in trans in 293 cells which contain the E1 region of adenovirus type 5. Five fold dilutions of the test article are utilized to quantify the titer.

The test method is as follows. Human 293 cells are seeded in 66 well tissue culture plates and the cells are allowed to grow to greater than 90% confluence before infection. Vector dilutions are made to target 5-80 plaques per well. A reference virus is used as a control. Two concentrations are tested for the positive control using six replicates. Four concentrations are tested for each sample using six replicates. The vector is allowed to infect for one hour during which the plates are rocked every 15 minutes to ensure even coverage of the virus. After the incubation period, the cells are overlaid with a 0.5% agarose solution, and the virus-infected cells are incubated for six days at which time they are stained with Neutral Red. The plaques are counted between four and 25 hours after staining, depending on the size of the plaques. Wells which contain greater than 80 plaques are scored TNTC (Too Numerous To Count), and wells that cannot be counted are marked as NC (Not Counted) and the reason is noted on the record. Plaque counts and their respective dilutions are used to calculate the sample titer. For the assay to be considered valid, the negative control wells should preferably contain no plaques, the titer of the positive control should preferably be within one quarter (0.25) log of the official titer of the virus being used as the positive control, the % CV for the positive control should preferably be less than or equal to 25%, and for any one dilution in the positive control, there should preferably be no more than three wells designated "NC".

At the final product testing step, the test article should preferably have a titer of $1 \times 10^7$ to $1 \times 10^{12}$ pfu/mL. It is more preferable to have a titer of $1 \times 10^9$ to $1 \times 10^{12}$ pfu/mL, even more preferable to have a titer of $1 \times 10^{10}$ to $1 \times 10^{12}$ pfu/mL, even more preferable to have a titer of $5 \times 10^{10}$ to $1 \times 10^{12}$ pfu/mL, and most preferable to have a titer of $8 \times 10^{10}$ to $1 \times 10^{12}$ pfu/ml. Using purification techniques in accordance with the present disclosure, titer values as high as $5 \times 10^{12}$ virus particles/mL have been obtained at the final product step.

Determination of Viral Particle Concentration and Particle/PFU Ratio

This assay measures the concentration, in viral particles/mL, for a sample of adenoviral material. This assay is a spectrophotometric assay that determines the total number of particles in a sample based on absorbance at 260 nm. The extinction coefficient used to convert to viral particles is 1 $OD_{260}=10^{12}$ viral particles.

The test method is as follows. Three replicates are prepared for each sample using an appropriate dilution to fall within the linear range of the spectrophotometer. The virus sample is combined with 1% SDS (or 10% SDS for dilute test samples) and water to achieve a total volume of 150 microliters. The sample is incubated at room temperature for 15-30 minutes to disrupt the virion. Each sample is read at $A_{260}$ and $A_{280}$ and the mean optical density for replicate samples is multiplied by the dilution factor to determine viral particles/mL. The Particle/PFU ratio is determined using the titer determined by the plaque assay described previously. For the assay to be considered valid, the % CV for the three sample replicates should preferably be less than or equal to 10%. The test sample should preferably contain $1 \times 10^7$ to $2 \times 10^{13}$ viral particles/mL at the final product step. It is more preferable that the test sample contain between about $0.8 \times 10^{12}$ and $2 \times 10^{13}$ viral particles/mL, and most preferable that the sample contain between about $1.2 \times 10^{12}$ and $2 \times 10^{13}$ particles/mL It is most preferable that the $A_{260}/A_{280}$ is 1.2 to 1.4. It is preferable that the Particle/PFU ratio is less than 100, even more preferable that it is less than 75, and most preferable that it is 10 to 60. Using purification techniques in accordance with the present disclosure, viral particle concentration values as high as $5 \times 10^{12}$ virus particles/mL have been obtained at the final product step.

Adenoviral p53 Bioactivity Assay

The SAOS LM assay is a bioactivity assay which is conducted for the purpose of determining the activity of the p53 component of Ad5CMV-p53. The assay measures the inhibition of growth of SAOS-LM cells (human osteocarcinoma cell line with a homozygous p53 deletion). Any significant loss of inhibitory activity compared with a standard would indicate the presence of an unacceptable amount of inactive vector. The inhibition of growth of SAOS cells is followed using the Alamar Blue indicator dye, which is used to quantitatively measure cell proliferation. This dye contains a colorimetric oxidation/reduction (REDOX) indicator. As cellular activity results in chemical reduction of the cellular environment, inhibition of growth results in an oxidized environment that allows the measurement of p53 activity.

The test method is as follows. SAOS cells are plated in 96 well plates and grown overnight at 37 degrees Celsius to greater than 75% confluence. Media is removed from the wells and the cells are challenged with either a media control, positive control virus (MOI=1000) or varying dilutions of the test sample. Following challenge, the cells are incubated at 37 degrees Celsius for four days. Alamar Blue is added to the wells and the plates are incubated approximately eight hours at 37 degrees Celsius. Cell density is determined by reading the plates at 570 nm. To accept the assay the $OD_{570}$ of the positive control must be less than 0.1 and the media control cell density must be at least 75% confluent. It is preferable that the MOI of the test article that causes 50% cell death is less than 1000 viral particles. It is more preferable that the test article have an MOI that causes 50% cell death of less than 700 viral particles, and most preferable that the MOI that causes 50% cell death is less than 400 viral particles. Using purification techniques in accordance with the present disclosure, bioactivity values as high as 250-260 have been obtained at the final product step.

HPLC Assay for p53.

This assay is a quantitative evaluation of Ad5CMV-p53 particle number and purity of in-process samples and of final product stability samples. The method allows quantitation of Ad5CMV-p53 particles by an ion exchange HPLC method.

The test method is as follows. A Toso Haas TSK-Gel-Q-5PW column is used with a buffered salt gradient mobile phase for separation of virus particles and impurities. A reference control calibration curve is run on a newly installed column and scanned at $A_{260}$. A blank is prepared and run using the same column and method. The sample to be tested is prepared by dilution with the same low salt buffer used in gradient formation. The sample absorbance is detected at 260 and 280 nm wavelengths, and the total are for all peaks detected is determined. The ratio of the area for the $A_{260}/A_{280}$ peak is determined, and the concentration for the 260 nm peak is determined by comparison to the reference calibration curve. Assay acceptance criteria include similar profile to historical samples, and a $A_{260}/A_{280}$ ratio of 1.3+/−0.1 The test sample should preferably have a purity of greater than or equal to 98%. It is more preferable that the purity be greater than 99%, and most preferable that the purity is greater than 99.9%. Using purification techniques in accordance with the present disclosure, virus purity values as high as 99.8% have been obtained at the final product step.

C. Identity Assays

Restriction Enzyme Mapping Assay for Ad5CMV-p53

This method allows evaluation of Ad5CMV-p53 DNA by restriction enzyme analysis. Restriction enzymes recognize specific base pair sequences on DNA, cutting the DNA at these restriction sites. There are a limited number of recognition sites within a vector for any particular restriction enzyme. Test sample DNA is digested with two restriction enzymes and the fragments separated electrophoretically in an agarose gel matrix. The DNA fragments are checked for number and size.

The test method is as follows. DNA is extracted from vector particles using a commercially available ion exchange spin column. The extracted DNA is quantified and checked for purity by analyzing the $A_{260}/A_{280}$ ratio. Approximately 0.4-5 micrograms of the extracted DNA is digested with a cocktail of two restriction enzymes, Eco RI and Cla I. The digested DNA is loaded onto a 1% agarose gel containing ethidium bromide alongside an equal amount of unrestricted DNA from the same sample. The samples are separated by electrophoresis and visualized using an ultraviolet light source. Data is captured by photography. The assay acceptance criteria that should preferably be met for the assay to be considered valid is a $A_{260}/A_{280}$ ratio of extracted DNA of greater than 1.6. The test article should preferably have restriction fragment sizes that match the theoretical fragment sizes expected from the sequence of Ad5CMV-p53. The expected band sizes are 486, 2320, 8494 and 24008 base pairs.

SDS Page Assay

This method allows evaluation of total proteins in final product ranging in size from 5 to 100 kDa by separation according to molecular weight.

The test method is as follows. Total proteins are determined using a Pierce BCA method according to the protocol described previously in this section. The test sample, internal standard and molecular weight standards are prepared in sample buffer and denatured by heating. All samples and standards are loaded into wells of a pre-cast Tris-glycine gel and set in an electrophoresis tank containing running buffer. The gel is run on a constant current setting for approximately 90 minutes. The gel is then removed from the cassette, stained using Coomassie Brilliant Blue stain and destained. The gel is then analyzed using a densitometric scanning instrument, and the data captured by photography. Alternatively, the gel is dried for archiving. In all controls, the presence of expected proteins is preferable and there should preferably be no contaminating proteins. In the test sample, the expected bands should preferably be observed, with no significant extra bands.

Western Blot Assay:

This method tests for the presence of p53 protein in Ad5CMV-p53 transduced cells. The test method is as follows. Individual 60 mm tissue culture dishes for product samples and control samples are seeded at a density of $7\times10^5$ cells and grown to greater than 80% confluence. The test article is diluted in media to provide $3.5\times10^8$ viral particles/mL. A reference control is diluted to $3.5\times10^8$ vp/mL and a negative control with no vector is also prepared. The cells are exposed to media containing product for one hour during which the plates are rocked to ensure even distribution of vector. At the end of the hour, additional media is added to the dishes and they are incubated for approximately five hours to allow time for expression of p53. At the end of the incubation period, the cells are treated with trypsin to allow harvest, washed with DPBS and solubilized with a detergent buffer. The total amount of protein in each sample and control is determined by a colorimetric quantitation method (Pierce BCA). For each sample and method, 3-5 micrograms of protein are loaded onto a gel alongside a commercially purchased p53 protein reference and separated by polyacrylamide gel electrophoresis (PAGE). The proteins in the gel are transferred to a PVDF membrane and the membrane is exposed to a milk buffer to block non-specific binding sites and then sequentially exposed to antibodies. The primary antibody, a mouse anti-human p53 antibody specifically binds to p53. The secondary antibody is a goat anti-mouse IgG with horseradish peroxidase (HRP) covalently bound. A colorimetric substrate is exposed to the bound HRP enzyme which enables visualization of p53 protein on the blot. For the assay to be considered valid, the control p53 band should preferably be visible, and the negative control should preferably show no expression of p53. The test article should preferably show expression of p53.

Recoverable Fill Volume Assay

This method is a gravimetric determination of volume recoverable from the container closure for Ad5CMV-p53 final product. Product is recovered from seven vials using tared 3 cc syringes and 21G 1.5 inch needles. The product is weighed, and the weights are converted to volume using the specific gravity of the product of 1.03 g/mL. The balance calibration must be met before weighing of the samples and it is preferable that all seven vials tested must meet specification of 1.0 to 1.4 mL of recoverable fill volume. It is more preferable that the recoverable fill volume be 1.1 to 1.3 mL. It will be understood by those of skill in the art that this assay is an example for the Ad5CMVp53 product, and that those of skill in the art will be able to modify this assay for other products in other types of container closures.

Physical Description Assay

This method allows evaluation of the physical description of final product. Approximately seven milliliters of product are pooled in a clear plastic tube. The product is inspected by an analyst to document the color, transparency, and the presence of any gross particulate matter. The test article should preferably be clear to opalescent and contain no gross particulate matter by visual inspection.

pH Assay

This method is a pH determination of the Ad5CMV-p53 final product. Approximately 0.5 mL of the product is placed in a tube. The pH is determined using a calibrated pH meter at a temperature of 25+/−5 degrees Celsius. The pH standard solutions should preferably demonstrate a slope range of 80-120%. The pH of the final product should preferably be between about 6 and about 9. It is more preferable that the pH is between about 6.5 and about 8.8, even more preferable that the pH is between about 7.0 and about 8.6, and most preferable that the pH is between about 7.5 and about 8.5.

Restriction Enzyme Mapping for Identity Testing of Master Viral Bank or Working Viral Bank The goal of this test is to assess the identity of the Ad5CMV-p53 genome through measurement of the DNA fragments generated after cleavage of the whole viral genome (approximately 35308 base pairs). When the unpurified viruses are contained in a cell mixture such as a virus bank, the viral DNA first has to be extracted from the crude cell lysate. An aliquot of the sample is digested by proteinase K in the presence of SDS. The DNA is then extracted using a mixture of phenol/chloroform/isoamyl alcohol and precipitated with ethanol. The DNA concentration is measured by UV spectrometry. Approximately one microgram of the viral DNA is then submitted to restriction enzyme digestion. Four individual digests are performed utilizing a battery of three restriction enzymes in different combinations. The digests and DNA size markers are then separated on an agarose gel using electrophoresis and stained with Syb-Green. The gels are integrated using a camera and a calibration curve calculated from the standards. The size of the fragments greater than 500 bp and less than 8000 bp is then determined. The size of the fragments obtained should preferably correspond to the theoretical size of the fragments obtained from the expected theoretical sequence. The fragment sizes of the test sample should preferably correspond to those expected from the DNA sequence.

PCR to Detect E1 DNA Sequences in 293 MCB and WCB

This assay is used to determine the identity of the 293 Master and Working Cell Banks by demonstrating the presence of the E1 region. Using two specific pairs of PCR primers, one targeted against the E1 region present in both 293 cells and wild-type adenovirus and another one targeted against the E1 region only present in the wild type adenovirus. The method should demonstrate the identity of the 293 cell line contained in the test article.

The test method is as follows. After thawing, cells from the test article are grown using standard conditions in a cell culture dish until a monolayer of cells is obtained. The cells are then digested with proteinase K to remove the proteins, and DNA isolated using phenol/chloroform/isoamyl alcohol extractions followed by ethanol precipitation. The extracted DNA is quantified and checked for purity by an absorbance scan from OD260-OD280. The PCR reaction is performed using the two E1 targeted pairs of primers on the test article and on both positive and negative DNA controls. The negative control is a mammalian cell line which does not contain the E1 region. The positive control is a wild type adenovirus. The PCR products from each reaction are loaded onto an agarose gel and the size of the fragments obtained after electrophoresis and staining are recorded using photography. The non-bearing E1 mammalian cell line must exhibit no amplification product with both pairs of PCR primers, while the wild type adenovirus must show the correct amplification product with both pairs of PCR primers. The test article must demonstrate the correct amplification product with the pair of primers located in the E1 region described to be present in the 293 cell, and must be negative with the second pair of primers known only to be present in the wild type adenoviral genome.

11. PHARMACEUTICAL COMPOSITIONS AND FORMULATIONS

When purified according to the methods set forth above, it is contemplated that the viral particles of the present invention may be administered in vitro, ex vivo or in vivo. Thus, it will be desirable to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct and nucleic acid, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The viral particles of the present invention may include classic pharmaceutical preparations for use in therapeutic regimens, including their administration to humans. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal, or intravenous injection. Such compositions would normally be administered as pharmaceutically acceptable compositions that include physiologically acceptable carriers, buffers or other excipients. For application against tumors, direct intratumoral injection, inject of a resected tumor bed, regional (i.e., lymphatic) or general administration is contemplated. It also may be desired to perform continuous perfusion over hours or days via a catheter to a disease site, e.g., a tumor or tumor site.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations which are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal, for example (i) inhibition of tumor cell proliferation, (ii) elimination or killing of tumor cells, (iii) vaccination, or (iv) gene transfer for long term expression of a therapeutic gene. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the result desired. Multiple gene therapeutic regimens are expected, especially for adenovirus.

In certain embodiments of the present invention, an adenoviral vector encoding a tumor suppressor gene will be used to treat cancer patients. Typical amounts of an adenovirus vector used in gene therapy of cancer is $10^3$-$10^{15}$ viral particles/dose, ($10^3$, $10^4$, $10^5$, $10^6$, $10^7$, $10^8$, $10^9$, $10^{10}$, $10^{11}$, $10^{12}$, $10^{13}$, $10^{14}$, $10^{15}$) wherein the dose may be divided into several injections at different sites within a solid tumor. The treatment regimen also may involve several cycles of administration of the gene transfer vector over a period of 3-10 weeks. Administration of the vector for longer periods of time from months to years may be necessary for continual therapeutic benefit.

In another embodiment of the present invention, an adenoviral vector encoding a therapeutic gene may be used to vaccinate humans or other mammals. Typically, an amount of virus effective to produce the desired effect, in this case vaccination, would be administered to a human or mammal so that long term expression of the transgene is achieved and a strong host immune response develops. It is contemplated that a series of injections, for example, a primary injection followed by two booster injections, would be sufficient to induce an long term immune response. A typical dose would be from $10^6$ to $10^{15}$ PFU/injection depending on the desired result. Low doses of antigen generally induce a strong cell-mediated response, whereas high doses of antigen generally induce an antibody-mediated immune response. Precise amounts of the therapeutic composition also depend on the judgment of the practitioner and are peculiar to each individual.

12. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

A) Cells 293 cells (human epithelial embryonic kidney cells) from the Master Cell Bank were used for the studies.

B) Media

Dulbecco's modified Eagle's medium (DMEM, 4.5 g/L glucose)+10% fetal bovine serum (FBS) was used for the cell growth phase. For the virus production phase, the FBS concentration in DMEM was lowered to 2%.

C) Virus

AdCMVp53 is a genetically engineered, replication-incompetent human type 5 adenovirus expressing the human wild type p53 protein under control of the cytomegalovirus (CMV) immediate early promoter.

D) Celligen bioreactor

A Celligen bioreactor (New Brunswick Scientific, Co. Inc.) with 5 L total volume (3.5 L working volume) was used to produce virus supernatant using microcarrier culture. 13 g/L glass coated microcarrier (SoloHill) was used for culturing cells in the bioreactor.

E) Production of Virus Supernatant in the Celligen Bioreactor 293 cells from master cell bank (MCB) were thawed and expanded into Cellfactories (Nunc). Cells were generally split at a confluence of about 85-90%. Cells were inoculated into the bioreactor at an inoculation concentration of $1 \times 10^5$ cells/ml. Cells were allowed to attach to the microcarriers by intermittent agitation. Continuous agitation at a speed of 30 rpm was started 6-8 hr post cell inoculation. Cells were cultured for 7 days with process parameters set at pH=7.20, dissolved oxygen (DO)=60% of air saturation, temperature=37° C. On day 8, cells were infected with AdCMVp53 at an MOI of 5. Fifty hr post virus infection, agitation speed was increased from 30 rpm to 150 rpm to facilitate cell lysis and release of the virus into the supernatant. The virus supernatant was harvested 74 hr post-infection. The virus supernatant was then filtered for further concentration/diafiltration.

F) Cellcube™ Bioreactor System

A Cellcube™ bioreactor system (Corning-Costar) was also used for the production of AdCMVp53 virus. It is composed of a disposable cell culture module, an oxygenator, a medium recirculation pump and a medium pump for perfusion. The cell culture module used has a culture surface area of 21,550 cm² (1 mer).

G) Production of Virus in the Cellcube™

293 cells from master cell bank (MCB) were thawed and expanded into Cellfactories (Nunc). Cells were generally split at a confluence of about 85-90%. Cells were inoculated into the Cellcube™ according to the manufacturer's recommendation. Inoculation cell densities were in the range of $1$-$1.5 \times 10^4/cm^2$. Cells were allowed to grow for 7 days at 37° C. under culture conditions of pH=7.20, DO=60% air saturation. Medium perfusion rate was regulated according to the glucose concentration in the Cellcube™. One day before viral infection, medium for perfusion was changed from DMEM+10% FBS to DMEM+2% FBS. On day 8, cells were infected with AdCMVp53 virus at a multiplicity of infection (MOI) of 5. Medium perfusion was stopped for 1 hr immediately after infection then resumed for the remaining period of the virus production phase. Culture was harvested 45-48 hr post-infection.

H) Lysis Solution

Tween-20 (Fisher Chemicals) at a concentration of 1% (v/v) in 20 mM Tris+0.25 M NaCl+1 mM MgCl$_2$, pH=7.50 buffer was used to lyse cells at the end of the virus production phase in the Cellcube™.

I) Clarification and Filtration

Virus supernatant from the Celligen bioreactor and virus solution from the Cellcube™ were first clarified using a depth filter (Preflow, GelmanSciences), then was filtered through a 0.8/0.22 µm filter (SuporCap 100, GelmanSciences).

J) Concentration/Diafiltration

Tangential flow filtration (TFF) was used to concentrate and buffer exchange the virus supernatant from the Celligen bioreactor and the virus solution from the Cellcube™. A Pellicon II mini cassette (Millipore) of 300 K nominal molecular weight cut off (NMWC) was used for the concentration and diafiltration. Virus solution was first concentrated 10-fold. This was followed by 4 sample volume of buffer exchange against 20 mM Tris+1.0 M NaCl+1 mM $MgCl_2$, pH=9.00 buffer using the constant volume diafiltration method.

Similar concentration/diafiltration was carried out for the column purified virus. A Pellicon II mini cassette of 100 K NMWC was used instead of the 300 K NMWC cassette. Diafiltration was done against 20 mM Tris+0.25 M NaCl+1 mM $MgCl_2$, pH=9.00 buffer or Dulbecco's phosphate buffered saline (DPBS).

K) Benzonase Treatment

The concentrated/diafiltrated virus solution was treated with Benzonase™ (American International Chemicals) at a concentration of 100 u/ml, room temperature overnight to reduce the contaminating nucleic acid concentration in the virus solution.

L) CsCl Gradient Ultracentrifugation

Crude virus solution was purified using double CsCl gradient ultracentrifugation using a SW40 rotor in a Beckman ultracentrifuge (XL-90). First, 7 ml of crude virus solution was overlaid on top of a step CsCl gradient made of equal volume of 2.5 ml of 1.25 g/ml and 1.40 g/ml CsCl solution, respectively. The CsCl gradient was centrifuged at 35,000 rpm for 1 hr at room temperature. The virus band at the gradient interface was recovered. The recovered virus was then further purified through a isopicnic CsCl gradient. This was done by mixing the virus solution with at least 1.5-fold volume of 1.33 g/ml CsCl solution. The CsCl solution was centrifuged at 35,000 rpm for at least 18 hr at room temperature. The lower band was recovered as the intact virus. The virus was immediately dialyzed against 20 mM Tris+1 mM $MgCl_2$, pH=7.50 buffer to remove CsCl. The dialyzed virus was stored at −70° C. for future use.

M) Ion Exchange Chromatography (IEC) Purification

The Benzonase treated virus solution was purified using IEC. Strong anionic resin Toyopearl SuperQ 650M (Tosohaas) was used for the purification. A FPLC system (Pharmacia) with a XK16 column (Pharmacia) were used for the initial method development. Further scale-up studies were carried out using a BioPilot system (Pharmacia) with a XK 50 column (Pharmacia). Briefly, the resin was packed into the columns and sanitized with 1 N NaOH, then charged with buffer B which was followed by conditioning with buffer A. Buffers A and B were composed of 20 mM Tris+0.25 M NaCl+1 mM $MgCl_2$, pH=9.00 and 20 mM Tris+2M NaCl+1 mM $MgCl_2$, pH=9.00, respectively. Viral solution sample was loaded onto the conditioned column, followed by washing the column with buffer A until the UV absorption reached base line. The purified virus was eluted from the column by using a 10 column volume of linear NaCl gradient.

N) HPLC Analysis

A HPLC analysis procedure was developed for evaluating the efficiency of virus production and purification. Tris(hydroxymethyl)aminomethane (tris) was obtained from Fisher-Biotech (Cat# BP154-1; Fair Lawn, N.J., U.S.A.); sodium chloride (NaCl) was obtained from Sigma (Cat# S-7653, St. Louis, Mo., U.S.A.). Both were used directly without further purification. HPLC analyses were performed on an Analytical Gradient System from Beckman, with Gold Workstation Software (126 binary pump and 168 diode array detector) equipped with an anion-exchange column from TosoHaas (7.5 cm×7.5 mm ID, 10 µM particle size, Cat# 18257). A 1-ml Resource Q (Pharmacia) anion-exchange column was used to evaluate the method developed by Huyghe et al. using their HEPES buffer system. This method was only tried for the Bioreactor system:

The buffers used in the present HPLC system were Buffer A: 10 mM tris buffer, pH 9.0. Buffer B: 1.5 M NaCl in buffer A, pH 9.0. The buffers were filtered through a 0.22 µm bottle top filter by Corning (Cat# 25970-33). All of the samples were filtered through a 0.8/0.22 µm Acrodisc PF from Gelman Sciences (Cat# 4187) before injection.

The sample is injected onto the HPLC column in a 60-100 µl volume. After injection, the column (TosoHaas) is washed with 20% B for 3 min at a flow rate of 0.75 ml/min. A gradient is then started, in which B is increased from 20% to 50% over 6 min. Then the gradient is changed from 50% to 100% B over 3 min, followed by 100% B for 6 min. The salt concentration is then changed back stepwise to 20% again over 4 min, and maintained at 20% B for another 6 min. The retention time of the Adp53 is 9.5±0.3 min with $A_{260}/A_{280} \cong 1.26 \pm 0.03$. Cleaning of the column after each chromatographic run is accomplished by injecting 100 µl of 0.15 M NaOH and then running the gradient.

Example 2

Effect of Medium Perfusion Rate in Cellcube™ on Virus Production and Purification For a perfusion cell culture system, such as the Cellcube™, medium perfusion rate plays an important role on the yield and quality of product. Two different medium perfusion strategies were examined. One strategy was to keep the glucose concentration in the Cellcube™ $\geq 2$ g/L (high perfusion rate). The other one was to keep the glucose concentration $\geq 1$ g/L (low medium perfusion rate).

No significant changes in the culture parameters, such as pH, DO, was observed between the two different perfusion rates. Approximately equivalent amount of crude viruses (before purification) were produced after harvesting using 1% Tween-20 lysis solution as shown in Table 7. However, dramatic difference was seen on the HPLC profiles of the viral solutions from the high and low medium perfusion rate production runs.

TABLE 7

| Effect of medium glucose concentration on virus yield | | |
|---|---|---|
| Glucose concentration (g/L) | $\geq 2.0$ | $\geq 1.0$ |
| Crude virus yield (PFU) | $4 \times 10^{12}$ | $4.9 \times 10^{12}$ |

Figure 1B:
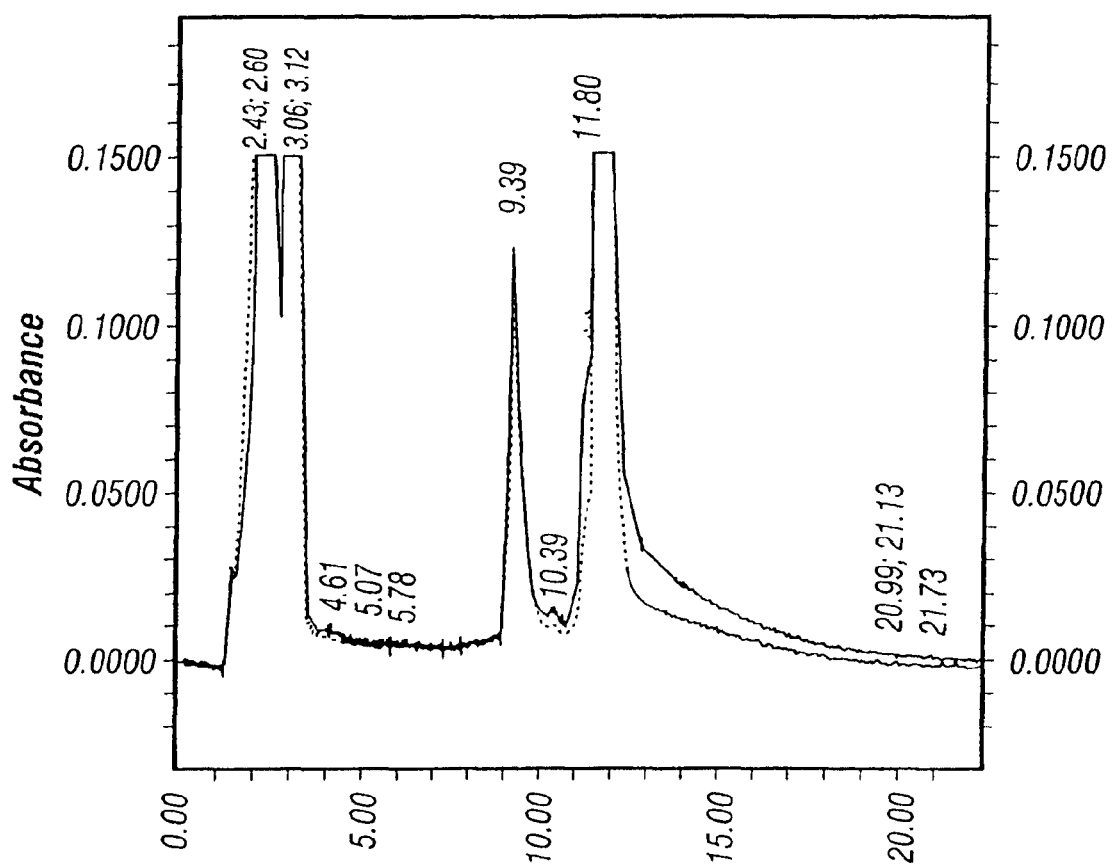

As shown in FIG. 1, a very well separated virus peak (retention time 9.39 min) was produced from viral solution using low medium perfusion rate. It was found that virus with adequate purity and biological activity was attained after a single step ion exchange chromatographic purification of the virus solution produced under low medium perfusion rate. On the other hand, no separated virus peak in the retention time of 9.39 min was observed from viral solution produced using high medium perfusion rate. This suggests that contaminants which have the same elution profile as the virus were produced under high medium perfusion rate. Although the nature of the contaminants is not yet clear, it is expected that the contaminants are related to the increased extracellular matrix protein production under high medium perfusion rate (high serum feeding) from the producer cells. This poor separation characteristic seen on the HPLC created difficulties for process IEC purification as shown in the following Examples. As a result, medium perfusion rate used during the cell growth and the virus production phases in the Cellcube™ has a significant effect on the downstream IEC purification of the virus. Low medium perfusion rate is recommended. This not only produces easy to purify crude product but also offers more cost-effective production due to the reduced medium consumption.

Example 3

Methods of Cell Harvest and Lysis

Based on previous experience, the inventors first evaluated the freeze-thaw method. Cells were harvested from the Cellcube™ 45-48 hr post-infection. First, the Cellcube™ was isolated from the culture system and the spent medium was drained. Then, 50 mM EDTA solution was pumped into the Cube to detach the cells from the culture surface. The cell suspension thus obtained was centrifuged at 1,500 rpm (Beckman GS-6KR) for 10 min. The resultant cell pellet was resuspended in Dulbecco's phosphate buffered saline (DPBS). The cell suspension was subjected to 5 cycles of freeze/thaw between 37° C. water bath and dry-ice ethanol bath to release virus from the cells. The crude cell lysate (CCL) thus generated was analyzed on HPLC.

Figure 2:
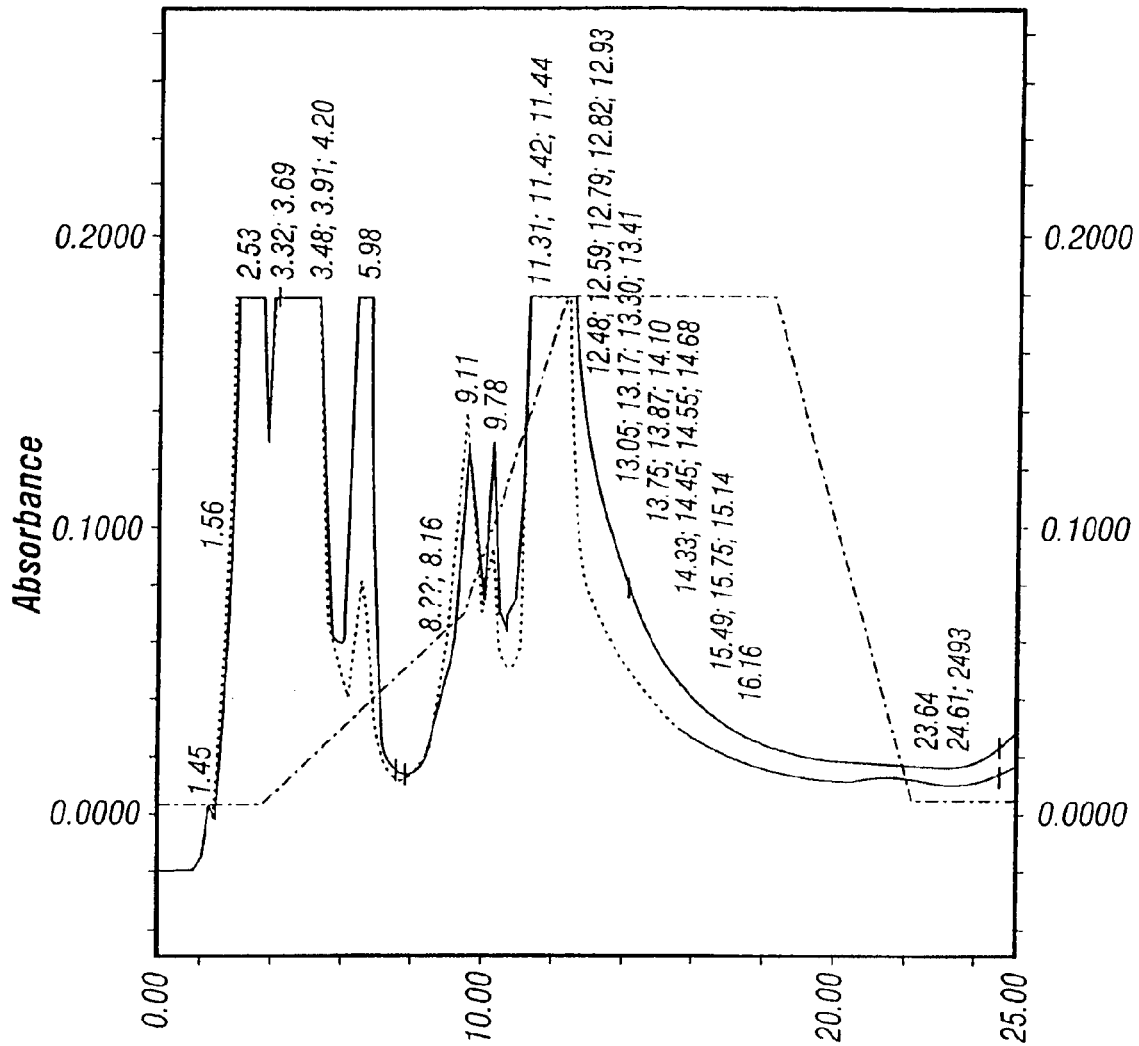
FIG. 2. The HPLC profile of crude cell lysate (CCL) from CellCube™ (solid line $A_{260}$; dotted line $A_{280}$).
Figure 3A:
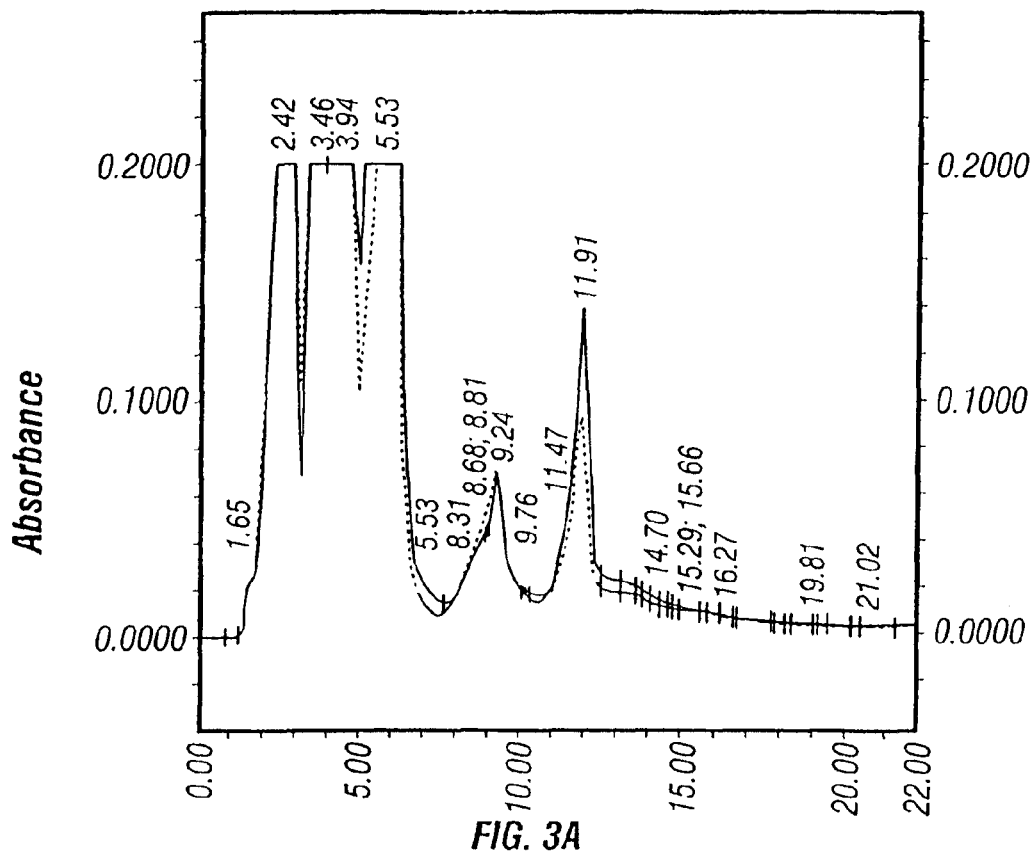
FIG. 3A, FIG. 3B, FIG. 3C, FIG. 3D and FIG. 3E. The HPLC profiles of lysis solutions from CellCube™ using different detergents.
Figure 3B:
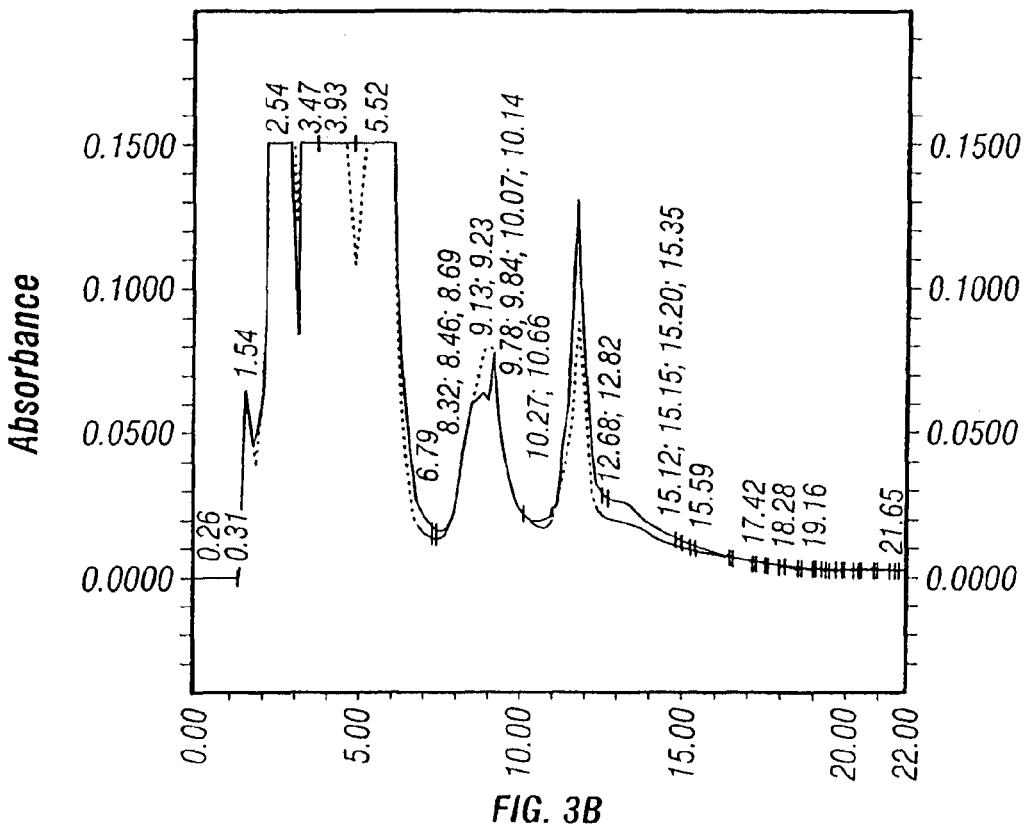
Figure 3C:
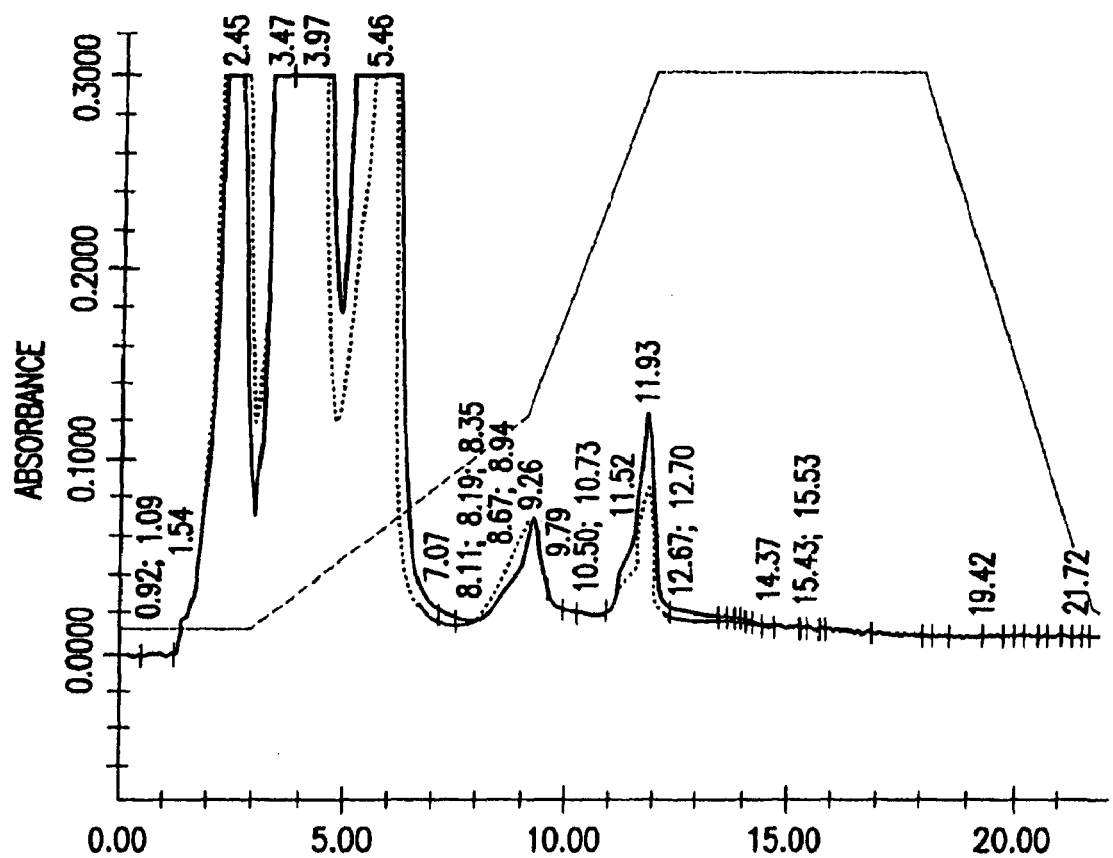
Figure 3D:
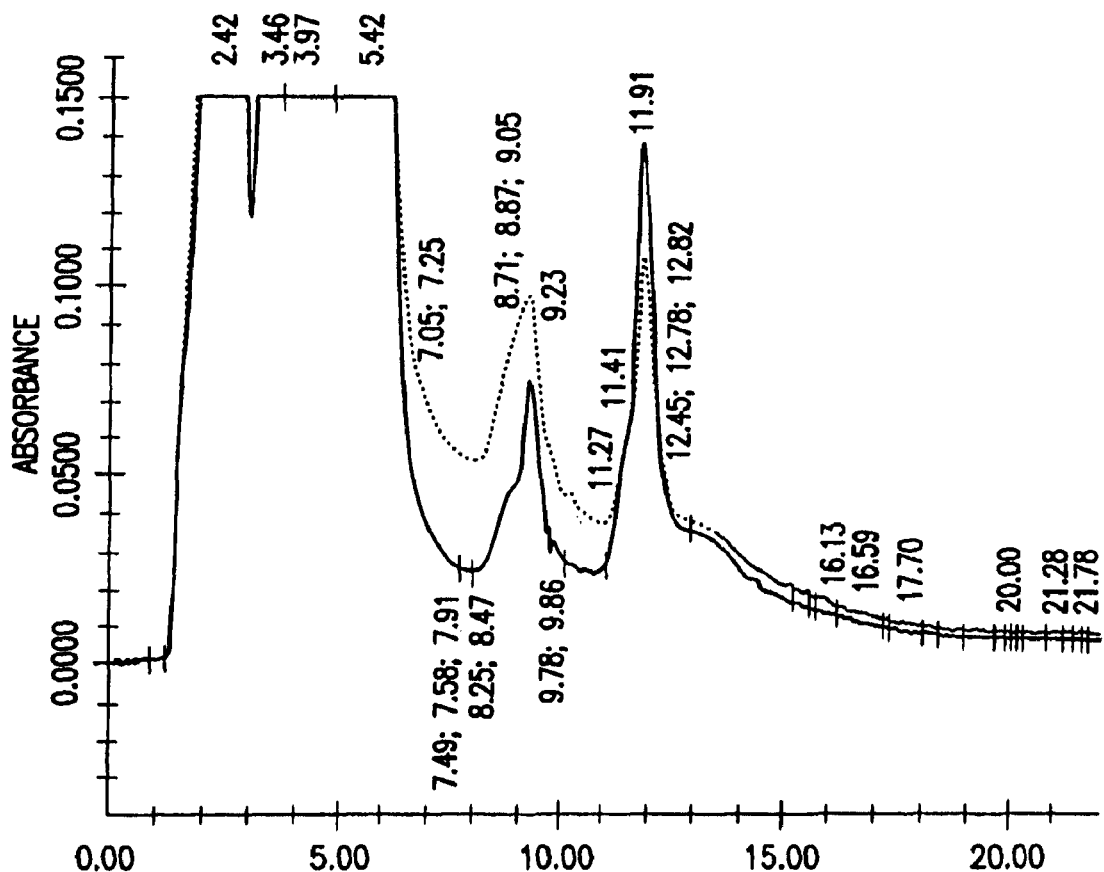
Figure 3E:
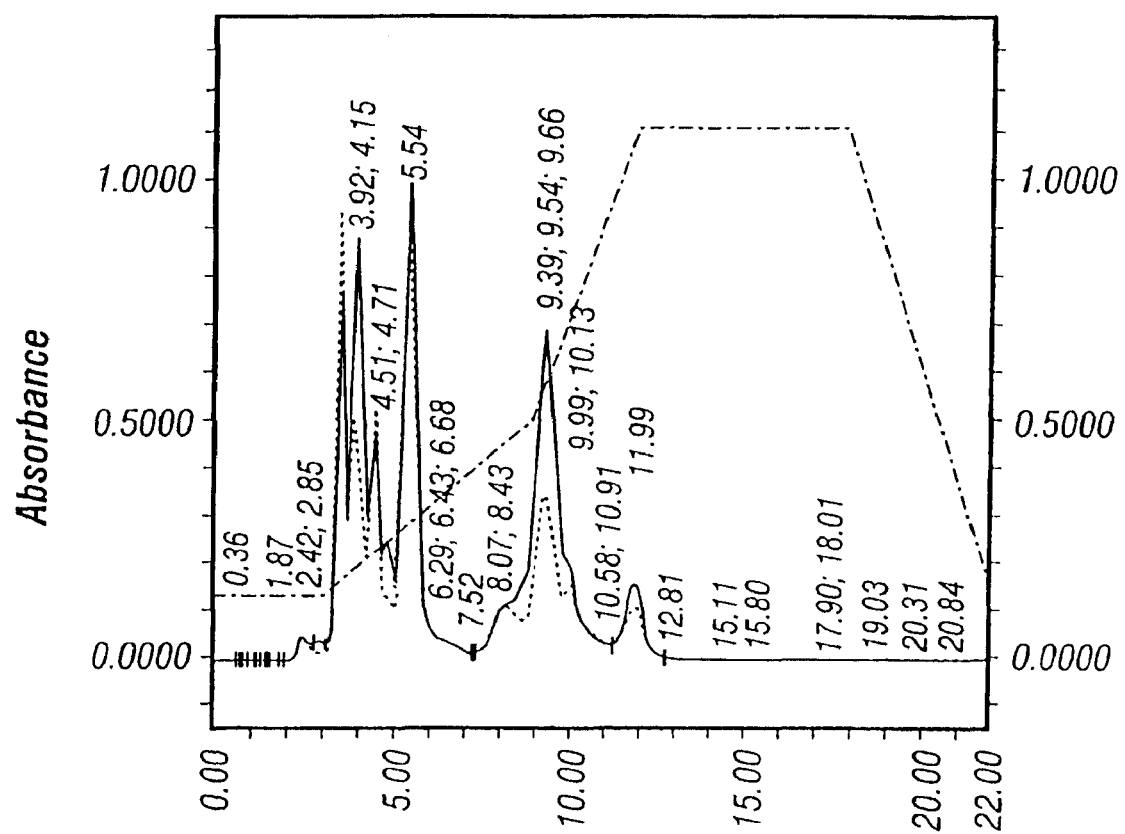

FIG. 2 shows the HPLC profile. No virus peak is observed at retention time of 9.32 min. Instead, two peaks at retention times of 9.11 and 9.78 min are produced. This profile suggests that the other contaminants having similar elution time as the virus exist in the CCL and interfere with the purification of the virus. As a result, very low purification efficiency was observed when the CCL was purified by IEC using FPLC.

In addition to the low purification efficiency, there was a significant product loss during the cell harvest step into the EDTA solution as indicated in Table 8. Approximately 20% of the product was lost into the EDTA solution which was discarded. In addition, about 24% of the crude virus product is present in the spent medium which was also discarded. Thus, only 56% of the crude virus product is in the CCL. Furthermore, freeze-thaw is a process of great variation and very limited scalability. A more efficient cell lysis process with less product loss needed to be developed.

TABLE 8

Loss of virus during EDTA harvest of cells from Cellcube ™

| | Waste Spent Medium | EDTA harvest Solution | Crude product Crude cell lysate | Total crude product (PFU) |
|---|---|---|---|---|
| Volume (ml) | 2800 | 2000 | 82 | — |
| Titer (PFU/ml) | $2.6 \times 10^8$ | $3 \times 10^8$ | $2 \times 10^{10}$ | — |
| Total virus (PFU) | $7.2 \times 10^{11}$ | $6 \times 10^{11}$ | $1.64 \times 10^{12}$ | $3 \times 10^{12}$ |
| Percentage | 24% | 20% | 56% | |

Data was generated from 1 mer Cellcube ™.

TABLE 9

Evaluation of non-ionic detergents for cell lysis

| Detergents | Concentrations (w/v) | Chemistry | Comments |
|---|---|---|---|
| Thesit | 1% 0.5% 0.1% | Dodecylpoly(ethylene glycol ether)$_n$, n = 9-10 | Large Precipitate |

TABLE 9-continued

Evaluation of non-ionic detergents for cell lysis

| Detergents | Concentrations (w/v) | Chemistry | Comments |
|---|---|---|---|
| NP-40 | 1% 0.5% 0.1% | Ethylphenolpoly (ethylene-glycolether)$_n$ n = 9-11 | Large precipitate |
| Tween-20 | 1% 0.5% 0.1% | Poly(oxyethylene)$_n$-sorbitan-monolaurate n = 20 | Small precipitate |
| Brij-58 | 1% 0.5% 0.1% | Cetylpoly (ethylene-glycolether)$_n$ n = 20 | Cloudy Solution |
| Triton X-100 | 1% 0.5% 0.1% | Octylphenolpoly(ethylene-glycoether)$_n$ n = 10 | Large precipitate |

Detergents have been used to lyse cells to release intracellular organelles. Consequently, the inventors evaluated the detergent lysis method for the release of adenovirus. Table 9 lists the 5 different non-ionic detergents that were evaluated for cell lysis. Cells were harvested from the Cellcube™ 48 hr post-infection using 50 mM EDTA. The cell pellet was resuspended in the different detergents at various concentrations listed in Table 9.

Cell lysis was carried out at either room temperature or on ice for 30 min. Clear lysis solution was obtained after centrifugation to remove the precipitate and cellular debris. The lysis solutions were treated with Benzonase and then analyzed by HPLC. FIG. 3 shows the HPLC profiles of lysis solutions from the different detergents. Thesit and NP-40 performed similarly as Triton X-100. Lysis solution generated from 1% Tween-20 gave the best virus resolution with the least virus resolution being observed with Brij-58. More efficient cell lysis was found at detergent concentration of 1% (w/v). Lysis temperature did not contribute significantly to the virus resolution under the detergent concentrations examined. For the purpose of process simplicity, lysis at room temperature is recommended. Lysis solution composed of 1% Tween-20 in 20 mM Tris+0.25M NaCl+1 mM MgCl$_2$, pH=7.50 was employed for cell lysis and virus harvest in the Cellcube™.

Example 4

Effects of Concentration/Diafiltration on Virus Recovery

Virus solution from the lysis step was clarified and filtered before concentration/diafiltration. TFF membranes of different NMWCs, including 100K, 300K, 500K, and 1000K, were evaluated for efficient concentration/diafiltration. The highest medium flux with minimal virus loss to the filtrate was obtained with a membrane of 300K NMWC. Bigger NMWC membranes offered higher medium flux, but resulted in greater virus loss to the filtrate, while smaller NMWC membranes achieved an insufficient medium flux. Virus solution was first concentrated 10-fold, which was followed by 4 sample volumes of diafiltration against 20 mM Tris+0.25 M NaCl+1 mM MgCl$_2$, pH=9.00 buffer using the constant volume method. During the concentration/diafiltration process, pressure drop across the membrane was kept $\leq$5 psi. Consistent, high level virus recovery was demonstrated during the concentration/diafiltration step as indicated in Table 10.

TABLE 10

Concentration/diafiltration of crude virus solution

| | Titer (PFU/ml) | | Volume (ml) | | Total virus (PFU) | | Recovery | |
|---|---|---|---|---|---|---|---|---|
| | Run #1 | Run #2 | Run #1 | Run #2 | Run #1 | Run #2 | Run #1 | Run #2 |
| Before conc./diafl. | $2.6 \times 10^9$ | $2 \times 10^9$ | 1900 | 2000 | $4.9 \times 10^{12}$ | $4 \times 10^{12}$ | | |
| Post conc./diafl. | $2.5 \times 10^{10}$ | $1.7 \times 10^{10}$ | 200 | 200 | $5 \times 10^{12}$ | $3.4 \times 10^{12}$ | 102% | 85% |
| Conc. Factor | | | 9.5 | 10 | | | | |
| Filtrate | $5 \times 10^5$ | $1 \times 10^6$ | 3000 | 3000 | $1.5 \times 10^9$ | $3 \times 10^9$ | | |

Example 5

Effect of Salt Addition on Benzonase Treatment

Virus solution after concentration/diafiltration was treated with Benzonase (nuclease) to reduce the concentration of contaminating nucleic acid in virus solution. Different working concentrations of Benzonase, which included 50, 100, 200, 300 units/ml, were evaluated for the reduction of nucleic acid concentrations. For the purpose of process simplicity, treatment was carried out at room temperature overnight. Significant reduction in contaminating nucleic acid that is hybridizable to human genomic DNA probe was seen after Benzonase treatment.

Figure 4A:
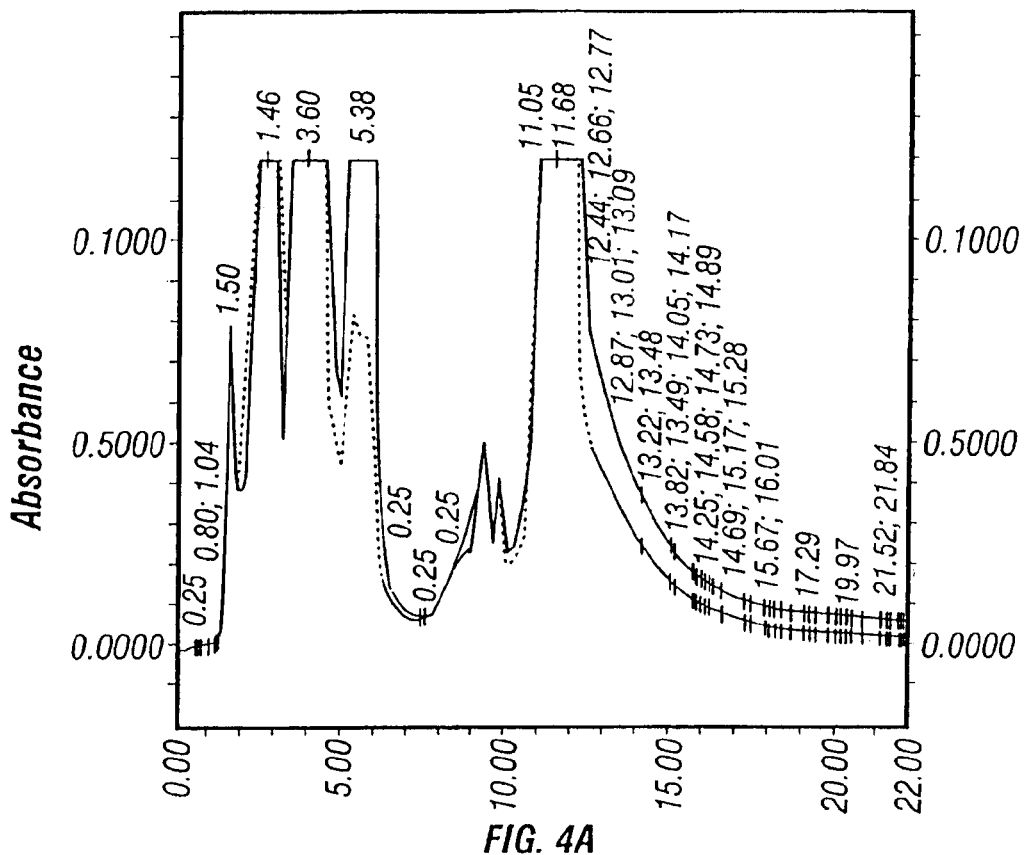
FIG. 4A and FIG. 4B. The HPLC profiles of virus solution before (FIG. 4A) and after (FIG. 4B) Benzonase treatment. (solid line $A_{260}$; dotted line $A_{280}$).
Figure 4B:
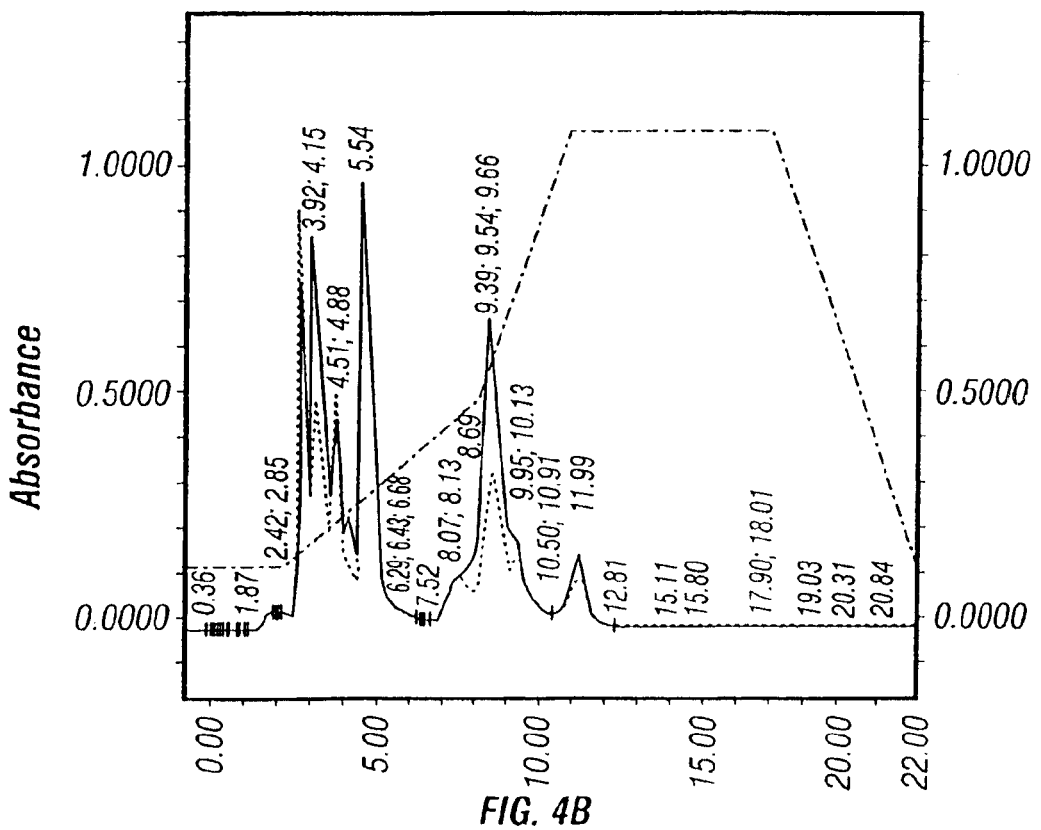

Table 11 shows the reduction of nucleic acid concentration before and after Benzonase treatment. Virus solution was analyzed on HPLC before and after Benzonase treatment. As shown in FIG. 4A and FIG. 4B, dramatic reduction in the contaminating nucleic acid peak was observed after Benzonase treatment. This is in agreement with the result of the nucleic acid hybridization assay. Because of the effectiveness, a Benzonase concentration of 100 u/ml was employed for the treatment of the crude virus solution.

TABLE 11

Reduction of contaminating nucleic acid concentration in virus solution

| | Before Treatment | After Treatment | Reduction |
|---|---|---|---|
| Contaminating nucleic acid concentration | 200 μg/ml | 10 ng/ml | $2 \times 10^4$-fold |

Treatment condition: Benzonase concentration: 100 u/ml, temperature: room temperature, time: overnight.

Considerable change in the HPLC profile was observed pre- and post-Benzonase treatment. No separated virus peak was detected at retention time of 9.33 min after Benzonase treatment. At the same time, a major peak with high 260 nm adsorption at retention time of 9.54 min was developed. Titer assay results indicated that Benzonase treatment did not negatively affect the virus titer and virus remained intact and infectious after Benzonase treatment. It was reasoned that cellular nucleic acid released during the cell lysis step interacted with virus and either formed aggregates with the virus or adsorbed onto the virus surface during Benzonase treatment.

Figure 5:
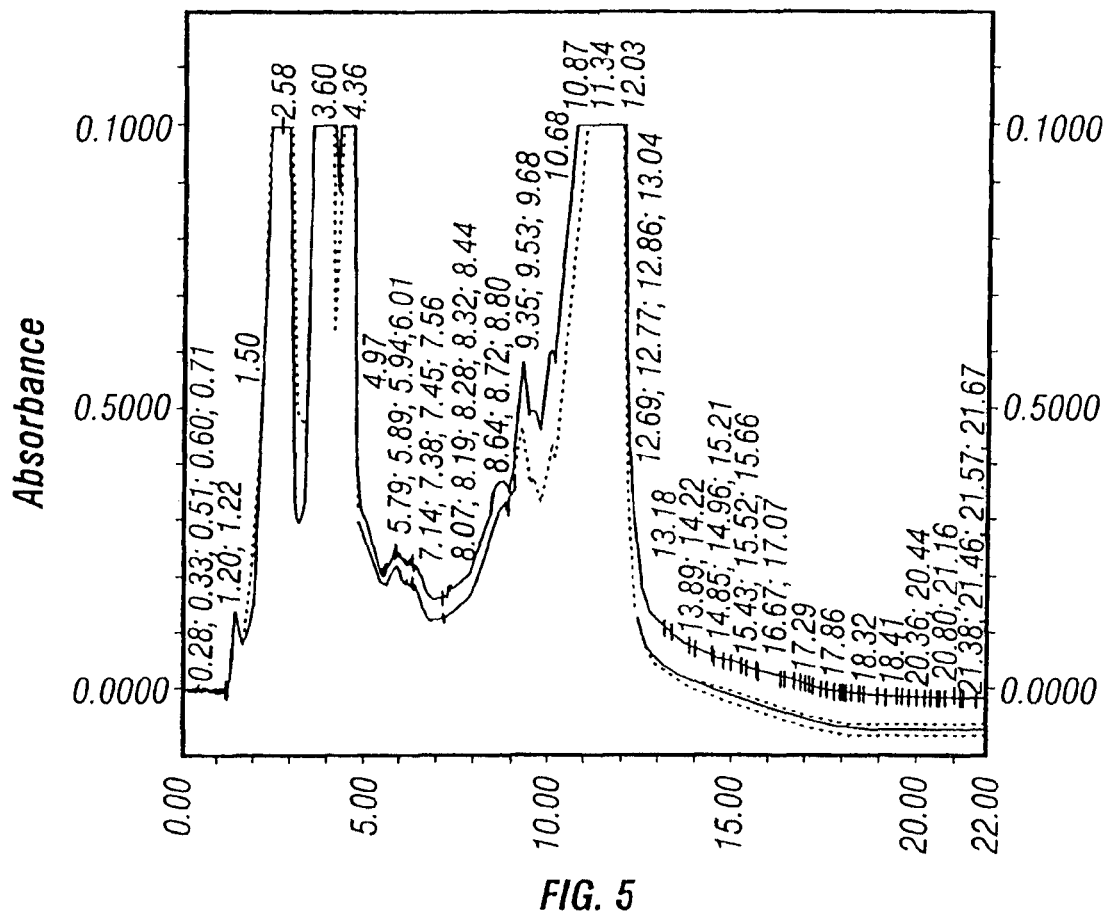
FIG. 5. The HPLC profile of virus solution after Benzonase treatment in the presence of 1M NaCl. (solid line $A_{260}$; dotted line $A_{280}$).

To minimize the possible nucleic acid virus interaction during Benzonase treatment, different concentrations of NaCl was added into the virus solution before Benzonase treatment. No dramatic change in the HPLC profile occurred after Benzonase treatment in the presence of 1 M NaCl in the virus solution. FIG. 5 shows the HPLC profile of virus solution after Benzonase treatment in the presence of 1M NaCl. Unlike that shown in FIG. 4B, virus peak at retention time of 9.35 min still exists post Benzonase treatment. This result indicates that the presence of 1M NaCl prevents the interaction of nucleic acid with virus during Benzonase treatment and facilitates the further purification of virus from contaminating nucleic acid.

Example 6

Ion Exchange Chromatographic Purification

The presence of negative charge on the surface of adenovirus at physiological pH conditions prompted evaluation of anionic ion exchangers for adenovirus purification. The strong anionic ion exchanger Toyopearl Super Q 650M was used for the development of a purification method. The effects of NaCl concentration and pH of the loading buffer (buffer A) on virus purification was evaluated using the FPLC system.

A) Method Development

For ion exchange chromatography, buffer pH is one of the most important parameters and can have dramatic influence on the purification efficiency. In reference to the medium pH and conductivity used during virus production, the inventors formulated 20 mM Tris+1 mM $MgCl_2$+0.2M NaCl, pH=7.50 as buffer A. A XK16 column packed with Toyopearl SuperQ 650M with a height of 5 cm was conditioned with buffer A.

A sample of 5 ml of Benzonase treated concentrated/diafiltrated virus supernatant from the Celligen bioreactor was loaded onto the column. After washing the column, elution was carried out with a linear gradient of over 10 column volumes to reach buffer B (20 mM Tris+1 mM $MgCl_2$+2M NaCl, pH=7.50).

Figure 6:
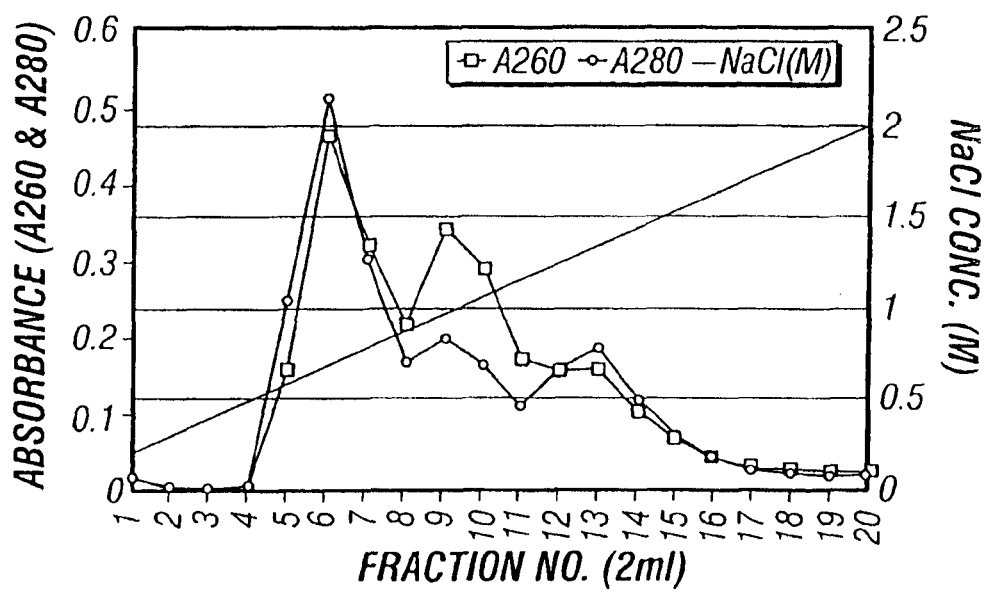
FIG. 6. Purification of AdCMVp53 virus under buffer A condition of 20 mM Tris+1 mM $MgCl_2$+0.2M NaCl, pH=7.5.
Figure 7:
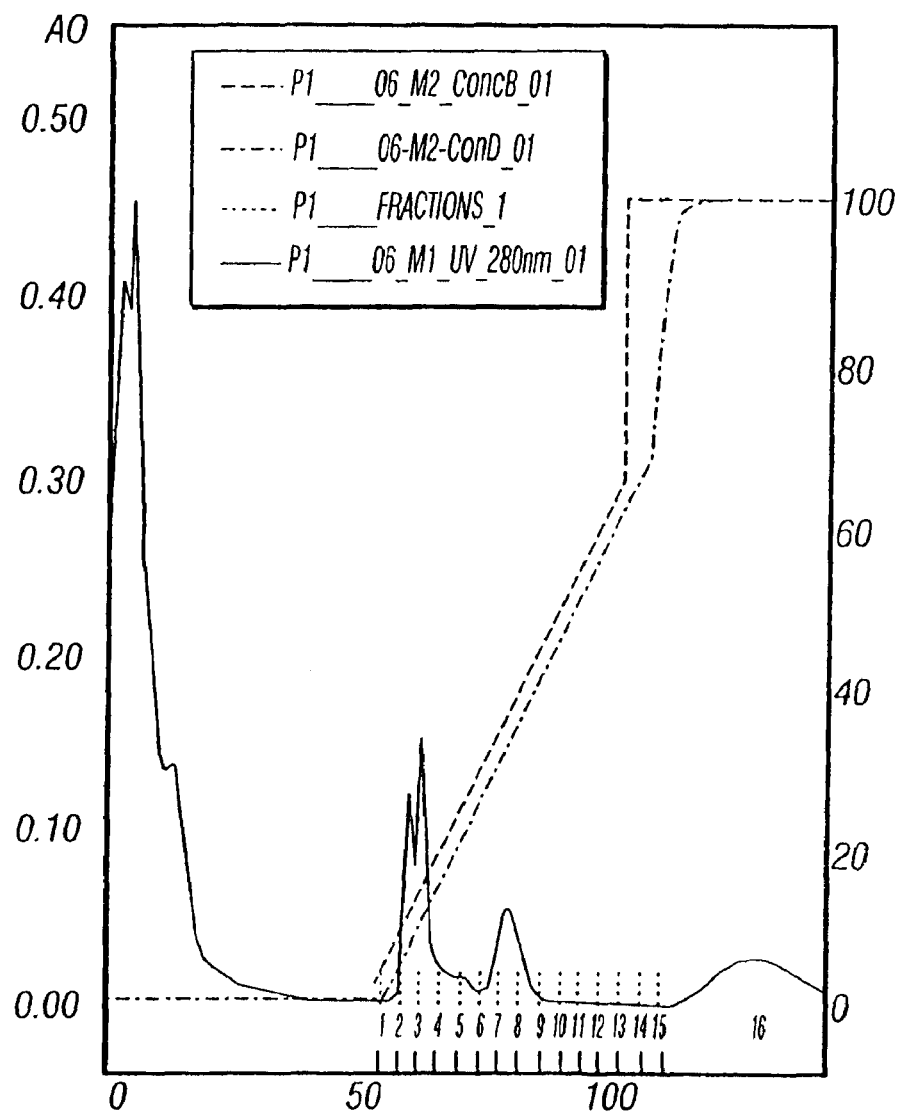
FIG. 7. Purification of AdCMVp53 virus under buffer A condition of 20 mM Tris+1 mM $MgCl_2$+0.2M NaCl, pH=9.0.

FIG. 6 shows the elution profile. Three peaks were observed during elution without satisfactory separation among them. Control study performed with 293 cell conditioned medium (with no virus) showed that the first two peaks are virus related. To further improve the separation efficiency, the effect of buffer pH was evaluated. Buffer pH was increased to 9.00 while keeping other conditions constant. Much improved separation, as shown in FIG. 7, was observed as compared to that of buffer pH of 7.50. Fractions #3, #4, and #8 were analyzed on HPLC.

Figure 8A:
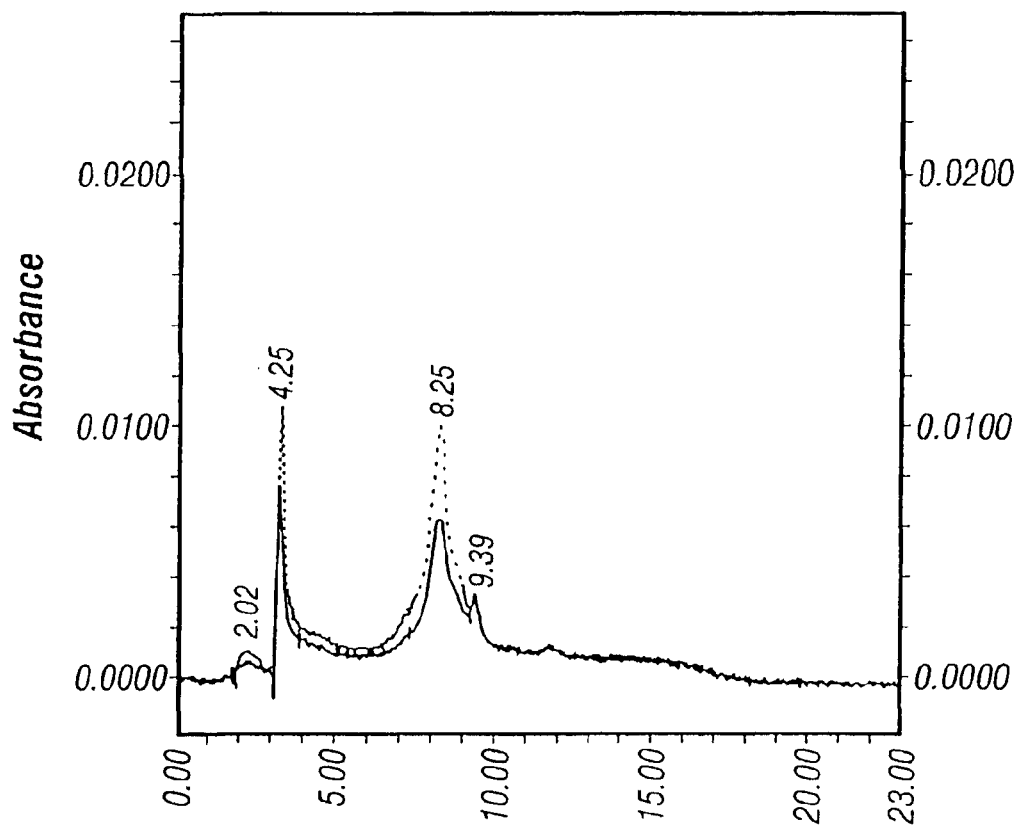
FIG. 8A, FIG. 8B, and FIG. 8C. HPLC analysis of fractions obtained during purification FIG. 8A fraction 3.
Figure 8B:
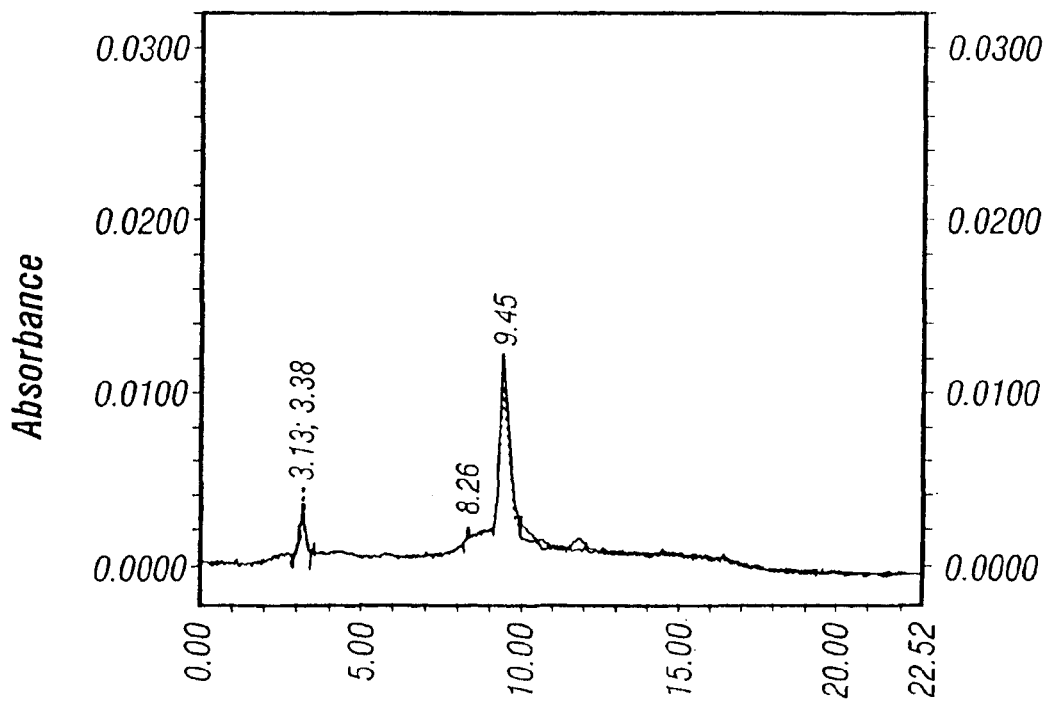
Figure 8C:
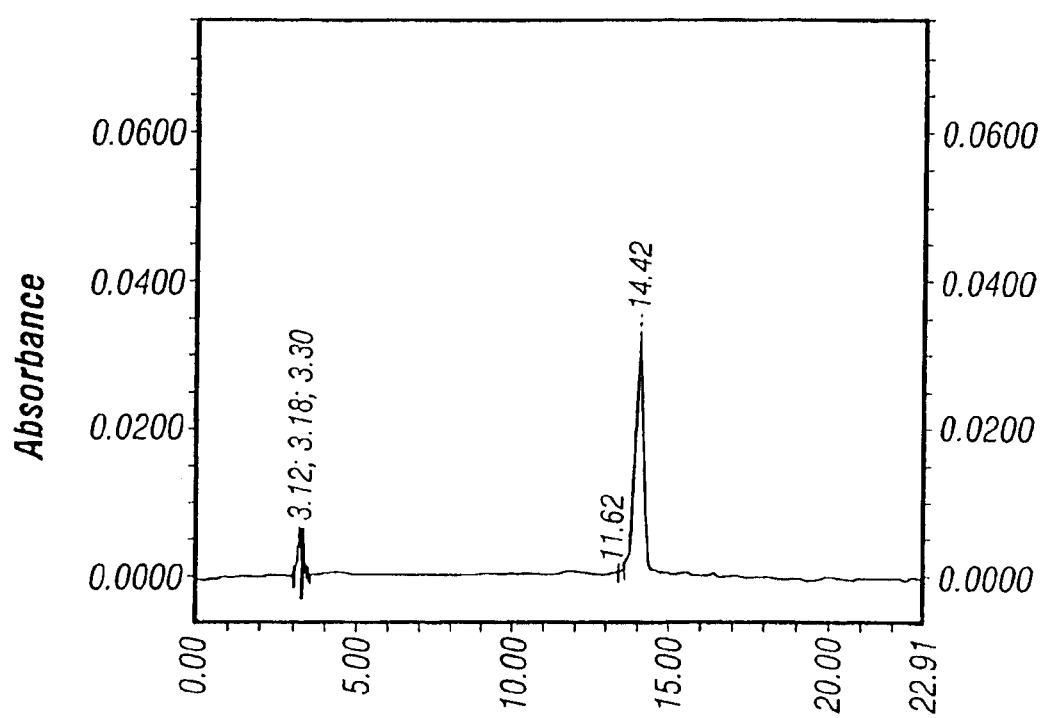

As shown in FIG. 8, the majority of virus was found in fraction #4, with no virus being detected in fractions #3 and #8. Fraction #8 was found to be mainly composed of contaminating nucleic acid. However, the purification was still not optimal. There is overlap between fractions #3 and #4 with contaminants still detected in fraction #4.

Figure 9:
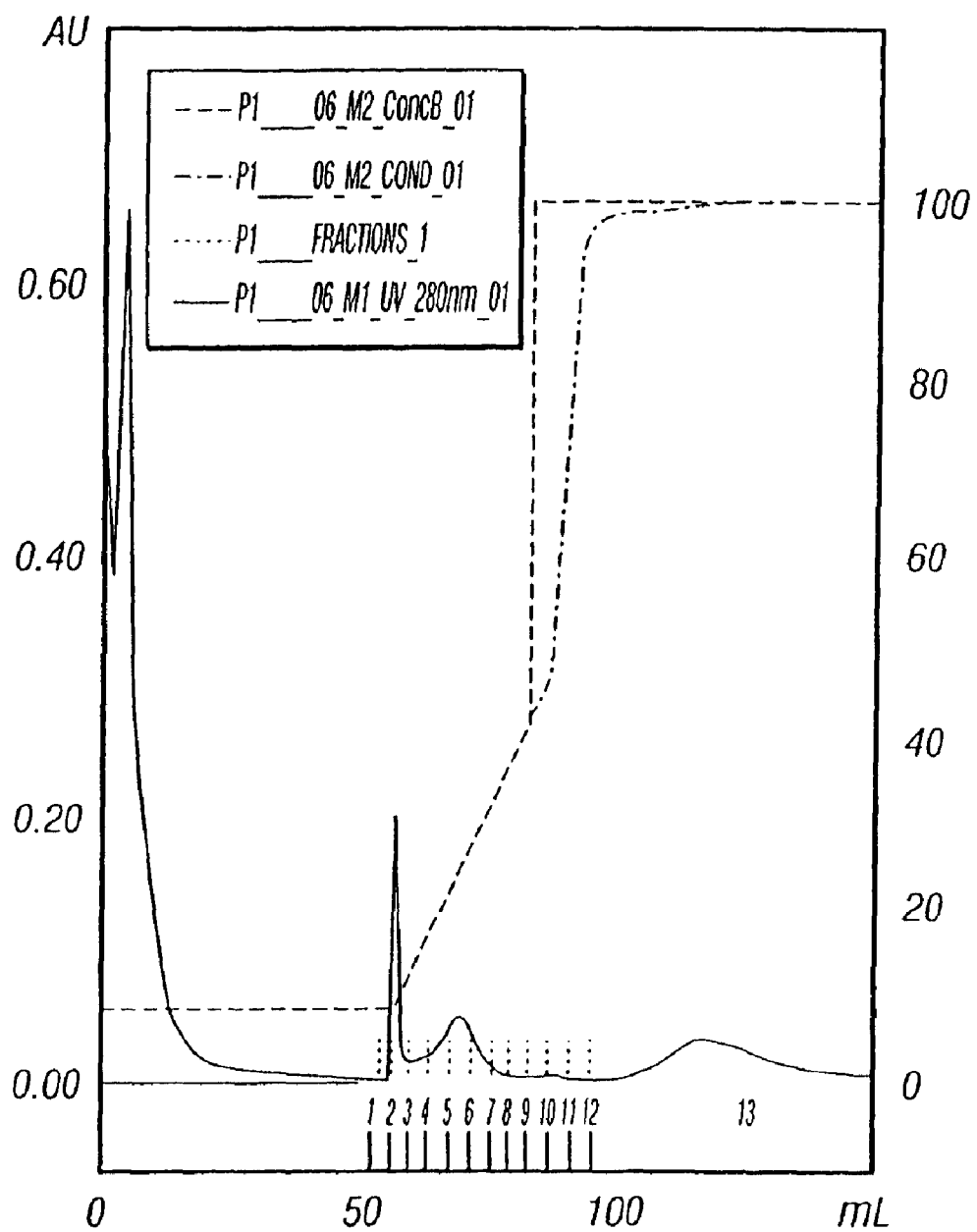
FIG. 9. Purification of AdCMVp53 virus under buffer A condition of 20 mM Tris+1 mM $MgCl_2$+0.3M NaCl, pH=9.
Figure 10A:
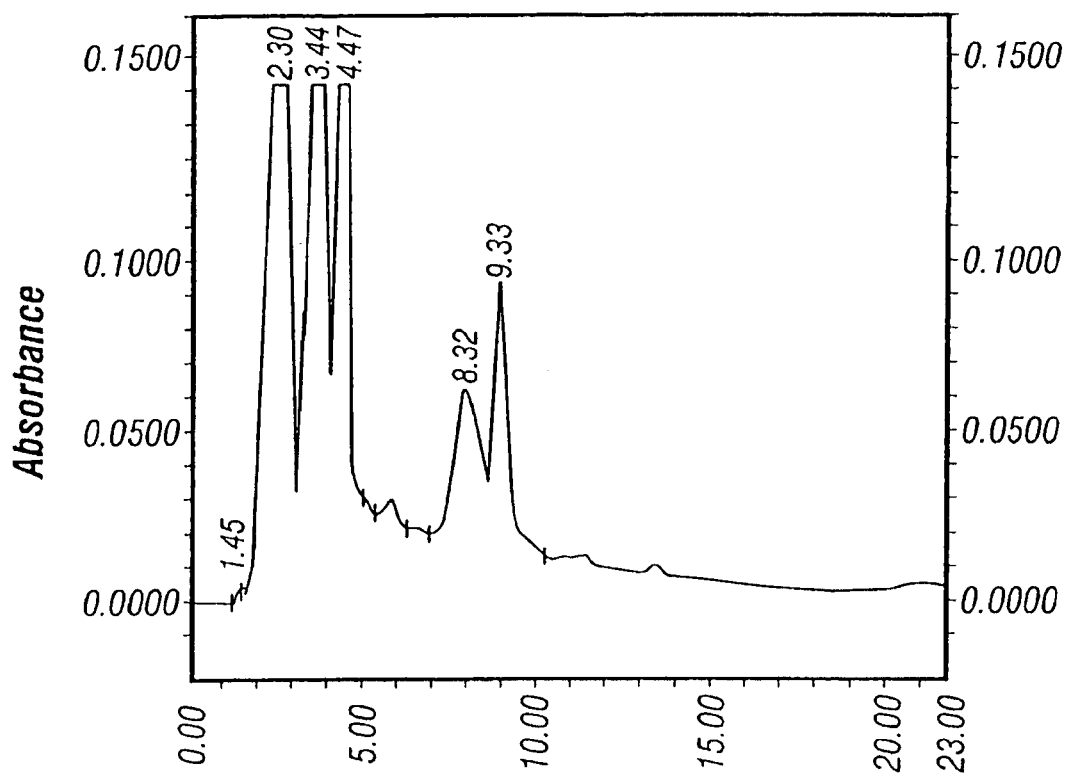
FIG. 10A, FIG. 10B, FIG. 10C, FIG. 10D and FIG. 10E. HPLC analysis of crude virus fractions obtained during purification and CsCl gradient purified virus.
Figure 10B:
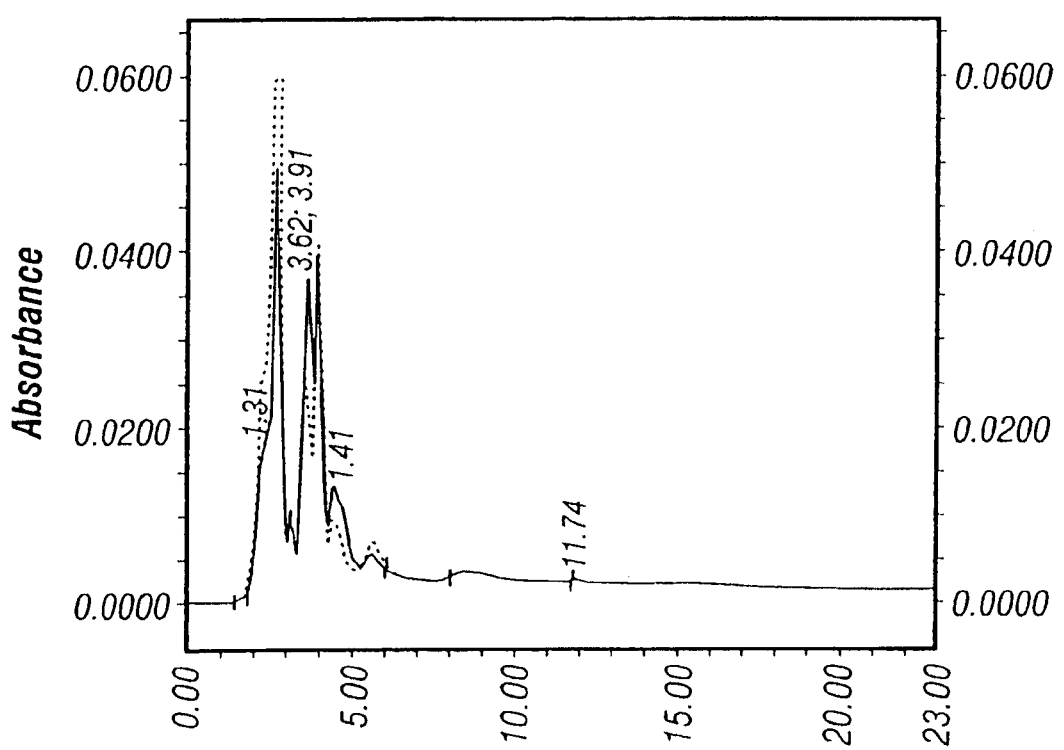
Figure 10C:
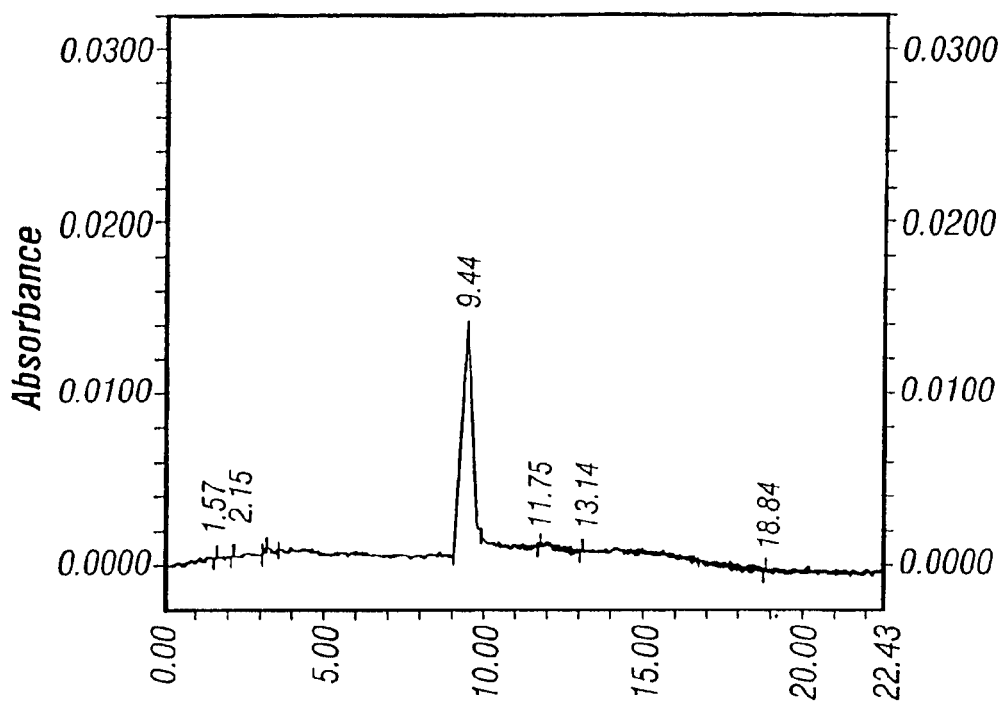
Figure 10D:
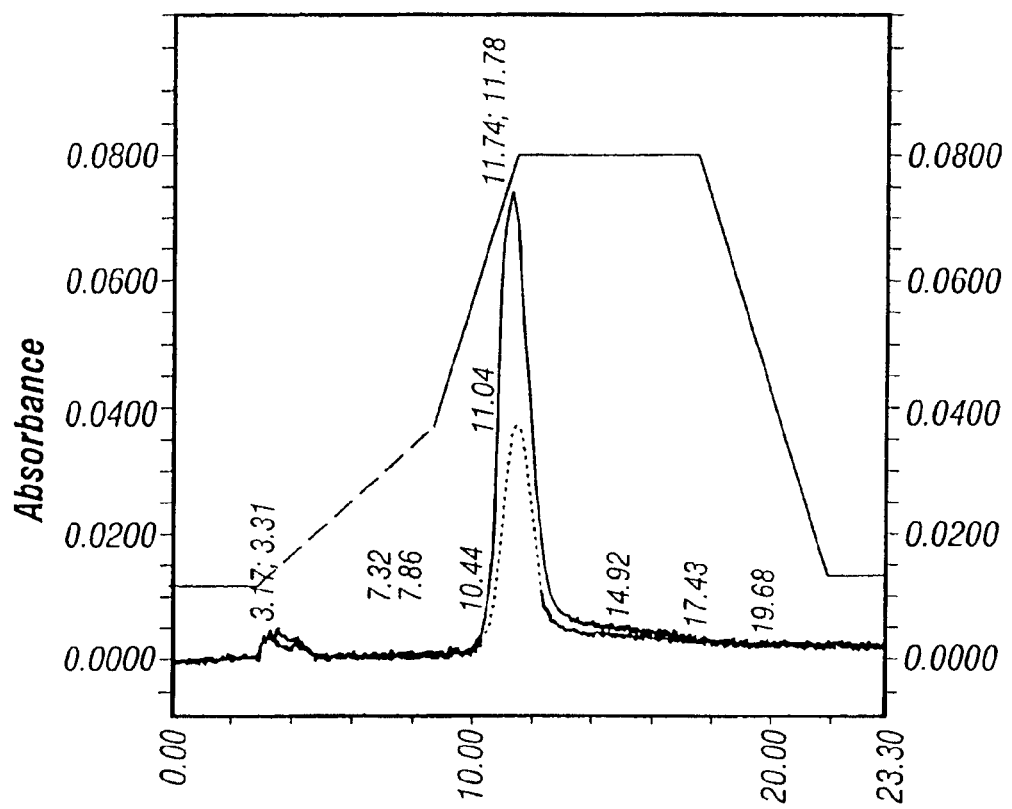
Figure 10E:
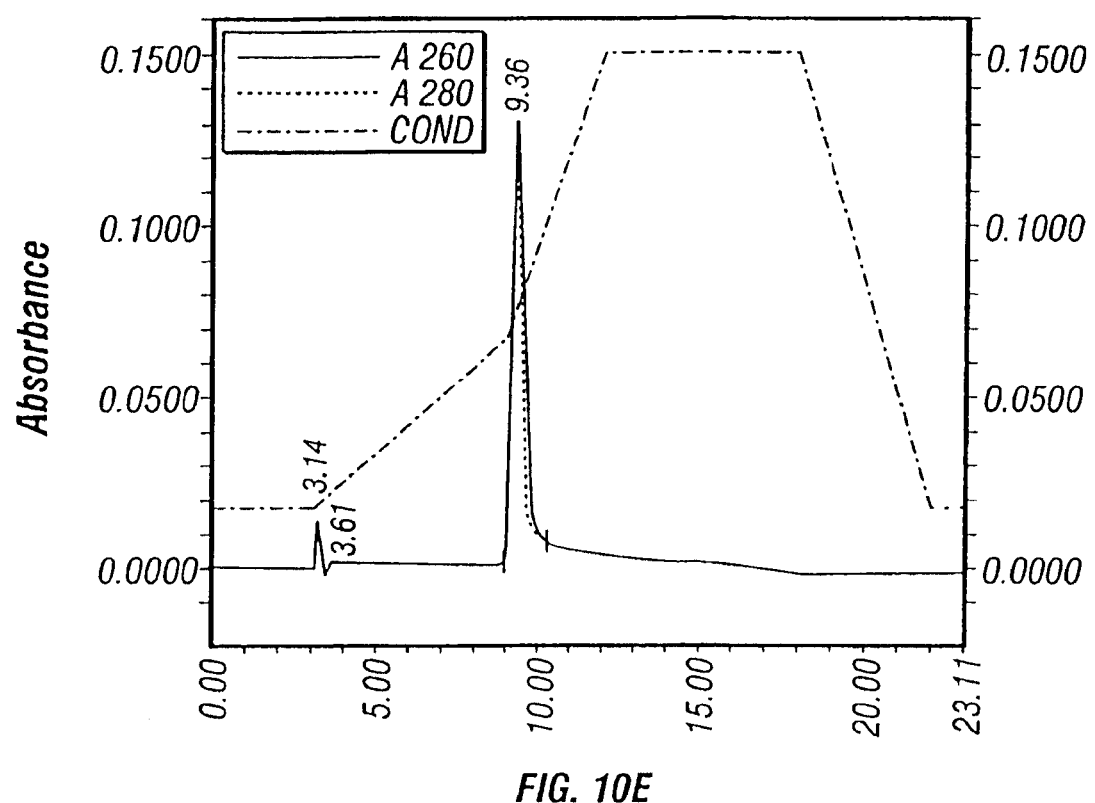

Based on the chromatogram in FIG. 7, it was inferred that further improvement of virus purification could be achieved by increasing the salt concentration in buffer A. As a result, the contaminants present in the fraction #3, which is prior to the virus peak, can be shifted to the flow through faction. The NaCl concentration in buffer A was increased to 0.3 M while keeping other conditions constant. FIG. 9 shows the elution profile under the condition of 0.3 M NaCl in buffer A.

Dramatic improvement in purification efficiency was achieved. As expected the contaminant peak observed in FIG. 7 was eliminated under the increased salt condition. Samples from crude virus sup, flow through, peak #1, and peak #2 were analyzed on HPLC and the results are shown in FIG. 10. No virus was detected in the flow through fraction. The majority of the contaminants present in the crude material were found in the flow through. HPLC analysis of peak #1 showed a single well defined virus peak. This HPLC profile is equivalent to that obtained from double CsCl gradient purified virus. Peaks observed at retention times of 3.14 and 3.61 min in CsCl gradient purified virus are glycerol related peaks. The purified virus has a A260/A280 ratio of 1.27±0.03. This similar to the value of double CsCl gradient purified virus as well as the results reported by Huyghe et al. (1996). Peak #2 is composed mainly of contaminating nucleic acid. Based on the purification result, the inventors proposed the following method for IEC purification of adenovirus sup from the bioreactor.

Buffer A: 20 mM Tris+1 mM $MgCl_2$+0.3M NaCl, pH=9.00

Buffer B: 20 mM Tris+1 mM $MgCl_2$+2M NaCl, pH=9.00

Elution: 10 column volume linear gradient

B) Method Scale-Up

Figure 11:
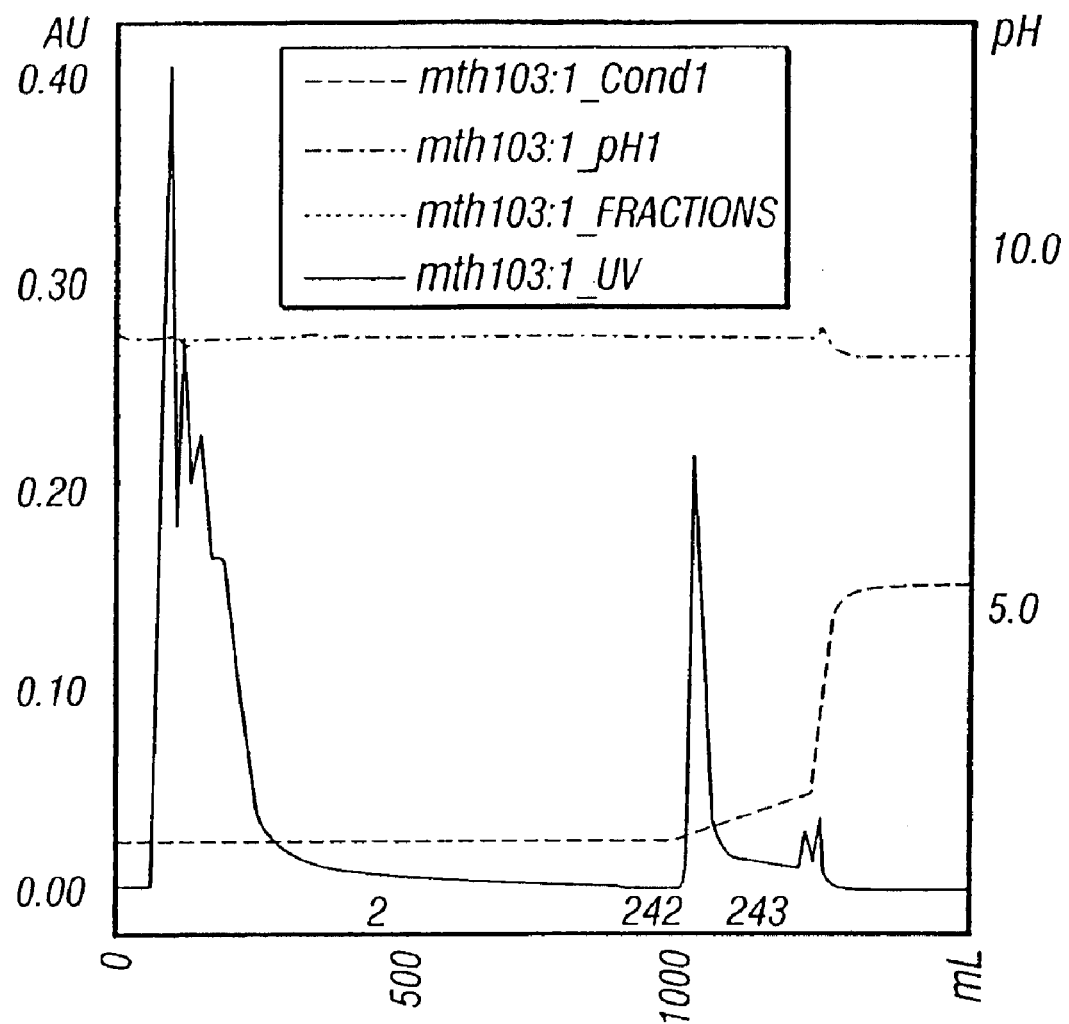
FIG. 11. HPLC purification profile from a 5 cm id column.

Following the development of the method, purification was scaled-up from the XK16 column (1.6 cm I.D.) to a XK50 column (5 cm I.D., 10-fold scale-up) using the same purification method. A similar elution profile was achieved on the XK50 column as shown in FIG. 11. The virus fraction was analyzed on HPLC, which indicated equivalent virus purity to that obtained from the XK16 column.

During the scale-up studies, it was found that it was more convenient and consistent to use conductivity to quantify the salt concentration in buffer A. The optimal conductivity of buffer A is in the range of 25±2 mS/cm at approximately room temperature (21° C.). Samples produced during the purification process together with double CsCl purified virus were analyzed on SDS-PAGE.

Figure 12:
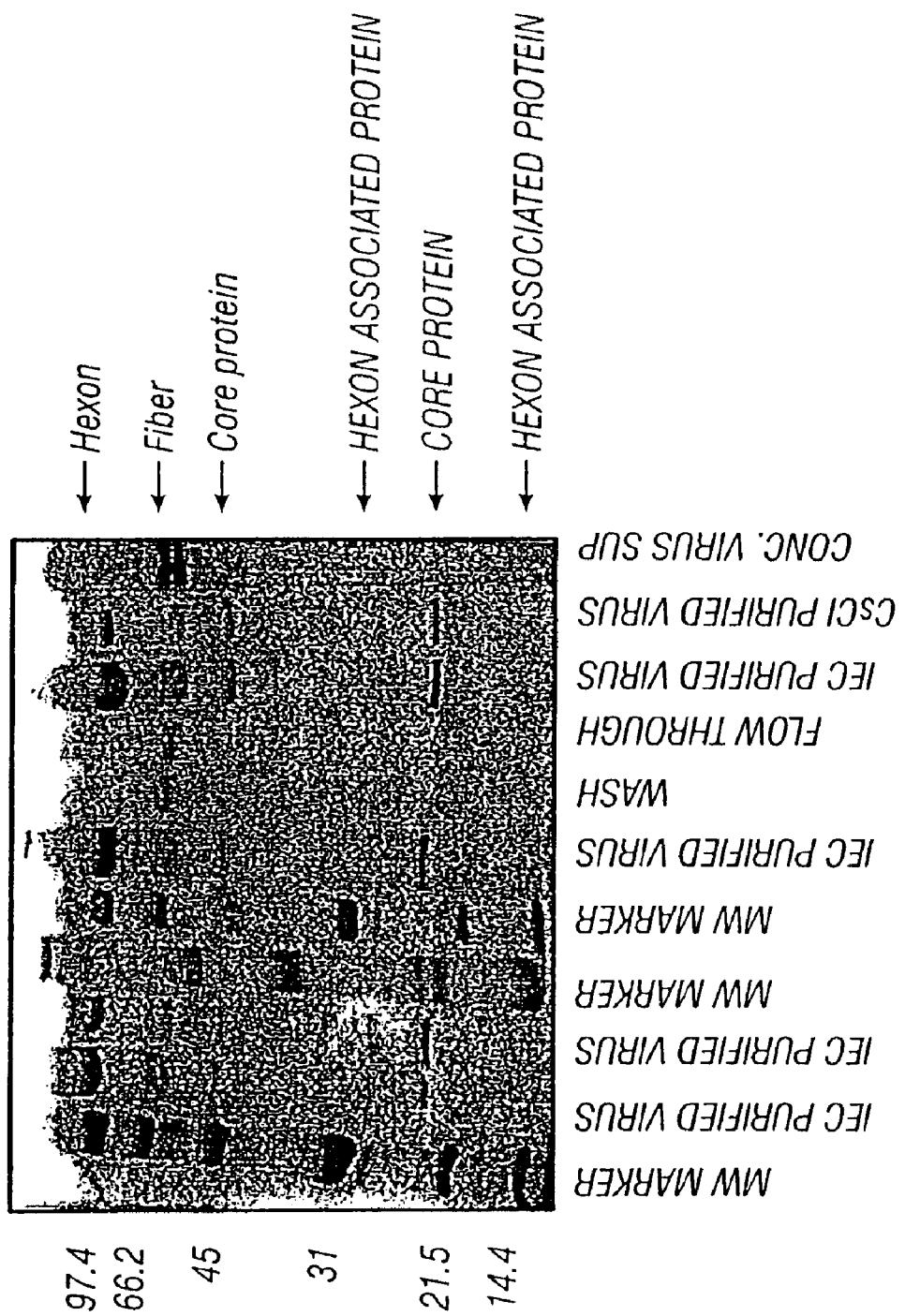
FIG. 12. The major adenovirus structure proteins detected on SDS-PAGE.
Figure 13:
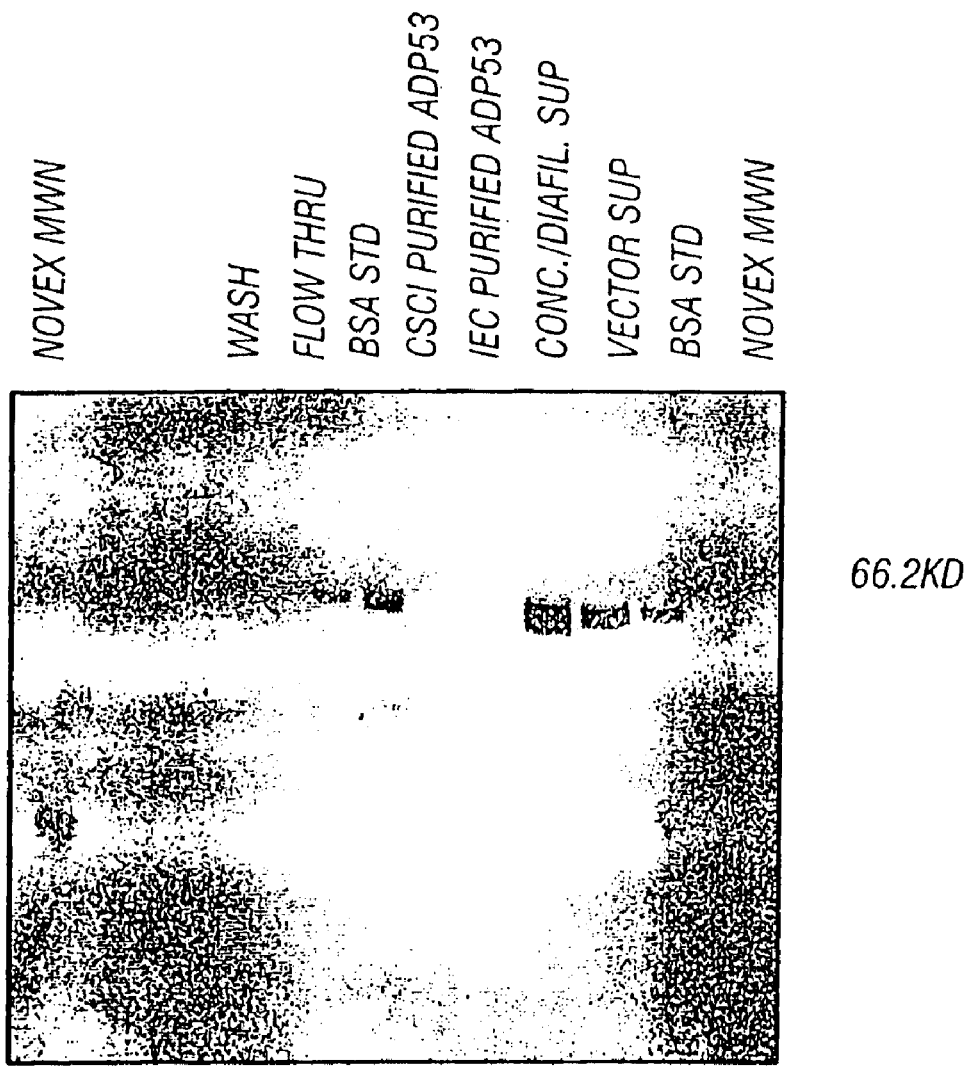
FIG. 13. The BSA concentration in the purified virus as detected level of the western blot assay.

As shown in FIG. 12, all the major adenovirus structure proteins are detected on the SDS-PAGE. The IEC purified virus shows equivalent staining as that of the double CsCl purified virus. Significant reduction in bovine serum albumin (BSA) concentration was achieved during purification. The BSA concentration in the purified virus was below the detection level of the western blot assay as shown in FIG. 13.

The reduction of contaminating nucleic acid concentration in virus solution during the purification process was determined using nucleic acid slot blot. $^{32}P$ labeled human genomic DNA was used as the hybridization probe (because 293 cells are human embryonic kidney cells). Table 12 shows the nucleic acid concentration at different stages of the purification process. Nucleic acid concentration in the final purified virus solution was reduced to 60 pg/ml, an approximate $3.6 \times 10^6$-fold reduction compared to the initial virus supernatant. Virus titer and infectious to total particle ratio were determined for the purified virus and the results were compared to that from double CsCl purification in Table 11. Both virus recovery and particle/PFU ratio are very similar between the two purification methods. The titer of the column purified virus solution can be further increased by performing a concentration step.

TABLE 12

Removal of contaminating nucleic acids during purification

| Steps during purification | Contaminating nucleic acid concentration |
|---|---|
| Virus supernatant from bioreactor | 220 µg/ml |
| Concentrated/diafiltrated sup | 190 µg/ml |
| Sup post Benzonase treatment (O/N, RT, 100 u/ml) | 10 ng/ml |
| Purified virus from column | 210 pg/ml |
| Purified virus post concentration/diafiltration | 60 pg/ml |
| CsCl purified virus | 800 pg/ml |

Example 7

Other Purification Methods

In addition to the strong anionic ion exchange chromatography, other modes of chromatographic methods, were also evaluated for the purification of AdCMVp53 virus (e.g. size exclusion chromatography, hydrophobic interaction chromatography, cation exchange chromatography, or metal ion affinity chromatography). Compared to the Toyopearl Super Q, all those modes of purification offered much less efficient purification with low product recovery. Therefore, Toyopearl Super Q resin is recommended for the purification of AdCMVp53. However, other quaternary ammonium chemistry based strong anionic exchangers are likely to be suitable for the purification of AdCMVp53 with some process modifications.

Example 8

Purification of Crude AdCMVp53 Virus Generated from Cellcube™

Two different production methods were developed to produce AdCMVp53 virus. One was based on microcarrier culture in a stirred tank bioreactor. The other was based on a Cellcube™ bioreactor. As described above, the purification method was developed using crude virus supernatant generated from the stirred tank bioreactor. It was realized that although the same medium, cells and viruses were used for virus production in both the bioreactor and the Cellcube™, the culture surface onto which cells attached was different.

In the bioreactor, cells were grown on a glass coated microcarrier, while in the Cellcube™ cells were grown on proprietary treated polystyrene culture surface. Constant medium perfusion was used in the Cellcube™, on the other hand, no medium perfusion was used in the bioreactor. In the Cellcube™, the crude virus product was harvested in the form of virally infected cells, which is different from the virus supernatant harvested from the bioreactor.

Figure 14:
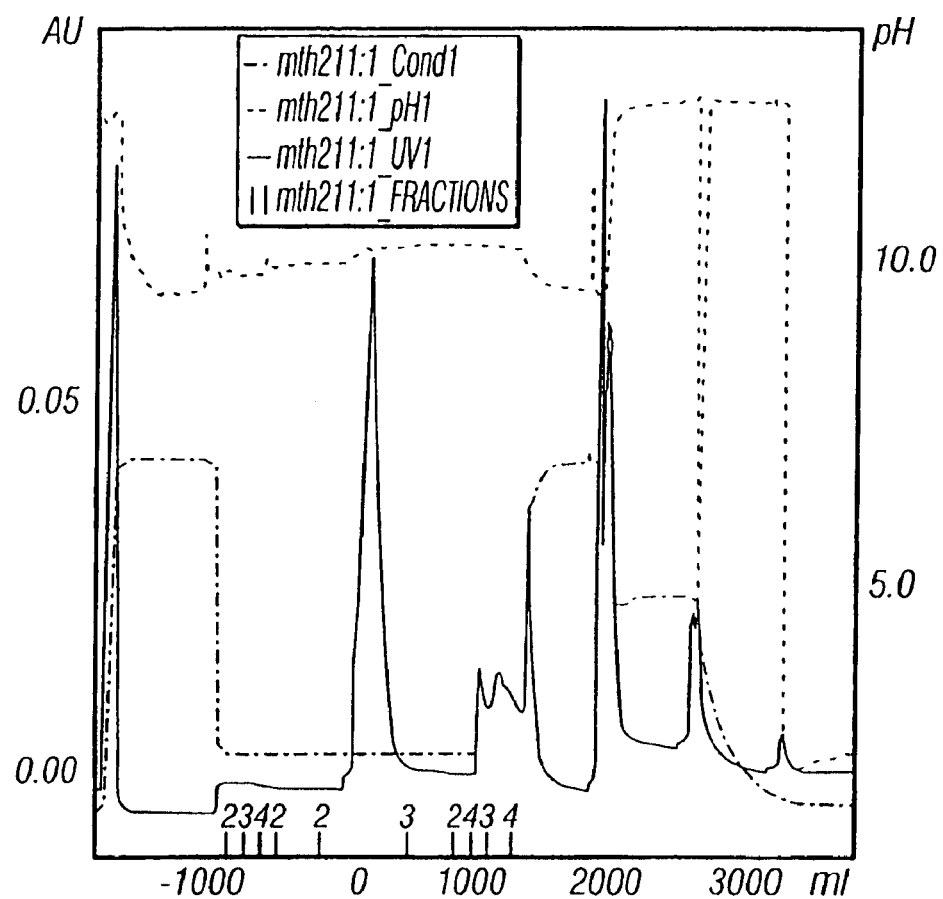
FIG. 14. The chromatogram for the crude cell lysate material generated from the CellCube™.

Crude cell lysate (CCL), produced after 5 cycles freeze-thaw of the harvested virally infected cells, was purified by IEC using the above described method. Unlike the virus supernatant from the bioreactor, no satisfactory purification was achieved for the CCL material generated from the Cellcube™. FIG. 14 shows the chromatogram. The result suggests that crude virus solution generated from the Cellcube™ by freeze-thawing harvested cells is not readily purified by the IEC method.

Other purification methods, including hydrophobic interaction and metal chelate chromatography, were examined for the purification of virus in CCL. Unfortunately, no improvement in purification was observed by either method. Considering the difficulties of purification of virus in CCL and the disadvantages associated with a freeze-thaw step in the production process, the inventors decided to explore other cell lysis methods.

A) Purification of Crude Virus Solution in Lysis Buffer

As described in Examples 1 and 3, HPLC analysis was used to screen different detergent lysis methods. Based on the HPLC results, 1% Tween-20 in 20 mM Tris+0.25 M NaCl+1 mM $MgCl_2$, pH=7.50 buffer was employed as the lysis buffer. At the end of the virus production phase, instead of harvesting the infected cells, the lysis buffer was pumped into the Cellcube™ after draining the spent medium. Cells were lysed and virus released into the lysis buffer by incubating for 30 min.

Figure 15:
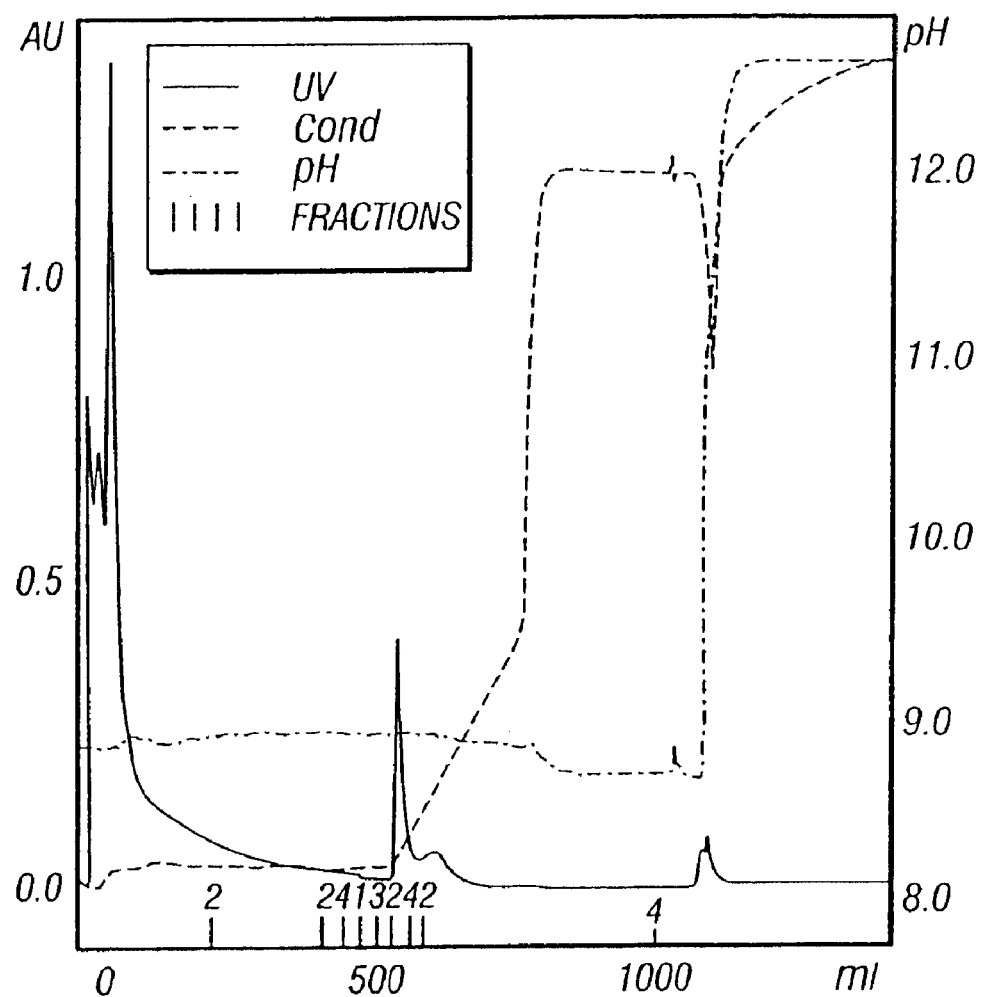
FIG. 15. The elution profile of treated virus solution purified using the method of the present invention using Toyopearl SuperQ resin.
Figure 16A:
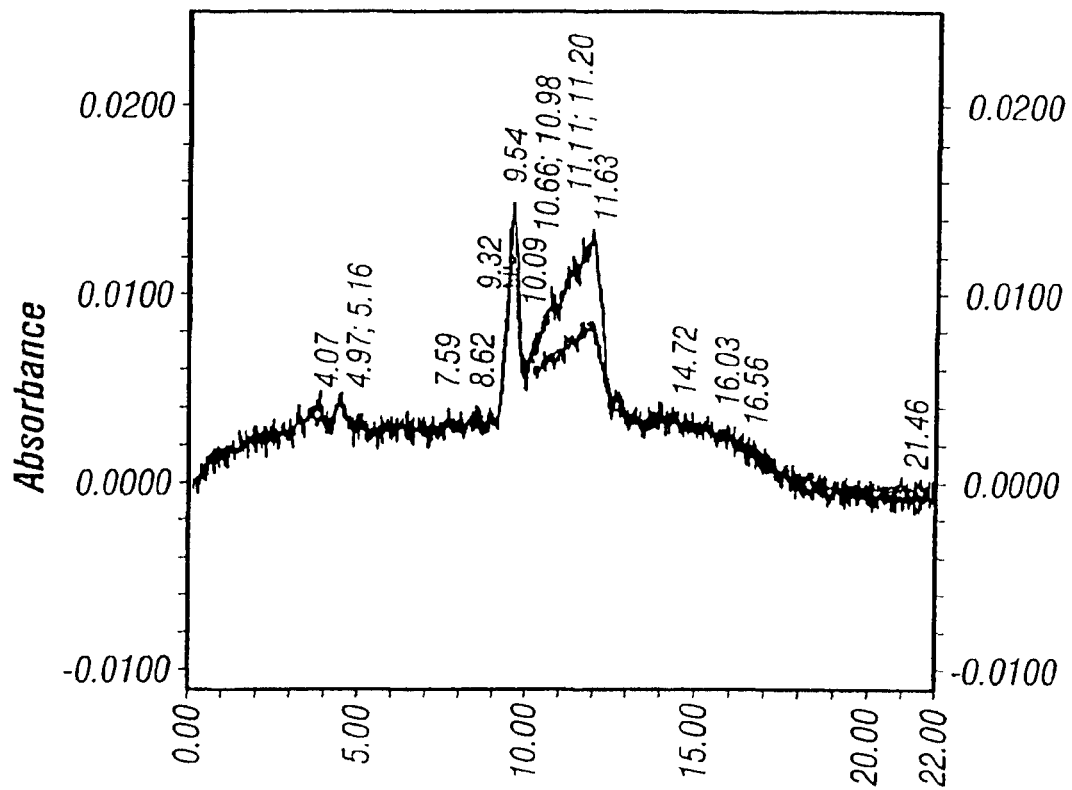
FIG. 16A and FIG. 16B. HPLC analysis of virus fraction from purification protocol.

After clarification and filtration, the virus solution was concentrated/diafiltrated and treated with Benzonase to reduce the contaminating nucleic acid concentration. The treated virus solution was purified by the method developed above using Toyopearl SuperQ resin. Satisfactory separation, similar to that obtained using virus supernatant from the bioreactor, was achieved during elution. FIG. 15 shows the elution profile. However, when the virus fraction was analyzed on HPLC, another peak in addition to the virus peak was detected. The result is shown in FIG. 16A.

Figure 16B:
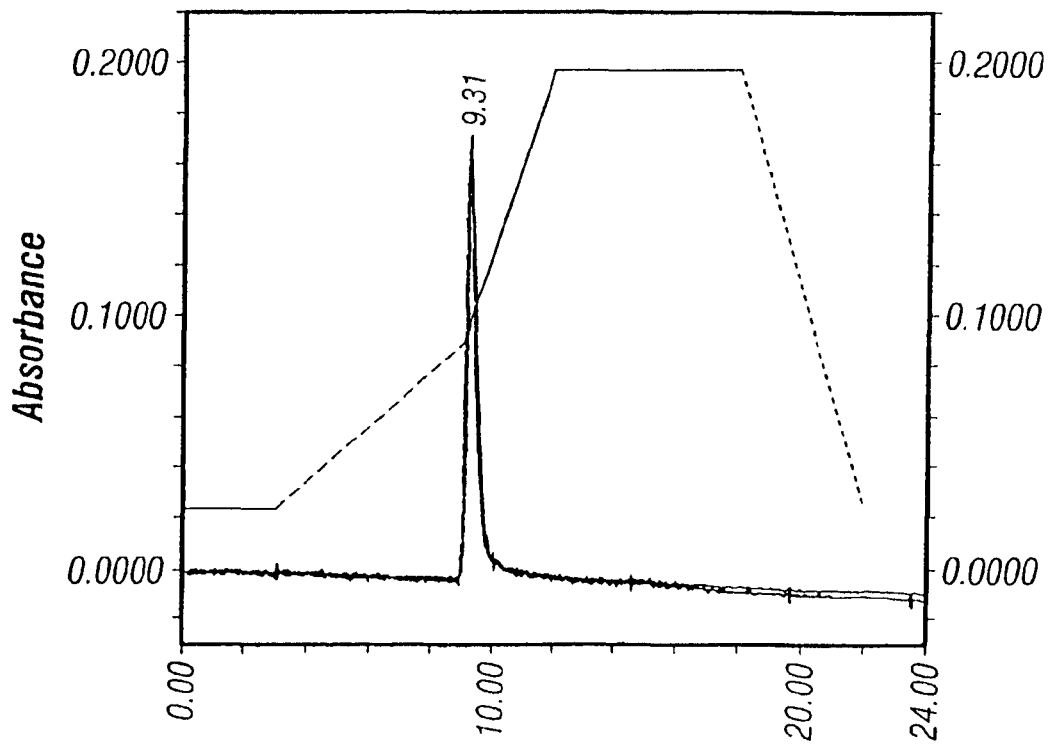

To further purify the virus, the collected virus fraction was re-purified using the same method. As shown in FIG. 16B, purity of the virus fraction improved considerably after the second purification. Metal chelate chromatography was also evaluated as a candidate for the second purification. Similar improvement in virus purity as seen with the second IEC was achieved. However, because of its simplicity, IEC is preferred as the method of choice for the second purification.

As described above in Example 2, medium perfusion rate employed during the cell growth and virus production phases has a considerable impact on the HPLC separation profile of the Tween-20 crude virus harvest. For crude virus solution produced under high medium perfusion rate, two ion exchange columns are required to achieve the required virus purity.

Figure 17:
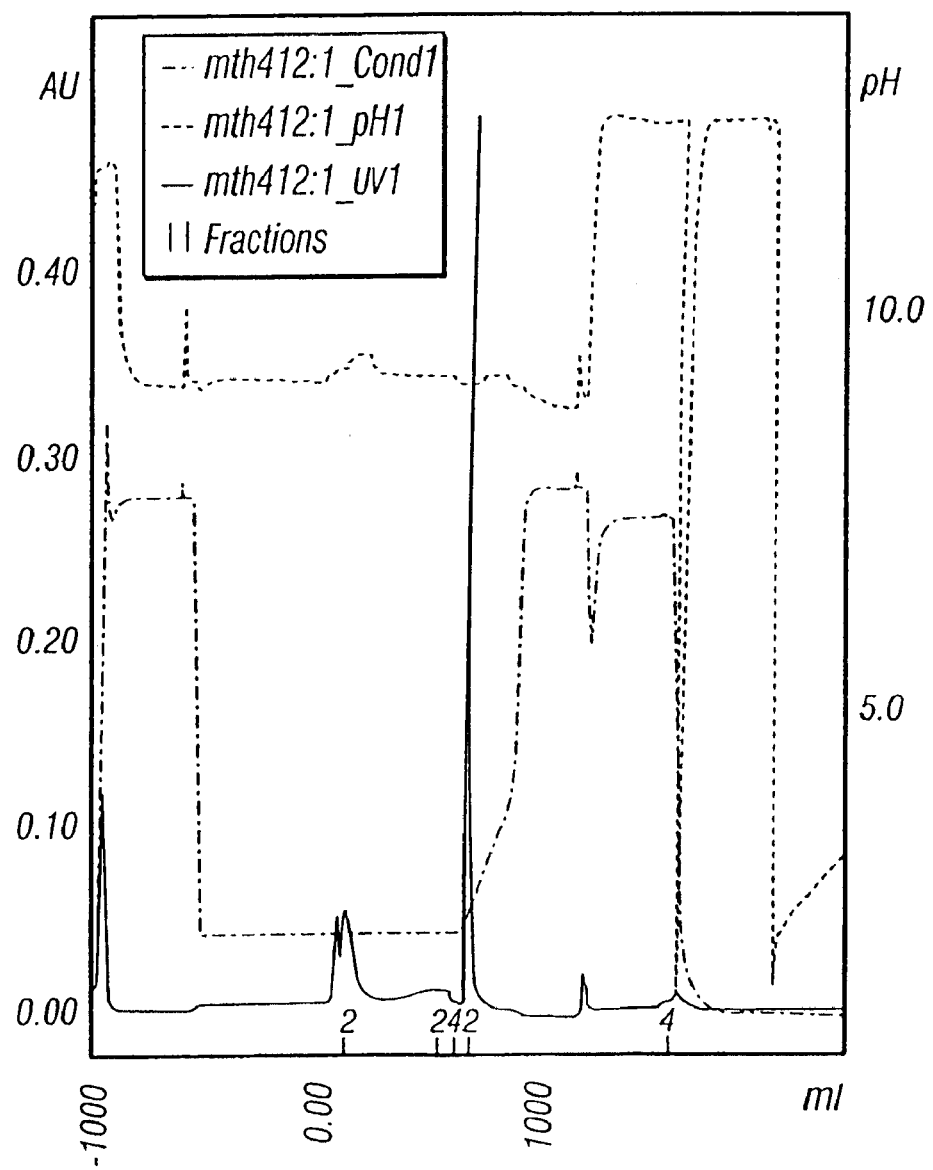
FIG. 17. Purification of 1% Tween® harvest virus solution under low medium perfusion rate.
Figure 18:
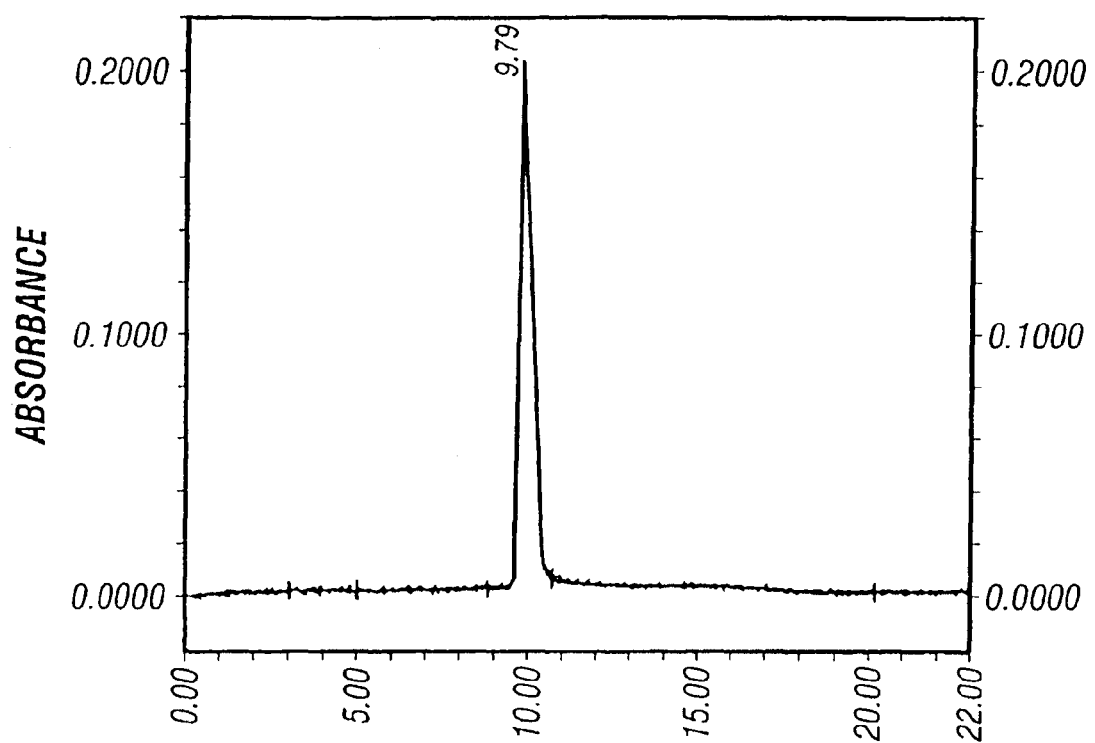
FIG. 18. HPLC analysis of the virus fraction produced under low medium perfusion rate.

Based on the much improved separation observed on HPLC for virus solution produced under low medium perfusion rate, it is likely that purification through one ion exchange column may achieve the required virus purity. FIG. 17 shows the elution profile using crude virus solution produced under low medium perfusion rate. A sharp virus peak was attained during elution. HPLC analysis of the virus fraction indicates virus purity equivalent to that of CsCl gradient purified virus after one ion exchange chromatography step. FIG. 18 shows the HPLC analysis result.

Figure 19A:
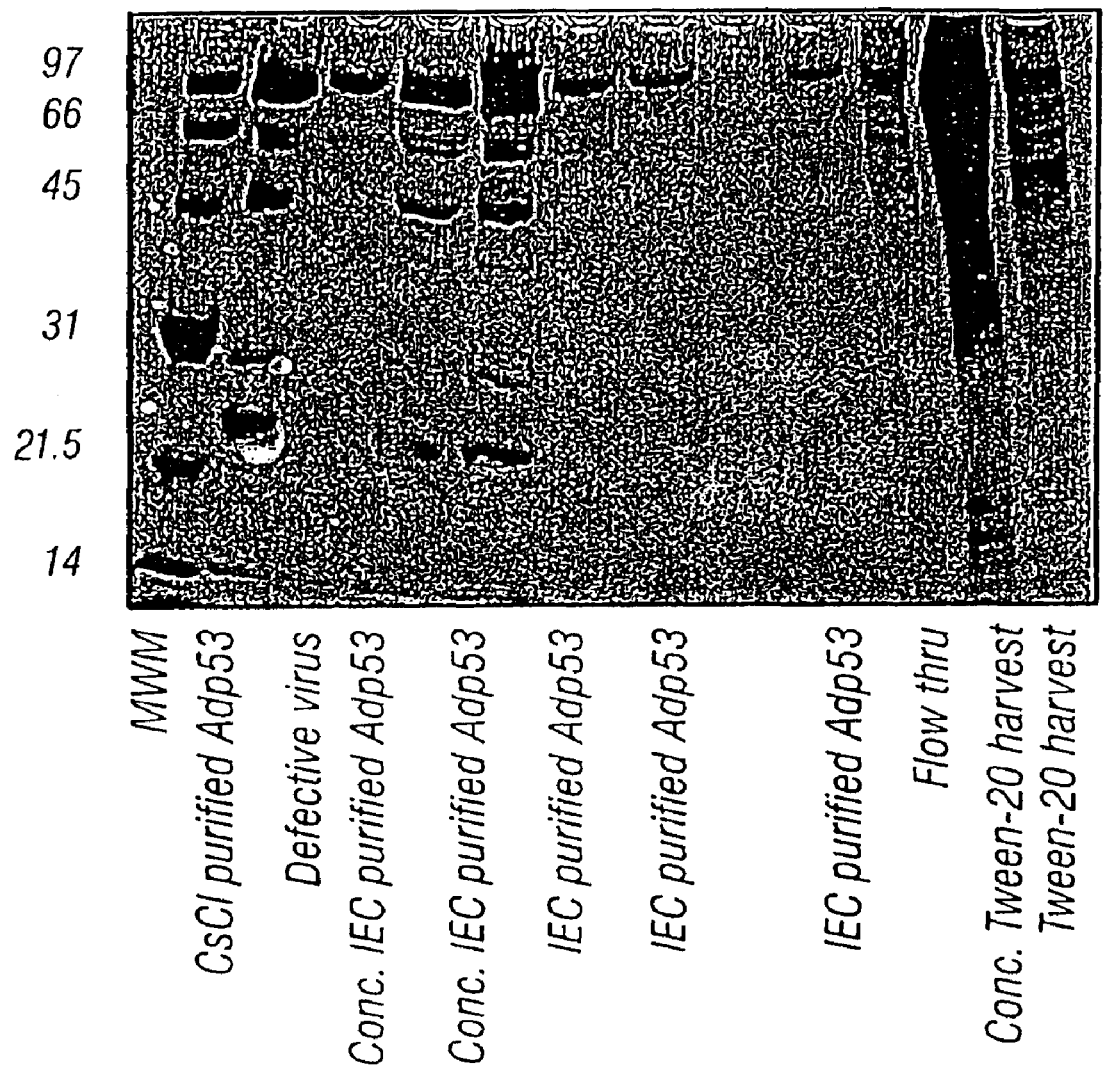
FIG. 19A, FIG. 19B and FIG. 19C. Analysis of column purified virus.
Figure 19B:
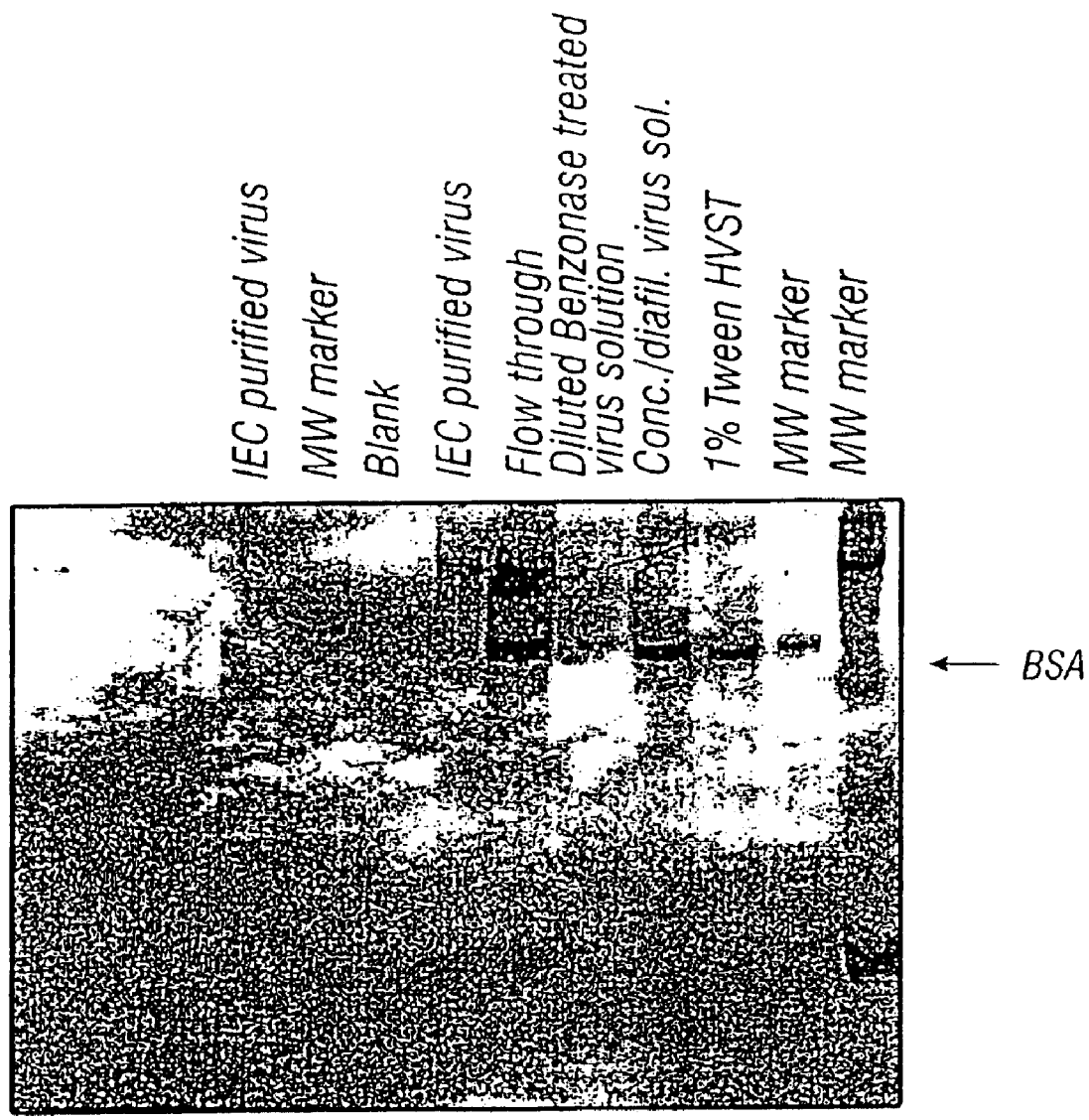
Figure 19C:
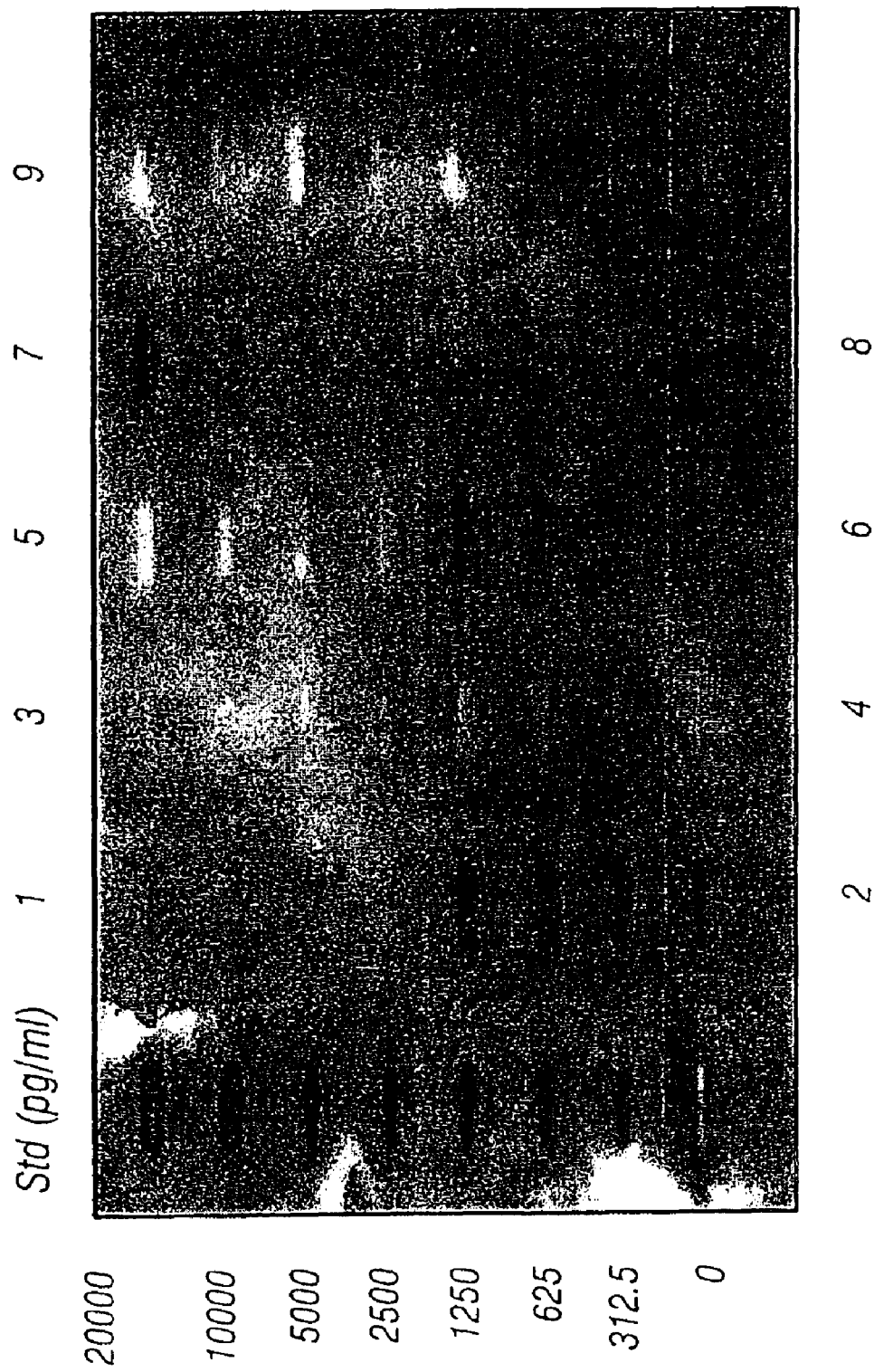
Figure 20A:
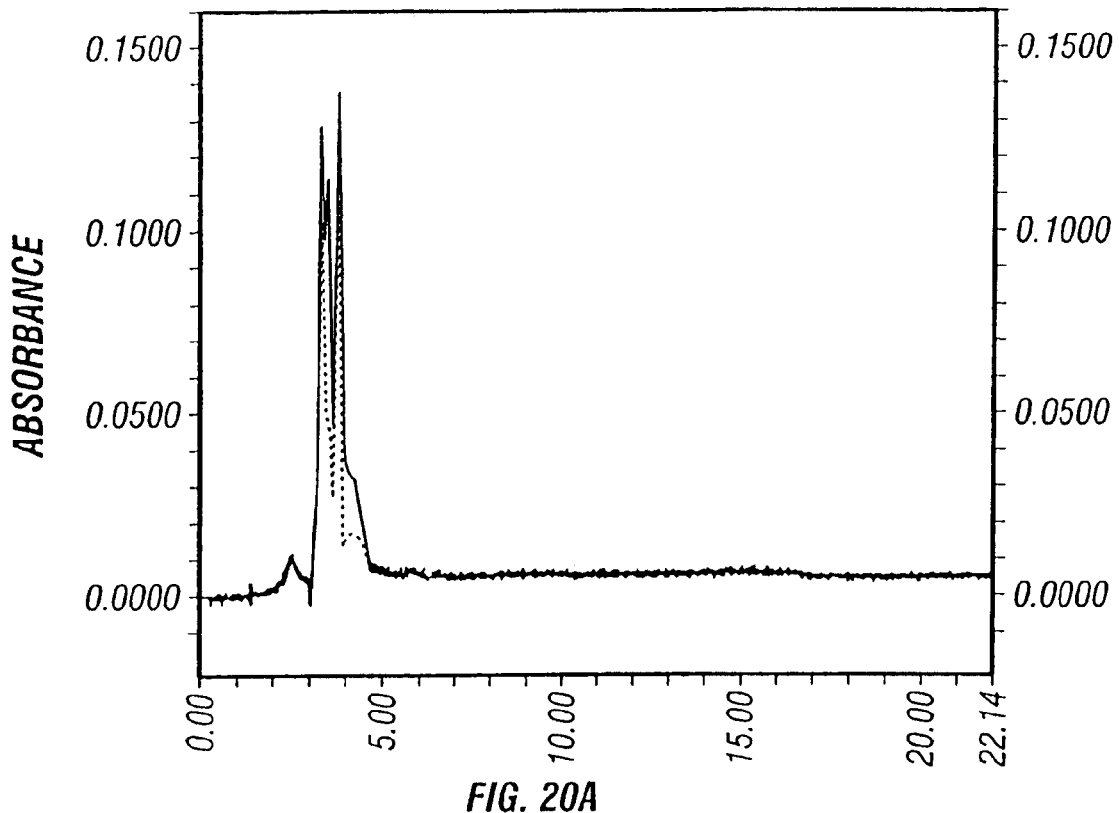
FIG. 20A, FIG. 20B, FIG. 20C, FIG. 20D, FIG. 20E and FIG. 20F. Capacity study of the Toyopearl SuperQ 650M resin.
Figure 20B:
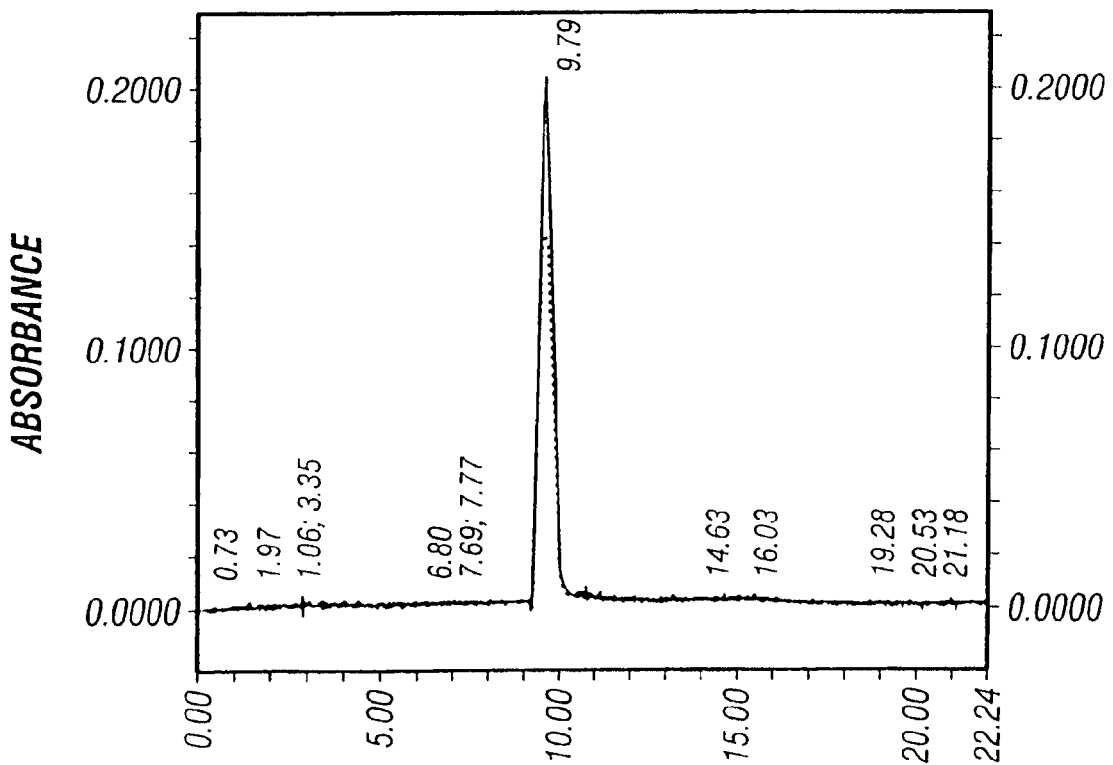
Figure 20C:
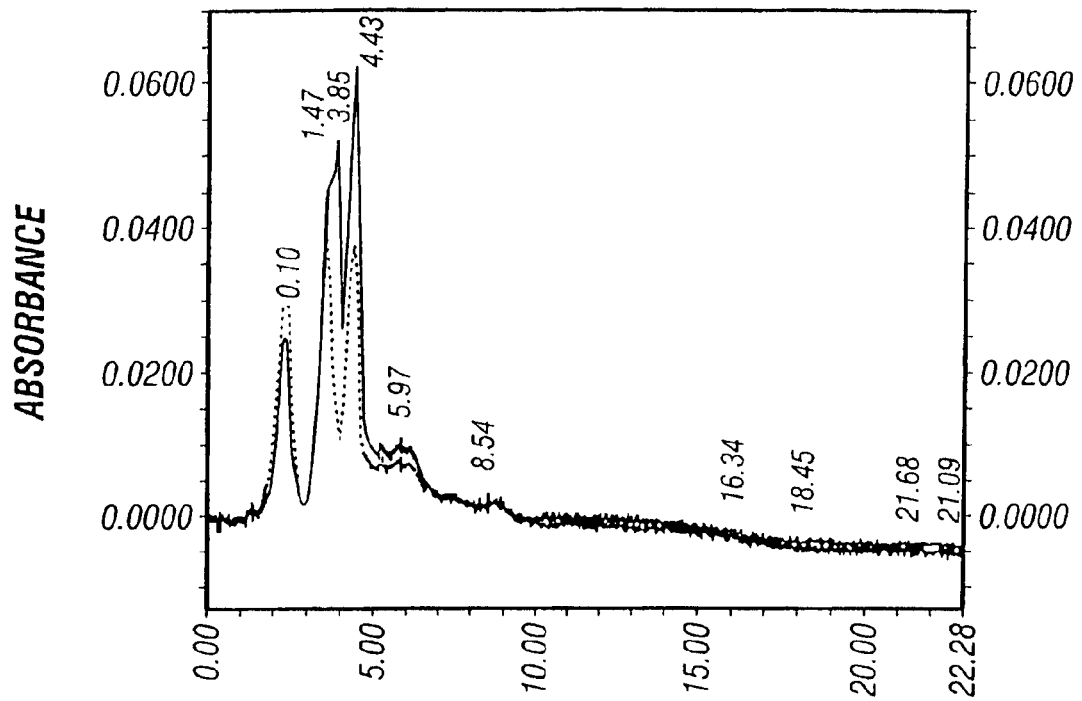
Figure 20D:
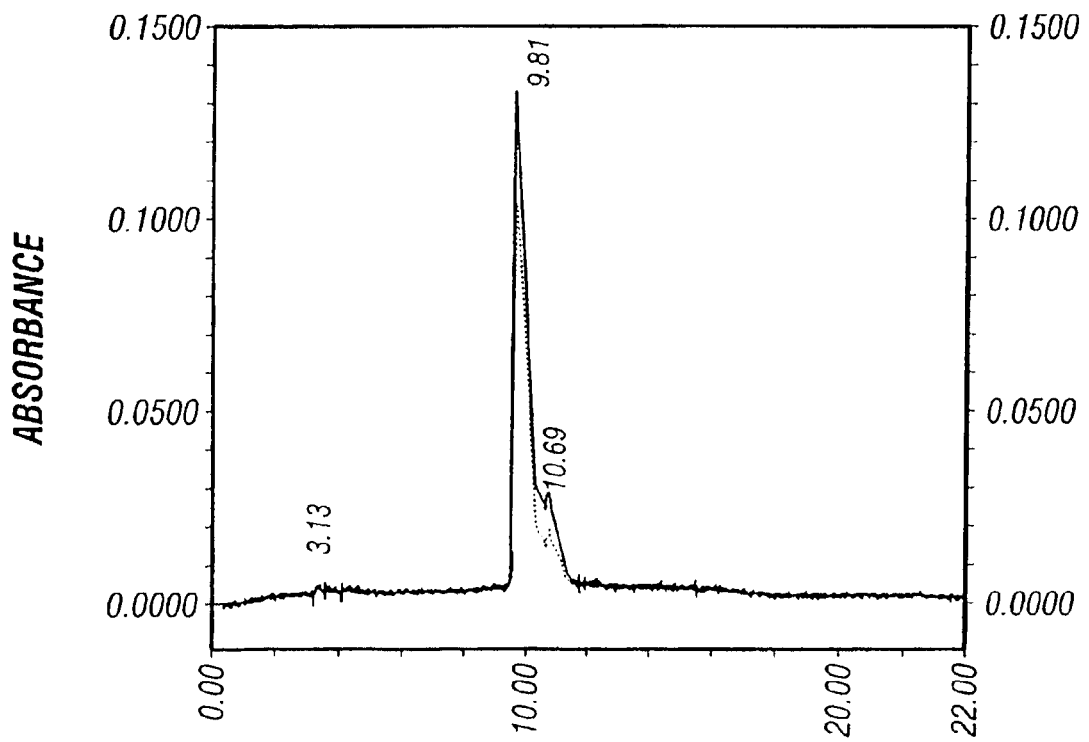
Figure 20E:
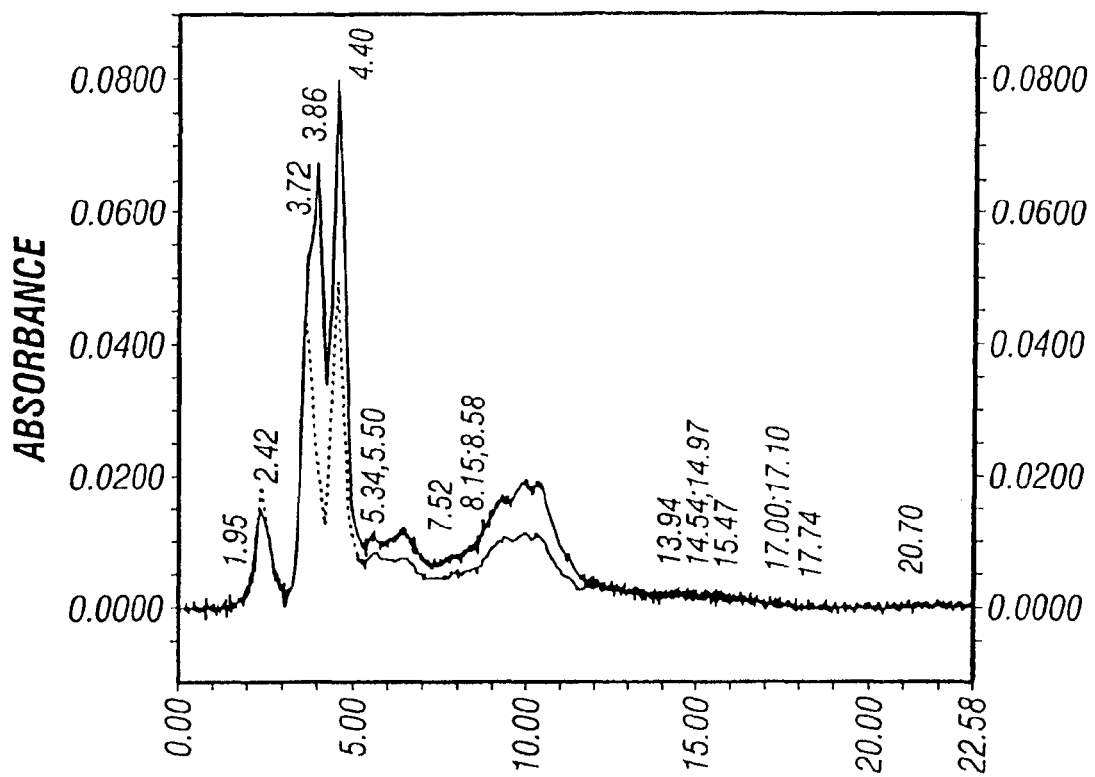
Figure 20F:
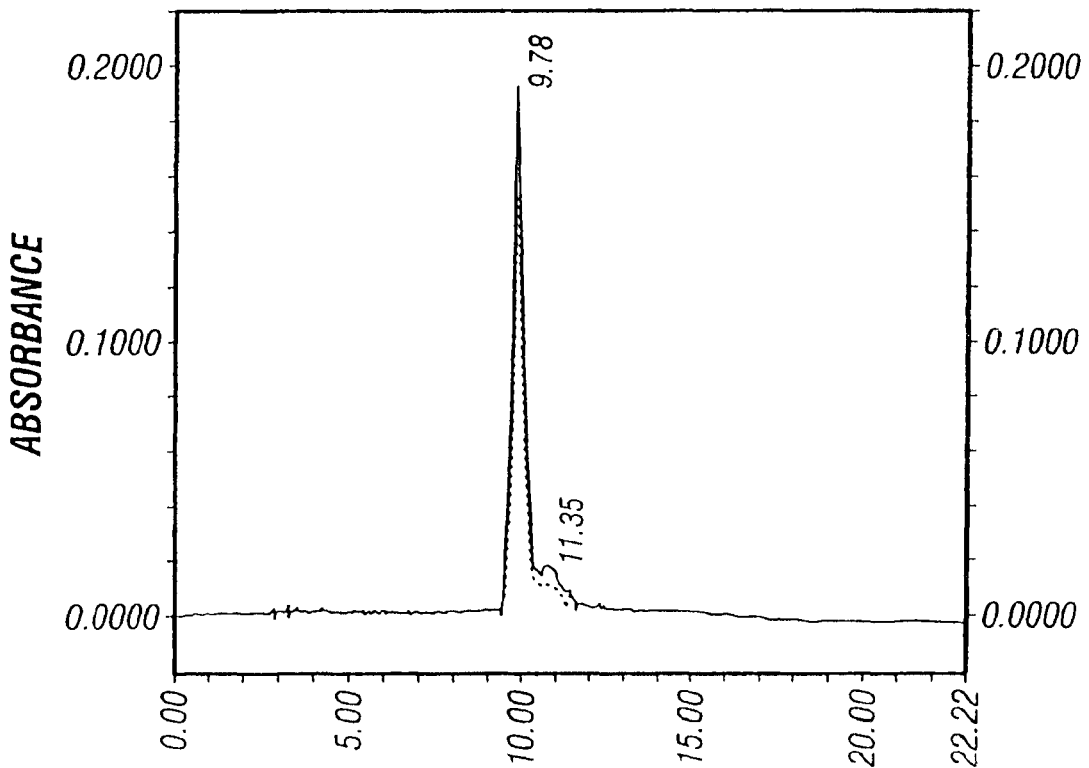

The purified virus was further analyzed by SDS-PAGE, western blot for BSA, and nucleic acid slot blot to determine the contaminating nucleic acid concentration. The analysis results are given in FIG. 19A, FIG. 19B and FIG. 19C, respectively. All those analyses indicate that the column purified virus has equivalent purity compared to the double CsCl gradient purified virus. Table 13 shows the virus titer and recovery before and after the column purification. For comparison purposes, the typical virus recovery achieved by double CsCl gradient purification was also included. Similar virus recoveries were achieved by both methods.

TABLE 13

Comparison of IEC and double CsCl gradient ultracentrifugation purification of AdCMVp53 from Cellcube ™

|  | Titer (PFU/ml) | A260/A280 | Particle/PFU | Recovery |
|---|---|---|---|---|
| IEC | $1 \times 10^{10}$ | 1.27 | 36 | 63% |
| Ultracentrifugation | $2 \times 10^{10}$ | 1.26 | 38 | 60% |

A) Resin Capacity Study

The dynamic capacity of the Toyopearl Super Q resin was evaluated for the purification of the Tween-20 harvested virus solution produced under low medium perfusion rate. One hundred ml of resin was packed in a XK50 column. Different amount of crude virus solution was purified through the column using the methods described herein.

Virus breakthrough and purification efficiency were analyzed on HPLC. FIG. 20 shows the HPLC analysis results. At a column loading factor greater than sample/column volume ratio of 2:1, purity of the virus fraction was reduced. Contaminants co-eluted with the virus. At a loading factor of greater than 3:1, breakthrough of the virus into the flow through was observed. Therefore, it was proposed that the working loading capacity of the resin be in the range of sample/column volume ratio of 1:1.

B) Concentration/Diafiltration Post Purification

A concentration/diafiltration step after column purification serves not only to increase the virus titer, if necessary, but also to exchange to the buffer system specified for the virus product. A 300K NMWC TFF membrane was employed for the concentration step. Because of the absence of proteinacious and nucleic acid contaminants in the purified virus, very high buffer flux was achieved without noticeable pressure drop across the membrane.

Approximately 100% virus recovery was achieved during this step by changing the buffer into 20 mM Tris+1 mM $MgCl_2$+0.15 M NaCl, pH=7.50. The purified virus was also successfully buffer exchanged into DPBS during the concentration/diafiltration step. The concentration factor can be determined by the virus titer that is desired in the final product and the titer of virus solution eluted from the column. This flexibility will help to maintain the consistency of the final purified virus product.

C) Evaluation of Defective Adenovirus in the IEC Purified AdCMVp53

Due to the less than 100% packaging efficiency of adenovirus in producer cells, some defective adenoviruses generally exist in crude virus solution. Defective viruses do not have DNA packaged inside the viral capsid and therefore can be separated from intact virus on CsCl gradient ultracentrifugation based the density difference. It is likely that it would be difficult to separate the defective from the intact viruses based on ion exchange chromatography assuming both viruses have similar surface chemistry. The presence of excessive amount of defective viruses will impact the quality of the purified product.

Figure 21:
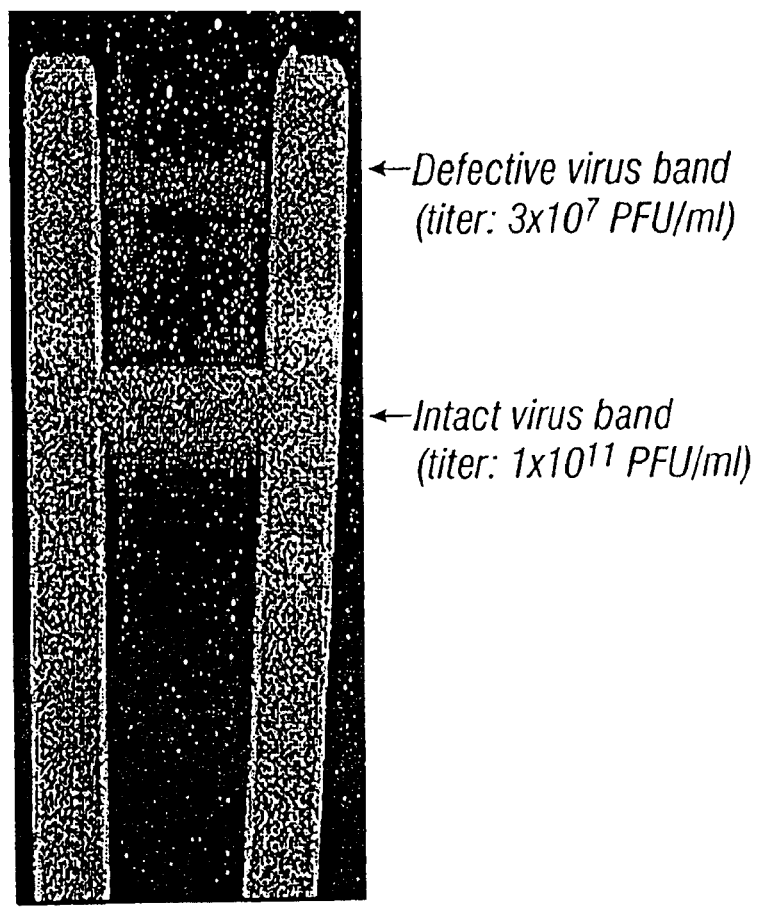
FIG. 21. Isopycnic CsCl ultracentrifugation column purified virus.
Figure 22A:
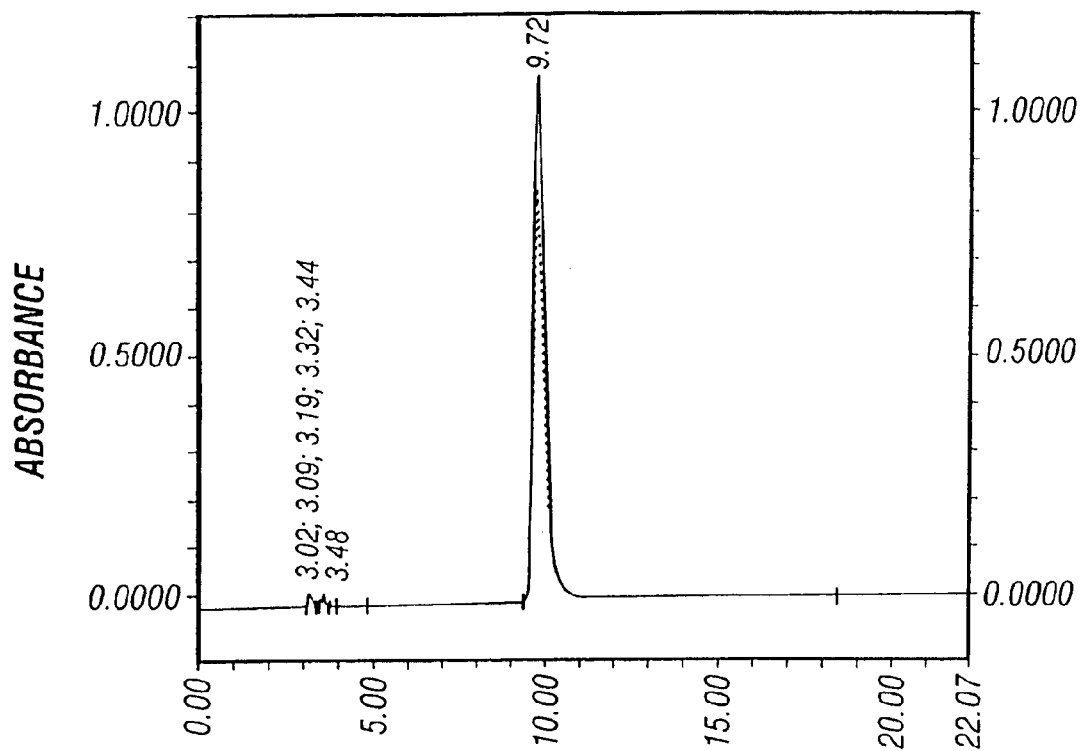
FIG. 22. The HPLC profiles of intact viruses present in the column purified virus. A. Intact virus B. Defective virus. (solid line $A_{260}$; dotted line $A_{280}$).
Figure 22B:
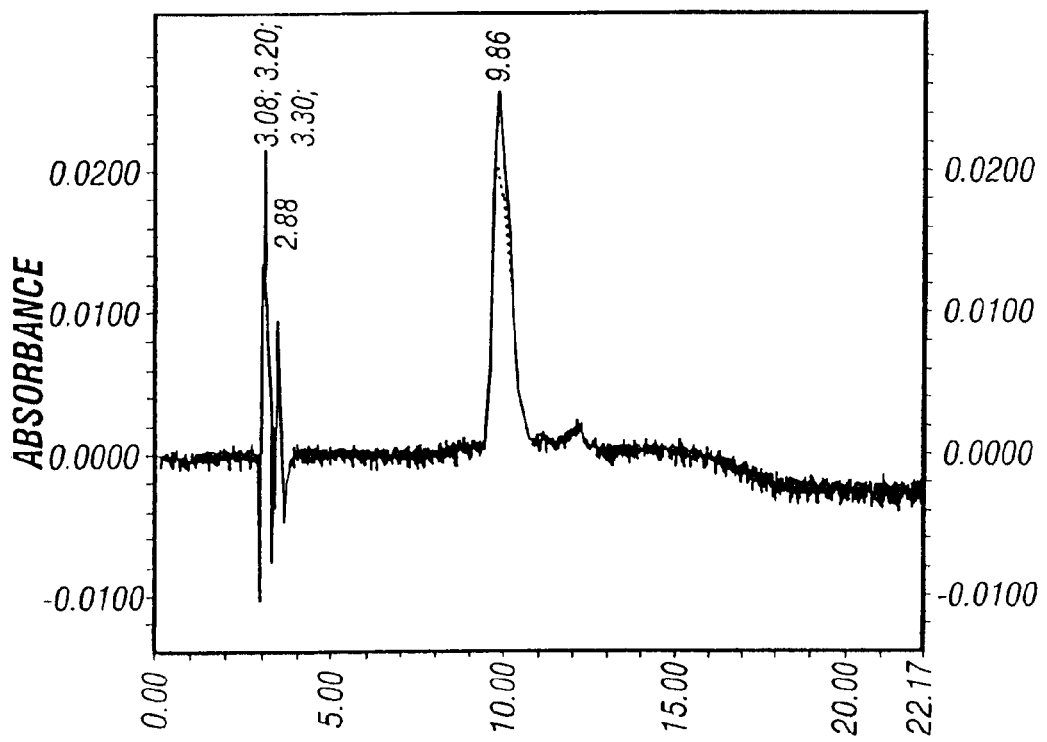

To evaluate the percentage of defective virus particles present, the purified and concentrated viruses were subjected to isopicnic CsCl ultracentrifugation. As shown in FIG. 21, a faint band on top of the intact virus band was observed after centrifugation. Both bands were recovered and dialyzed against 20 mM Tris+1 mM $MgCl_2$, pH=7.50 buffer to remove CsCl. The dialyzed viruses were analyzed on HPLC and the results are shown in FIG. 22. Both viruses show similar retention time. However, the defective virus has a smaller A260/

A280 ratio than that of the intact virus. This is indicative of less viral DNA in the defective virus.

The peaks seen at retention times between 3.02 to 3.48 min are produced by glycerol which is added to the viruses (10% v/v) before freezing at −70° C. The percentage of the defective virus was less than 1% of the total virus. This low percentage of defective virus is unlikely to impact the total particle to infectious virus (PFU) ratio in the purified virus product. Both viruses were analyzed by SDS-PAGE (shown in FIG. 19A). Compared to the intact viruses, defective viruses lack the DNA associated core proteins banded at 24 and 48.5 KD. This result is in agreement with the absence of DNA in defective virus.

D) Process Overview of the Production and Purification of AdCMVp53 Virus

Based on the above process development results, the inventors propose a production and purification flow chart for AdCMVp53 as shown in FIG. 23. The step and accumulative virus recovery is included with the corresponding virus yield based on a 1 mer Cellcube™. The final virus recovery is about 70±10%. This is about 3-fold higher than the virus recovery reported by Huyghe et al. (1996) using a DEAE ion exchanger and a metal chelate chromatographic purification procedure for the purification of p53 protein encoding adenovirus. Approximately $3 \times 10^{12}$ PFU of final purified virus product was produced from a 1 mer Cellcube™. This represents a similar final product yield compared to the current production method using double CsCl gradient ultracentrifugation for purification.

E) Scale-Up

Successful scale-up studies have been performed with the 4 mer Cellcube™ system, and are currently underway to evaluate virus production in the 16 mer Cellcube™ system. The crude virus solution produced will be filtered, concentrated and diafiltrated using a bigger Pellicon cassette. The quality and recovery of the virus will be determined. After Benzonase treatment, the crude virus solution will be purified using a 20 cm and a 30 cm BioProcess column for the 4 mer and 16 mer, respectively.

Example 9

Improved Ad-p53 Production in Serum-Free Suspension Culture

Adaptation of 293 Cells 293 cells were adapted to a commercially available IS293 serum-free media (Irvine Scientific; Santa Ana, Calif.) by sequentially lowering down the FBS concentration in T-flasks. The frozen cells in one vial of PDWB were thawed and placed in 10% FBS DMEM media in T-75 flask and the cells were adapted to serum-free IS 293 media in T-flasks by lowering down the FBS concentration in the media sequentially. After 6 passages in T-75 flasks the FBS % was estimated to be about 0.019%. The cells were subcultured two more times in the T flasks before they were transferred to spinner flasks.

Serum Free Adapted 293 Cells in T Flasks were Adapted to Suspension Culture

The above serum-free adapted cells in T-flasks were transferred to a serum-free 250 mL spinner suspension culture (100 mL working volume) for the suspension culture. The initial cell density was 1.18E+5 vc/mL. During the cell culture the viability decreased and the big clumps of cells were observed. After 2 more passages in T-flasks the adaptation to suspension culture was tried again. In a second attempt the media was supplemented with heparin, at a concentration of 100 mg/L, to prevent aggregation of cells and the initial cell density was increased to 5.22E+5 vc/mL. During the cell culture there was some increase of cell density and cell viability was maintained. Afterwards the cells were subcultured in the spinner flasks for 7 more passages and during the passages the doubling time of the cells was progressively reduced and at the end of seven passages it was about 1.3 day which is comparable to 1.2 day of the cells in 10% FBS media in the attached cell culture. In the serum-free IS 293 media supplemented with heparin almost all the cells existed as individual cells not forming aggregates of cells in the suspension culture (Table 14).

TABLE 14

Serum-Free Suspension Culture: Adaptation to Suspension

| Passage No. | Flask No. | Average Doubling Time (days) |
|---|---|---|
| 11 | | Viability decreased |
| 13 | | 3.4 |
| 14 | | 3.2 |
| 15 | 1 | Viability decreased |
| Heparin added | 2 | 4.7 |
| | 3 | 5.0 |
| | 4 | 3.1 |
| 16 | 1 | 5.5 |
| | 2 | 4.8 |
| | 3 | 4.3 |
| | 4 | 4.3 |
| 17 | 1 | 2.9 |
| | 2 | 3.5 |
| | 3 | 2.4 |
| | 4 | 1.7 |
| 18 | 1 | 3.5 |
| | 2 | 13.1 |
| | 3 | 6.1 |
| | 4 | 3.8 |
| 19 | 1 | 2.5 |
| | 2 | 2.6 |
| | 3 | 2.3 |
| | 4 | 2.5 |
| 20 | 1 | 1.3 (97% viability) |
| | 2 | 1.5 (99% viability) |
| | 3 | 1.8 (92% viability) |
| | 4 | 1.3 (96% viability) |

Viral Production and Growth of Cells in Serum Free Suspension Culture in Spinner Flask To test the production of Ad5-CMVp53 vectors in the serum-free suspension culture the above cells adapted to the serum-free suspension culture were grown in 100 mL serum-free IS293 media supplemented with 0.1% Pluronic F-68 and Heparin (100 mg/L) in 250 mL spinner flasks. the cells were infected at 5 MOI when the cells reached 1.36E+06 viable cells/mL on day 3. The supernatant was analyzed everyday for HPLC viral particles/mL after the infection. No viruses were detected other than day 3 sample. On day 3 it was 2.2E+09 vps/mL. The pfu/mL on day 6 was 2.6+/−0.6E+07 pfu/mL. The per cell pfu production was estimated to be 19 which is approximately 46 times below the attached culture in the serum-supplemented media. As a control the growth of cells was checked in the absence of an infection.

TABLE 15

Serum-Free Suspension Culture: Viral Production and Cell Growth

|  | Control w/o viral infection | Viral infection w/o media exchange | Viral infection w/media exchange |
|---|---|---|---|
| Initial Density (vc/mL) | $2.1 \times 10^5$ | $2.1 \times 10^5$ | $2.1 \times 10^5$ |
| Cell Density at infection (vc/mL) | $9.1 \times 10^5$ | $1.4 \times 10^6$ | $1.5 \times 10^6$ |
| Volumetric viral production (pfu/mL) 6 days P.I. | NA | $2.6 \times 10^7$ | $2.8 \times 10^8$ |
| Volumetric viral production (HPLC vps/mL) 6 days P.I. | NA | NA | $1.3 \times 10^{10}$ |
| Per cell viral production (HPLC vps/cell) | NA | NA | $1.3 \times 10^4$ |

Preparation of Serum-Free Suspension Adapted 293 Cell Banks

As described above, after it was demonstrated the cells produce the Ad-p53 vectors, the cells were propagated in the serum-free IS293 media with 0.1% F-68 and 100 mg/L heparin in the spinner flasks to make serum-free suspension adapted cell banks which contain 1.0E+07 viable cells/mL/vial. To collect the cells they were centrifuged down when they were at mid-log phase growth and the viability was over 90% and resuspended in the serum-free, supplemented IS293 media and centrifuged down again to wash out the cells. Then the cells were resuspended again in the cryopreservation media which is cold IS293 with 0.1% F-68, 100 mg/L heparin, 10% DMSO and 0.1% methylcellulose resulting in 1E+07 viable cells/mL. The cell suspension was transferred to sterile cryopreservation vials and they were sealed and frozen in cryocontainer at −70 C overnight. The vials were transferred to liquid nitrogen storage. The mycoplasma test was negative.

To revive the frozen cells one vial was thawed into the 50 mL serum-free IS293 media with 0.1% F-68 and 100 mg/L heparin in a T-150. Since then the cultures were subcultured three times in 250 mL spinner flasks. In the other study one vial was thawed into 100 mL serum-free, supplemented IS293 media in a 250 mL spinner flask. Since then these were subcultured in serum-free spinner flasks 2 times. In both of the studies the cells grew very well.

Media Replacement and Viral Production in Serum Free Suspension Culture in Spinner Flask In the previous serum-free viral production in the suspension culture in the spinner flask the per cell viral production was too low for the serum-free suspension production to be practical. It was supposed that this might be due to the depletion of nutrients and/or the production of inhibitory byproducts. To replace the spent media with fresh serum-free, supplemented IS293 media the cells were centrifuged down on day 3 and resuspended in a fresh serum-free IS-293 medium supplemented with F-68 and heparin (100 mg/L) and the resulting cell density was 1.20E+06 vc/mL and the cells were infected with Ad5-CMVp53 vectors at 5 MOI. The extracellular HPLC vps/mL was 7.7E+09 vps/mL on day 3, 1.18E+10 vps/mL on day 4, 1.2E+10 vps/mL on day 5 and 1.3E+10 vps/mL on day 6 and the pfu/mL on day 6 was 2.75+/−0.86E+08 tvps/mL. The ratio of HPLC viral particles to pfus was about 47. Also the cells have been centrifuged down and lysed with the same type of the detergent lysis buffer as used in the harvest of CellCube. The cellular HPLC vps/mL was 1.6E+10 vps/mL on day 2, 6.8E+09 vps/mL on day 3, 2.2E+09 vps/mL on day 4, 2.24E+09 vps/mL on day 5 and 2.24E+09 vps/mL on day 6.

The replacement of the spent media with a fresh serum-free, supplemented IS 293 media resulted in the significant increase in the production of Ad-p53 vectors. The media replacement increased the production of extracellular HPLC viral particles 3.6 times higher above the previous level on day 3 and the production of extracellular pfu titer ten times higher above the previous level on day 6. Per cell production of Ad-p53 vectors was estimated to be approximately 1.33E+04 HPLC vps.

The intracellular HPLC viral particles peaked on day 2 following the infection and then the particle numbers decreased. In return the extracellular viral particles increased progressively to the day 6 of harvest. Almost all the Ad-p53 vectors were produced for the 2 days following the infection and intracellularly localized and then the viruses were released outside of the cells. Almost half of the viruses were released outside of the cells into the supernatant between day 2 and day 3 following the infection and the rate of release decreased as time goes on.

All the cells infected with Ad-p53 vectors lost their viability at the end of 6 days after the infection while the cells in the absence of infection was 97% viable. In the presence of infection the pH of the spent media without the media exchange and with the media exchange was 6.04 and 5.97, respectively, while the one in the absence of the infection was 7.00 (Table 14).

Viral Production and Cell Culture in Stirred Bioreactor with Media Replacement and Gas Overlay To increase the production of Ad-p53 vectors, a 5 L CelliGen bioreactor was used to provide a more controlled environment. In the 5 L CelliGen bioreactor the pH and the dissolved oxygen as well as the temperature were controlled. Oxygen and carbon dioxide gas was connected to the solenoid valve for oxygen supply and the pH adjustment, respectively. For a better mixing while generating low shear environment a marine-blade impeller was implemented. Air was supplied all the time during the operation to keep a positive pressure inside the bioreactor.

To inoculate the bioreactor a vial of cells was thawed into 100 mL serum-free media in a 250 mL spinner flask and the cells were expanded in 250 or 500 mL spinner flasks. 800 mL cell inoculum, grown in 500 mL flasks, was mixed with 2700 mL fresh media in a 10 L carboy and transferred to the CelliGen bioreactor by gas pressure. The initial working volume of the CelliGen bioreactor was about 3.5 L culture. The agitation speed of the marine-blade impeller was set at 80 rpm, the temperature at 37° C., pH at 7.1 at the beginning and 7.0 after the infection and the DO at 40% all the time during the run.

The initial cell density was 4.3E+5 vc/mL (97% viability) and 4 days later when the cell density reached to 2.7E+6 vc/mL (93% viability) the cells were centrifuged down and the cells were resuspended in a fresh media and transferred to the CelliGen bioreactor. After the media exchange the cell density was 2.1E+6 vc/mL and the cells were infected at MOI of 10. Since then the DO dropped to below 40%. To keep the DO above 40%, about 500 mL of culture was withdrawn from the CelliGen bioreactor to lower down the oxygen demand by the cell culture and the upper marine-blade was positioned close to the interface between the gas and the liquid phase to improve the oxygen transfer by increasing the surface renewal. Since then the DO could be maintained above 40% until the end of the run.

For pH control, $CO_2$ gas was used to acidify the cell culture and 1 N $NaHCO_3$ solution to make the cell culture alkaline. The pH control was initially set at 7.10. The initial pH of the cell culture was about pH 7.41. Approximately 280 mL 1N $NaHCO_3$ solution was consumed until the pH of cell culture stabilized around pH 7.1. After the viral infection of the cell culture, the pH control was lowered down to pH 7.0 and the $CO_2$ gas supply line was closed off to reduce the consumption of $NaHCO_3$ solution. The consumption of too much $NaHCO_3$ solution for pH adjustment would increase the cell culture volume undesirably. Since then 70 mL 1N $NaHCO_3$ solution was consumed and the pH was in the range between 7.0 and 7.1 most of the time during the run. The temperature was controlled between 35° C. and 37° C.

After the infection the viability of the cells decreased steadily until day 6 of harvest after the infection. On the harvest day none of the cells was viable. The volumetric viral production of the CelliGen bioreactor was 5.1E+10 HPLC vps/mL compared to the 1.3E+10 vps/mL in the spinner flask. The controlled environment in the CelliGen bioreactor increased the production of Ad-p53 vectors 4-fold compared to the spinner flasks with media replacement. This is both due to the increase of the cell density at the time of infection from 1.2E+6 to 2.1E+6 vc/mL and the increase of per cell viral production from 1.3E+4 to 2.5E+4 vps/mL. The 2.5E+4 vps/mL is comparable to the 3.5E+4 vps/cell in the serum-supplemented, attached cell culture.

Viral Production and Cell Culture in Stirred and Sparged Bioreactor

In the first study the cells were successfully grown in an stirred bioreactor for viral production, and the oxygen and $CO_2$ were supplied by gas overlay in the headspace of a bioreactor. However, this method will limit the scale-up of the cell culture system because of its inefficient gas transfer. Therefore in the second study, to test the feasibility of the scale up of the serum-free suspension culture was investigated by growing of cells and producing Ad-p53 in a sparged bioreactor. Pure oxygen and $CO_2$ gases were supplied by bubbling through the serum-free IS293 media supplemented with F-68 (0.1%) and heparin (100 mg/L).

Pure oxygen was bubbled through the liquid media to supply the dissolved oxygen to the cells and the supply of pure oxygen was controlled by a solenoid valve to keep the dissolved oxygen above 40%. For efficient oxygen supply while minimizing the damage to the cells, a stainless steel sintered air diffuser, with a nominal pore size of approximately 0.22 micrometer, was used for the pure oxygen delivery. The $CO_2$ gas was also supplied to the liquid media by bubbling from the same diffuser as the pure oxygen to maintain the pH around 7.0. For pH control, $Na_2CO_3$ solution (106 g/L) was also hooked up to the bioreactor. Air was supplied to the head space of the bioreactor to keep a positive pressure inside the bioreactor. Other bioreactor configuration was the same as the first study.

Inoculum cells were developed from a frozen vial. One vial of frozen cells (1.0E+7 vc) was thawed into 50 mL media in a T-150 flask and subcultured 3 times in 200 mL media in 500 mL spinner flasks. 400 mL of inoculum cells grown in 2 of 500 mL spinner flasks were mixed with IS293 media with F-68 and heparin in a 10 L carboy to make 3.5 L cell suspension and it was transferred to the 5 L CelliGen bioreactor.

The initial cell density in the bioreactor was 3.0E+4 vc/mL. The initial cell density is lower than the first study. In the first study four of 500 mL spinner flasks were used as the inoculum. Even with the lower initial cell density the cells grew up to 1.8E+6 vc/mL on day 7 in the sparged environment and the viability was 98%. During the 7 days' growth, glucose concentration decreased from 5.4 g/L to 3.0 g/L and lactate increased from 0.3 g/L to 1.8 g/L.

On day 7, when the cell density reached 1.8E+6 vc/mL, the cells in the bioreactor were centrifuged down and resuspended in 3.5 L fresh serum-free IS293 media with F-68 and heparin in a 10 L carboy. The 293 cells were infected with 1.25E+11 pfu Ad-p53 and transferred to the CelliGen bioreactor. In the bioreactor, cell viability was 100% but the cell density was only 7.2E+5 vc/mL. There was a loss of cells during the media exchange operation. The viral titer in the media was measured as 2.5E+10 HPLC vps/mL on day 2, 2.0E+10 on day 3, 2.8E+10 on day 4, 3.5E+10 on day 5 and 3.9E+10 HPLC vps/mL on day 6 of harvest. The first CelliGen bioreactor study with gas overlay produced 5.1E+10 HPLC vps/mL. The lower virus concentration in the second run was likely due to the lower cell density at the time of infection. Compared to the 7.2E+5 vc/mL in the second run, 2.1E+6 vc/mL was used in the first run. Actually the per cell production of Ad-p53 in the second sparged CelliGen bioreactor is estimated to be 5.4E+4 vps/cell which is the highest per cell production ever achieved so far. The per cell production in the first serum-free CellGen bioreactor without sparging and the serum-supplemented T-flask was 2.5E+4 vps/cell and 3.5E+4 vps/cell, respectively.

After the viral infection, the viability of the cells decreased from 100% to 13% on day 6 of harvest. During those 6 days after the infection the glucose concentration decreased from 5.0 g/L to 2.1 g/L and the lactate increased from 0.3 g/L to 2.9 g/L. During the entire period of operation about 20 mL of $Na_2CO_3$ (106 g/L) solution was consumed.

The experimental result shows that it is technically and economically feasible to produce Ad-p53 in the sparged and stirred bioreactor. Scale-up and large-scale unit operation of sparged and stirred bioreactor are well established.

Example 10

Blanche et al Production Process

The following example is text excerpted from pages 4-14 of Blanche et al in U.S. Ser. No. 60/076,662. This text is descriptive of the methods used by Blanche et al in production of recombinant adenovirus.

Recombinant adenoviruses are usually produced by the introduction of viral DNA into the encapsulation line, followed by lysis of the cells after approximately 2 or 3 days (with the kinetics of the adenoviral cycle being 24 to 36 hours). After lysis of the cells, the recombinant viral particles are isolated by centrifugation on a cesium chloride gradient.

For implementation of the process, the viral DNA introduced may be the complete recombinant viral genome, possibly constructed in a bacterium (ST 95010) or in a yeast (WO95/03400), transfected in the cells. It may also be a recombinant virus used to infect the encapsulation line. It is further possible to introduce the viral DNA in the form of fragments, each carrying a portion of the recombinant viral genome and a homology zone permitting the recombinant viral genome to be reconstituted by homologous recombination between the different fragments after introduction into the encapsulation cell. Thus a classical adenovirus production process includes the following steps: The cells (for example, cells 293) are infected in a culture plate with a viral prestock at the rate of 3 to 5 viral particles per cell (Multiplicity of Infection (MOI)=3 to 5), or transfected with viral DNA. The incubation then lasts 40 to 72 hours. The virus is subsequently released from the nucleus by lysis of the cells, generally by several successive thaw cycles. The cellular lysate obtained is then centrifuged at low speed (2000 to 4000 rpm), after which the supernatant (clarified cellular lysate) is purified by centrifugation in the presence of cesium chloride in two steps:

A first rapid 1.5 hour centrifugation on two layers of cesium chloride of densities 1.25 and 1.40 surrounding the density of the virus (1.34) in such a way as to separate the virus from the proteins of the medium;

A second, longer centrifugation in a gradient (from 10 to 40 hours according to the rotor used), which constitutes the true and only purification step of the virus.

Generally, after the second centrifugation step, the band of the virus is intensified. Nevertheless, two finer, less dense bands are observed. Observation under the electron microscope has shown that these bands are made up of empty or broken viral particles for the denser band and of viral subunits (pentons, hexons) for the less dense band. After this step, the virus is harvested by needle puncture in the centrifugation tube and the cesium is eliminated by dialysis or deionization.

Although the purity levels obtained are satisfactory, this type of process presents certain drawbacks. In particular, it is based on the use of cesium chloride, which is a reagent incompatible with therapeutic use in man. Thus, it is imperative to eliminate the cesium chloride at the end of purification. This process also has certain other disadvantages mentioned below, limiting its use to an industrial scale.

To remedy these problems, it has been proposed to purify the virus obtained after lysis, not by gradient of cesium chloride, but by chromatography. Thus the article of Huyghe et at. (*Hum. Gen. Ther.* 6 (1996) 1403) describes a study of different types of chromatographies applied to the purification of recombinant adenoviruses. This article describes in particular a study of recombinant adenovirus purification using weak anion exchange chromatography (DEAE). Earlier studies already described the use of this type of chromatography toward that goal (Klemperer et al., *Virology* 9 (1959) 536; Philipson, L., *Virology* 10 (1960) 459; Haruna et al., *Virology* 13 (1961) 264). The results presented in the article by Huyghe et al. show a rather poor efficacy of the ion exchange chromatography protocol recommended. Thus, the resolution obtained is average, with the authors indicating that virus particles are present in several chromatographic peaks; the yield is low (viral particle yield: 67%; infectious particle yield: 49%); and the viral preparation obtained following this chromatographic step is impure. In addition, pretreatment of the virus with different enzymes/proteins is necessary. This same article also describes a study of the use of gel permeation chromatography, showing very poor resolution and very low yields (15-20%).

The present invention describes a new process for the production of recombinant adenoviruses. The process according to the invention results from changes in previous processes in the production phase and/or in the purification phase. The process according to the invention now makes it possible in a very rapid and industrializable manner to obtain stocks of virus of very high quantity and quality.

One of the first features of the invention concerns more particularly a process for the preparation of recombinant adenoviruses in which the viruses are harvested from the culture supernatant. Another aspect of the invention concerns a process for the preparation of adenoviruses including an ultrafiltration step. According to yet another aspect, the invention concerns a process for the purification of recombinant adenoviruses including an anion exchange chromatography step. The present invention also describes an improved purification process, using gel permeation chromatography, possibly coupled with anion exchange chromatography. The process according to the invention makes it possible to obtain viruses of high quality in terms of purity, stability, morphology, and infectivity, with very high yields and under production conditions completely compatible with the industrial requirements and with the regulations concerning the production of therapeutic molecules.

In particular, in terms of industrialization, the process according to the invention uses methods of the treatment of supernatants of cultures tested on a large scale for recombinant proteins, such as microfiltration or deep filtration, and tangential ultrafiltration. Furthermore, because of the stability of the virus at 37° C., this process permits better organization at the industrial stage inasmuch as, contrary to the intracellular method, the harvesting time does not need to be precise to within a half day. Moreover, it guarantees maximum harvesting of the virus, which is particularly important in the case of viruses defective in several regions. In addition, the process according to the invention permits an easier and more precise follow-up of the production kinetics directly on homogenous samples of supernatant, without pretreatment, which permits better reproducibility of the productions. The process according to the invention also makes it possible to eliminate the cell lysis step. The lysis of the cells presents a number of drawbacks. Thus, it may be difficult to consider breaking the cells by freeze/thaw cycles at the industrial level. Besides, the alternative lysis methods (Dounce, X-press, sonification, mechanical shearing, etc.) present drawbacks as well: they are potential generators of sprays that are difficult to confine for L2 or L3 viruses (level of confinement of the viruses, depending on their pathogenicity or their mode of dissemination), with these viruses having a tendency to be infectious through airborne means; they generate shear forces and/or a liberation of heat that are difficult to control, diminishing the activity of the preparations. The solution of using detergents to lyse the cells would demand validation and would also require that elimination of the detergent be validated. Finally, cellular lysis leads to the presence in the medium of a large quantity of cellular debris, which makes purification more difficult. In terms of virus quality, the process according to the invention potentially permits better maturation of the virus, leading to a more homogenous population. In particular, provided that the packing of the viral DNA is the last step in the viral cycle, the premature lysis of the cells potentially liberates empty particles which, although not replicative, are a priori infectious and capable of participating in the distinctive toxic effect of the virus and of increasing the ratio of specific activity of the preparations obtained. The ratio of specific infectivity of a preparation is defined as the ratio of the total number of viral particles, measured by biochemical methods (OD 260 nm, HPLC, CRP, immuno-enzymatic methods, etc.), to the number of viral particles generating a biologic effect (formation of lysis plaques on cells in culture and solid medium, translation of cells). In practice, for a purified preparation, this ratio is determined by dividing the concentration of particles measured by OD at 260 nm by the concentration of plaque-forming units in the preparation. This ratio should be less than 100.

The results obtained show that the process according to the invention makes it possible to obtain a virus of a purity comparable to the homologous one purified by centrifugation in cesium chloride gradient, in a single step and without preliminary treatment, starting from a concentrated viral supernatant.

A first goal of the invention thus concerns a process for the production of recombinant adenoviruses characterized by the fact that the viral DNA is introduced into a culture of encapsulation cells and the viruses produced are harvested after release into the culture supernatant. Contrary to the previous processes in which the viruses are harvested following premature cellular lysis performed mechanically or chemically, in the process according to the invention the cells are not lysed by means of an external factor. Culturing is pursued during a longer period of time, and the viruses are harvested directly in the supernatant, after spontaneous release by the encapsulation cells. In this way the virus according to the invention is recovered in the cellular supernatant, while in the previous processes it is an intracellular and more particularly an intranuclear virus that is involved.

The applicant has now shown that despite that elongation in duration of the culture and despite the use of larger volumes, the process according to the invention makes it possible to generate viral particles in large quantity and of better quality.

In addition, as indicated above, this process makes it possible to avoid the lysis steps, which are cumbersome from the industrial standpoint and generate numerous impurities.

The principle of the process thus lies in the harvesting of the viruses released into the supernatant. This process may involve a culture time longer than that used in the previous techniques based on lysis of the cells. As indicated above, the harvesting time does not have to be precise to within a half day. It is essentially determined by the kinetics of release of the viruses into the culture supernatant.

The kinetics of liberation of the viruses can be followed in different ways. In particular, it is possible to use analysis methods such as reverse-phase HPLC, ion exchange analytic chromatography, semiquantitative PCR (example 4.3), staining of dead cells with trypan blue, measurement of liberation of LDH type intracellular enzymes, measurement of particles in the supernatant by Coulter type equipment or by light diffraction, immunologic (ELISA, RIA, etc.) or nephelometric methods, titration by aggregation in the presence of antibodies, etc.

Harvesting is preferably performed when at least 50% of the viruses have been released into the supernatant. The point in time at which 50% of the viruses have been released can easily be determined by doing a kinetic study according to the methods described above. Even more preferably, harvesting is performed when at least 70% of the viruses have been released into the supernatant. It is particularly preferred to do the harvesting when at least 90% of the viruses have been released into the supernatant, i.e., when the kinetics reach a plateau. The kinetics of liberation of the virus are essentially based on the replication cycle of the adenovirus and can be influenced by certain factors. In particular, they may vary according to the type of virus used, and especially according to the type of deletion done in the recombinant viral genome. In particular, deletion of region E3 seems to slow liberation of the virus. Thus, in the presence of region E3, the virus can be harvested between 24 and 48 hours post-infection. In contrast, in the absence of region E3, a longer culturing time seems necessary. In this regard, the applicant has had experience with the kinetics of liberation of an adenovirus deficient in regions E1 and E3 into the supernatant of the cells, and has shown that liberation begins approximately 4 to 5 days post-infection and lasts up to about day 14. Liberation generally reaches a plateau between day 8 and day 14, and the titer remains stable for at least 20 days post-infection.

Preferably, in the process according to the invention, the cells are cultured during a period ranging between 2 and 14 days. Furthermore, liberation of the virus may be induced by expression in the encapsulation cell of a protein, for example a viral one, involved in the liberation of the virus. Thus, in the case of the adenovirus, liberation may be modulated by expression of the Death protein coded by region E3 of the adenovirus (protein E3-11.6K), possibly expressed under the control of an inducible promoter. Consequently, it is possible to reduce the virus liberation time and to harvest in the culture supernatant more than 50% of the viruses 24-48 hours post-infection.

To recover the viral particles, the culture supernatant is advantageously first filtered. Since the adenovirus is approximately 0.1 μm (120 nm) in size, filtration is performed with membranes whose pores are sufficiently large to let the virus pass through, but sufficiently fine to retain the contaminants. Preferably, filtration is performed with membranes having a porosity greater than 0.2 μm. According to a particularly advantageous exemplified embodiment, filtration is performed by successive filtrations on membranes of decreasing porosity. Particularly good results have been obtained by doing filtration on filters with a range of decreasing porosity—10 μm, 1.0 μm, then 0.8-0.2 μm. According to another preferred variant, filtration is performed by tangential microfiltration on flat membranes or hollow fibers. More particularly, it is possible to use flat Millipore membranes or hollow fibers ranging in porosity between 0.2 and 0.6 μm. The results presented in the examples show that this filtration step has a yield of 100% (no loss of virus was observed by retention on the filter having the lowest porosity).

According to another aspect of the invention, the applicant has now developed a process making it possible to harvest and purify the virus from the supernatant. Toward this goal, a supernatant thus filtered (or clarified) is subjected to ultrafiltration. This ultrafiltration makes is possible (i) to concentrate the supernatant, with the volumes used being important; (ii) to do a first purification of the virus and (iii) to adjust the buffer of the preparation in the subsequent preparation steps. According to a preferred exemplified embodiment, the supernatant is subjected to tangential ultrafiltration. Tangential ultrafiltration consists of concentrating and fractionating a solution between two compartments, retentate and filtrate, separated by membranes of specified cutoff thresholds, by producing a flow in the retentate compartment of the apparatus and by applying a transmembrane pressure between this compartment and the filtrate compartment. The flow is generally produced with a pump in the retentate compartment of the apparatus, and the transmembrane pressure is controlled by a valve on the liquid channel of the retentate circuit or by a variable-speed pump on the liquid channel of the filtrate circuit. The speed of the flow and the transmembrane pressure are chosen so as to generate low shear forces (Reynolds number less than 5000 $\sec^{-1}$, preferably below 3000 $\sec^{-1}$, pressure below 1.0 bar), while preventing plugging of the membranes. Different systems can be used to accomplish ultrafiltration, e.g., spiral membranes (Millipore, Amicon), as well as flat membranes or hollow fibers (Amicon, Millipore, Sartorius, Pall, GF, and Sepracor). Since the adenovirus has a mass of ca. 1000 kDa, it is advantageous within the scope of the invention to use membranes having a cutoff thresh below 1000 kDa, and preferably ranging between 100 kDa and 1000 kDa. The use of membranes having a cutoff threshold of 1000 kDa or higher in effect causes a large loss of virus at this stage. It is preferable to use membranes having a cutoff threshold ranging between 200 and 600 kDa, and even more preferable, between 300 and 500 kDa. The experiences presented in the examples show that the use of a membrane having a cutoff threshold at 300 kDa permits more than 90% of the viral particles to be retained, while eliminating the contaminants from the medium (DNA, proteins in the medium, cellular proteins, etc.). The use of a cutoff threshold of 500 kDa offers the same advantages.

The results presented in the examples show that this step makes it possible to concentrate large volumes of supernatant without loss of virus (90% yield), with generation of a better quality virus. In particular, concentration factors of 20- to 100-fold can easily be obtained.

This ultrafiltration step thus includes an additional purification compared to the classical model inasmuch as the contaminants of mass below the cutoff threshold (300 or 500 kDa) are eliminated at least in part. A distinct improvement in the quality of the viral preparation may be seen upon comparing the appearance of the separation after the first ultracentrifugation step according to the two processes. In the classical process involving lysis, the viral preparation tube presents a cloudy appearance with a coagulum (lipids, proteins) sometimes touching the virus band, while in the process according to the invention, following liberation and ultrafiltration, the preparation presents a band that is already well resolved of the contaminants of the medium that persist in the upper phase. An improvement in quality is also demonstrated upon comparing the profiles on ion exchange chromatography of a virus obtained by cellular lysis with a virus obtained by ultrafiltration as described in the present invention. In addition, it is possible to further enhance the quality by pursuing ultrafiltration with diafiltration of the concentrate. This diafiltration is performed based on the same principle as tangential ultrafiltration, and makes it possible to more completely eliminate the large-sized contaminants at the cutoff threshold of the membrane, while achieving equilibration of the concentrate in the purification buffer.

In addition, the applicant has also shown that this ultrafiltration makes it possible to purify the virus directly by ion exchange chromatography or by gel permeation chromatography, permitting excellent resolution of the viral particle peak without requiring treatment of the preparation beforehand with chromatography. This is particularly unexpected and advantageous. In fact, as indicated in the article by Huyghe et al. mentioned above, purification by chromatography of viral preparations gives poor results and also requires pretreatment of the viral suspension with benzonase and cyclodextrins.

Example 11

Optimization of Production Process

Figure 28:
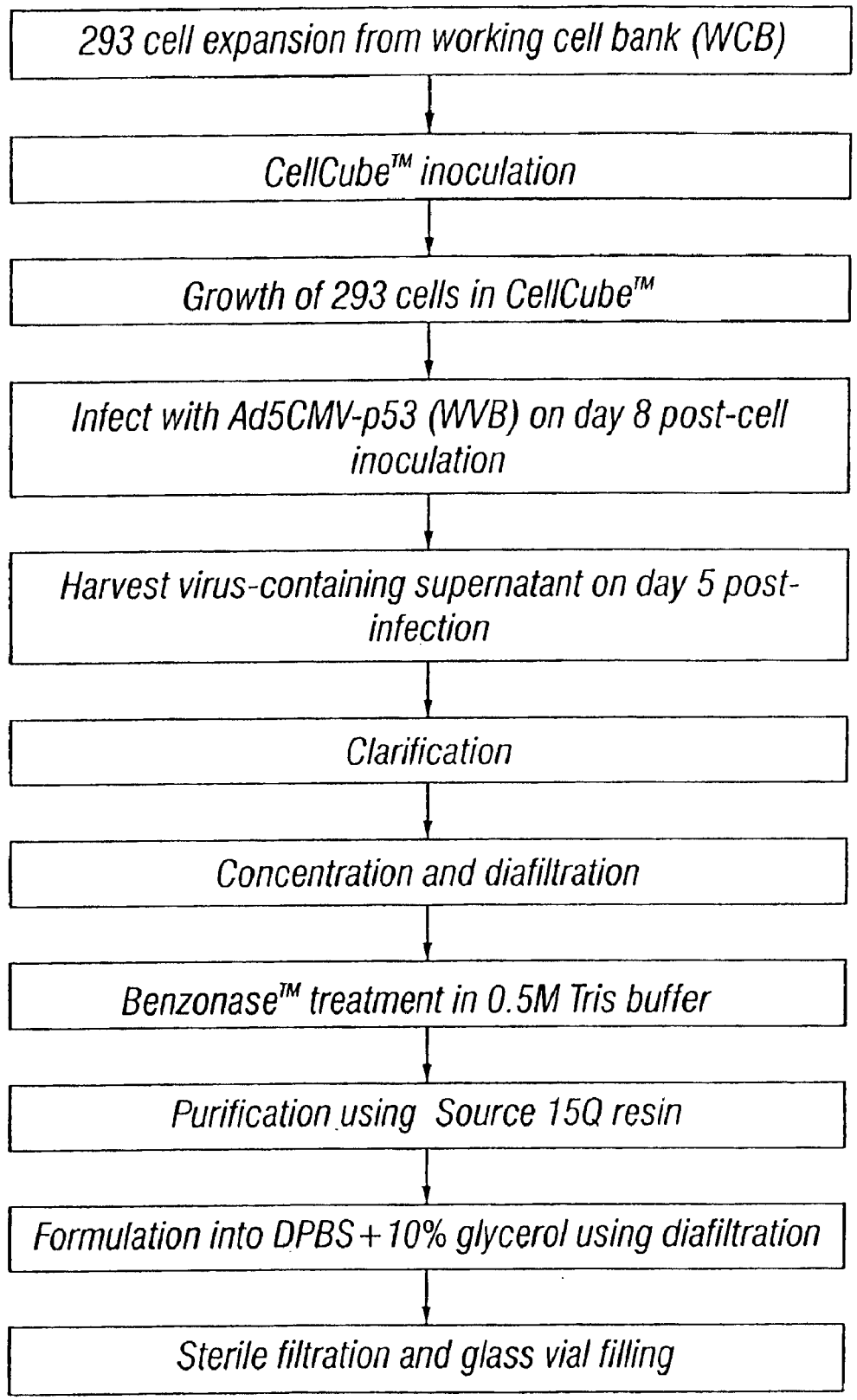
FIG. 28. Production and Purification flow chart for Ad5CMV-p53 optimized process.

To arrive at an optimized process that may be used for adenovirus production for clinical therapeutic production, a few steps in the above process as well as that of Blanche et al in PCT Publication No. WO 98/00524 (incorporated by reference) have been modified to enhance large scale production. Those steps involve modification to the virus harvest step, the nuclease treatment step, and the resin used for purification. The optimized process is depicted by the flow chart in FIG. 28.

Virus Harvest Step

Figure 24:
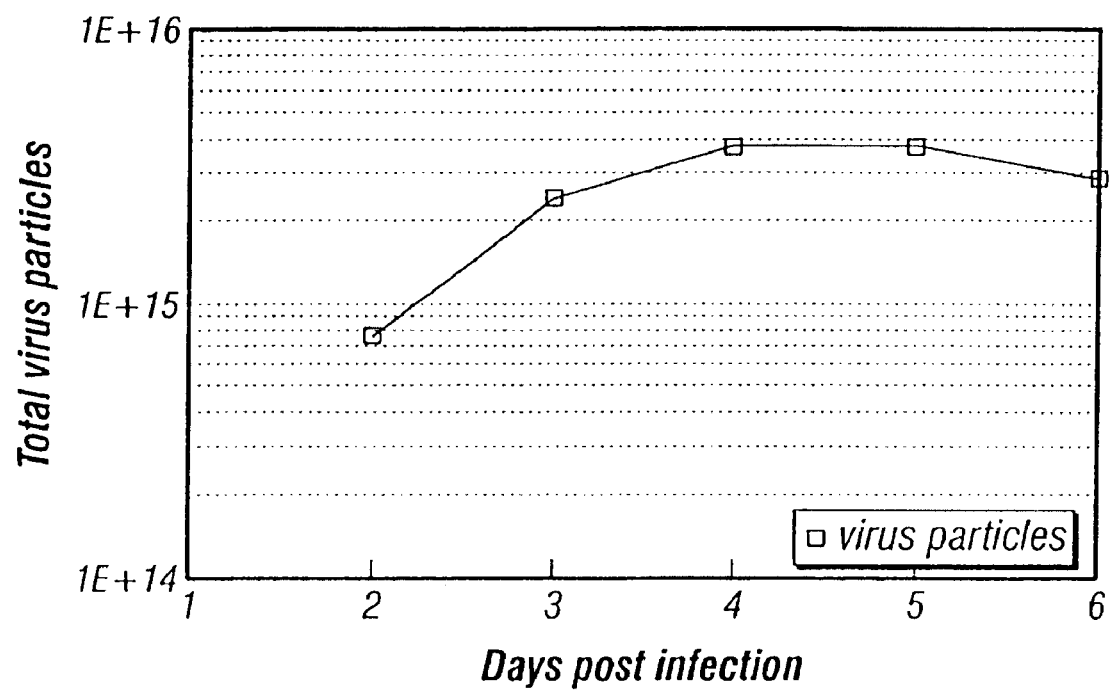
FIG. 24. Kinetics of virus release in the supernatant in a 4×100 CellCube™.

In the process described above, virus was harvested by lysing the 293 cells using a 1% Tween-20 lysis solution 2 days post-viral infection. This harvest method required the introduction of a lysis step into the process and the addition of one substance (Tween-20) into the crude viral harvest. In consideration of the lytic nature of the adenovirus life cycle, an alternative strategy was used to harvest the virus-containing supernatant after complete viral-mediated 293 cell lysis. Viral release kinetics were determined by analyzing daily samples of supernatant from the CellCube™ system after infection. Viral release into the supernatant reached a plateau on day 5 post-infection. The kinetics of viral release were found to be consistent. FIG. 24 shows the typical viral release kinetics for Ad5CMV-p53. Equivalent viral yield was obtained by using either the Tween-20 lysis or the autolysis supernatant harvest methods. The supernatant harvest method, however, simplified the production process by removing the lysis step in the process and the added lysis agent (Tween-20) in the crude viral harvest. As a result, the supernatant harvest method will preferably be used for the optimized process.

Nuclease Treatment Step

In the above process and that of Blanch et al in PCT Publication No. WO 98/00524, 1M NaCl was included in the Benzonase™ treatment buffer to prevent viral precipitation during enzyme treatment. Unfortunately, the presence of 1M NaCl in the buffer was found to significantly inhibit the Benzonase™ enzymatic activity. As a result, other buffers which could prevent viral precipitation without retarding the Benzonase™ enzymatic activity were examined. A 0.5M Tris/HCl+1 mM $MgCl_2$, pH=8.0, buffer was found to meet both criteria. In addition, this buffer has a conductivity of 19 mS/cm, which makes it possible to load the Benzonase™-treated viral solution directly onto the chromatographic column for purification As a result, changing to the 0.5M Tris/HCl+1 mM $MgCl_2$, pH=8.0, buffer will not only improve the Benzonase™ treatment efficiency but also simplify the downstream process.

Resin for Purification

Figure 25:
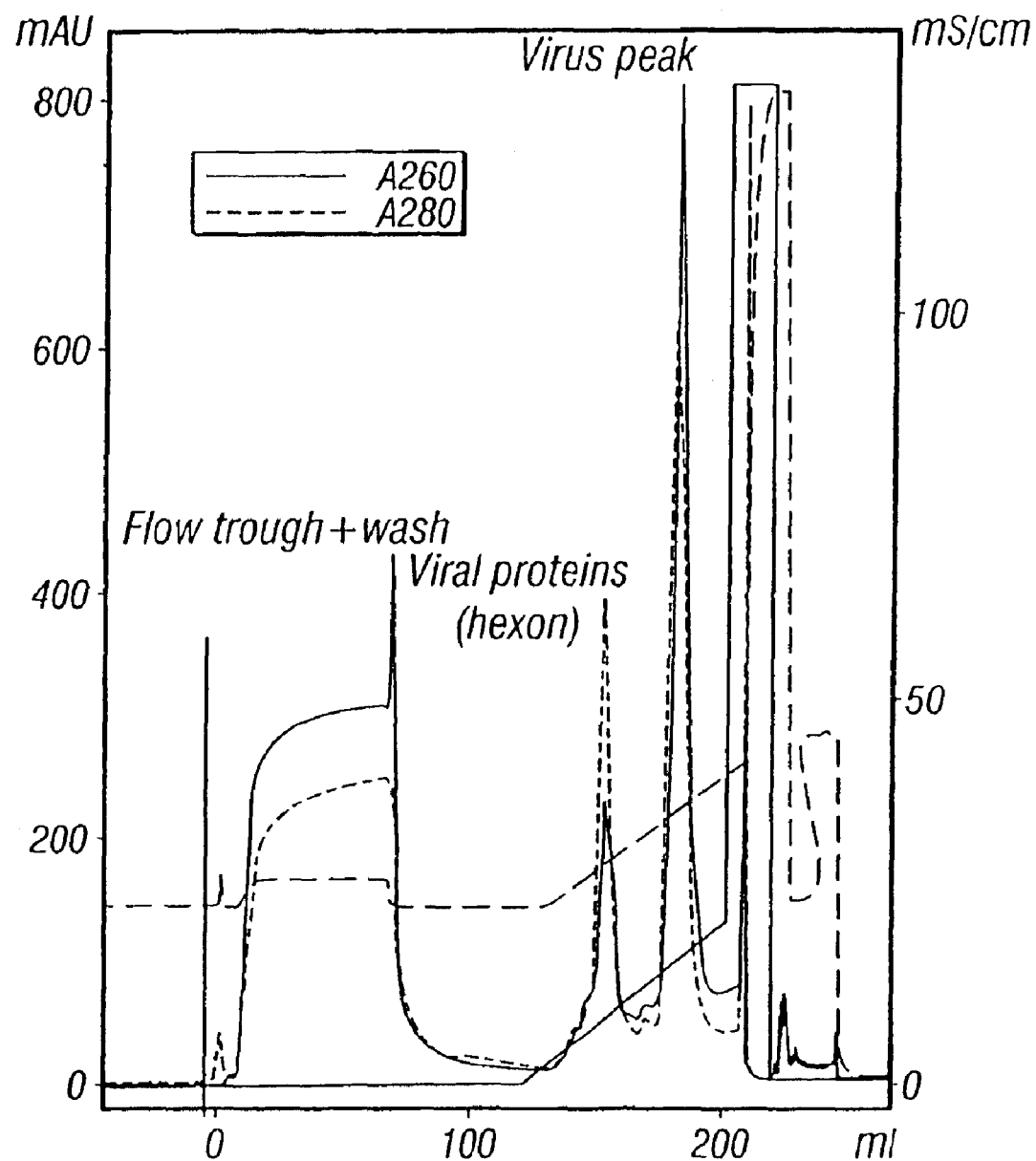
FIG. 25. Chromatogram using Source 15Q resin for purification.
Figure 26:
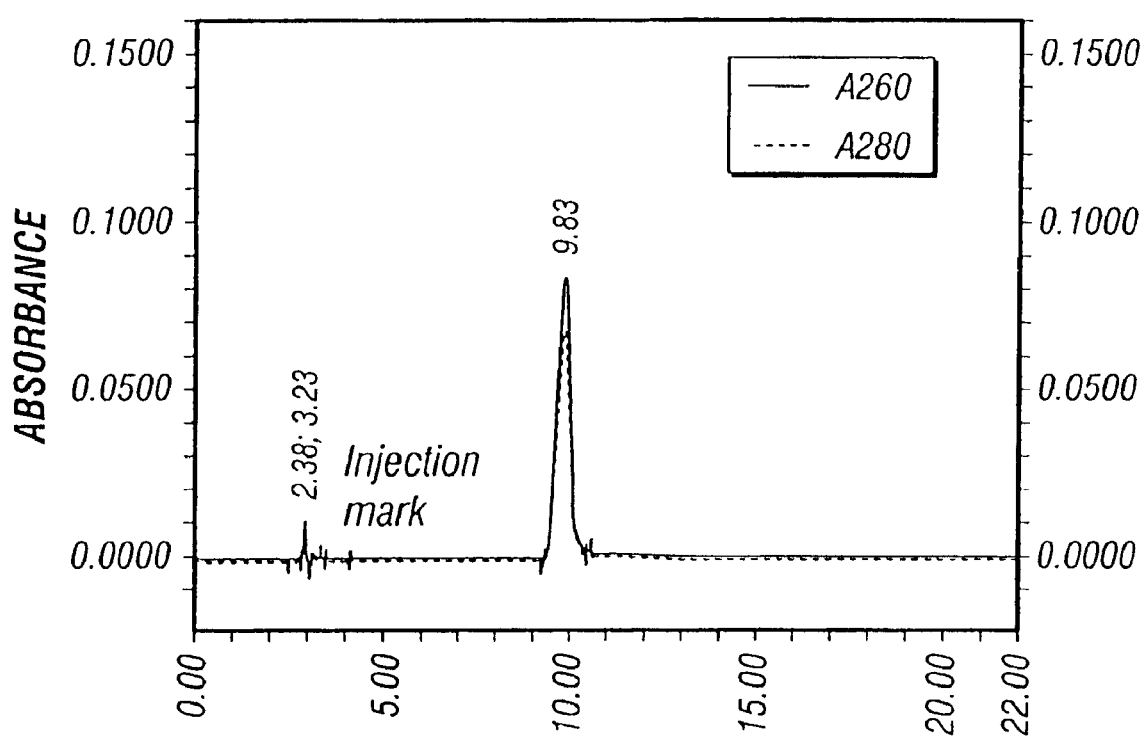
FIG. 26. HPLC profile of purified Ad5CMV-p53 product from Source 15Q resin.

The Fractogel TMAE(s) resin and Toyopearl SuperQ 650M resin employed in the above process and that of Blanche et al performed consistently well. However because of supply and technical support problems, alternative resins were chosen for use in virus purification. Source 15Q resin manufactured by Pharmacia Biotech was found to perform as well as the Fractogel and Toyopearl resins. FIG. 25 shows a typical chromatogram from the Source 15Q resin. Surprisingly, viral material was found to interact slightly stronger with the Source 15Q resin than with the Fractogel and Toyopearl resin. As a result, a larger viral protein peak was seen at the beginning of the gradient elution. The purified virus fraction was also eluted relatively later in the gradient. However, the overall purification profile was not significantly different from that of the Fractogel or Toyopearl resin. HPLC analysis of the purified viral fraction from the Source 15Q resin showed an equivalent profile to that from the Fractogel resin. FIG. 26 shows the HPLC profile.

Figure 27A:
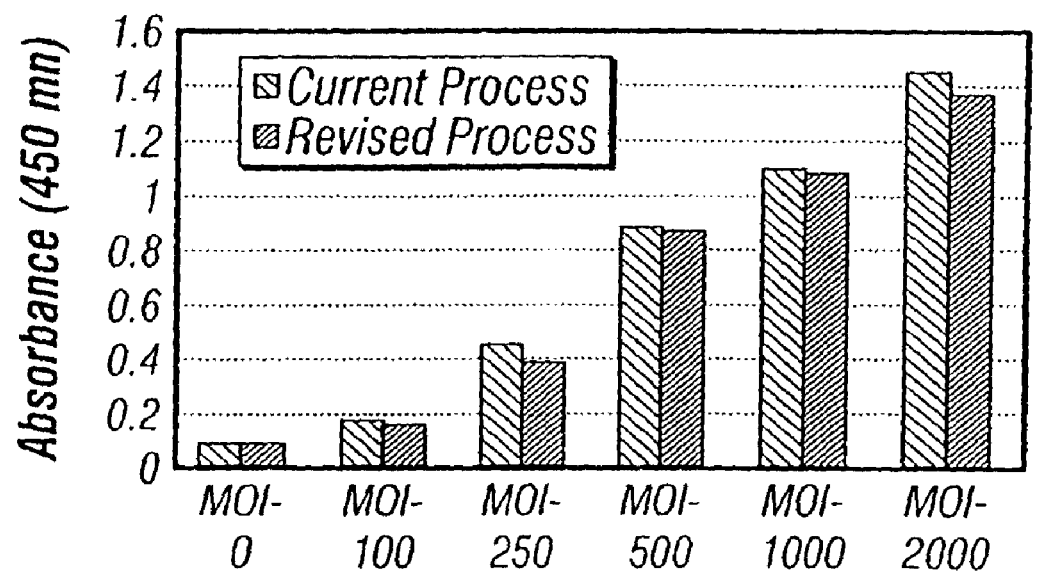
FIG. 27. Comparison of bioactivity of original process vs. optimized process to produce Ad5CMV-p53 product.
Figure 27B:
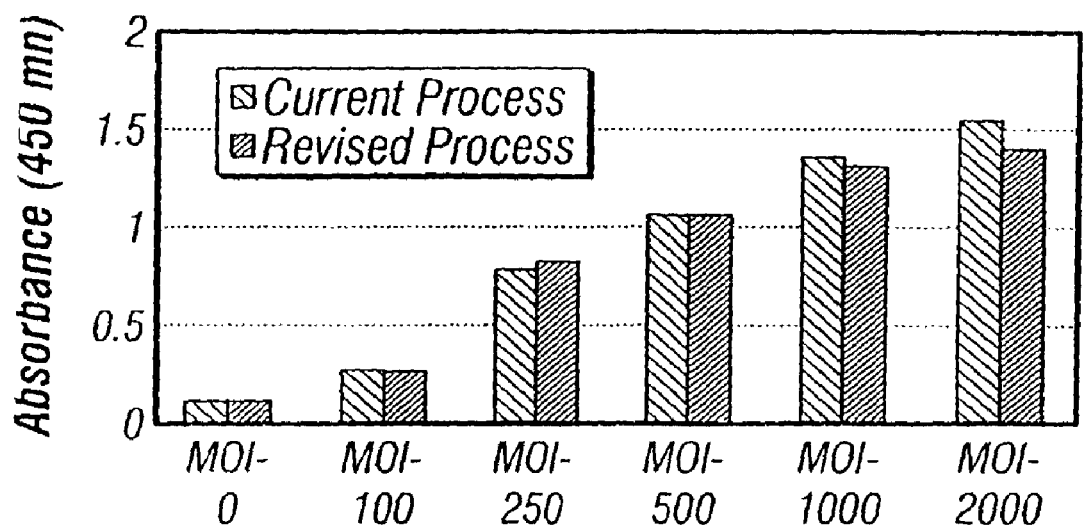

Ad5CMV-p53 made by the optimized process was also assessed for biological activity compared to material made by the above process and that of Blanche et al. Two cell lines, H1299 and SAOS-LM, which express no endogenous p53, were transduced with materials made by the two processes at equal multiplicities of infection (viral particles/cell). p53 expression was monitored at 6 hours post-transduction in H1299 and 24 hours post-transduction in SAOS-2. The level of p53 expression mediated by the two materials was equivalent and dose-dependent in both recipient cell lines (FIG. 27).

Process Hold Points

The freeze and thaw stability of the purified viral fraction eluted from the chromatography column (purified bulk) was evaluated. The purified viral fraction eluted from the column was frozen bulk at $\leq-60°$ C. after supplementing with glycerol to a final concentration of 10% (v/v). The frozen bulk was thawed successfully without detrimental effects on titer. The freeze and thaw data are given in Table 16.

TABLE 16

Freeze and thaw of purified bulk

|  | No freeze | Post freeze-thaw | |
|---|---|---|---|
|  |  | Bulk freeze (45 ml) | Small volume freeze (1 ml) |
| Viral particles/ml | $4.0 \times 10^{11}$ | $3.8 \times 10^{11}$ | $4.1 \times 10^{11}$ |

Furthermore, no change in HPLC profiles was observed pre- and post-freeze and thaw. Therefore, viral material at the post-chromatography step can be held at <−60° C. for further processing, and a process hold can be introduced at the post-chromatography step (purified bulk).

Similar freeze and thaw stability was observed for formulated sterile bulk product. Table 17 shows the freeze and thaw data.

TABLE 17

Freeze and thaw of formulated sterile bulk product

|  | No freeze | Post freeze-thaw | |
|---|---|---|---|
|  |  | Bulk freeze (45 ml) | Small volume freeze (1 ml) |
| Viral particles/ml | $1.3 \times 10^{13}$ | $1.4 \times 10^{13}$ | $1.3 \times 10^{13}$ |

As a result, the formulated sterile bulk product can be held at <−60° C. before aseptic filling without damaging effects on the viral titer and a process hold point can be introduced at the post-formulation step (sterile bulk).

Example 12

Parameters for Large Scale Production

During the scale up and optimization of the large scale process (16-mer), several parameters were found by the inventors to be desirable for successful production runs and high virus yield. These desirable parameters are centered around the cell culturing system, the most upstream portion of the adenovirus production process, and are believed to be applicable to other types of cell culturing systems and at larger scales. In particular, it can be easily envisioned that the changes described below which result in functional changes to the system will be useful to enable modification and optimization of other cell culture systems.

For the present example, the culture control parameters are as follows. Cells are cultured at 37° C. with 10% $CO_2$. Cell culture medium is DMEM+10% FBS, and the inoculation cell density for cell expansion is <$4 \times 10^4$ cells/cm². The parameters that involve the set up and execution of the CellCube™ system and are listed below.

CellCube™ setup: In the full scale set up (4×100 or "16-mer"), it is desirable to use one separate cell culture medium recirculation loop for each cube module (4-mer) to achieve even medium perfusion. For example, in the present 16-mer set-up, the 16-mer is composed of four 4-mers linked together in a series, each 4-mer having it's own medium recirculation loop. The 16-mer is considered one unit and is controlled by a single control module that modulates the rate of medium perfusion and measures the culture control parameters. Other setups such as using one medium recirculation loop for every two 4-mer modules results in uneven medium perfusion due to pressure drops in the system, and is detrimental to the health of the cells in the second cube with lower levels of nutrients and freshly oxygenated medium. Thus, in a cell culture system used for adenovirus production, it is preferable that the cell culture medium perfusion be maintained at a constant pressure and rate, ensuring consistent and optimal health of the producer cells. The perfusion rate is determined by monitoring one or more of the cell culture control parameters, such as glucose concentration.

Seeding Density: In order to achieve maximal cell expansion and growth, it is most preferable to inoculate the CellCube™ with $1-2 \times 10^4$ cells/cm². Higher numbers of cells used in the cell inoculation step results in a cell density that is too high and the result is an over-confluence of cells at the time of viral infection, thus lowering yields. It is well within one of skill in the art to determine that in other types of cell culturing systems, similar optimization of the seeding density for a particular system could easily be determined.

Seeding Method: It has been found that for full scale production, it is advantageous to use one homogeneous cell pool for seeding of all CellCube™ modules. Prior to seeding the cell culture apparatus, producer cells from the working cell bank are expanded from stock cultures. This cell expansion is accomplished by growing the cells in tissue culture flasks or other similar cell culture devices, and continual splitting of the cells into larger tissue culture devices. Upon reaching the total number of needed cells for inoculation of the large scale cell culture apparatus, all of the cells from each of the cell culture devices used for cell expansion are pooled together. This homogeneous cell pool is used to inoculate each of the CellCube™ modules of the 16-mer. Seeding of each of the modules using separate cell populations, for example from individual cell culture devices used in the cell expansion phase, can result in uneven cell density, and therefore uneven confluency levels at the time of infection. It is believed that the use of a homogeneous cell pool for seeding overcomes these problems.

Length of Cell Inoculation: During inoculation of each of the CellCube™ modules, cells are added to the module and allowed a period of a few hours to attach to the surface of the module. During this time there is no medium perfusion or recirculation. It has been found by the inventors that it is advantageous to complete this cell seeding in one day (24 hrs). Thus for example, one side of the module is inoculated and left for a period of 6-8 hours to allow cell attachment, and then the other side of the module is inoculated and left overnight to allow the cells to attach to the surface of the module. During this seeding process, the cell culture medium from each side of the module is kept separate, and not allowed to flow to the other side of the module. It has been observed that if the cell inoculation procedure is done over a period of time longer than one day, and/or with medium exchange between sides of the module, that there is a greater likelihood of cell detachment from the cell culture surface due to weak attachment. Possible reasons for this weak attachment may include: 1) the medium exchange between sides of the module which may produce shear forces with the potential to dislodge cells undergoing the attachment process, and 2) the longer time period before medium perfusion is started may result in low levels of nutrients in the media, and therefore the health of the cells deteriorates, leading to less efficient attachment.

Culture Control Parameters: The inventors have found that glucose concentration of the cell culture medium should preferably be maintained at 1-2 g/L. Previous studies using glucose concentrations at higher levels has been shown to reduce product yield.

Infection Method: Eight days post-cell seeding, the cells are infected with adenovirus. During the infection process, medium perfusion is stopped for one hour, however medium recirculation is maintained, thus keeping high levels of fresh oxygen in the medium. It has been found by the inventors that if medium recirculation is also stopped during the infection step, there is an increased possibility of cell death due to oxygen starvation.

Example 13

Optimized Large Scale Production and Purification of Adenovirus

The example described below is descriptive of the methods and materials used in a large scale production and purification process for recombinant Ad5CMV-p53 adenovirus. This process uses a CellCube™ bioreactor apparatus as the cell culturing system, and large scale in this example refers to a CellCube 4×100 set up or multiples thereof. Total maximum virus yields that may be obtained from one CellCube 4×100 system are about $1-5 \times 10^{15}$ viral particles at harvest.

Cell Expansion and Culture

The CellCube™ 4×100 was set up as described above, with 4 CellCube™ 100 modules in parallel, all in a medium recirculation loop, and the whole system being controlled by a single control unit. The producer cells, 293 cells from a working cell bank (WCB), were thawed and expanded in T flasks and Cellfactories (Nunc) seeding at densities from $1-8 \times 10e4$ cells/cm². Cells were generally split at a confluence of about 85-90% and continually expanded until enough cells were obtained for inoculation of the Cellcube™. At the end of the cell expansion phase, all the cells from each of the Cellfactories were pooled to make one homogeneous mixture of 293 cells. This cell pool was used to inoculate the Cellcube™ at a total cell number in the range of $1-3 \times 10e9$ viable cells per side. During cell inoculation, medium perfusion and recirculation is suspended for a period of time to allow the cells to attach to the substrate. Cells are allowed to attach to side one for 4-6 hours; then side two is inoculated and the cells allowed to attach for no more than 18 hours before recirculation is restarted. After cell attachment, medium perfusion and recirculation was restarted and the cells were allowed to grow for 7 days at 37° C. under culture conditions of pH=6.90-7.45, DO=40-50% air saturation. Medium perfusion rate is regulated according to the glucose concentration in the Cellcube™, and was maintained at between 1-2 g/L. One day before viral infection, medium for perfusion was changed from DMEM+10% FBS to Basal DMEM (no FBS). On day 8, cells were infected with AdCMVp53 virus at a multiplicity of infection (MOI) of 5-50 viral particles per cell based on $8 \times 10^{10}$ cells total. Medium perfusion was stopped for 1 hr at the time of infection and then resumed for approximately two days. Medium recirculation was maintained throughout the virus infection period.

Virus Harvest and Purification

Previous studies looking at virus release kinetics after Ad5CMV-p53 infection of 293 cells determined that maximal virus release from the producer cells due to the lytic nature of adenovirus was obtained four to six days after infection. Thus, four to six days after virus infection, the supernatant from the Cellcube™ modules was removed as a pool. The virus supernatant was then clarified by filtration through two Polyguard 5.0 micron filters, followed by a 5.0 micron Polysep filter (Millipore). The supernatant was then concentrated approximately 10-fold using tangential flow filtration through a Pellicon cassette (Millipore) of 300 K nominal molecular weight cut-off (NMWC). The buffer was then exchanged by diafiltration against 0.5 M Tris+1 mM $MgCl_2$, pH=8. The supernatant was then treated at room temperature with 100 U/ml Benzonase™ in a buffer of 0.5M Tris/HCl+1 mM $MgCl_2$, pH=8.0; 0.2 micron filtered, and incubated overnight at room temperature to remove contaminating cellular nucleic acids. The crude virus preparation is then 0.2 micron filtered and loaded directly onto an ion exchange column (BPG 200/500, Pharmacia) containing Source 15Q resin equilibrated with 20 mM Tris+1 mM $MgCl_2$+250 mM NaCl, pH=8.0. The virus was eluted with a 40 column linear gradient using an elution buffer composed of 20 mM Tris+1 mM $MgCl_2$+2 M NaCl, pH=8.0. The purified virus was then subjected to another concentration and diafiltration step to place the virus in the final formulation for the virus product. The concentration step used a 300 NMWC Pellicon TFF membrane, and for diafiltration the buffer was exchanged using 8-10 column volumes of Dulbecco's Phosphate Buffered Saline+10% Glycerol. The purified virus was then sterile filtered through a 0.2 micron Millipak (Millipore) filter. The formulated product was then filled into sterile glass vials with stoppers. Flip off crimp caps were applied prior to final product inspection and labeling.

Two process hold points may be introduced into the process as described in Example 10. The first process hold may be introduced after the IEC step, at which time 10% glycerol may be added to the eluate and frozen for later processing. The second process hold step may be introduced after the final product is obtained but prior to sterile filtering and vialing. The final bulk product can at this point can be frozen and held for final filtering and vialing.

The following list of parameters was measured throughout the production and purification process. The Specification is the desired measurement that the test article should meet. The result of each test is shown to the right on the table.

| Test | Specification | Result |
|---|---|---|
| Mycoplasma PTC 1993 | Negative | PASS |
| Bioburden | <10 CFU/100 ML | 0 CFU/100 ML |
| In Vitro Adventitious Virus | NEGATIVE | PASS |
| In Vivo Adventitious Virus | NEGATIVE | PASS |
| Adeno-Associated Virus (PCR) | NEGATIVE | PASS |
| Bioburden | ≦1 cfu/10 mL | 0 cfu/10 mL |
| Bacterial Endotoxins Test | <5 EU/mL | <0.15 EU/mL |
| Sterility | STERILE | Pass |
| Sterility | Sterile | Pass |
| Bacterial Endotoxins Test | <5 EU/mL | <0.15 EU/mL |
| Titration of Adenovirus Vector | $2 \times 10^{10} - 8 \times 10^{10}$ pfu/mL | $5 \times 10^{10}$ pfu/mL |
| Virus Particle Enumeration | $8.0 \times 10^{11} - 1.2 \times 10^{12}$ Viral Particles/mL Ratio 260/280 | $9.4 \times 10^{11}$ Viral Particles/mL Ratio 260/280 |
| Particle/pfu Ratio | 10-60 | 20 |
| Western Blot (anti-p53) | Express p53 Protein | Pass |
| Bioactivity (SAOS) | MOI Causing 50% Cell Death is <1000 vp/cell | <1000 vp/cell |
| Restriction Mapping | Molecular Size as Expected | Pass |
| Protein Content by | ≦320 µg/1 × $10^{12}$ | 245 µg/1 × $10^{12}$ |

-continued

| Test | Specification | Result |
|---|---|---|
| BCA | Viral Particles | Viral Particles |
| SDS-PAGE | Bands as Expected No Significant Extra Bands | Pass |
| HPLC Ion Exchange | ≧98% Purity | ≧99.57% |
| Bovine Serum Albumin (ELISA) | ≦50 ng BSA/$10^{12}$ Viral Particles | <1.9 ng BSA/$10^{12}$ Viral Particles |
| Recoverable Fill Volume | 1.0 to 1.4 mL | 7 of 7 vials in the range of 1.1 to 1.2 mL |
| Physical Description | Clear to opalescent with no gross particles by visual inspection | Pass |
| huDNA | <10 ng/1 × $10^{12}$ Viral Particles | 0.4 ng/1 × $10^{12}$ Viral Particles |
| General Safety | Pass | Pass |
| Replication Competent Adenovirus | <1 pfu in 2.5 × $10^9$ Viral Particles | Report Value at 2.5 × $10^9$ and 2.5 × $10^{10}$ |
| p53 Mutation Frequency | <3% | <1% |
| pH | 6.0 - 8.0 | 7.5 |

Example 14

Summary of Formulation Development for Adenovirus

Currently, clinical Adp53 product is stored frozen at ≦60° C. This deep frozen storage condition is not only expensive, but also creates problems for shipment and inconvenience for clinic use. The goal of the formulation development effort is to develop either a liquid or a lyophilized formulation for Adp53 that can be stored at refrigerated condition and be stable for extended period of time. Formulation development for Adp53 is focused on both lyophilization and liquid formulations. From manufacturing and marketing economics point of view, liquid formulation is preferred to a lyophilized formulation. Preliminary results from both fronts of formulation development are summarized here.

Materials and Equipment

Lyophilizer

A Dura-stop μp lyophilizer (FTSsystems) with in process sample retrieving device was used. The lyophilizer is equipped with both thermocouple vacuum gauge and capacitance manometer for vacuum measurement. Condenser temperature is programmed to reach to −80° C. Vials were stoppered at the end of each run with a build-in mechanical stoppering device.

Residual Moisture Measurement

Residual moisture in freeze dried product was analyzed by a Karl-Fisher type coulometer (Mettler DL37, KF coulometer).

HPLC Analysis

HPLC analysis of samples was done on a Beckman Gold HPLC system.

Vials and Stoppers

Borosilicate 3 ml with 13 mm opening lyo vials and their corresponding butyl rubber stoppers (both from Wheaton) were used for both lyophilization and liquid formulation development. The stoppered vials were capped with Flip-off aluminum caps using a capping device (LW312 Westcapper, The West Company).

Results

Lyophilization

Initial Cycle and Formulation Development

Figure 29:
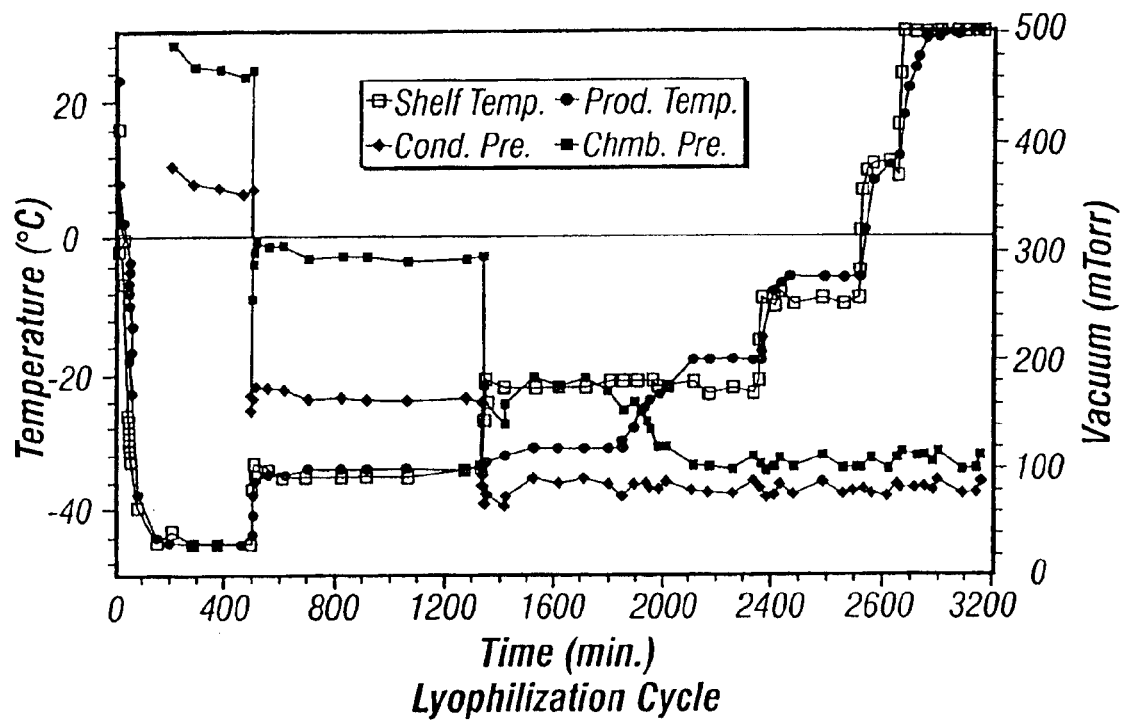
FIG. 29. Lyophilization cycle for adenovirus formulations.

There are three main process variables that can be programmed to achieve optimal freeze-drying. Those are shelf temperature, chamber pressure, and lyophilization step duration time. To avoid cake collapse, shelf temperature need to be set at temperatures 2-3° C. below the glass transition or eutectic temperature of the frozen formulation. Both the glass transition and eutectic temperatures of a formulation can be determined by differential scanning colorometry (DSC) analysis. Chamber pressure is generally set at below the ice vapor pressure of the frozen formulation. The ice vapor pressure is dependent on the shelf temperature and chamber pressure. Too high a chamber pressure will reduce the drying rate by reducing the pressure differential between the ice and the surrounding, while too low a pressure will also slow down drying rate by reducing the heat transfer rate from the shelf to the vials. The development of a lyophilization cycle is closely related with the formulation and the vials chosen for lyophilization. Formulation excipient selection was based on the classical excipients found in most lyophilized pharmaceuticals. The excipients in a lyophilization formulation should provide the functions of bulking, cryoprotection, and lyoprotection. The excipients chosen were mannitol (M, bulking agent), sucrose (S, cryo- and lyoprotectant), and human serum albumin (HSA, lyoprotectant). These excipients were formulated in 10 mM Tris+1 mM $MgCl_2$, pH=7.50 at various percentages and filled into the 3 ml vials at a fill volume of 1 ml. To start with, a preliminary cycle was programmed to screen a variety of formulations based on the criteria of residual moisture and physical appearance after drying. The cycle used is plotted in FIG. 29. Extensive screening was carried out by variation of the percentages of the individual excipients. Table 18 shows briefly some of the results.

TABLE 18

Evaluation of different formulations under the same cycle

| Formulation M %/S %/HSA % | Appearance | Moisture (% weight) |
|---|---|---|
| 10/5/0.5 | good cake | 0.89 |
| 5/5/0.5 | good cake | 1.5 |
| 3/5/0.5 | loose cake (partial collapse) | 3.4 |
| 1/5/0.5 | no cake (collapse) | 6.4 |

The results suggest that a minimum amount of 3% mannitol is required in the formulation in order to achieve pharmaceutically elegant cake. The percentages of sucrose in the formulation were also examined. No significant effect on freeze-drying was observed at sucrose concentrations of ≦10%. HSA concentration was kept constant to 0.5% during the initial screening stage.

After the evaluation of the formulations, freeze-drying cycle was optimized by changing the shelf temperature, chamber vacuum and the duration of each cycle step. Based on the extensive cycle optimization, the following cycle (cycle #14) was used for further virus lyophilization development.

Load sample at room temperature onto shelf

Set shelf temperature to −45° C. and freeze sample. Step time 2 h.

Set shelf temperature at −45° C., turn vacuum pump and set vacuum at 400 mT. Step time 5 h Set shelf temperature at −35° C., set vacuum at 200 mT. Step time 13 h Set shelf temperature at −22° C., set vacuum at 100 mT. Step time 15 h Set shelf temperature at −10° C., set vacuum at 100 mT. Step time 5 h Set shelf temperature at 10° C., set vacuum at 100 mT, Step time 4 h Vial stoppering under vacuum Cycle and Formulation Development with Virus in Formulation Effect of Sucrose Concentration in Formulation Cycle and formulation were further optimized according to virus recovery after lyophilization analyzed by both HPLC and plaque forming unit (PFU) assays. Table 19 shows the virus recoveries immediate after drying in different formulations using the above drying cycle. Variation of the percentage of sucrose in the formulation had significant effect on virus recoveries.

TABLE 19

Recoveries of virus after lyophilization

| Formulation M %/S %/HSA % | Appearance | Residual moisture | Recovery (%) |
|---|---|---|---|
| 6/0/0.5 | Good cake | 0.44% | 0 |
| 6/3.5/0.5 | Good cake | 2.2% | 56 |
| 6/5/0.5 | Good cake | 2.5% | 81 |
| 6/6/0.5 | Good cake | 2.7% | 120 |
| 6/7/0.5 | Good cake | 2.8% | 120 |
| 6/8/0.5 | Good cake | 3.3% | 93 |
| 6/9/0.5 | Good cake | 3.7% | 120 |

Residual moisture in the freeze-dried product increased as the sucrose percentage increased. A minimum sucrose concentration of 5% is required in the formulation to maintain a good virus recovery after lyophilization. Similar sucrose effects in formulation that had 5% instead of 6% mannitol were observed. However, good virus recovery immediately after drying does not necessary support a good long-term storage stability. As a result, formulations having 4 different sucrose concentrations of 6, 7, 8, and 9%, were incorporated for further evaluation.

Effect of HSA in Formulation

The contribution of HSA concentrations in the formulation on virus recovery after drying was examined using the same freeze drying cycle. Table 20 shows the results

TABLE 20

Effects of HSA concentration on lyophilization

| Formulation M %/S %/HSA % | Appearance | Residual moisture | Recovery (%) |
|---|---|---|---|
| 6/7/0 | Good cake | 0.98 | 83 |
| 6/7/0.5 | Good cake | 1.24 | 120 |
| 6/7/2 | Good cake | 1.5 | 110 |
| 6/7/5 | Good cake | 1.7 | 102 |

The results indicate that inclusion of HSA in the formulation had positive effect on virus recovery after drying. Concentrations higher than 0.5% did not further improve the virus recovery post drying. As a result, 0.5% HSA is formulated in all the lyophilization formulations.

Cycle Optimization

As indicated in Table 19, relatively high residual moistures were present in the dried product. Although there has not been a known optimal residual moisture for freeze dried viruses, it could be beneficial for long term storage stability to further reduce the residual moisture in the dried product. After reviewing of the drying cycle, it was decided to increase the secondary drying temperature from 10° C. to 30° C. without increasing the total cycle time. As indicated in Table 21, significant reduction in residual moisture had been achieved in all the formulations without negative effects on virus recoveries. With the improved drying cycle, residual moisture was less than 2% in all the formulations immediately after drying. It is expected that the reduced residual moisture will improve the long-term storage stability of the dried product.

TABLE 21

Effects of secondary drying temperature on lyophilization

| Formulation M %/S %/HAS % | Secondary drying at 10° C. | | Secondary drying at 30° C. | |
|---|---|---|---|---|
| | Residual moisture (w %) | Recovery (%) | Residual moisture | Recovery |
| 6/6/0.5 | 2.2 | 100 | 0.8 | 93 |
| 6/7/0.5 | 2.5 | 86 | 1.1 | 100 |
| 6/8/0.5 | 2.7 | 83 | 1.3 | 87 |
| 6/9/0.5 | 3.3 | 93 | 1.5 | 86 |
| 5/6/0.5 | 2.3 | 110 | 1.0 | 94 |
| 5/7/0.5 | 2.7 | 88 | 1.2 | 85 |
| 5/8/0.5 | 3.5 | 97 | 1.6 | 88 |
| 5/9/0.5 | 4 | 90 | 1.9 | 86 |

$N_2$ Backfilling (Blanketing)

Lyophilization was done similarly as above except that dry $N_2$ was used for gas bleeding for pressure control during the drying and backfilling at the end of the cycle. At the end of a drying run, the chamber was filled with dry $N_2$ to about 80% atmospheric pressure. Subsequently, the vials were stoppered. No difference was noticed between the air and $N_2$ blanketing runs immediate after drying. However, if oxygen present in the vial during air backfilling causes damaging effect (oxidation) on the virus or excipients used during long-term storage, backfilling with dry $N_2$ is likely to ameliorate the damaging effects and improve long term storage stability of the virus.

Removal of Glycerol from Formulation

During the preparation of virus containing formulations, stock virus solution was added to the pre-formulated formulations at a dilution factor of 10. Because of the presence of 10% glycerol in the stock virus solution, 1% glycerol was introduced into the formulations. To examine any possible effect of the presence of 1% glycerol on lyophilization, a freeze drying run was conducted using virus diafiltered into the formulation of 5% (M)/7% (S)/0.5% (HSA). Diafiltration was done with 5 vol of buffer exchange using a constant volume buffer exchange mode to ensure adequate removal of residual glycerol (99% removal). After diafiltration, virus solution was filled into vials and then lyophilized similarly. Table 22 shows the lyophilization results

TABLE 22

Lyophilization without glycerol

| Formulation M%/S%/HSA% | Residual moisture | Recovery (%) |
|---|---|---|
| 5/7/0.5 | 1.0 | 80 |

No significant difference after freeze drying was observed between formulations with and without 1% glycerol. Possible implications of this change on long term storage will be evaluated.

Long Term Storage Stability

Adp53 virus lyophilized under different formulations and different cycles was placed at −20° C., 4° C., and room temperature (RT) under dark for long term storage stability evaluation. Parameters measured during the stability study were PFU, HPLC viral particles, residual moisture, and vacuum inside vial (integrity). FIG. 30A and FIG. 30B show the data after 12-month storage with secondary drying at 10° C. without $N_2$ blanketing. Lyophilized virus is stable at both −20° C. and 4° C. storage for up to 12 months. However, virus was not stable at room temperature storage. More than 50% loss in infectivity was observed at RT after 1-month storage. The reason for the quick loss of infectivity at RT is not clear. However, it is likely that RT is above the glass transition temperature of the dried formulation and results in the accelerated virus degradation. A differential scanning colorimitry (DSC) analysis of the formulation could provide very useful information. Pressure change inside the vials during storage was not detected, which indicates that the vials maintained their integrity. The slight increase in residual moisture during storage can be attributed to the release of moisture from the rubber stopper into the dried product.

FIG. 31 and FIG. 32 show the storage stability data with secondary drying at 30° C. without and with $N_2$ backfilling, respectively. Because of the nearly identical stability observed at −20° C. and 4° C. storage conditions, and to reduce the consumption of virus, −20° C. was not included in the long-term storage stability study. Similar to the samples dried with secondary drying at 10° C., virus is stable at 4° C. but not stable at RT. However, relative better stability was observed at RT storage than those dried at 10° C. secondary drying. This is likely to be the result of the lower residual moisture attained at 30° C. secondary drying. This result suggests that residual moisture is an important parameter that affects storage stability during long term storage. Longer time storage is needed to reveal any beneficial effects of doing $N_2$ blanketing during lyophilization since no significant effect was observed for up to 3 months storage. During storage, HPLC analysis indicates that virus is stable at both −20° C. and 4° C. storage and not stable at RT, which is consistent with the results from PFU assay.

HSA Alternatives

The presence of HSA in the formulations could be a potential regulatory concern. As a result, a variety of excipients have been evaluated to substitute HSA in the formulation.

The substitutes examined included PEG, amino acids (glycine, arginine), polymers (polyvinylpyrrolidone), and surfactants (Tween-20 and Tween-80).

Liquid Formulation

Concurrent with the development of lyophilization of Adp53 product, experimentation was carried out to examine the possibility of developing a liquid formulation for Adp53 product. The goal was to develop a formulation that can provide enough stability to the virus when stored at above freezing temperatures. Four sets of liquid formulations have been evaluated. In the first set of formulation, the current 10% glycerol formulation was compared to HSA and PEG containing formulations. In the second set of formulation, various amino acids were examined for formulating Adp53. In the third set of formulation, the optimal formulation developed for lyophilization was used to formulate Adp53 in a liquid form. In the fourth set of formulation, detergents were evaluated for formulating Adp53. Viruses formulated with all those different formulations are being tested for long term storage stability at −20° C., 4° C., and RT.

Liquid Formulation Set #1

HSA containing formulation (5% sucrose+5% HSA in 10 mM Tris buffer, 150 mM NaCl, and 1 mM $MgCl_2$, pH=8.20 buffer) was compared with 10% glycerol in DPBS buffer and sucrose/PEG and Trehalose/PEG formulations. PEG has been recommended as a good preferential exclusion agent in formulations (Wong and Parasrampurita, *Pharmaceutical excipients for the stabilization of proteins, BioPharm*, 10(11) 52-61, 1997). It is included in this set of formulation to examine whether it can provide stabilization effect on Adp53. Formulations were filled into the 3 ml lyo vials at a fill volume of 0.5 ml. Vials were capped under either atmospheric or $N_2$ blanketing conditions to examine any positive effects $N_2$ blanketing may have on long term storage stability of Adp53. To ensure adequate degassing from the formulation and subsequent $N_2$ blanketing, the filled vials was partially stoppered with lyo stoppers and loaded onto the shelf of the lyophilizer under RT. The lyophilizer chamber was closed and vacuum was established by turning on the vacuum pump. The chamber was evacuated to 25 in. Hg. Then the chamber was purged completely with dry $N_2$. The evacuation and gassing were repeated twice to ensure complete $N_2$ blanketing. $N_2$ blanketed vials were placed with the non-$N_2$ blanketed vials at various storage conditions for storage stability evaluation. FIG. 33 shows the analysis data for up to 9 months storage at 4° C. and RT.

Statistically significant drops in virus PFU and HPLC viral particles were observed for 10% glycerol formulation after 3 months storage at both 4° C. and RT. No statistically significant virus degradation was observed for all other formulations at 4° C. storage. However, decrease in virus infectivity was observed when stored at RT. Longer time storage is needed to evaluate the effectiveness of the different formulations.

Liquid Formulation #2

Various combinations of amino acids, sugars, PEG and urea were evaluated for Adp53 stabilization during long storage. FIG. 34 shows the 6-month stability data. The results indicate that combination of 5% mannitol and 5% sucrose with other excipients gave better storage stability at RT. In this set of formulation, no human or animal derived excipients were included.

Liquid Formulation Set #3

The optimal formulations developed for lyophilization was evaluated for formulating Adp53 in a liquid form. This approach would be a good bridging between liquid formulation and lyophilization if satisfactory Adp53 stability can be achieved using lyophilization formulation for liquid fill. Filled samples were stored at −20° C. and 4° C. for stability study. FIG. 35 shows the 3-month stability data. Virus is stable at both −20° C. and 4° C. for the four different formulations. This is in agreement with the results from formulation set #2, which suggests that better virus stability is expected with the presence of both mannitol and sucrose in the formulation. Longer time storage stability data is being accrued.

Liquid Formulation Set #4

Detergents have been used in the formulations for a variety of recombinant proteins. In this set of formulation, various concentrations of detergents were examined for formulating Adp53. The detergents used were non-ionic (Tween-80) and zwitterionic (Chaps). FIG. 36 shows the 6-month stability data. Virus is stable at 4° C. storage. Better virus stability is observed in Tween-80 containing formulations. Further accumulation of stability data will help to optimize the detergent concentration. Similar to formulation set #2, no exogenous protein is included in this set of formulations.

Both lyophilization and liquid formulation have produced very interesting and promising data and information. A lyophilization cycle and corresponding formulations have been developed to produce lyophilized Adp53 that is stable at 4° C. for at least 12 months. Longer time storage stability is being collected. Because of the conservative approach taken in the initial development of the lyophilization cycle, we are investigating further to significantly reduce the lyophilization cycle time and to improve the lyophilization process efficiency. Somewhat to our surprise, very promising stability data was generated for liquid formulation at 4° C. storage. However, longer time storage data is needed to evaluate the feasibility of developing a liquid formulation for Adp53.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aboud et al., *Arch. Virol.*, 71:185-195, 1982.
Arap et al., *Cancer Res.*, 55:1351-1354, 1995.
Bahnemann et al., *Abs. Pap. ACS*, 180:5. 1980.
Baichwal and Sugden, In: Kucherlapati R, ed. Gene transfer. New York: Plenum Press, pp. 117-148, 1986.
Benvenisty and Neshif, *Proc. Nat. Acad. Sci. USA*, 83:9551-9555, 1986.
Berg et al., *BioTechniques*, 14(6):972-978, 1993.
Bett, A. J., *Proc Natl Acad Sci USA*, 91 (19):8802-8806, 1994.
Bussemakers et al., *Cancer Res.*, 52:2916-2922, 1992.
Caldas et al., *Nat. Genet.*, 8:27-32, 1994.
Casey et al, *Oncogene*, 6:1791-1797, 1991.
Chen and Okayama, *Mol. Cell. Biol.*, 7:2745-2752, 1987.
Cheng et al., *Cancer Res.*, 54:5547-5551, 1994.
Cheung et al., *Biochem. J*, 295:427-435, 1993c.
Cheung et al., *J. Biol. Chem.*, 268:24303-24310, 1993a.
Cheung et al., *J. Biol. Chem.*, 268:6139-6146, 1993b.
Coffin, In: Fields B N, Knipe D M, ed. Virology. New York: Raven Press, pp. 1437-1500, 1990.
Coupar et al., *Gene*, 68:1-10, 1988.
Crooks et al., *J. Chrom.*, 502: 59-68, 1990.
Dubensky et al., *Proc. Nat. Acad. Sci. USA*, 81:7529-7533, 1984.
Edelman and Crossin, *Annu. Rev. Biochem.*, 60:155-190, 1991
Edelman, *Annu. Rev. Biochem.*, 54:135-169, 1985.
Fechheimer et al., *Proc. Natl. Acad. Sci. USA*, 84:8463-8467, 1987.
Ferkol et al., *FASEB J*, 7:1081-1091, 1993.
Fraley et al., *Proc. Natl. Acad. Sci. USA*, 76:3348-3352, 1979.
Freedman et al., WO 94/17178 (Aug. 4, 1994)
Freshney, In Animal Cell Culture, A Practical Approach, $2^{nd}$ Ed., Oxford Press, UK, 1992
Freshney, in Culture of Animal Cells—A Manual of Basic Techniques, $2^{nd}$ Ed., Alan R. Liss, NY, 1987.
Frixen et al., *J. Cell Biol.*, 113:173-185, 1991.
Garnier et al., *Cytotechnol.*, 15:145-155, 1994.
Ghosh and Bachhawat, In: Wu G, Wu C ed. Liver diseases, targeted diagnosis and therapy using specific receptors and ligands. New York: Marcel Dekker, pp. 87-104, 1991.
Giancotti and Ruoslahti, *Cell*, 60:849-859, 1990.
Gilbert, "Adaptation of cells to serum free culture for production of adenovirus vectors and recombinant proteins," *Williamsburg BioProcessing Conference*, Nov. 18-21, 1996.
Gopal, *Mol. Cell. Biol.*, 5:1188-1190, 1985.
Graham and Prevec, In: Methods in Molecular Biology: Gene Transfer and Expression Protocols 7. Murray, E. J. Editors. Clifton, N.J.: Humana Press, 109-128 and 205-225, 1991.
Graham and Van Der Eb, *Virology*, 52:456-467, 1973.
Graham et al, *Journal of General Virology*, 36:59-74, 1977.
Graham, *J. Gen. Virol.*, 68:93 7-940, 1987.
Griffiths, J. B., In "*Animal Cell Biotechnology*", vol. 3, p179-220, (Eds. Spier, R. E. and Griffiths, J. B.), Academic Press, London., 1986
Harland and Weintraub, *J. Cell Biol.*, 101:1094-1099, 1985.
Hay et al., *Journal of Molecular Biology*, 175:493-510, 1984.
Hearing and Shenk, *Journal of Molecular Biology*, 167:809-822, 1983.
Hearing et al., *Journal of Virology*, 67:2555-2558, 1987.
Hermonat and Muzycska, *Proc. Nat. Acad. Sci. USA*, 81:6466-6470, 1984.
Hollestein et al., *Science*, 253:49-53 1991.
Hussussian et al., *Nature Genetics*, 15-21, 1994.
Huyghe et al., *Human Gene Therapy*, 6:1403-1416, 1996.
Jones and Shenk, *Cell*, 13:181-188, 1978.
Kamb et al., *Nature Genetics*, 8:22-26, 1994.
Kamb et al., *Science*, 2674:436-440, 1994.
Kaneda et al., *Science*, 243:375-378, 1989.
Kato et al., *J. Biol. Chem.*, 266:3361-3364, 1991.
Klein et al., *Nature*, 327:70-73, 1987.
Larsson and Litwin, *Dev. Biol. Standard*, 66:385-390, 1987.
Levrero et al., *Gene*, 101:195-202, 1991.
Lim, U.S. Pat. No. 4,352,883, Oct. 5, 1982.
Lin and Guidotti, *J. Biol. Chem.*, 264:14408-14414, 1989.
Mann et al., *Cell*, 33:153-159, 1983.
Matsura et al., *Brit. J. Cancer*, 66:1122-1130, 1992.
McGrath et al., *J. Virol.*, 25: 923-927, 1978.
Mercer, *Critic. Rev. Eukar. Gene Express.* 2:251-263, 1992.
Mizrahi, *Process Biochem.*, (August):9-12, 1983.
Montenarh, *Crit. Rev. Oncogen*, 3:233-256, 1992.
Mori et al., *Cancer Res.*, 54:3396-3397, 1994.
Morris et al., "Serum-free production of adenoviral vectors for gene therapy," *Williamsburg BioProcessing Conference*, Nov. 18-21, 1996.
Myers, EPO 0273085
Nicolas and Rubenstein, In: Rodriguez R L, Denhardt D T, ed. Vectors: A survey of molecular cloning vectors and their uses. Stoneham: Butterworth, pp. 493-513, 1988.
Nicolau and Sene, *Biochim. Biophys. Acta*, 721:185-190, 1982.
Nicolau et al., *Methods Enzymol.*, 149:157-176, 1987.
Nilsson and Mosbach, *Dev. Biol. Standard*, 66:183-193,
Nobri et al., *Nature (London)*, 368:753-756, 1995.
O'Neil and Balkovic, *Bio/Technol.*, 11:173-178, 1993.
Obrink, *BioEssays.*, 13:227-233, 1991.
Odin and Obrink, *Exp. Cell Res.*, 171:1-15, 1987.

Okamoto et al., *Proc. Natl. Acad. Sci. USA,* 91:11045-11049, 1994.
Orlow et al., *Cancer Res.,* 54:2848-2851, 1994.
Paskind et al., *Virology,* 67:242-248, 1975.
Perales et al., *Proc. Natl. Acad. Sci. USA,* 91:4086-4090, 1994.
Perrin et al., *Vaccine,* 13(13):1244-1250, 1995.
Petricciani, *Dev. Biol. Standard.,* 66:3-12, 1985.
Phillips et al., In: *Large Scale Mammalian Cell Culture* (Feder, J. and Tolbert, W. R., eds.), Academic Press, Orlando, Fla., U.S.A., 1985.
Potter et al., *Proc. Nat. Acad. Sci. USA,* 81:7161-7165, 1984.
Renan, *Radiother. Oncol.,* 19:197-218, 1990.
Ridgeway, In: Rodriguez R L, Denhardt D T, ed. Vectors: A survey of molecular cloning vectors and their uses. Stoneham: Butterworth, pp. 467-492, 1988.
Rippe et al., *Mol. Cell. Biol.,* 10:689-695, 1990.
Roux et al., *Proc. Nat'l Acad. Sci. USA,* 86:9079-9083, 1989.
Serrano et al., *Nature,* 366:704-707, 1993.
Serrano et al., *Science,* 267:249-252, 1995.
Smith and Lee, *Analytical Biochem.,* 86: 252-263, 1978.
Takahashi et al., *Cancer Res.,* 52:2340-2342, 1992.
Temin, In: Kucherlapati R, ed. Gene transfer. New York: Plenum Press, pp. 149-188, 1986.
Tibbetts, *Cell,* 12:243-249, 1977.
Tur-Kaspa et al., *Mol. Cell. Biol.,* 6:716-718, 1986.
Umbas et al., *Cancer Res.,* 52:5104-5109, 1992.
van Wezel, *Nature,* 216:64-65, 1967.
Wagner et al., *Proc. Nat'l. Acad. Sci.,* 87(9):3410-3414, 1990.
Wagner et al., *Science,* 260:1510-1513, 1993.
Wang et al., In: Animal Cell Technology: Basic & Applied Aspects, S. Kaminogawa et al., (eds), vol. 5, pp 463-469, Kluwer Academic Publishers, Netherlands, 1993.
Wang et al., *Cytotechnology,* 9:41-49, 1992.
Wang et al., Proceeding of the Japanese Society for Animal Cell Technology, 1994.
Watt et al., *Proc. Nat'l Acad. Sci.,* 83(2):3166-3170, 1986.
Weinberg, R. A., *Science,* 254:1138-1146, 1991.
Wong et al., *Gene,* 10:87-94, 1980.
Wu and Wu, *J. Biol. Chem.,* 262:4429-4432, 1987.
Wu and Wu, *Adv. Drug Delivery Rev.,* 12:159-167, 1993.
Wu and Wu, *Biochemistry,* 27:887-892, 1988.
Yang et al., *Proc. Nat'l Acad. Sci. USA,* 87:9568-9572, 1990.

What is claimed is:

1. A process for preparing adenovirus, the process comprising:
    (a) preparing a culture of producer cells in a selected media;
    (b) infecting producer cells in the culture with the adenovirus in a bioreactor system, a microcarrier culture system, a multiplate culture system, a perfused packed bed reactor system, or a microencapsulation culture system, wherein the producer cells are infected between late-log phase and stationary phase of growth; and
    (c) harvesting adenovirus from the cell culture.

2. The process of claim 1, wherein the producer cells are perfused for at least a portion of the time that the cells are cultured.

3. The process of claim 2, wherein the producer cells are perfused at a rate that will maintain a glucose level of between about 0.5 and about 3.0 gm glucose/liter.

4. The process of claim 3, wherein the producer cells are perfused at a rate that will maintain a glucose level of between about 0.7 and about 2.0 gm glucose/liter.

5. The process of claim 4, wherein the producer cells are perfused at a rate that maintains a glucose level of between about 1 and about 1.5 gm glucose/liter.

6. The process of claim 1, wherein the producer cells are seeded into the culture medium and allowed to attach to a culture surface for between about 3 hours and about 24 hours prior to infection with adenovirus.

7. The process of claim 1, wherein the culture medium is at least partially recirculated during the adenovirus infection step.

8. The process of claim 1, wherein the culture medium is seeded with between about $0.5 \times 10^4$ and about $3 \times 10^4$ cells/cm2.

9. The process of claim 8, wherein the culture medium is seeded with between about $7.5 \times 10^3$ and about $2.0 \times 10^4$ cell/cm2.

10. The process of claim 9, wherein the culture medium is seeded with between about $9 \times 10^3$ and $1.5 \times 10^4$ cells/cm2.

11. The process of claim 1, wherein the harvested adenovirus is subjected to purification and placed into a pharmaceutically acceptable composition.

12. The process of claim 11, the adenovirus is purified by steps which include chromatography.

13. The process of claim 12, wherein the chromatography step involves subjecting the adenovirus to more than one chromatographic separations.

14. The process of claim 12, wherein the chromatography step involves subjecting the adenovirus to only one chromatographic separation.

15. The process of claim 14, wherein the chromatographic separation includes ion-exchange chromatography.

16. The process of claim 1, wherein said adenovirus is a replication-deficient adenovirus encoding a selected gene operably linked to a promoter.

17. The process of claim 16, wherein said replication deficient adenovirus is lacking at least a portion of the E1 region.

18. The process of claim 17, wherein said producer cells complement the growth of replication deficient adenovirus.

19. The process of claim 1, wherein said producer cells are selected from the group consisting of 293, PER.C6, 911 and IT293SF cells.

20. The process of claim 19, wherein said producer cells are 293 cells.

21. The process of claim 16, wherein said selected gene is selected from the group consisting of antisense ras, antisense myc, antisense raf, antisense erb, antisense src, antisense fms, antisense jun, antisense trk, antisense ret, antisense gsp, antisense hst, antisense bcl antisense abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF, mda-7, thymidine kinase or p53.

22. The process of claim 21, wherein said selected gene is a p53 gene.

23. The process of claim 16, wherein said promoter is an SV40 IE, RSV LTR, β-actin, CMV-IE, adenovirus major late, polyoma F9-1, or tyrosinase promoter.

24. The process of claim 1, wherein the adenovirus is harvested by steps that include lysing the producer cells by means other than freeze-thaw.

25. The process of claim 24, wherein the producer cells are lysed by means of a detergent lysis.

26. The process of claim 24, wherein the producer cells are lysed by means of autolysis.

27. The process of claim 1, further comprising purifying the harvested adenovirus to obtain a purified adenovirus composition having one or more of the following properties:

(a) a virus titer of between about 1×109 and about 1×1013 pfu/ml;
(b) a virus particle concentration between about 1×1010 and about 2×1013 particles/ml;
(c) a particle:pfu ratio between about 10 and about 60;
(d) having less than 50 ng BSA per $1\times10^{e12}$ viral particles;
(e) between about 50 pg and 1 ng of contaminating human DNA per 1×1012 viral particles,
(f) a single HPLC elution peak consisting essentially of 97 to 99% of the area under the peak.

28. The process of claim 27, further comprising formulating the purified adenovirus composition into a pharmaceutically acceptable composition.

29. The process of claim 28, wherein the pharmaceutically acceptable composition is administered to a subject.

30. The process of claim 29, wherein the subject is a mammal.

31. The process of claim 30, wherein the mammal is a human or a mouse.

32. The process of claim 29, wherein administering is intravenously, intradermally, intramuscularly, intraarterially, intralesionally, percutaneously, subcutaneously, or by inhalation.

33. The process of claim 32, wherein administering is intratumorally.

34. The process of claim 1, wherein the adenovirus is a recombinant adenovirus.

35. The process of claim 1, wherein the producer cells are cultured in a bioreactor system.

36. The process of claim 35, wherein the bioreactor system is a stirred tank reactor.

37. The process of claim 35, wherein the bioreactor system is a airlift reactor.

38. The process of claim 35, wherein the bioreactor system is a sparged bioreactor.

39. The process of claim 1, wherein the producer cells are cultured in a microcarrier culture system.

40. The process of claim 1, wherein the producer cells are cultured in a multiplate cell culture system.

41. The process of claim 1, wherein the producer cells are cultured in a perfused packed bed reactor system.

42. The process of claim 1, wherein the producer cells are cultured in a microencapsulation culture system.

43. A process for preparing adenovirus, the process comprising:
(a) preparing a culture of producer cells in a selected media;
(b) infecting producer cells in the culture with the adenovirus, wherein the producer cells are infected between mid-log phase of growth and stationary phase of growth and the producer cells are essentially homogeneous with respect to the phase of cell growth; and
(c) harvesting adenovirus from the cell culture.

44. The process of claim 43, wherein infecting producer cells in the culture with the adenovirus occurs in a bioreactor system, a microcarrier culture system, a multiplate culture system, a perfused packed bed reactor system, or a microencapsulation culture system.

45. A method for producing adenovirus that includes culturing producer cells and infecting the cultured producer cells with an adenovirus, wherein the improvement comprises infecting said producer cells with the adenovirus when the cells in culture are between late-log phase of growth and stationary phase of growth.

46. A method of claim 45, wherein the further improvement comprises infecting the cultured producer cells in a bioreactor system, a microcarrier culture system, a multiplate culture system, a perfused packed bed reactor system, or a microencapsulation culture system.

47. A method of claim 45, wherein the improvement further comprises harvesting adenovirus from the cell culture.

48. A method of claim 45, wherein said adenovirus is a recombinant adenovirus.

49. A method of claim 48, wherein said recombinant adenovirus comprises a selected gene operably linked to a promoter.

50. A method of claim 45, wherein said adenovirus is a replication-deficient adenovirus.

51. A method of claim 50, wherein said replication deficient adenovirus is lacking at least a portion of the E1 region.

52. A method of claim 45, wherein said producer cells complement the growth of replication deficient adenovirus.

53. A method of claim 52, wherein said producer cells are selected from the group consisting of 293, PER.C6, 911 and IT293SF cells.

54. A method of claim 53, wherein said producer cells are 293 cells.

55. A method of claim 49, wherein said selected gene is selected from the group consisting of antisense ras, antisense myc, antisense raf, antisense erb, antisense src, antisense fms, antisense jun, antisense trk, antisense ret, antisense gsp, antisense hst, antisense bcl antisense abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF, mda-7, thymidine kinase or p53.

56. A method of claim 55, wherein said selected gene is a p53 gene.

57. A method of claim 49, wherein said promoter is an SV40 IE, RSV LTR, β-actin, CMV-IE, adenovirus major late, polyoma F9-1, or tyrosinase promoter.

58. A method of claim 47, wherein the improvement further comprises purifying the harvested adenovirus to obtain a purified adenovirus composition having one or more of the following properties:
(a) a virus titer of between about $1\times10^9$ and about $1\times10^{13}$ pfu/ml;
(b) a virus particle concentration between about $1\times10^{10}$ and about $2\times10^{13}$ particles/ml;
(c) a particle:pfu ratio between about 10 and about 60;
(d) having less than 50 ng BSA per $1\times10^{e12}$ viral particles;
(e) between about 50 pg and 1 ng of contaminating human DNA per 1×1012 viral particles,
(f) a single HPLC elution peak consisting essentially of 97 to 99% of the area under the peak.

59. In a method for producing adenovirus that includes culturing producer cells and infecting the cultured producer cells with an adenovirus, wherein the improvement comprises infecting said producer cells with the adenovirus when the cells in culture are between mid-log phase of growth and stationary phase of growth and the producer cells are essentially homogeneous with respect to the phase of cell growth.

* * * * *